(12) United States Patent
El Qacemi et al.

(10) Patent No.: US 10,517,294 B2
(45) Date of Patent: Dec. 31, 2019

(54) DIHYDROTHIOPHENE DERIVATIVES AS INSECTICIDAL COMPOUNDS

(71) Applicant: Syngenta Participations AG, Basel (CH)

(72) Inventors: Myriem El Qacemi, Stein (CH); Jerome Yves Cassayre, Stein (CH); Guillaume Berthon, Stein (CH); Girish Rawal, Goa (IN); Rupesh Patre, Goa (IN)

(73) Assignee: SYNGENTA PARTICIPATIONS AG, Basel (CH)

( * ) Notice: Subject to any disclaimer, the term of this patent is extended or adjusted under 35 U.S.C. 154(b) by 416 days.

(21) Appl. No.: 14/441,304

(22) PCT Filed: Nov. 8, 2013

(86) PCT No.: PCT/EP2013/073421
§ 371 (c)(1),
(2) Date: May 7, 2015

(87) PCT Pub. No.: WO2014/072480
PCT Pub. Date: May 15, 2014

(65) Prior Publication Data
US 2015/0272120 A1 Oct. 1, 2015

(30) Foreign Application Priority Data

Nov. 9, 2012 (IN) .......................... 3500/DEL/2012

(51) Int. Cl.
*A01N 43/10* (2006.01)
*C07D 333/40* (2006.01)
(Continued)

(52) U.S. Cl.
CPC ............ *A01N 43/10* (2013.01); *A01N 37/10* (2013.01); *A01N 43/20* (2013.01); *A01N 43/40* (2013.01);
(Continued)

(58) Field of Classification Search
None
See application file for complete search history.

(56) References Cited

U.S. PATENT DOCUMENTS 3,755,364 A * 8/1973 Magee .................. C07D 307/30
504/288

FOREIGN PATENT DOCUMENTS

| CN | 102114433 | * | 7/2011 |
|---|---|---|---|
| EP | 1932836 | | 6/2008 |
| IL | 47687 | | 1/1979 |
| WO | 20110101229 | | 8/2011 |

OTHER PUBLICATIONS

Duus F. A Study of the Tautomerism of 2- and 4-Ethoxycarbonylthiolan-3-Ones Implicating Stereochemical Effects of Ring-Substitution. Tetrahedron vol. 37, No. 15, pp. 2633 to 2640, 1981.*
(Continued)

*Primary Examiner* — Joseph R Kosack
(74) *Attorney, Agent, or Firm* — BakerHostetler LLP; Toni-Junell Herbert

(57) ABSTRACT

The present invention provides compounds of formula (I) wherein Q is Q1 or Q2 P is P0, heterocyclyl or heterocyclyl substituted by one to five Z; $Y^1$, $Y^2$, $Y^3$ and $Y^4$ are independently of each other C—H, C—$R^5$, or nitrogen; $G^1$ is oxygen or sulfur; $R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-; $X^4$ is $C_1$-$C_8$haloalkyl; $R^4$ is aryl or aryl substituted by one to five $R^9$, or heteroaryl or heteroaryl substituted by one to five $R^9$; n is 0, 1 or 2; and Z, $R^2$, $R^5$ and $R^9$ are as defined in the claims. The invention also provides methods of controlling insects, acarines, nematodes or molluscs comprising applying to a pest, to a locus of a pest, or to a plant susceptible to attack by a pest an insecticidally, acaricidally, nematicidally or molluscicidally effective amount of a compound of formula (I).

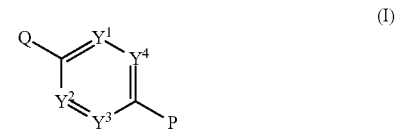

(I)

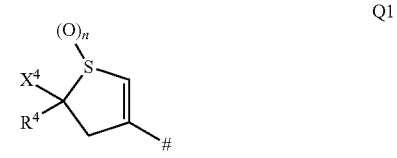

Q1

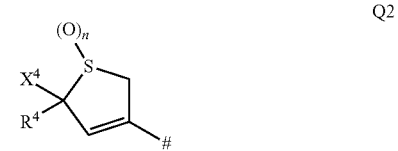

Q2

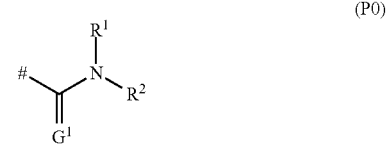

(P0)

24 Claims, No Drawings

(51) Int. Cl.

| | |
|---|---|
| *C07D 333/24* | (2006.01) |
| *C07D 409/12* | (2006.01) |
| *A01N 43/20* | (2006.01) |
| *C07D 413/12* | (2006.01) |
| *A01N 43/80* | (2006.01) |
| *A01N 43/40* | (2006.01) |
| *C07D 333/32* | (2006.01) |
| *C07D 333/48* | (2006.01) |
| *C07D 409/10* | (2006.01) |
| *A01N 43/653* | (2006.01) |
| *A01N 37/10* | (2006.01) |
| *C07D 333/38* | (2006.01) |

(52) U.S. Cl.
CPC ........... *A01N 43/653* (2013.01); *A01N 43/80* (2013.01); *C07D 333/24* (2013.01); *C07D 333/32* (2013.01); *C07D 333/38* (2013.01); *C07D 333/40* (2013.01); *C07D 333/48* (2013.01); *C07D 409/10* (2013.01); *C07D 409/12* (2013.01); *C07D 413/12* (2013.01)

(56) References Cited

OTHER PUBLICATIONS

Thornber CW. Isosterism and Molecular Modification in Drug Design. Chem. Soc. Rev., 1979,8, 563-580. (Year: 1979).*
Patani et al. "Bioisosterism: A Rational Approach in Drug Design" Chemical Reviews, 1996, vol. 96, pp. 3147-3176.*
Database CA, Chemical Abstracts Service, Columbus, OH, US, Hutchinson, Douglas K. et al: "Phenyloxazolidinones Having a C—C Bond to 4-8 Membered Heterocyclic Rings, and Their Use As Antimicrobials.", retrieved from STN Database accession No. 1997:302929, Mar. 13, 1997.
International Search Report dated Feb. 25, 2014 for International Patent Application No. PCT/EP2013/073421.

* cited by examiner

DIHYDROTHIOPHENE DERIVATIVES AS INSECTICIDAL COMPOUNDS

RELATED APPLICATION INFORMATION

This application is a 371 of International Application No. PCT/EP2013/073421, filed 8 Nov. 2013, which claims priority to IN Patent Application No. 3500/DEL/2012, filed 9 Nov. 2012, the contents of which are incorporated by reference herein.

The present invention relates to certain dihydrothiophene derivatives, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain isoxazoline derivatives with insecticidal properties are disclosed, for example, in EP 1,731,512 and WO 2011/101229. However there is a continuing need to find new biologically active compounds as well as new biologically active compounds displaying superior properties for use as agrochemical active ingredients, for example greater biological activity, different spectrum of activity, increased safety profile, or increased biodegradability.

It has now surprisingly been found that certain dihydrothiophenederivatives have highly potent insecticidal properties.

The present invention provides compounds of formula (I)

(I)

[Structure: six-membered ring with Q, Y¹, Y², Y³, Y⁴, P substituents]

wherein Q is Q1 or Q2

Q1

[Structure: dihydrothiophene ring with (O)$_n$, S, X⁴, R⁴, #]

Q2

[Structure: dihydrothiophene ring with (O)$_n$, S, X⁴, R⁴, #]

wherein
P is P0, heterocyclyl or heterocyclyl substituted by one to five Z;

(P0)

[Structure: #—C(=G¹)—N(R¹)(R²)]

$Y^1$, $Y^2$, $Y^3$ and $Y^4$ are independently of each other C—H, C—$R^5$, or nitrogen;

$G^1$ is oxygen or sulfur;
$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, $C_3$-$C_{10}$cycloalkyl-$C_1$-$C_4$alkylene or $C_3$-$C_{10}$cycloalkyl-$C_1$-$C_4$alkylene substituted by one to five $R^7$, $C_3$-$C_{10}$cycloalkenyl or $C_3$-$C_{10}$cycloalkenyl substituted by one to five $R^7$, $C_3$-$C_{10}$ cycloalkenyl-$C_1$-$C_4$ alkylene or $C_3$-$C_{10}$ cycloalkenyl-$C_1$-$C_4$ alkylene substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$ alkylene- wherein the heterocyclyl moiety is substituted by one to five $R^8$, aryl-N($R^{20}$)— or aryl-N($R^{20}$)— wherein the aryl moiety is substituted by one to five $R^8$, heterocyclyl-N($R^{20}$)— or heterocyclyl-N($R^{20}$)— wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, $C_1$-$C_8$alkylaminocarbonyl-, $C_1$-$C_8$haloalkylaminocarbonyl, $C_3$-$C_8$cycloalkyl-aminocarbonyl, $C_1$-$C_6$alkyl-O—N=CH—, $C_1$-$C_6$haloalkyl-O—N=CH—, and wherein a bridging alkylene moiety may include a —C($R^{21}$)($R^{22}$)— unit as bridge member; or $R^1$ and $R^2$ together represent group A (A)

[Structure: $G^2$=C(#)—$G^3$ (or similar)]

$G^2$ is O($R^{13}$), N($R^{14}$)($R^{15}$) or S($R^{16}$);
$G^3$ is N($R^{17}$)($R^{18}$) or S($R^{19}$);
$X^4$ is $C_1$-$C_8$haloalkyl;
$R^4$ is aryl or aryl substituted by one to five $R^9$, or heteroaryl or heteroaryl substituted by one to five $R^9$; each $R^5$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-; or two $R^5$ on adjacent carbon atoms together form a —CH=CH—CH=CH— bridge;
each $R^6$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, $C_1$-$C_8$alkoxy-, $C_1$-$C_8$haloalkoxy-, aryloxy or aryloxy substituted by one to five $R^{10}$, aryloxy-$C_1$-$C_4$alkylene or aryloxy-$C_1$-$C_4$alkylene wherein the aryl moiety is substituted by one to five $R^{10}$, $C_1$-$C_8$ alkylcarbonyl-, $C_1$-$C_8$ alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, aryl-$C_1$-$C_4$alkylthio or aryl-$C_1$-$C_4$alkylthio wherein the aryl moiety is substituted by one to five $R^{10}$;
each $R^7$ is independently halogen, cyano, $C_1$-$C_8$alkyl, $C_2$-$C_8$alkenyl, $C_2$-$C_8$alkynyl, $C_1$-$C_8$alkyl-O—N=, $C_1$-$C_8$haloalkyl-O—N=, $C_1$-$C_8$alkoxy, $C_1$-$C_4$alkoxy-$C_1$-$C_4$ alkyl, $C_1$-$C_8$alkoxycarbonyl;

each $R^8$ is independently halogen, cyano, nitro, oxo, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy-, $C_1$-$C_8$haloalkoxy-, mercapto, $C_1$-$C_5$ alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$ alkylaminosulfonyl, $(C_1$-$C_8$ alkyl$)_2$ aminosulfonyl-, $C_1$-$C_8$ alkylcarbonyl-, $C_1$-$C_8$ alkoxycarbonyl-, aryl or aryl substituted by one to five $R^{10}$, heterocyclyl or heterocyclyl substituted by one to five $R^{10}$, aryl-$C_1$-$C_4$alkylene or aryl-$C_1$-$C_4$alkylene wherein the aryl moiety is substituted by one to five $R^{10}$, heterocyclyl-$C_1$-$C_4$ alkylene or heterocyclyl-$C_1$-$C_4$ alkylene wherein the heterocyclyl moiety is substituted by one to five $R^{10}$, aryloxy or aryloxy substituted by one to five $R^{10}$, aryloxy-$C_1$-$C_4$alkylene or aryloxy-$C_1$-$C_4$alkylene wherein the aryl moiety is substituted by one to five $R^{10}$;

each $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$ alkylthio-, $C_1$-$C_8$haloalkylthio-, $C_1$-$C_8$ alkylsulfinyl-, $C_1$-$C_8$haloalkylsulfinyl-, $C_1$-$C_8$ alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{10}$, or heterocyclyl or heterocyclyl substituted by one to five $R^{10}$;

each $R^{10}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;

each Z is independently halogen, $C_1$-$C_{12}$ alkyl or $C_1$-$C_{12}$ alkyl substituted by one to five $R^6$, nitro, $C_1$-$C_{12}$ alkoxy or $C_1$-$C_{12}$ alkoxy substituted by one to five $R^6$, cyano, $C_1$-$C_{12}$ alkylsulfinyl, $C_1$-$C_{12}$ alkylsulfonyl, $C_1$-$C_{12}$haloalkylsulfinyl, $C_1$-$C_{12}$haloalkylsulfonyl, hydroxyl or thiol;

$R^{13}$, $R^{16}$ and $R^{19}$ are independently $C_1$-$C_4$alkyl;

$R^{14}$, $R^{15}$, $R^{17}$, and $R^{18}$ are independently hydrogen or $C_1$-$C_4$alkyl;

$R^{20}$ is hydrogen or $C_1$-$C_4$alkyl;

each $R^{21}$ and $R^{22}$ is independently halogen or $C_1$-$C_4$alkyl, or may together form a $C_3$-$C_4$alkylene bridge;

n is 0, 1 or 2;

or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds. For example, a tautomer of $C_1$-$C_6$alkyl-O—N=CH—NH—C(=O)— is $C_1$-$C_6$alkyl-O—NH—CH=N—C(=O)—.

The invention also covers N-oxides and salts. The compounds of the invention may contain one or more additional asymmetric carbon atoms and may exist as enantiomers (or as pairs of diastereo-isomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazolyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include isoxazolyl, thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of P, Q, $Y^1$, $Y^2$, $Y^3$, $Y^4$, $G^1$, Z, $R^1$, $R^2$, $X^4$, $R^4$, $R^5$, $R^6$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$, $R^{21}$, $R^{22}$, are, in any combination, as set out below.

Preferably, Q is Q1, more preferably Q1 wherein n is 0.

Preferably, P is P0, or a heterocycle selected from H1 to H9

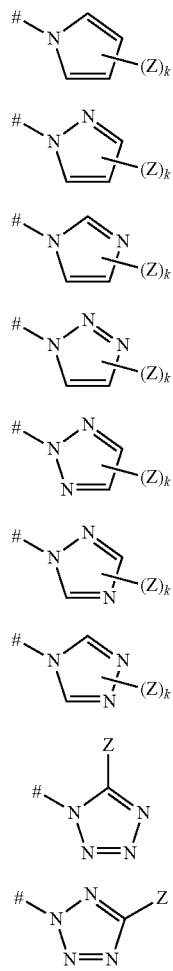

k is 0, 1 or 2.

When P is a heterocycle, P is preferably H2 or H6.

More preferably P is P0.

In one group of compounds P is P0. In another group of compounds P is a heterocycle, preferably selected form H1 to H9, more preferably H2 or H6.

Preferably no more than two of $Y^1$, $Y^2$, $Y^3$ and $Y^4$ are nitrogen, more preferably no more than one of $Y^1$, $Y^2$, $Y^3$ and $Y^4$ is nitrogen.

Preferably $Y^1$ is C—H or C—$R^5$, most preferably $Y^1$ is C—H.

Preferably $Y^2$ is C—H or C—$R^5$, most preferably $Y^2$ is C—H.

Preferably $Y^3$ is C—H or C—$R^5$, most preferably $Y^3$ is C—H.

Preferably $Y^4$ is C—H or C—$R^5$, most preferably $Y^4$ is C—$R^5$.

In one preferred group of compounds $Y^1$ is C—$R^{5b}$, C—H or nitrogen, $Y^2$ and $Y^3$ are independently C—H or nitrogen and $Y^4$ is C—$R^5$; wherein no more than two of $Y^1$, $Y^2$ and $Y^3$ are nitrogen and wherein $Y^2$ and $Y^3$ are not both nitrogen, and wherein $R^{5b}$ when present forms a —CH=CH— bridge with $R^5$.

In another preferred group of compounds $Y^1$ is C—H, $Y^2$ is C—H or nitrogen, $Y^3$ is C—H or nitrogen and $Y^4$ is C—$R^5$, wherein $Y^2$ and $Y^3$ are not both nitrogen.

In another preferred group of compounds $Y^1$ is C—H, $Y^2$ is C—H, $Y^3$ is C—H and $Y^4$ is C—$R^5$.

Preferably $G^1$ is oxygen.

Preferably $R^1$ is hydrogen, methyl, ethyl, methylcarbonyl-, or methoxycarbonyl-, more preferably hydrogen, methyl or ethyl, most preferably hydrogen.

Preferably, $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$ alkylene- or heterocyclyl-$C_1$-$C_4$ alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1

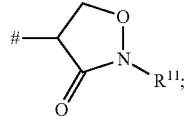

(C1)

wherein $R^{11}$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^{12}$, or $R^{11}$ is pyridyl-methyl- or pyridyl-methyl-substituted by one to three $R^{12}$; and each $R^{12}$ is independently fluoro, chloro, bromo, trifluoromethyl, trifluoromethoxy, cyano or methoxy. In one group of compounds $R^{11}$ is $C_1$-$C_4$alkyl or $C_1$-$C_4$haloalkyl. ethyl and trifluoroethyl are particularly preferred.

A heterocyclyl group as defined for $R^2$ is preferably a 4- to 6-membered saturated or partially saturated heterocyclic ring containing one or two heteroatoms independently selected from O, S, SO, $SO_2$, N and N($R^{11}$) as ring atoms, or is a 5- or 6-membered heteroaryl ring containing one to three heteroatoms independently selected from O, N and S as ring atoms, more preferably the heterocyclyl is a 4- to 6-membered saturated or partially saturated heterocyclic ring containing one or two heteroatoms independently selected from O, S, SO, $SO_2$, N and N($R^{11}$) as ring atoms or is a 5- or 6-membered heteroaryl ring containing one to three heteroatoms independently selected from O, N and S as ring atoms, even more preferably heterocyclyl is pyridyl, pyridyl-N-oxide, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, thiadiazolyl or group C1 or C2.

More preferably $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$ alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1 wherein each aryl group is a phenyl group and each heterocyclyl group is independently selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, dihydrothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo[1,4]dioxinyl.

More preferably $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$ alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1, wherein each aryl group is a phenyl group and each heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1, wherein each aryl group is a phenyl group and each heterocyclyl group is selected from pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^6$, $C_3$-$C_{10}$cycloalkyl or $C_3$-$C_{10}$ substituted by one to five $R^7$, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to four $R^8$, tetrahydrofuranyl-$C_1$-$C_4$alkylene- or tetrahydrofuranyl-$C_1$-$C_4$alkylene- wherein the tetrahydrofuranyl moiety is substituted by one to five $R^8$, imidazolyl-$C_1$-$C_4$alkylene- or imidazolyl-$C_1$-$C_4$alkylene- wherein the imidazolyl moiety is substituted by one to three $R^8$, pyrazolyl-$C_1$-$C_4$alkylene- or pyryazolyl-$C_1$-$C_4$alkylene- wherein the pyrazolyl moiety is substituted by one to three $R^8$, pyrrolyl-$C_1$-$C_4$alkylene- or pyrrolyl-$C_1$-$C_4$alkylene- wherein the pyrrolyl moiety is substituted by one to four $R^8$, thiazolyl-$C_1$-$C_4$alkylene- or thiazolyl-$C_1$-$C_4$alkylene- wherein the thiazolyl moiety is substituted by one to four $R^8$, oxetanyl-$C_1$-$C_4$ alkylene or oxetanyl-$C_1$-$C_4$ alkylene wherein the oxetanyl moiety is substituted by one to five $R^8$, thietanyl-$C_1$-$C_4$ alkylene or thietanyl-$C_1$-$C_4$ alkylene wherein the thietanyl moiety is substituted by one to five $R^8$, oxo-thietanyl-$C_1$-$C_4$ alkylene or oxo-thietanyl-$C_1$-$C_4$ alkylene wherein the oxo-thietanyl moiety is substituted by one to five $R^8$, dioxo-thietanyl-$C_1$-$C_4$ alkylene or dioxo-thietanyl-$C_1$-$C_4$ alkylene wherein the dioxo-thietanyl moiety is substituted by one to five $R^8$, oxetanyl or oxetanyl substituted by one to five $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group C1.

Even more preferably $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to four $R^8$, oxetanyl or oxetanyl substituted by one to five $R^8$, thietanyl-$C_1$-$C_4$ alkylene or thietanyl-$C_1$-$C_4$ alkylene wherein the thietanyl moiety is substituted by one to five $R^8$, oxo-thietanyl-$C_1$-$C_4$ alkylene or oxo-thietanyl-$C_1$-$C_4$ alkylene wherein the oxo-thietanyl moiety is substituted by one to five $R^8$, dioxo-thietanyl-$C_1$-$C_4$ alkylene or dioxo-thietanyl-$C_1$-$C_4$ alkylene wherein the dioxo-thietanyl moiety is substituted by one to five $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, or group C1.

Yet even more preferably $R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two groups independently selected from fluoro and methyl, phenyl-$C_1$-$C_4$ alkylene- or phenyl-$C_1$-$C_4$ alkylene- wherein the phenyl moiety is substituted by one to five $R^8$, pyridyl-$C_1$-$C_4$alkylene- or pyridyl-$C_1$-$C_4$ alkylene- wherein the pyridyl moiety is substituted by one to four $R^8$, thietanyl, oxo-thietanyl, dioxo-thietanyl, $C_1$-$C_8$alkylaminocarbonyl-methylene, $C_1$-$C_8$haloalkylaminocarbonyl-methylene, $C_3$-$C_8$cycloalkyl-aminocarbonyl-methylene, group C1, $C_1$-$C_6$alkyl-O—N=CH— or $C_1$-$C_6$haloalkyl-O—N=CH—.

Yet even more preferably $R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two groups independently selected from fluoro and methyl, phenyl-$C_1$-$C_2$ alkylene- or phenyl-$C_1$-$C_2$ alkylene- wherein the phenyl moiety is substituted by one to five $R^8$, pyridyl-$C_1$-$C_2$alkylene- or pyridyl-$C_1$-$C_2$alkylene- wherein the pyridyl moiety is substituted by one to four $R^8$, thietanyl, oxo-thietanyl, dioxo-thietanyl, $C_1$-$C_4$alkylaminocarbonyl-methylene, $C_1$-$C_4$haloalkylaminocarbonyl-methylene, $C_3$-$C_8$cycloalkyl-aminocarbonyl-methylene, group C1, $C_1$-$C_4$alkyl-O—N=CH— or $C_1$-$C_4$haloalkyl-O—

N=CH— and wherein each $R^8$ is independently bromo, chloro, fluoro, cyano or methyl.

A group of preferred compounds are those wherein $R^2$ is $C_1$-$C_6$alkyl or $C_1$-$C_6$alkyl substituted by one to five $R^6$, for example ethyl-, butyl-, but-2-yl-, 3-bromo-propyl-, 2,2,2-trifluoro-ethyl-, 3,3,3-trifluoro-propyl-, 2-methoxy-ethyl-, and 1-methoxy-prop-2-yl-.

A group of preferred compounds are those wherein $R^2$ is $C_3$-$C_8$cycloalkyl or $C_3$-$C_8$cycloalkyl substituted by one to five $R^7$, for example cyclobutyl-, 2-fluoro-cyclopropyl and 2-methyl-cyclohex-1-yl-.

A group of preferred compounds are those wherein $R^2$ is aryl-$C_1$-$C_2$alkylene- or aryl-$C_1$-$C_2$alkylene- wherein the aryl moiety is substituted by one to five $R^8$, for example phenyl-methyl-, 1-phenyl-eth-1-yl-, 2-phenyl-eth-1-yl-, (3-chloro-phenyl)-methyl-, (2-fluoro-phenyl)-methyl-, (4-methoxy-phenyl)-methyl-, (2-trifluoromethyl-phenyl)-methyl-, and (2-trifluoromethoxy-phenyl)-methyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^8$, for example (pyrid-2-yl)-methyl-, (pyrid-3-yl)-methyl-, (2-chloro-pyrid-5-yl)-methyl-, (1-methyl-1H-imidazol-4-yl)-methyl-, (furan-2-yl)-methyl-, 2-(thiophen-2'-yl)-eth-1-yl-, 2-(indol-3'-yl)-eth-1-yl-, (1H-benzimidazol-2-yl)-methyl-, (oxetan-2-yl)-methyl-, (tetrahydrofuran-2-yl)-methyl-, 2-([1',3']dioxolan-2'-yl)-eth-1-yl-, 2-(morpholin-4'-yl)-eth-1-yl-, 2-(benzo[1',3']dioxol-5'-yl)-eth-1-yl-, (2,3-dihydro-benzo[1,4]dioxin-6-yl)-methyl-, thietan-2-yl-methyl-, 1-oxo-thietan-2-yl-methyl-, 1,1-dioxo-thietan-2-yl-methyl-, thietan-3-yl-methyl-, 1-oxo-thietan-3-yl-methyl-, 1,1-dioxo-thietan-3-yl-methyl-, thietan-3-yl-ethyl-, 1-oxo-thietan-3-yl-ethyl-, and 1,1-dioxo-thietan-3-yl-ethyl-, preferably thietan-2-yl-methyl-, 1-oxo-thietan-2-yl-methyl-, 1,1-dioxo-thietan-2-yl-methyl-, thietane-3-yl-methyl-, 1-oxo-thietan-3-yl-methyl-, 1,1-dioxo-thietan-3-yl-methyl-, thietan-3-yl-ethyl-, 1-oxo-thietan-3-yl-ethyl-, and 1,1-dioxo-thietan-3-yl-ethyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^8$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl, preferably the heterocyclyl group is selected from thietanyl, oxo-thietanyl and dioxo-thietanyl.

A group of preferred compounds are those wherein $R^2$ is heteroaryl-$C_1$-$C_2$alkylene- or heteroaryl-$C_1$-$C_2$alkylene- wherein the heteroaryl moiety is substituted by one to five $R^8$.

A group of preferred compounds are those wherein $R^2$ is aryl or aryl substituted by one to five $R^8$, for example 2-chloro-phenyl-, 3-fluoro-phenyl-, 2-methyl-phenyl-, 2-chloro-6-methyl-phenyl-, 2-trifluoromethyl-phenyl-, and 2,4-dimethoxy-phenyl-.

A group of preferred compounds are those wherein $R^2$ is heterocyclyl or heterocyclyl substituted by one to five $R^8$, for example 3-methyl-pyrid-2-yl-, 1,3-dimethyl-1H-pyrazol-5-yl-, 4-methyl-thiazol-2-yl-, 5-methyl-thiadiazol-2-yl-, quinolin-2-yl-, quinolin-5-yl-, benzothiazol-6-yl-, 4-methyl-benzothiazol-2-yl-, thietan-3-yl-, 1-oxo-thietan-3-yl-, 1,1-dioxo-thietan-3-yl-, and 3-methyl-thietan-3-yl-, more preferably $R^2$ is oxetanyl, thietanyl, oxo-thietanyl or dioxo-thietanyl each optionally substituted by one to five $R^8$, most preferably $R^2$ is thietanyl, oxo-thietanyl or dioxo-thietanyl each optionally substituted by one to five $R^8$. It is particularly preferred that the oxetanyl, thietanyl, oxo-thietanyl or dioxo-thietanyl ring is linked via the 3-position.

A group of preferred compounds are those wherein $R^2$ is heterocyclyl- or heterocyclyl substituted by one to five $R^8$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl, preferably the heterocyclyl group is selected from thietanyl, oxo-thietanyl and dioxo-thietanyl.

A group of preferred compounds are those wherein $R^2$ is $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, more preferably $C_1$-$C_4$alkylaminocarbonyl-$C_1$-$C_4$ alkylene, $C_1$-$C_4$haloalkylaminocarbonyl-$C_1$-$C_4$ alkylene, or $C_3$-$C_6$cycloalkyl-aminocarbonyl-$C_1$-$C_4$ alkylene, most preferably $C_1$-$C_4$alkylaminocarbonyl-$C_1$-$C_2$ alkylene or $C_1$-$C_4$haloalkylaminocarbonyl-$C_1$-$C_2$ alkylene.

A group of preferred compounds are those wherein $R^1$ and $R^2$ together represent group A

(A)

wherein $G^2$ and $G^3$ are as defined above, for example group A1, A2, A3 or A4

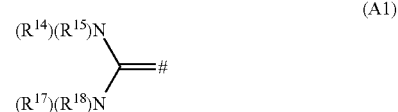

(A1)

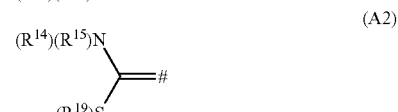

(A2)

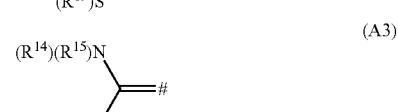

(A3)

(A4)

wherein $R^{13}$, $R^{14}$, $R^{15}$, $R^{16}$, $R^{17}$, $R^{18}$ and $R^{19}$ are as defined above.

$R^{13}$, $R^{17}$, $R^{18}$ and $R^{19}$ are preferably $C_1$-$C_4$alkyl, more preferably methyl or ethyl.

$R^{14}$ and $R^{15}$ are preferably hydrogen.

A group of preferred compounds are those wherein $R^2$ is group C1.

A group of preferred compounds are those wherein $R^2$ is group C2.

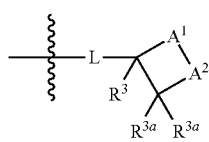
(C2)

wherein L is a bond, methylene or ethylene; one of $A^1$ and $A^2$ is S, SO or $SO_2$ and the other is $-C(R^{3a})R^{3a}-$; $R^3$ is hydrogen or methyl; each $R^{3a}$ is independently hydrogen or methyl; and preferably L is a bond, preferably $R^3$ and each $R^{3a}$ is hydrogen; preferably $A^1$ is $-C(R^4)R^4-$, more preferably $-CH_2-$; preferably $A^2$ is S, SO or $SO_2$.

In one group of compounds P is selected from P0 and P1 to P44 and $R^2$ is group C1 or C2

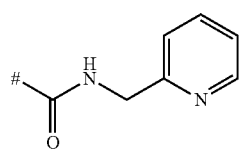
P1

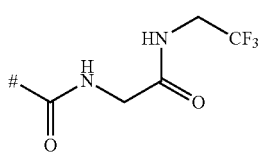
P2

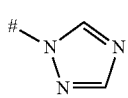
P3

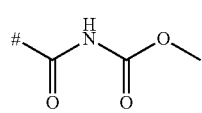
P4

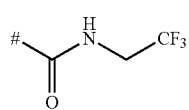
P5

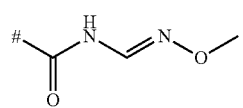
P6

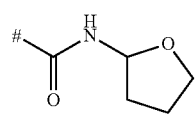
P7

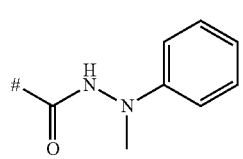
P8

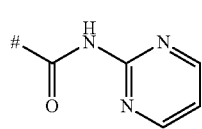
P9

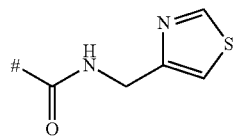
P10

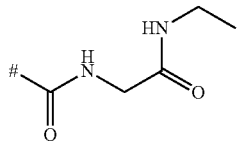
P11

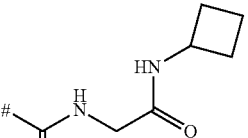
P12

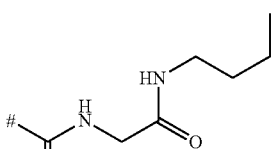
P13

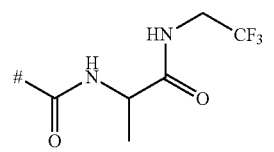
P14

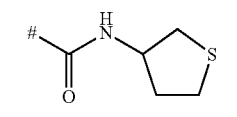
P15

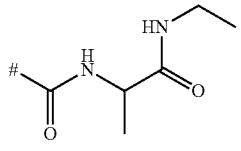
P16

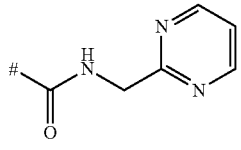
P17

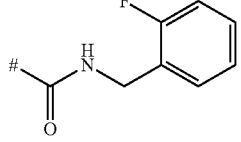
P18

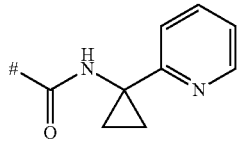
P19

-continued
P20 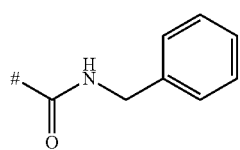
P21 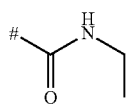
P22 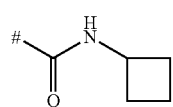
P23 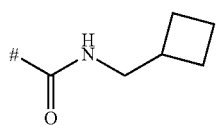
P24 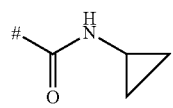
P25 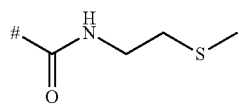
P26 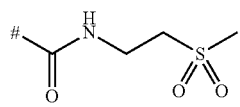
P27 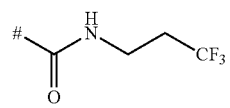
P28 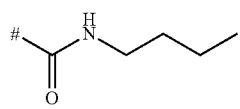
P29 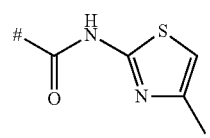
P30 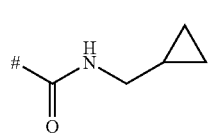
P31 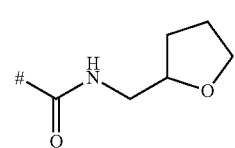
P32 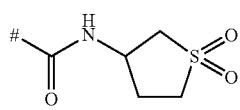
-continued
P33 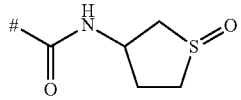
P34 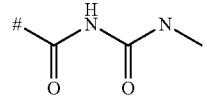
P35 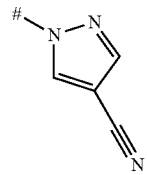
P36 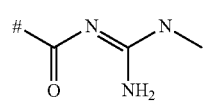
P37 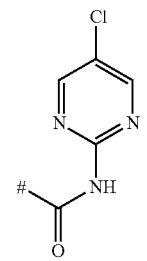
P38 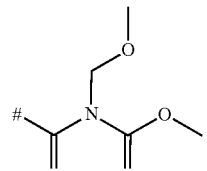
P39 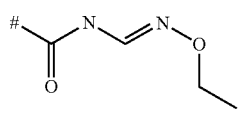
P40 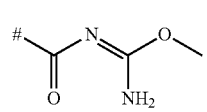
P41 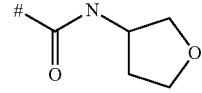
P42 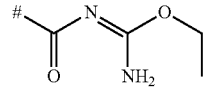
P43 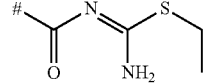

-continued

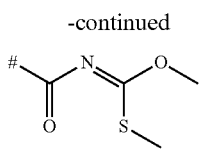

P44

Preferably X⁴ is trifluoromethyl, difluoromethyl or chlorodifluoromethyl, most preferably trifluoromethyl.

Preferably $R^4$ is aryl or aryl substituted by one to five $R^9$, more preferably aryl substituted by one to three $R^9$, more preferably phenyl substituted by one to three $R^9$. In one group of compounds R is group

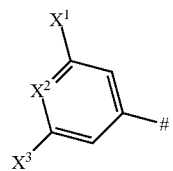

(B)

wherein $X^2$ is C—$X^6$ or nitrogen (preferably C—$X^6$); $X^1$, $X^3$ and $X^6$ are independently hydrogen, halogen or trihalomethyl, e.g. wherein at least two of $X^1$, $X^3$ and $X^6$ are not hydrogen; even more preferably $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, 3-bromo-5-(trifluoromethyl)phenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl) phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably $R^2$ is 3,5-dichloro-phenyl, 3,5-dichloro-4-fluorophenyl- or 3,4, 5-trichloro-phenyl, most preferably 3,5-dichloro-phenyl.

In one group of compounds $R^4$ is 3,5-dichloro-phenyl. In one group of compounds $R^4$ is 3,5-dichloro-4-fluorophenyl-. In one group of compounds $R^4$ is 3,4,5-trichlorophenyl-. In one group of compounds $R^4$ is 3,5-bis(trifluoromethyl)phenyl.

Preferably each $R^5$ is independently halogen, cyano, nitro, $NH_2$, $C_1$-$C_8$alkyl, $C_1$-$C_8$haloalkyl, $C_3$-$C_5$cycloalkyl, $C_3$-$C_5$halocycloalkyl, $C_1$-$C_8$alkenyl, $C_1$-$C_8$haloalkenyl, $C_1$-$C_8$alkoxy-, or $C_1$-$C_8$haloalkoxy-, preferably halogen, cyano, nitro, $NH_2$, $C_1$-$C_2$alkyl, $C_1$-$C_2$haloalkyl, $C_3$-$C_5$cycloalkyl, $C_3$-$C_5$halocycloalkyl, $C_1$-$C_2$alkoxy, $C_1$-$C_2$haloalkoxy; more preferably chloro, bromo, fluoro, trifluoromethyl, methyl, ethyl, methoxy, nitro, trifluoromethoxy, cyano, cyclopropyl, even more preferably $R^5$ is chloro, bromo, fluoro, methyl or trifluoromethyl, most preferably methyl.

In one group of compounds $R^5$ is chloro. In one group of compounds $R^5$ is bromo. In one group of compounds $R^5$ is methyl. In one group of compounds $R^5$ is halogen.

Preferably each $R^6$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$ alkylsulfinyl-, $C_1$-$C_8$haloalkylsulfinyl-, $C_1$-$C_8$ alkylsulfonyl-, or $C_1$-$C_8$haloalkylsulfonyl-, more preferably each $R^6$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-, more preferably bromo, chloro, fluoro, methoxy, or methylthio, most preferably chloro, fluoro, or methoxy.

Preferably each $R^7$ is independently halogen or $C_1$-$C_8$alkyl, more preferably each $R^7$ is independently chloro, fluoro or methyl, most preferably fluoro or methyl.

Preferably each $R^8$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$ alkylthio-, $C_1$-$C_8$haloalkylthio-, $C_1$-$C_8$ alkylsulfinyl-, $C_1$-$C_8$haloalkylsulfinyl-, $C_1$-$C_8$ alkylsulfonyl-, $C_1$-$C_8$haloalkylsulfonyl-, $C_1$-$C_8$ alkylcarbonyl-, $C_1$-$C_8$alkoxycarbonyl-, aryl or aryl substituted by one to five $R^{10}$, or heterocyclyl or heterocyclyl substituted by one to five $R^{10}$, more preferably each $R^8$ is independently halogen, cyano, nitro, $C_1$-$C_8$alkyl, $C_1$-$C_8$haloalkyl, $C_1$-$C_8$alkoxy-, $C_1$-$C_8$haloalkoxy-, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Preferably each $R^9$ is independently halogen, $C_1$-$C_8$alkyl, $C_1$-$C_8$haloalkyl, $C_1$-$C_8$alkoxy-, $C_1$-$C_8$haloalkoxy-, $C_1$-$C_8$alkylthio-, or $C_1$-$C_8$haloalkylthio-, more preferably bromo, chloro, fluoro, trifluoromethyl, methoxy, or methylthio, most preferably bromo or chloro.

Preferably each $R^{10}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

Preferably $R^{11}$ is methyl, ethyl or trifluoroethyl.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, more preferably each Z is independently hydrogen, halogen, cyano, methyl, halomethyl, methoxy or halomethoxy.

Preferably n is 0 or 1, more preferably 0.

In the following embodiments reference to "Het" means heterocyclyl or heterocyclyl substituted by one to five Z as defined for P above.

In one embodiment E1 the present invention provides compounds of formula (Ia-1)

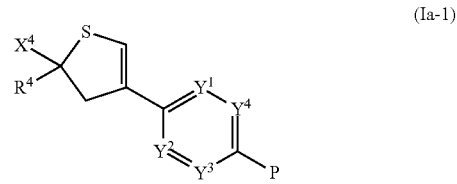

(Ia-1)

wherein P, $X^4$, $Y^1$, $Y^2$, $Y^3$, $Y^4$ and $R^4$ are as defined for compounds of formula (I); or a salt or N-oxide thereof. The preferences for P, $X^4$, $Y^1$, $Y^2$, $Y^3$, $Y^4$ and $R^4$ are the same as the preferences set out for the corresponding substituents of compounds of the formula (I).

In one embodiment E2 the present invention provides compounds of formula (Ia-2)

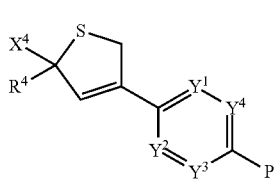
(Ia-2)

wherein P, $X^4$, $Y^1$, $Y^2$, $Y^3$, $Y^4$ and $R^4$ are as defined for compounds of formula (I); or a salt or N-oxide thereof. The preferences for P, $X^4$, $Y^1$, $Y^2$, $Y^3$, $Y^4$ and $R^4$ are the same as the preferences set out for the corresponding substituents of compounds of the formula (I).

In a further embodiment E3 the present invention provides compounds of formula (Ib-1)

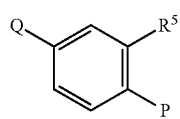
(Ib-1)

wherein Q, P and $R^5$ are as defined for compounds of formula (I); or a salt or N-oxide thereof. The preferences for Q, P and $R^5$ are the same as the preferences set out for the corresponding substituents of compounds of the formula (I).

In a further embodiment E4 the present invention provides compounds of formula (Ib-2)

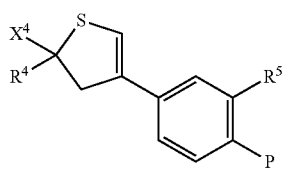
(Ib-2)

wherein P, $X^4$, $R^4$ and $R^5$ are as defined for compounds of formula (I); or a salt or N-oxide thereof. The preferences for P, $X^4$, $R^4$ and $R^5$ are the same as the preferences set out for the corresponding substituents of compounds of the formula (I).

In a further embodiment E5 the present invention provides compounds of formula (Ib-3)

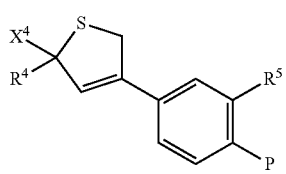
(Ib-3)

wherein P, $X^4$, $R^4$ and $R^5$ are as defined for compounds of formula (I); or a salt or N-oxide thereof. The preferences for P, $X^4$, $R^4$ and $R^5$ are the same as the preferences set out for the corresponding substituents of compounds of the formula (I).

In a further embodiment E6 the present invention provides compounds of formula (Ic-1)

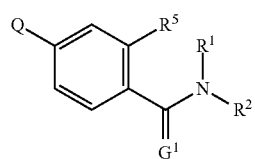
(Ic-1)

wherein Q, $G^1$, $R^1$, $R^2$ and $R^5$ are as defined for compounds of formula (I); or a salt or N-oxide thereof. The preferences for Q, $G^1$, $R^1$, $R^2$ and $R^5$ are the same as the preferences set out for the corresponding substituents of compounds of the formula (I).

In a further embodiment E7 the present invention provides compounds of formula (Ic-2)

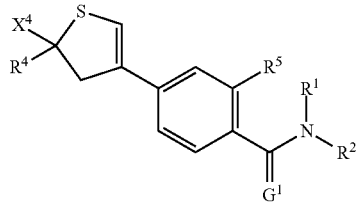
(Ic-2)

wherein $G^1$, $X^4$, $R^1$, $R^2$, $R^4$ and $R^5$ are as defined for compounds of formula (I); or a salt or N-oxide thereof. The preferences for $G^1$, $X^4$, $R^1$, $R^2$, $R^4$ and $R^5$ are the same as the preferences set out for the corresponding substituents of compounds of the formula (I).

In a further embodiment E8 the present invention provides compounds of formula (Ic-3)

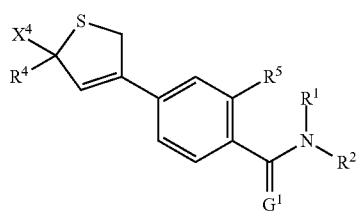
(Ic-3)

wherein $G^1$, $X^4$, $R^1$, $R^2$, $R^4$ and $R^5$ are as defined for compounds of formula (I); or a salt or N-oxide thereof. The preferences for $G^1$, $X^4$, $R^1$, $R^2$, $R^4$ and $R^5$ are the same as the preferences set out for the corresponding substituents of compounds of the formula (I).

In a further embodiment E9 the present invention provides compounds of formula (Id-1)

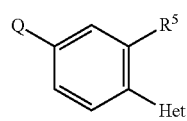
(Id-1)

wherein Q, Het and $R^5$ are as defined for compounds of formula (I); or a salt or N-oxide thereof. The preferences for Q, Het and $R^5$ are the same as the preferences set out for the corresponding substituents of compounds of the formula (I).

In a further embodiment E10 the present invention provides compounds of formula (Id-2)

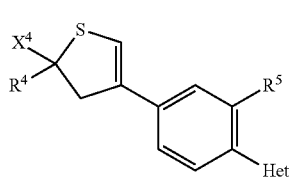

(Id-2)

wherein Het, $X^4$, $R^4$ and $R^5$ are as defined for compounds of formula (I); or a salt or N-oxide thereof. The preferences for Het, $X^4$, $R^4$ and $R^5$ are the same as the preferences set out for the corresponding substituents of compounds of the formula (I).

In a further embodiment E11 the present invention provides compounds of formula (Id-3)

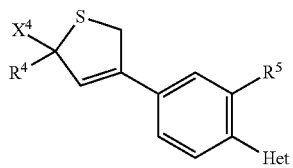

(Id-3)

wherein Het, $X^4$, $R^4$ and $R^5$ are as defined for compounds of formula (I); or a salt or N-oxide thereof. The preferences for Het, $X^4$, $R^4$ and $R^5$ are the same as the preferences set out for the corresponding substituents of compounds of the formula (I).

In a further embodiment E12 the present invention provides compounds of formula (Ie-1)

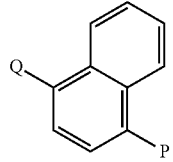

(Ie-1)

wherein Q and P are as defined for compounds of formula (I); or a salt or N-oxide thereof. The preferences for Q and P are the same as the preferences set out for the corresponding substituents of compounds of the formula (I).

In a further embodiment E13 the present invention provides compounds of formula (Ie-2)

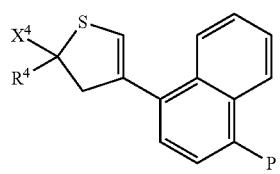

(Ie-2)

wherein P, $X^4$ and $R^4$ are as defined for compounds of formula (I); or a salt or N-oxide thereof. The preferences for P, $X^4$ and $R^4$ are the same as the preferences set out for the corresponding substituents of compounds of the formula (I).

In a further embodiment E14 the present invention provides compounds of formula (Ie-3)

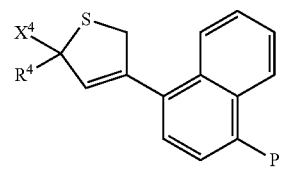

(Ie-3)

wherein P, $X^4$ and $R^4$ are as defined for compounds of formula (I); or a salt or N-oxide thereof. The preferences for P, $X^4$ and $R^4$ are the same as the preferences set out for the corresponding substituents of compounds of the formula (I).

In a further embodiment E15 the present invention provides compounds of formula (If-1)

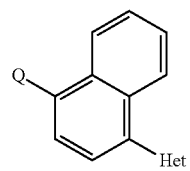

(If-1)

wherein Q and Het are as defined for compounds of formula (I); or a salt or N-oxide thereof. The preferences for Q and Het are the same as the preferences set out for the corresponding substituents of compounds of the formula (I).

In a further embodiment E16 the present invention provides compounds of formula (If-2)

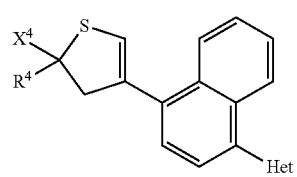

(If-2)

wherein Het, $X^4$ and $R^4$ are as defined for compounds of formula (I); or a salt or N-oxide thereof. The preferences for Het, $X^4$ and $R^4$ are the same as the preferences set out for the corresponding substituents of compounds of the formula (I).

In a further embodiment E17 the present invention provides compounds of formula (If-3)

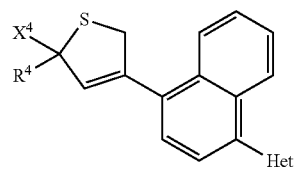

(If-3)

wherein Het, $X^4$ and $R^4$ are as defined for compounds of formula (I); or a salt or N-oxide thereof. The preferences for Het, $X^4$ and $R^4$ are the same as the preferences set out for the corresponding substituents of compounds of the formula (I).

In a further embodiment E18 the present invention provides compounds of formula (Ig-1)

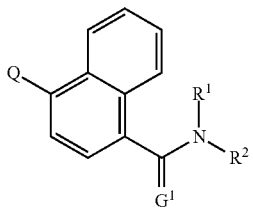

(Ig-1)

wherein Q, $G^1$, $R^1$ and $R^2$ are as defined for compounds of formula (I); or a salt or N-oxide thereof. The preferences for Q, $G^1$, $R^1$ and $R^2$ are the same as the preferences set out for the corresponding substituents of compounds of the formula (I).

In a further embodiment E19 the present invention provides compounds of formula (Ig-2)

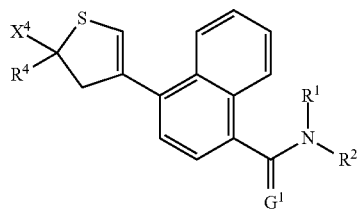

(Ig-2)

wherein $X^4$, $G^1$, $R^1$, $R^2$ and $R^4$ are as defined for compounds of formula (I); or a salt or N-oxide thereof. The preferences for $X^4$, $G^1$, $R^1$, $R^2$ and $R^4$ are the same as the preferences set out for the corresponding substituents of compounds of the formula (I).

In a further embodiment E20 the present invention provides compounds of formula (Ig-3)

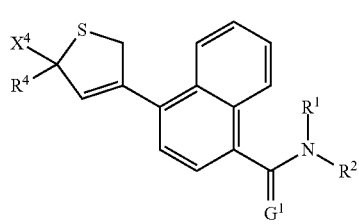

(Ig-3)

wherein $X^4$, $G^1$, $R^1$, $R^2$ and $R^4$ are as defined for compounds of formula (I); or a salt or N-oxide thereof. The preferences for $X^4$, $G^1$, $R^1$, $R^2$ and $R^4$ are the same as the preferences set out for the corresponding substituents of compounds of the formula (I).

In a further embodiment E21 the present invention provides compounds of formula (Ih-1)

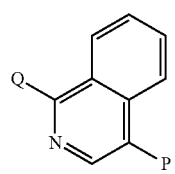

(Ih-1)

wherein Q and P are as defined for compounds of formula (I); or a salt or N-oxide thereof. The preferences for Q and P are the same as the preferences set out for the corresponding substituents of compounds of the formula (I).

In a further embodiment E22 the present invention provides compounds of formula (Ih-2)

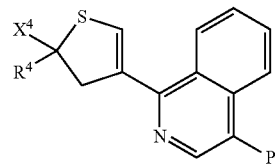

(Ih-2)

wherein P, $X^4$ and $R^4$ are as defined for compounds of formula (I); or a salt or N-oxide thereof. The preferences for P, $X^4$ and $R^4$ are the same as the preferences set out for the corresponding substituents of compounds of the formula (I).

In a further embodiment E23 the present invention provides compounds of formula (Ih-3)

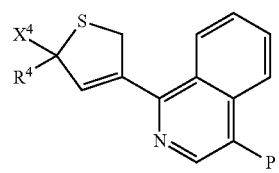

(Ih-3)

wherein P, $X^4$ and $R^4$ are as defined for compounds of formula (I); or a salt or N-oxide thereof. The preferences for QP, $X^4$ and $R^4$ are the same as the preferences set out for the corresponding substituents of compounds of the formula (I).

In a further embodiment E24 the present invention provides compounds of formula (Ii-1)

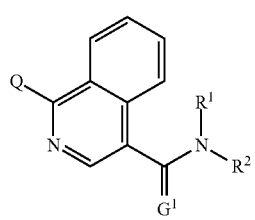

(Ii-1)

wherein Q, $G^1$, $R^1$ and $R^2$ are as defined for compounds of formula (I); or a salt or N-oxide thereof. The preferences for Q, $G^1$, $R^1$ and $R^2$ are the same as the preferences set out for the corresponding substituents of compounds of the formula (I).

In a further embodiment E25 the present invention provides compounds of formula (Ii-2)

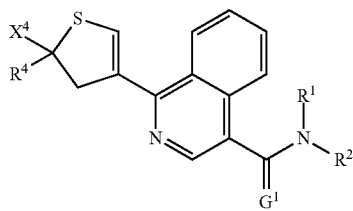

(Ii-2)

wherein $X^4$, $G^1$, $R^1$, $R^2$ and $R^4$ are as defined for compounds of formula (I); or a salt or N-oxide thereof. The preferences for $X^4$, $G^1$, $R^1$, $R^2$ and $R^4$ are the same as the preferences set out for the corresponding substituents of compounds of the formula (I).

In a further embodiment E26 the present invention provides compounds of formula (Ii-3)

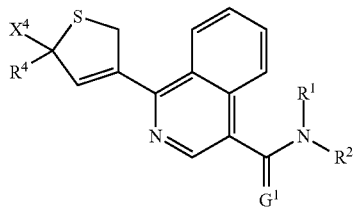

(Ii-3)

wherein $X^4$, $G^1$, $R^1$, $R^2$ and $R^4$ are as defined for compounds of formula (I); or a salt or N-oxide thereof. The preferences for $X^4$, $G^1$, $R^1$, $R^2$ and $R^4$ are the same as the preferences set out for the corresponding substituents of compounds of the formula (I).

In a further embodiment E27 the present invention provides compounds of formula (Ij-1)

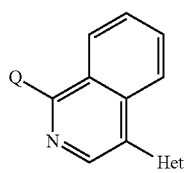

(Ij-1)

wherein Q and Het are as defined for compounds of formula (I); or a salt or N-oxide thereof. The preferences for Q and Het are the same as the preferences set out for the corresponding substituents of compounds of the formula (I).

In a further embodiment E28 the present invention provides compounds of formula (Ij-2)

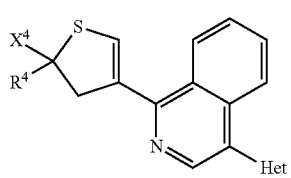

(Ij-2)

wherein Het, $X^4$ and $R^4$ are as defined for compounds of formula (I); or a salt or N-oxide thereof. The preferences for Het, $X^4$ and $R^4$ are the same as the preferences set out for the corresponding substituents of compounds of the formula (I).

In a further embodiment E29 the present invention provides compounds of formula (Ij-3)

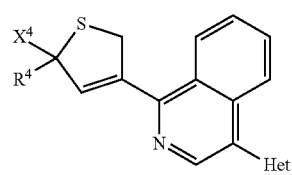

(Ij-3)

wherein Het, $X^4$ and $R^4$ are as defined for compounds of formula (I); or a salt or N-oxide thereof. The preferences for Het, $X^4$ and $R^4$ are the same as the preferences set out for the corresponding substituents of compounds of the formula (I).

In a further embodiment E30 the present invention provides compounds of formula (Ik-1)

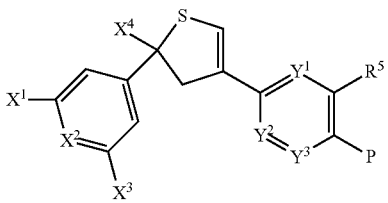

(Ik-1)

wherein P, $X^1$, $X^2$, $X^3$, $X^4$, $X^4$, $Y^1$, $Y^2$, $Y^3$ and $R^5$ are as defined for compounds of formula (I); or a salt or N-oxide thereof. The preferences for P, $X^1$, $X^2$, $X^3$, $X^4$, $Y^1$, $Y^2$, $Y^3$ and $R^5$ are the same as the preferences set out for the corresponding substituents of compounds of the formula (I).

In a further embodiment E31 the present invention provides compounds of formula (Ik2)

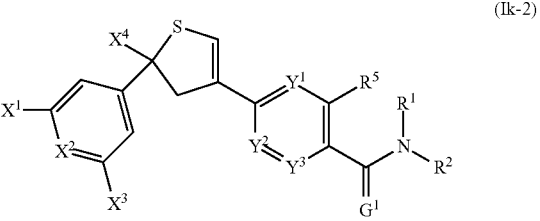

(Ik-2)

wherein $X^1$, $X^2$, $X^3$, $X^4$, $Y^1$, $Y^2$, $Y^3$, $R^1$, $R^2$ and $R^5$ are as defined for compounds of formula (I); or a salt or N-oxide thereof. The preferences for $X^1$, $X^2$, $X^3$, $X^4$, $Y^1$, $Y^2$, $Y^3$, $R^1$, $R^2$ and $R^5$ are the same as the preferences set out for the corresponding substituents of compounds of the formula (I).

In a further embodiment E32 the present invention provides compounds of formula (Ik-3)

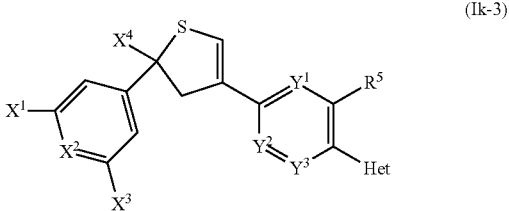
(Ik-3)

wherein Het, $X^1$, $X^2$, $X^3$, $X^4$, $Y^1$, $Y^2$, $Y^3$ and $R^5$ are as defined for compounds of formula (I); or a salt or N-oxide thereof. The preferences for Het, $X^1$, $X^2$, $X^3$, $X^4$, $Y^1$, $Y^2$, $Y^3$ and $R^5$ are the same as the preferences set out for the corresponding substituents of compounds of the formula (I).

In a further embodiment E33 the present invention provides compounds of formula (II-1)

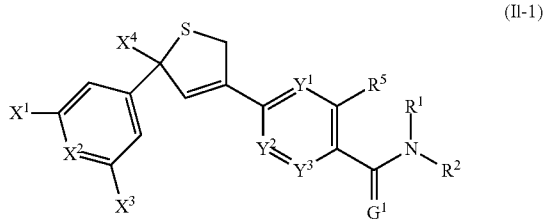
(II-1)

wherein $X^1$, $X^2$, $X^3$, $X^4$, $Y^1$, $Y^2$, $Y^3$, $R^1$, $R^2$ and $R^5$ are as defined for compounds of formula (I); or a salt or N-oxide thereof. The preferences for $X^1$, $X^2$, $X^3$, $X^4$, $Y^1$, $Y^2$, $Y^3$, $R^1$, $R^2$ and $R^5$ are the same as the preferences set out for the corresponding substituents of compounds of the formula (I).

In a further embodiment E34 the present invention provides compounds of formula (II-2)

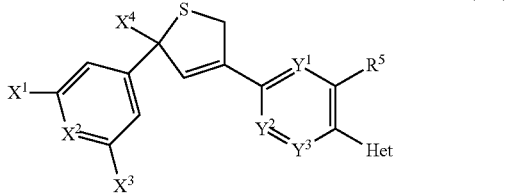
(II-2)

wherein Het, $X^1$, $X^2$, $X^3$, $X^4$, $Y^1$, $Y^2$, $Y^3$ and $R^5$ are as defined for compounds of formula (I); or a salt or N-oxide thereof. The preferences for Het, $X^1$, $X^2$, $X^3$, $X^4$, $Y^1$, $Y^2$, $Y^3$ and $R^5$ are the same as the preferences set out for the corresponding substituents of compounds of the formula (I).

In a further embodiment E35 the present invention provides compounds of formula (II-3)

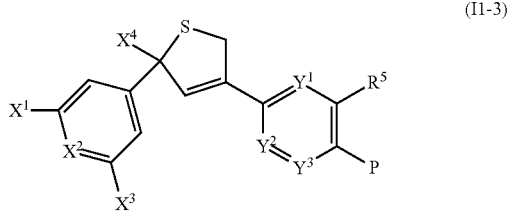
(II-3)

wherein P, $X^1$, $X^2$, $X^3$, $X^4$, $Y^1$, $Y^2$, $Y^3$ and $R^5$ are as defined for compounds of formula (I); or a salt or N-oxide thereof. The preferences for P, $X^1$, $X^2$, $X^3$, $X^4$, $Y^1$, $Y^2$, $Y^3$ and $R^5$ are the same as the preferences set out for the corresponding substituents of compounds of the formula (I).

In a further embodiment E36

$R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl-N($R^{20}$)— or aryl-N($R^{20}$)— wherein the aryl moiety is substituted by one to five $R^8$, heterocyclyl-N($R^{20}$)— or heterocyclyl-N($R^{20}$)— wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, $C_1$-$C_8$alkylaminocarbonyl-, $C_1$-$C_8$haloalkylaminocarbonyl, $C_3$-$C_8$cycloalkyl-aminocarbonyl, $C_1$-$C_6$alkyl-O—N=CH—, $C_1$-$C_6$haloalkyl-O—N=CH—;

each $R^7$ is independently halogen, $C_1$-$C_8$alkyl, $C_1$-$C_8$alkenyl, $C_1$-$C_8$alkynyl, $C_1$-$C_6$alkyl-O—N=, $C_1$-$C_8$haloalkyl-O—N=; $C_1$-$C_8$alkoxy, $C_1$-$C_8$akoxycarbonyl;

and all other substituents are as defined for the compound of formula (I).

In a preferred embodiment E37

Q is Q1;

P is P0, or H1 to H9;

$Y^1$, $Y^2$, $Y^3$ and $Y^4$ are independently of each other C—H;

$Y^4$ is C—$R^5$;

$G^1$ is oxygen or sulfur;

$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;

$R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, $C_1$-$C_8$alkylaminocarbonyl-, $C_1$-$C_8$haloalkylaminocarbonyl, $C_3$-$C_8$cycloalkyl-aminocarbonyl, $C_1$-$C_6$alkyl-O—N=CH—, $C_1$-$C_6$haloalkyl-O—N=CH—;

and $X^4$, $R^4$, $R^5$, $R^6$, $R^7$, $R^8$, n, Z and k are as defined for compounds of formula I.

A preferred embodiment is E30, wherein $Y^1$ is C—$R^{5b}$, CH or nitrogen;

$Y^2$ and $Y^3$ are independently CH or nitrogen wherein no more than two of $Y^1$, $Y^2$ and $Y^3$ are nitrogen and wherein $Y^2$ and $Y^3$ are not both nitrogen;

$R^5$ is hydrogen, halogen, cyano, nitro, $NH_2$, $C_1$-$C_2$alkyl, $C_1$-$C_2$haloalkyl, $C_3$-$C_5$cycloalkyl, $C_3$-$C_5$halocycloalkyl, $C_1$-$C_2$alkoxy, $C_1$-$C_2$haloalkoxy;

$R^{5b}$ when present together with $R^5$ forms a —CH=CH—CH=CH— bridge;

$X^2$ is C—$X^6$ or nitrogen;

$X^1$, $X^2$, $X^3$ and $X^6$ are independently hydrogen, halogen or trihalomethyl, e.g. wherein at least two of $X^1$, $X^3$ and $X^6$ are not hydrogen;

$X^4$ is trifluoromethyl, difluoromethyl or chlorodifluoromethyl;

A more preferred embodiment is E30, wherein

P is P0, H2 or H6;

$Y^1$ is C—H, $Y^2$ is C—H, $Y^3$ is C—H;

$G^1$ is oxygen;

$R^1$ is hydrogen;

$R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two groups independently selected from fluoro and methyl, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$ alkylene- wherein the pyridyl moiety is substituted by one to four $R^8$, thietanyl, oxo-thietanyl, dioxo-thietanyl, $C_1$-$C_8$ alkylaminocarbonyl-methylene, $C_1$-$C_8$haloalkylaminocarbonyl-methylene, $C_3$-$C_8$cycloalkyl-aminocarbonyl-methylene, group C1, $C_1$-$C_6$alkyl-O—N=CH—, $C_1$-$C_6$haloalkyl-O—N=CH—;

$R^5$ is chloro, bromo, fluoro, methyl or trifluoromethyl;

$R^8$ is bromo, chloro, fluoro, cyano, nitro, methyl, ethyl, trifluoromethyl;

$X^2$ is C—$X^6$;

$X^1$, $X^3$ and $X^6$ are independently hydrogen, halogen or trihalomethyl, e.g. wherein at least two of $X^1$, $X^3$ and $X^6$ are not hydrogen;

$X^4$ is trifluoromethyl, difluoromethyl or chlorodifluoromethyl;

k is 0, 1;

each Z is independently hydrogen, halogen, cyano, methyl, halomethyl, methoxy or halomethoxy.

A particularly preferred embodiment is E31 in which $Y^1$ is C—H, $Y^2$ is C—H, $Y^3$ is C—H;

$G^1$ is oxygen;

$R^1$ is hydrogen;

$R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two groups independently selected from fluoro and methyl, phenyl-$C_1$-$C_4$alkylene- or phenyl-$C_1$-$C_4$ alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to four $R^8$, thietanyl, oxo-thietanyl, dioxo-thietanyl, $C_1$-$C_8$alkylaminocarbonyl-methylene, $C_1$-$C_8$haloalkylaminocarbonyl-methylene, $C_3$-$C_8$cycloalkyl-aminocarbonyl-methylene, group C1, $C_1$-$C_6$alkyl-O—N=CH—, $C_1$-$C_6$haloalkyl-O—N=CH—;

$R^5$ is chloro, bromo, fluoro, methyl or trifluoromethyl;

$R^8$ is bromo, chloro, fluoro, cyano, nitro, methyl, ethyl, trifluoromethyl;

$X^2$ is C—$X^6$;

$X^1$, $X^3$ and $X^6$ are independently hydrogen, halogen or trihalomethyl, e.g. wherein at least two of $X^1$, $X^3$ and $X^6$ are not hydrogen;

$X^4$ is trifluoromethyl.

A further particularly preferred embodiment is E31 in which $Y^1$ is C—H, $Y^2$ is C—H, $Y^3$ is C—H;

$G^1$ is oxygen;

$R^1$ is hydrogen;

$R^2$ is $C_1$-$C_8$alkyl or $C_1$-$C_8$alkyl substituted by one to three halogen atoms, $C_3$-$C_6$cycloalkyl or $C_3$-$C_6$cycloalkyl substituted by one or two groups independently selected from fluoro and methyl, phenyl-$CH_2$ or phenyl-$CH_2$— wherein the phenyl moiety is substituted by one to five $R^8$, pyridyl-$CH_2$— or pyridyl-$CH_2$— wherein the pyridyl moiety is substituted by one to four $R^8$, thietanyl, oxo-thietanyl, dioxo-thietanyl, $C_1$-$C_8$alkylaminocarbonyl-methylene, $C_1$-$C_8$haloalkylaminocarbonyl-methylene, $C_3$-$C_8$cycloalkyl-aminocarbonyl-methylene, group C1, $C_1$-$C_6$alkyl-O—N=CH—, $C_1$-$C_6$haloalkyl-O—N=CH—;

$R^5$ is chloro, bromo, fluoro, methyl or trifluoromethyl;

$R^8$ is bromo, chloro, fluoro, cyano, nitro, methyl, ethyl, trifluoromethyl;

$X^2$ is C—$X^6$;

$X^1$, $X^3$ and $X^6$ are independently hydrogen, halogen or trihalomethyl, e.g. wherein at least two of $X^1$, $X^3$ and $X^6$ are not hydrogen;

$X^4$ is trifluoromethyl.

The present invention also provides intermediates useful for the preparation of compounds of formula I. One group of novel intermediates are compounds of formula (Int-I)

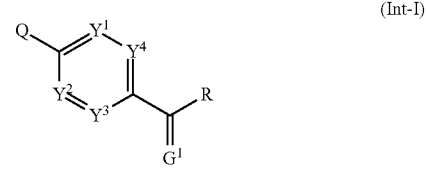

wherein Q, $G^1$, $Y^1$, $Y^2$, $Y^3$ and $Y^4$ are as defined for a compound of formula (I), and R is hydroxy, $C_1$-$C_{15}$ alkoxy or halogen, such as bromo, chloro or fluoro; or a salt or N-oxide thereof. The preferences for Q, $G^1$, $Y^1$, $Y^2$, $Y^3$ and $Y^4$ are the same as the preferences set out for the corresponding substituents of a compound of formula (I). Preferably R is hydroxy, $C_1$-$C_6$alkoxy or chloro. In one embodiment Q is Q1.

In a further embodiment Q is Q2.

A further group of novel intermediates are compounds of formula (Int-II)

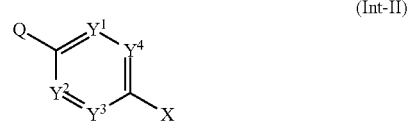

wherein Q, $Y^1$, $Y^2$, $Y^3$ and $Y^4$ are as defined for a compound of formula (I), and X is a leaving group such as halogen, $C_1$-$C_8$ alkoxy, cyano, $C_1$-$C_8$ alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. X is —$N_2^+Cl^-$, —$N_2^+BF_4^-$, —$N_2^+Br$, —$N_2^+F_6^-$), phosphonate esters (e.g. —OP(O)(OR)$_2$, wherein R is methyl or ethyl), preferably bromo, iodo, chloro, trifluoromethylsulfoxy, p-toluenesulfoxy, diazonium chloride; or a salt or N-oxide thereof. The preferences for Q, $Y^1$, $Y^2$, $Y^3$ and $Y^4$ are the same as the preferences set out for the corresponding substituents of a compound of formula (I). In one embodiment Q is Q1. In a further embodiment Q is Q2.

A further group of novel intermediates are compounds of formula (Int-III)

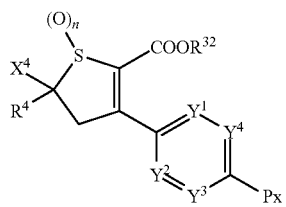

(Int-III)

wherein n, $X^4$, $Y^1$, $Y^2$, $Y^3$, $Y^4$ and $R^4$ are as defined for compounds of formula (I), Px is P as defined above, a leaving group as defined for X in compounds of formula Int-II, or C(O)R wherein R is halogen, OH or $C_1$-$C_{15}$ alkoxy, and $R^{32}$ is hydrogen or $C_1$-$C_{15}$ alkyl, or a salt or N-oxide thereof. The preferences for $X^4$, $Y^1$, $Y^2$, $Y^3$, $Y^4$ and $R^4$ and the preferences at position Px when Px is P are the same as the preferences set out for the corresponding substituents of a compound of formula (I). In one embodiment Px is P0. In a further embodiment Px is heterocyclyl or heterocyclyl substituted by one to five Z. In a further embodiment Px is a leaving group as defined for X in compounds of formula Int-II. In a further embodiment Px is C(O)R wherein R is halogen, OH or $C_1$-$C_{15}$ alkoxy.

A further group of novel intermediates are compounds of formula (Int-IV)

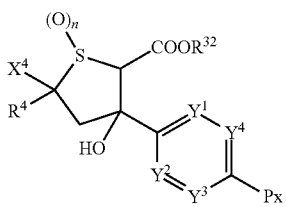

(Int-IV)

wherein n, $X^4$, $Y^1$, $Y^2$, $Y^3$, $Y^4$ and $R^4$ are as defined for compounds of formula (I), Px is P as defined above, a leaving group as defined for X in compounds of formula Int-II, or C(O)R wherein R is halogen, OH or $C_1$-$C_{15}$ alkoxy, and $R^{32}$ is hydrogen or $C_1$-$C_{15}$ alkyl, or a salt or N-oxide thereof. The preferences for $X^4$, $Y^1$, $Y^2$, $Y^3$, $Y^4$ and $R^4$ and the preferences at position Px when Px is P are the same as the preferences set out for the corresponding substituents of a compound of formula (I). In one embodiment Px is P0. In a further embodiment Px is heterocyclyl or heterocyclyl substituted by one to five Z. In a further embodiment Px is a leaving group as defined for X in compounds of formula Int-II. In a further embodiment Px is C(O)R wherein R is halogen, OH or $C_1$-$C_{15}$ alkoxy.

A further group of novel intermediates are compounds of formula (Int-V)

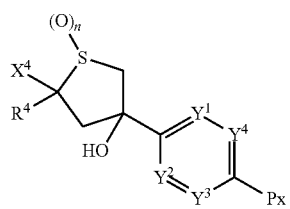

(Int-V)

wherein n, $X^4$, $Y^1$, $Y^2$, $Y^3$, $Y^4$ and $R^4$ are as defined for compounds of formula (I), Px is P as defined above, a leaving group as defined for X in compounds of formula Int-II, or C(O)R wherein R is halogen, OH or $C_1$-$C_{15}$ alkoxy, and $R^{32}$ is hydrogen or $C_1$-$C_{15}$ alkyl, or a salt or N-oxide thereof. The preferences for $X^4$, $Y^1$, $Y^2$, $Y^3$, $Y^4$ and $R^4$ and the preferences at position Px when Px is P are the same as the preferences set out for the corresponding substituents of a compound of formula (I). In one embodiment Px is P0. In a further embodiment Px is heterocyclyl or heterocyclyl substituted by one to five Z. In a further embodiment Px is a leaving group as defined for X in compounds of formula Int-II. In a further embodiment Px is C(O)R wherein R is halogen, OH or $C_1$-$C_{15}$ alkoxy.

A further group of novel intermediates are compounds of formula (Int-VI)

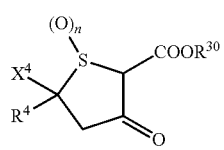

(Int-VI)

wherein n, $X^4$ and $R^4$ are as defined for compounds of formula (I) and $R^{30}$ is $C_1$-$C_{15}$ alkyl, or a salt or N-oxide thereof. The preferences for $X^4$ and $R^4$ are the same as the preferences set out for the corresponding substituents of a compound of formula (I).

A further group of novel intermediates are compounds of formula (Int-VII)

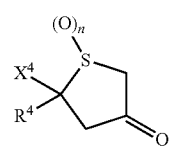

(Int-VII)

wherein n, $X^4$ and $R^4$ are as defined for compounds of formula (I), or a salt or N-oxide thereof. The preferences for $X^4$ and $R^4$ are the same as the preferences set out for the corresponding substituents of a compound of formula (I).

A further group of novel intermediates are compounds of formula (Int-VIII)

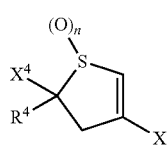

(Int-VIII)

wherein n, $X^4$ and $R^4$ are as defined for compounds of formula (I) and X is a leaving group as defined in compounds of formula Int-II, or a salt or N-oxide thereof. The preferences for $X^4$ and $R^4$ are the same as the preferences set out for the corresponding substituents of a compound of formula (I).

A further group of novel intermediates are compounds of formula (Int-IX).

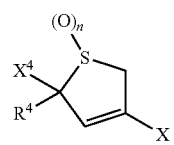
(Int-IX)

wherein n, $X^4$ and $R^4$ are as defined for compounds of formula (I) and X is a leaving group as defined in compounds of formula Int-II, or a salt or N-oxide thereof. The preferences for $X^4$ and $R^4$ are the same as the preferences set out for the corresponding substituents of a compound of formula (I).

Compounds of formula I include at least one chiral centre and may exist as compounds of formula Ia-1* or compounds of formula Ia-1** when Q is Q1, or compounds of formula Ia-2* or compounds of formula Ia-2** when Q is Q2

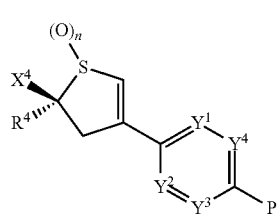
(Ia-1*)

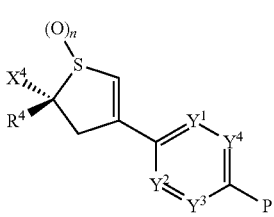
(Ia-1**)

Generally compounds of formula Ia-1** are more biologically active than compounds of formula Ia-1*. The invention includes mixtures of compounds Ia-1* and Ia-1 in any ratio e.g. in a molar ratio of 1:99 to 99:1, e.g. 10:1 to 1:10, e.g. a substantially 50:50 molar ratio. In an enantiomerically (or epimerically) enriched mixture of formula Ia-1, the molar proportion of compound Ia-1** compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula Ia-1*, the molar proportion of the compound of formula Ia-1* compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula Ia-1** are preferred. Each compound disclosed in Tables 1P-120P and Tables 1Q to 240Q represents a disclosure of a compound according to the compound of formula I*, and a disclosure according to the compound of formula I**.

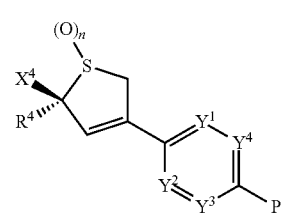
(Ia-2*)

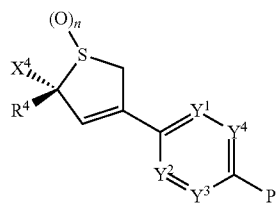
(Ia-2**)

Likewise, generally compounds of formula Ia-2** are more biologically active than compounds of formula Ia-2*. The invention includes mixtures of compounds Ia-2* and Ia-2 in any ratio e.g. in a molar ratio of 1:99 to 99:1, e.g. 10:1 to 1:10, e.g. a substantially 50:50 molar ratio. In an enantiomerically (or epimerically) enriched mixture of formula Ia-2, the molar proportion of compound Ia-2** compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula Ia-2*, the molar proportion of the compound of formula Ia-2* compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula Ia-2** are preferred.

TABLE G

| Group number | $R^2$ |
|---|---|
| G.001 | ethyl- |
| G.002 | butyl- |
| G.003 | but-2-yl- |
| G.004 | 3-bromo-propyl- |
| G.005 | 2,2,2-trifluoro-ethyl- |
| G.006 | 3,3,3-trifluoro-propyl- |
| G.007 | 2-methoxy-ethyl- |
| G.008 | 1-methoxy-prop-2-yl- |
| G.009 | cyclobutyl- |
| G.010 | 2-methyl-cyclohex-1-yl- |
| G.011 | phenyl-methyl- |
| G.012 | 1-phenyl-eth-1-yl- |
| G.013 | 2-phenyl-eth-1-yl- |
| G.014 | (3-chloro-phenyl)-methyl- |
| G.015 | (2-fluoro-phenyl)-methyl- |
| G.016 | (4-methoxy-phenyl)-methyl- |
| G.017 | (2-trifluoromethyl-phenyl)-methyl- |
| G.018 | (2-trifluoromethoxy-phenyl)-methyl- |
| G.019 | (pyrid-2-yl)-methyl- |
| G.020 | (pyrid-3-yl)-methyl- |
| G.021 | (2-chloro-pyrid-5-yl)-methyl- |
| G.022 | (1-methyl-1H-imidazol-4-yl)-methyl- |
| G.023 | (furan-2-yl)-methyl- |
| G.024 | 2-(thiophen-2'-yl)-eth-1-yl- |
| G.025 | 2-(indol-3'-yl)-eth-1-yl- |
| G.026 | (1H-benzimidazol-2-yl)-methyl- |
| G.027 | (oxetan-2-yl)-methyl- |
| G.028 | (tetrahydrofuran-2-yl)-methyl- |
| G.029 | 2-([1',3']dioxolan-2'-yl)-eth-1-yl- |
| G.030 | 2-(morpholin-4'-yl)eth-1-yl- |
| G.031 | 2-(benzo[1',3']dioxol-5'-yl)eth-1-yl- |

TABLE G-continued

| Group number | R² |
|---|---|
| G.032 | (2,3-dihydro-benzo[1,4]dioxin-6-yl)-methyl- |
| G.033 | 2-chloro-phenyl- |
| G.034 | 3-fluoro-phenyl- |
| G.035 | 2-methyl-phenyl- |
| G.036 | 2-chloro-6-methyl-phenyl- |
| G.037 | 2-trifluoromethyl-phenyl- |
| G.038 | 2,4-dimethoxy-phenyl- |
| G.039 | 3-methyl-pyrid-2-yl- |
| G.040 | 1,3-dimethyl-1H-pyrazol-5-yl- |
| G.041 | 4-methyl-thiazol-2-yl- |
| G.042 | 5-methyl-thiadiazol-2-yl- |
| G.043 | quinolin-2-yl- |
| G.044 | quinolin-5-yl- |
| G.045 | benzothiazol-6-yl- |
| G.046 | 4-methyl-benzothiazol-2-yl- |
| G.047 | thietan-3-yl- |
| G.048 | 1-oxo-thietan-3-yl- |
| G.049 | 1,1-dioxo-thietan-3-yl- |
| G.050 | 3-methyl-thietan-3-yl- |
| G.051 | N-(2,2,2-Trifluoro-ethyl)-acetamide-2-yl |
| G.052 | thietan-2-yl-methyl- |
| G.053 | 1-oxo-thietan-2-yl-methyl- |
| G.054 | 1,1-dioxo-thietan-2-yl-methyl- |
| G.055 | thietan-3-yl-methyl- |
| G.056 | 1-oxo-thietan-3-yl-methyl- |
| G.057 | 1,1,-dioxo-thietan-3-yl-methyl- |
| G.058 | thietan-3-yl-ethyl- |
| G.059 | 1-oxo-thietan-3-yl-ethyl- |
| G.060 | 1,1-dioxo-thietan-3-yl-ethyl- |
| G.061 | 2-fluoro-cyclopropyl |
| G.062 | n-Butyl |
| G.063 | 2-Methoxy-1-methyl-ethyl |
| G.064 | 1-Oxo-thietan-3-yl |
| G.065 | 2-ethyl-isoxazolidin-3-one-4-yl |
| G.066 | Dihydro-thiophen-2-one-3-yl |
| G.067 | 6-Ethoxycarbonyl-cyclohex-3-enyl |
| G.068 | 2-Benzylsulfanyl-ethyl |
| G.069 | 4-Methanesulfonyl-benzyl |
| G.070 | N',N'-Dimethylamino-ethyl |
| G.071 | sec-Butyl |
| G.072 | Butan-1-ol-2-yl |
| G.073 | 2,2-Difluoro-ethyl |
| G.074 | Ethynyl-cyclohexyl |
| G.075 | 2-Morpholin-4-yl-ethyl |
| G.076 | 3-Pyrrolidin-1-yl-propyl |
| G.077 | 3-Piperidin-1-yl-propyl |
| G.078 | [3-(4-Chloro-phenyl)isoxazol-5-yl]-methyl |
| G.079 | Phenethyl |
| G.080 | 1,2,2,6,6-Pentamethyl-piperidin-4-yl |
| G.081 | 2-Phenoxy-ethyl |
| G.082 | 3-Chloro-benzyl |
| G.083 | 2-Acetylamino-ethyl |
| G.084 | 4-Pyrazol-1-yl-benzyl |
| G.085 | 2-Methylsulfanyl-ethyl |
| G.086 | 2-Piperidin-1-yl-benzyl |
| G.087 | 4-Phenoxy-benzyl |
| G.088 | (6-Chloro-pyridin-3-yl)-methyl |
| G.089 | 1-Benzyl-pyrrolidin-3-yl |
| G.090 | 2-(4-Benzyl-piperazin-1-yl)-ethyl |
| G.091 | Furan-2-yl-methyl |
| G.092 | 1H-Indazol-5-yl |
| G.093 | 4-Pyrrol-1-yl-phenyl |
| G.094 | 4-Piperidin-1-yl-phenyl |
| G.095 | 2-Methylsulfanyl-phenyl |
| G.096 | 4-Methyl-2-oxo-2H-chromen-7-yl |
| G.097 | 4-Dimethylsulfamoyl-phenyl |
| G.098 | 2,5-Dimethyl-2H-pyrazol-3-yl |
| G.099 | 5-Methylsulfanyl-1H-[1,2,4]triazol-3-yl |
| G.100 | 4-Hydroxy-6-methyl-pyrimidin-2-yl |
| G.101 | Quinolin-2-yl |
| G.102 | 5-Methyl-3-phenyl-isoxazol-4-yl |
| G.103 | 9H-Purin-6-yl |
| G.104 | 5-Acetyl-4-methyl-thiazol-2-yl |
| G.105 | 4-Methyl-benzothiazol-2-yl |
| G.106 | 5-Methyl-[1,3,4]thiadiazol-2-yl |
| G.107 | 4,6-Dimethyl-2H-pyrazolo[3,4-b]pyridin-3-yl |
| G.108 | 3-(2,2,2-Trifluoro-ethoxyimino)-cyclobutyl |
| G.109 | 2-Thietan-3-yl-ethyl |
| G.110 | 2-(1,1-Dioxo-thietan-3-yl)-ethyl |
| G.111 | 3-Oxo-2-(2,2,2-trifluoro-ethyl)-isoxazolidin-4-yl |
| G.112 | ![structure with N-OMe oxime] |
| G.113 | ![structure with N-OEt oxime] |
| G.114 | 2-(2,2,2-trifluoro-ethyl)-isoxazolidin-3-one-4-yl |
| G.115 | 2-(2,2-Difluoro-ethyl)-isoxazolidin-3-one-4-yl |
| G.116 | 2-(2-Fluoro-ethyl)-isoxazolidin-3-one-4-yl |

TABLE P

| | X1, X2, X3 | X4 | R5 | Y1, Y2, Y3 |
|---|---|---|---|---|
| P.0001 | X¹ is chloro, X² is CH, X³ is chloro | chlorodifluoromethyl | bromo | Y¹ is CH, Y² is CH, Y³ is CH |
| P.0002 | X¹ is chloro, X² is CH, X³ is chloro | chlorodifluoromethyl | chloro | Y¹ is CH, Y² is CH, Y³ is CH |
| P.0003 | X¹ is chloro, X² is CH, X³ is chloro | chlorodifluoromethyl | cyano | Y¹ is CH, Y² is CH, Y³ is CH |
| P.0004 | X¹ is chloro, X² is CH, X³ is chloro | chlorodifluoromethyl | cyclopropyl | Y¹ is CH, Y² is CH, Y³ is CH |
| P.0005 | X¹ is chloro, X² is CH, X³ is chloro | chlorodifluoromethyl | ethyl | Y¹ is CH, Y² is CH, Y³ is CH |
| P.0006 | X¹ is chloro, X² is CH, X³ is chloro | chlorodifluoromethyl | fluoro | Y¹ is CH, Y² is CH, Y³ is CH |
| P.0007 | X¹ is chloro, X² is CH, X³ is chloro | chlorodifluoromethyl | hydrogen | Y¹ is CH, Y² is CH, Y³ is CH |
| P.0008 | X¹ is chloro, X² is CH, X³ is chloro | chlorodifluoromethyl | methoxy | Y¹ is CH, Y² is CH, Y³ is CH |
| P.0009 | X¹ is chloro, X² is CH, X³ is chloro | chlorodifluoromethyl | methyl | Y¹ is CH, Y² is CH, Y³ is CH |
| P.0010 | X¹ is chloro, X² is CH, X³ is chloro | chlorodifluoromethyl | nitro | Y¹ is CH, Y² is CH, Y³ is CH |
| P.0011 | X¹ is chloro, X² is CH, X³ is chloro | chlorodifluoromethyl | trifluoromethoxy | Y¹ is CH, Y² is CH, Y³ is CH |

TABLE P-continued

| | X1, X2, X3 | X4 | R5 | Y1, Y2, Y3 |
|---|---|---|---|---|
| P.0012 | $X^1$ is chloro, $X^2$ is CH, $X^3$ is chloro | chlorodifluoromethyl | trifluoromethyl | $Y^1$ is CH, $Y^2$ is CH, $Y^3$ is CH |
| P.0013 | $X^1$ is chloro, $X^2$ is CH, $X^3$ is chloro | difluoromethyl | bromo | $Y^1$ is CH, $Y^2$ is CH, $Y^3$ is CH |
| P.0014 | $X^1$ is chloro, $X^2$ is CH, $X^3$ is chloro | difluoromethyl | chloro | $Y^1$ is CH, $Y^2$ is CH, $Y^3$ is CH |
| P.0015 | $X^1$ is chloro, $X^2$ is CH, $X^3$ is chloro | difluoromethyl | cyano | $Y^1$ is CH, $Y^2$ is CH, $Y^3$ is CH |
| P.0016 | $X^1$ is chloro, $X^2$ is CH, $X^3$ is chloro | difluoromethyl | cyclopropyl | $Y^1$ is CH, $Y^2$ is CH, $Y^3$ is CH |
| P.0017 | $X^1$ is chloro, $X^2$ is CH, $X^3$ is chloro | difluoromethyl | ethyl | $Y^1$ is CH, $Y^2$ is CH, $Y^3$ is CH |
| P.0018 | $X^1$ is chloro, $X^2$ is CH, $X^3$ is chloro | difluoromethyl | fluoro | $Y^1$ is CH, $Y^2$ is CH, $Y^3$ is CH |
| P.0019 | $X^1$ is chloro, $X^2$ is CH, $X^3$ is chloro | difluoromethyl | hydrogen | $Y^1$ is CH, $Y^2$ is CH, $Y^3$ is CH |
| P.0020 | $X^1$ is chloro, $X^2$ is CH, $X^3$ is chloro | difluoromethyl | methoxy | $Y^1$ is CH, $Y^2$ is CH, $Y^3$ is CH |
| P.0021 | $X^1$ is chloro, $X^2$ is CH, $X^3$ is chloro | difluoromethyl | methyl | $Y^1$ is CH, $Y^2$ is CH, $Y^3$ is CH |
| P.0022 | $X^1$ is chloro, $X^2$ is CH, $X^3$ is chloro | difluoromethyl | nitro | $Y^1$ is CH, $Y^2$ is CH, $Y^3$ is CH |
| P.0023 | $X^1$ is chloro, $X^2$ is CH, $X^3$ is chloro | difluoromethyl | trifluoromethoxy | $Y^1$ is CH, $Y^2$ is CH, $Y^3$ is CH |
| P.0024 | $X^1$ is chloro, $X^2$ is CH, $X^3$ is chloro | difluoromethyl | trifluoromethyl | $Y^1$ is CH, $Y^2$ is CH, $Y^3$ is CH |
| P.0025 | $X^1$ is chloro, $X^2$ is CH, $X^3$ is chloro | trifluoromethyl | bromo | $Y^1$ is CH, $Y^2$ is CH, $Y^3$ is CH |
| P.0026 | $X^1$ is chloro, $X^2$ is CH, $X^3$ is chloro | trifluoromethyl | chloro | $Y^1$ is CH, $Y^2$ is CH, $Y^3$ is CH |
| P.0027 | $X^1$ is chloro, $X^2$ is CH, $X^3$ is chloro | trifluoromethyl | cyano | $Y^1$ is CH, $Y^2$ is CH, $Y^3$ is CH |
| P.0028 | $X^1$ is chloro, $X^2$ is CH, $X^3$ is chloro | trifluoromethyl | cyclopropyl | $Y^1$ is CH, $Y^2$ is CH, $Y^3$ is CH |
| P.0029 | $X^1$ is chloro, $X^2$ is CH, $X^3$ is chloro | trifluoromethyl | ethyl | $Y^1$ is CH, $Y^2$ is CH, $Y^3$ is CH |
| P.0030 | $X^1$ is chloro, $X^2$ is CH, $X^3$ is chloro | trifluoromethyl | fluoro | $Y^1$ is CH, $Y^2$ is CH, $Y^3$ is CH |
| P.0031 | $X^1$ is chloro, $X^2$ is CH, $X^3$ is chloro | trifluoromethyl | hydrogen | $Y^1$ is CH, $Y^2$ is CH, $Y^3$ is CH |
| P.0032 | $X^1$ is chloro, $X^2$ is CH, $X^3$ is chloro | trifluoromethyl | methoxy | $Y^1$ is CH, $Y^2$ is CH, $Y^3$ is CH |
| P.0033 | $X^1$ is chloro, $X^2$ is CH, $X^3$ is chloro | trifluoromethyl | methyl | $Y^1$ is CH, $Y^2$ is CH, $Y^3$ is CH |
| P.0034 | $X^1$ is chloro, $X^2$ is CH, $X^3$ is chloro | trifluoromethyl | nitro | $Y^1$ is CH, $Y^2$ is CH, $Y^3$ is CH |
| P.0035 | $X^1$ is chloro, $X^2$ is CH, $X^3$ is chloro | trifluoromethyl | trifluoromethoxy | $Y^1$ is CH, $Y^2$ is CH, $Y^3$ is CH |
| P.0036 | $X^1$ is chloro, $X^2$ is CH, $X^3$ is chloro | trifluoromethyl | trifluoromethyl | $Y^1$ is CH, $Y^2$ is CH, $Y^3$ is CH |
| P.0037 | $X^1$ is chloro, $X^2$ is C—F, $X^3$ is hydrogen | chlorodifluoromethyl | bromo | $Y^1$ is CH, $Y^2$ is CH, $Y^3$ is CH |
| P.0038 | $X^1$ is chloro, $X^2$ is C—F, $X^3$ is hydrogen | chlorodifluoromethyl | chloro | $Y^1$ is CH, $Y^2$ is CH, $Y^3$ is CH |
| P.0039 | $X^1$ is chloro, $X^2$ is C—F, $X^3$ is hydrogen | chlorodifluoromethyl | cyano | $Y^1$ is CH, $Y^2$ is CH, $Y^3$ is CH |
| P.0040 | $X^1$ is chloro, $X^2$ is C—F, $X^3$ is hydrogen | chlorodifluoromethyl | cyclopropyl | $Y^1$ is CH, $Y^2$ is CH, $Y^3$ is CH |
| P.0041 | $X^1$ is chloro, $X^2$ is C—F, $X^3$ is hydrogen | chlorodifluoromethyl | ethyl | $Y^1$ is CH, $Y^2$ is CH, $Y^3$ is CH |
| P.0042 | $X^1$ is chloro, $X^2$ is C—F, $X^3$ is hydrogen | chlorodifluoromethyl | fluoro | $Y^1$ is CH, $Y^2$ is CH, $Y^3$ is CH |
| P.0043 | $X^1$ is chloro, $X^2$ is C—F, $X^3$ is hydrogen | chlorodifluoromethyl | hydrogen | $Y^1$ is CH, $Y^2$ is CH, $Y^3$ is CH |
| P.0044 | $X^1$ is chloro, $X^2$ is C—F, $X^3$ is hydrogen | chlorodifluoromethyl | methoxy | $Y^1$ is CH, $Y^2$ is CH, $Y^3$ is CH |
| P.0045 | $X^1$ is chloro, $X^2$ is C—F, $X^3$ is hydrogen | chlorodifluoromethyl | methyl | $Y^1$ is CH, $Y^2$ is CH, $Y^3$ is CH |
| P.0046 | $X^1$ is chloro, $X^2$ is C—F, $X^3$ is hydrogen | chlorodifluoromethyl | nitro | $Y^1$ is CH, $Y^2$ is CH, $Y^3$ is CH |
| P.0047 | $X^1$ is chloro, $X^2$ is C—F, $X^3$ is hydrogen | chlorodifluoromethyl | trifluoromethoxy | $Y^1$ is CH, $Y^2$ is CH, $Y^3$ is CH |
| P.0048 | $X^1$ is chloro, $X^2$ is C—F, $X^3$ is hydrogen | chlorodifluoromethyl | trifluoromethyl | $Y^1$ is CH, $Y^2$ is CH, $Y^3$ is CH |
| P.0049 | $X^1$ is chloro, $X^2$ is C—F, $X^3$ is hydrogen | difluoromethyl | bromo | $Y^1$ is CH, $Y^2$ is CH, $Y^3$ is CH |
| P.0050 | $X^1$ is chloro, $X^2$ is C—F, $X^3$ is hydrogen | difluoromethyl | chloro | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0051 | $X^1$ is chloro, $X^2$ is C—F, $X^3$ is hydrogen | difluoromethyl | cyano | $Y^1$ is CH, $Y^2$ is CH, $Y^3$ is CH |
| P.0052 | $X^1$ is chloro, $X^2$ is C—F, $X^3$ is hydrogen | difluoromethyl | cyclopropyl | $Y^1$ is CH, $Y^2$ is CH, $Y^3$ is CH |
| P.0053 | $X^1$ is chloro, $X^2$ is C—F, $X^3$ is hydrogen | difluoromethyl | ethyl | $Y^1$ is CH, $Y^2$ is CH, $Y^3$ is CH |
| P.0054 | $X^1$ is chloro, $X^2$ is C—F, $X^3$ is hydrogen | difluoromethyl | fluoro | $Y^1$ is CH, $Y^2$ is CH, $Y^3$ is CH |
| P.0055 | $X^1$ is chloro, $X^2$ is C—F, $X^3$ is hydrogen | difluoromethyl | hydrogen | $Y^1$ is CH, $Y^2$ is CH, $Y^3$ is CH |
| P.0056 | $X^1$ is chloro, $X^2$ is C—F, $X^3$ is hydrogen | difluoromethyl | methoxy | $Y^1$ is CH, $Y^2$ is CH, $Y^3$ is CH |
| P.0057 | $X^1$ is chloro, $X^2$ is C—F, $X^3$ is hydrogen | difluoromethyl | methyl | $Y^1$ is CH, $Y^2$ is CH, $Y^3$ is CH |
| P.0058 | $X^1$ is chloro, $X^2$ is C—F, $X^3$ is hydrogen | difluoromethyl | nitro | $Y^1$ is CH, $Y^2$ is CH, $Y^3$ is CH |
| P.0059 | $X^1$ is chloro, $X^2$ is C—F, $X^3$ is hydrogen | difluoromethyl | trifluoromethoxy | $Y^1$ is CH, $Y^2$ is CH, $Y^3$ is CH |
| P.0060 | $X^1$ is chloro, $X^2$ is C—F, $X^3$ is hydrogen | difluoromethyl | trifluoromethyl | $Y^1$ is CH, $Y^2$ is CH, $Y^3$ is CH |
| P.0061 | $X^1$ is chloro, $X^2$ is C—F, $X^3$ is hydrogen | trifluoromethyl | bromo | $Y^1$ is CH, $Y^2$ is CH, $Y^3$ is CH |
| P.0062 | $X^1$ is chloro, $X^2$ is C—F, $X^3$ is hydrogen | trifluoromethyl | chloro | $Y^1$ is CH, $Y^2$ is CH, $Y^3$ is CH |
| P.0063 | $X^1$ is chloro, $X^2$ is C—F, $X^3$ is hydrogen | trifluoromethyl | cyano | $Y^1$ is CH, $Y^2$ is CH, $Y^3$ is CH |
| P.0064 | $X^1$ is chloro, $X^2$ is C—F, $X^3$ is hydrogen | trifluoromethyl | cyclopropyl | $Y^1$ is CH, $Y^2$ is CH, $Y^3$ is CH |
| P.0065 | $X^1$ is chloro, $X^2$ is C—F, $X^3$ is hydrogen | trifluoromethyl | ethyl | $Y^1$ is CH, $Y^2$ is CH, $Y^3$ is CH |
| P.0066 | $X^1$ is chloro, $X^2$ is C—F, $X^3$ is hydrogen | trifluoromethyl | fluoro | $Y^1$ is CH, $Y^2$ is CH, $Y^3$ is CH |
| P.0067 | $X^1$ is chloro, $X^2$ is C—F, $X^3$ is hydrogen | trifluoromethyl | hydrogen | $Y^1$ is CH, $Y^2$ is CH, $Y^3$ is CH |
| P.0068 | $X^1$ is chloro, $X^2$ is C—F, $X^3$ is hydrogen | trifluoromethyl | methoxy | $Y^1$ is CH, $Y^2$ is CH, $Y^3$ is CH |
| P.0069 | $X^1$ is chloro, $X^2$ is C—F, $X^3$ is hydrogen | trifluoromethyl | methyl | $Y^1$ is CH, $Y^2$ is CH, $Y^3$ is CH |
| P.0070 | $X^1$ is chloro, $X^2$ is C—F, $X^3$ is hydrogen | trifluoromethyl | nitro | $Y^1$ is CH, $Y^2$ is CH, $Y^3$ is CH |
| P.0071 | $X^1$ is chloro, $X^2$ is C—F, $X^3$ is hydrogen | trifluoromethyl | trifluoromethoxy | $Y^1$ is CH, $Y^2$ is CH, $Y^3$ is CH |
| P.0072 | $X^1$ is chloro, $X^2$ is C—F, $X^3$ is hydrogen | trifluoromethyl | trifluoromethyl | $Y^1$ is CH, $Y^2$ is CH, $Y^3$ is CH |
| P.0073 | $X^1$ is fluoro, $X^2$ is C—Cl, $X^3$ is hydrogen | chlorodifluoromethyl | bromo | $Y^1$ is CH, $Y^2$ is CH, $Y^3$ is CH |
| P.0074 | $X^1$ is fluoro, $X^2$ is C—Cl, $X^3$ is hydrogen | chlorodifluoromethyl | chloro | $Y^1$ is CH, $Y^2$ is CH, $Y^3$ is CH |
| P.0075 | $X^1$ is fluoro, $X^2$ is C—Cl, $X^3$ is hydrogen | chlorodifluoromethyl | cyano | $Y^1$ is CH, $Y^2$ is CH, $Y^3$ is CH |
| P.0076 | $X^1$ is fluoro, $X^2$ is C—Cl, $X^3$ is hydrogen | chlorodifluoromethyl | cyclopropyl | $Y^1$ is CH, $Y^2$ is CH, $Y^3$ is CH |
| P.0077 | $X^1$ is fluoro, $X^2$ is C—Cl, $X^3$ is hydrogen | chlorodifluoromethyl | ethyl | $Y^1$ is CH, $Y^2$ is CH, $Y^3$ is CH |
| P.0078 | $X^1$ is fluoro, $X^2$ is C—Cl, $X^3$ is hydrogen | chlorodifluoromethyl | fluoro | $Y^1$ is CH, $Y^2$ is CH, $Y^3$ is CH |
| P.0079 | $X^1$ is fluoro, $X^2$ is C—Cl, $X^3$ is hydrogen | chlorodifluoromethyl | hydrogen | $Y^1$ is CH, $Y^2$ is CH, $Y^3$ is CH |
| P.0080 | $X^1$ is fluoro, $X^2$ is C—Cl, $X^3$ is hydrogen | chlorodifluoromethyl | methoxy | $Y^1$ is CH, $Y^2$ is CH, $Y^3$ is CH |
| P.0081 | $X^1$ is fluoro, $X^2$ is C—Cl, $X^3$ is hydrogen | chlorodifluoromethyl | methyl | $Y^1$ is CH, $Y^2$ is CH, $Y^3$ is CH |
| P.0082 | $X^1$ is fluoro, $X^2$ is C—Cl, $X^3$ is hydrogen | chlorodifluoromethyl | nitro | $Y^1$ is CH, $Y^2$ is CH, $Y^3$ is CH |
| P.0083 | $X^1$ is fluoro, $X^2$ is C—Cl, $X^3$ is hydrogen | chlorodifluoromethyl | trifluoromethoxy | $Y^1$ is CH, $Y^2$ is CH, $Y^3$ is CH |
| P.0084 | $X^1$ is fluoro, $X^2$ is C—Cl, $X^3$ is hydrogen | chlorodifluoromethyl | trifluoromethyl | $Y^1$ is CH, $Y^2$ is CH, $Y^3$ is CH |
| P.0085 | $X^1$ is fluoro, $X^2$ is C—Cl, $X^3$ is hydrogen | difluoromethyl | bromo | $Y^1$ is CH, $Y^2$ is CH, $Y^3$ is CH |
| P.0086 | $X^1$ is fluoro, $X^2$ is C—Cl, $X^3$ is hydrogen | difluoromethyl | chloro | $Y^1$ is CH, $Y^2$ is CH, $Y^3$ is CH |
| P.0087 | $X^1$ is fluoro, $X^2$ is C—Cl, $X^3$ is hydrogen | difluoromethyl | cyano | $Y^1$ is CH, $Y^2$ is CH, $Y^3$ is CH |
| P.0088 | $X^1$ is fluoro, $X^2$ is C—Cl, $X^3$ is hydrogen | difluoromethyl | cyclopropyl | $Y^1$ is CH, $Y^2$ is CH, $Y^3$ is CH |
| P.0089 | $X^1$ is fluoro, $X^2$ is C—Cl, $X^3$ is hydrogen | difluoromethyl | ethyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0090 | $X^1$ is fluoro, $X^2$ is C—Cl, $X^3$ is hydrogen | difluoromethyl | fluoro | $Y^1$ is CH, $Y^2$ is CH, $Y^3$ is CH |
| P.0091 | $X^1$ is fluoro, $X^2$ is C—Cl, $X^3$ is hydrogen | difluoromethyl | hydrogen | $Y^1$ is CH, $Y^2$ is CH, $Y^3$ is CH |
| P.0092 | $X^1$ is fluoro, $X^2$ is C—Cl, $X^3$ is hydrogen | difluoromethyl | methoxy | $Y^1$ is CH, $Y^2$ is CH, $Y^3$ is CH |
| P.0093 | $X^1$ is fluoro, $X^2$ is C—Cl, $X^3$ is hydrogen | difluoromethyl | methyl | $Y^1$ is CH, $Y^2$ is CH, $Y^3$ is CH |
| P.0094 | $X^1$ is fluoro, $X^2$ is C—Cl, $X^3$ is hydrogen | difluoromethyl | nitro | $Y^1$ is CH, $Y^2$ is CH, $Y^3$ is CH |
| P.0095 | $X^1$ is fluoro, $X^2$ is C—Cl, $X^3$ is hydrogen | difluoromethyl | trifluoromethoxy | $Y^1$ is CH, $Y^2$ is CH, $Y^3$ is CH |
| P.0096 | $X^1$ is fluoro, $X^2$ is C—Cl, $X^3$ is hydrogen | difluoromethyl | trifluoromethyl | $Y^1$ is CH, $Y^2$ is CH, $Y^3$ is CH |
| P.0097 | $X^1$ is fluoro, $X^2$ is C—Cl, $X^3$ is hydrogen | trifluoromethyl | bromo | $Y^1$ is CH, $Y^2$ is CH, $Y^3$ is CH |
| P.0098 | $X^1$ is fluoro, $X^2$ is C—Cl, $X^3$ is hydrogen | trifluoromethyl | chloro | $Y^1$ is CH, $Y^2$ is CH, $Y^3$ is CH |
| P.0099 | $X^1$ is fluoro, $X^2$ is C—Cl, $X^3$ is hydrogen | trifluoromethyl | cyano | $Y^1$ is CH, $Y^2$ is CH, $Y^3$ is CH |
| P.0100 | $X^1$ is fluoro, $X^2$ is C—Cl, $X^3$ is hydrogen | trifluoromethyl | cyclopropyl | $Y^1$ is CH, $Y^2$ is CH, $Y^3$ is CH |
| P.0101 | $X^1$ is fluoro, $X^2$ is C—Cl, $X^3$ is hydrogen | trifluoromethyl | ethyl | $Y^1$ is CH, $Y^2$ is CH, $Y^3$ is CH |
| P.0102 | $X^1$ is fluoro, $X^2$ is C—Cl, $X^3$ is hydrogen | trifluoromethyl | fluoro | $Y^1$ is CH, $Y^2$ is CH, $Y^3$ is CH |
| P.0103 | $X^1$ is fluoro, $X^2$ is C—Cl, $X^3$ is hydrogen | trifluoromethyl | hydrogen | $Y^1$ is CH, $Y^2$ is CH, $Y^3$ is CH |
| P.0104 | $X^1$ is fluoro, $X^2$ is C—Cl, $X^3$ is hydrogen | trifluoromethyl | methoxy | $Y^1$ is CH, $Y^2$ is CH, $Y^3$ is CH |
| P.0105 | $X^1$ is fluoro, $X^2$ is C—Cl, $X^3$ is hydrogen | trifluoromethyl | methyl | $Y^1$ is CH, $Y^2$ is CH, $Y^3$ is CH |
| P.0106 | $X^1$ is fluoro, $X^2$ is C—Cl, $X^3$ is hydrogen | trifluoromethyl | nitro | $Y^1$ is CH, $Y^2$ is CH, $Y^3$ is CH |
| P.0107 | $X^1$ is fluoro, $X^2$ is C—Cl, $X^3$ is hydrogen | trifluoromethyl | trifluoromethoxy | $Y^1$ is CH, $Y^2$ is CH, $Y^3$ is CH |
| P.0108 | $X^1$ is fluoro, $X^2$ is C—Cl, $X^3$ is hydrogen | trifluoromethyl | trifluoromethyl | $Y^1$ is CH, $Y^2$ is CH, $Y^3$ is CH |
| P.0109 | $X^1$ is chloro, $X^2$ is C—Cl, $X^3$ is hydrogen | chlorodifluoromethyl | bromo | $Y^1$ is CH, $Y^2$ is CH, $Y^3$ is CH |
| P.0110 | $X^1$ is chloro, $X^2$ is C—Cl, $X^3$ is hydrogen | chlorodifluoromethyl | chloro | $Y^1$ is CH, $Y^2$ is CH, $Y^3$ is CH |
| P.0111 | $X^1$ is chloro, $X^2$ is C—Cl, $X^3$ is hydrogen | chlorodifluoromethyl | cyano | $Y^1$ is CH, $Y^2$ is CH, $Y^3$ is CH |
| P.0112 | $X^1$ is chloro, $X^2$ is C—Cl, $X^3$ is hydrogen | chlorodifluoromethyl | cyclopropyl | $Y^1$ is CH, $Y^2$ is CH, $Y^3$ is CH |
| P.0113 | $X^1$ is chloro, $X^2$ is C—Cl, $X^3$ is hydrogen | chlorodifluoromethyl | ethyl | $Y^1$ is CH, $Y^2$ is CH, $Y^3$ is CH |
| P.0114 | $X^1$ is chloro, $X^2$ is C—Cl, $X^3$ is hydrogen | chlorodifluoromethyl | fluoro | $Y^1$ is CH, $Y^2$ is CH, $Y^3$ is CH |
| P.0115 | $X^1$ is chloro, $X^2$ is C—Cl, $X^3$ is hydrogen | chlorodifluoromethyl | hydrogen | $Y^1$ is CH, $Y^2$ is CH, $Y^3$ is CH |
| P.0116 | $X^1$ is chloro, $X^2$ is C—Cl, $X^3$ is hydrogen | chlorodifluoromethyl | methoxy | $Y^1$ is CH, $Y^2$ is CH, $Y^3$ is CH |
| P.0117 | $X^1$ is chloro, $X^2$ is C—Cl, $X^3$ is hydrogen | chlorodifluoromethyl | methyl | $Y^1$ is CH, $Y^2$ is CH, $Y^3$ is CH |
| P.0118 | $X^1$ is chloro, $X^2$ is C—Cl, $X^3$ is hydrogen | chlorodifluoromethyl | nitro | $Y^1$ is CH, $Y^2$ is CH, $Y^3$ is CH |
| P.0119 | $X^1$ is chloro, $X^2$ is C—Cl, $X^3$ is hydrogen | chlorodifluoromethyl | trifluoromethoxy | $Y^1$ is CH, $Y^2$ is CH, $Y^3$ is CH |
| P.0120 | $X^1$ is chloro, $X^2$ is C—Cl, $X^3$ is hydrogen | chlorodifluoromethyl | trifluoromethyl | $Y^1$ is CH, $Y^2$ is CH, $Y^3$ is CH |
| P.0121 | $X^1$ is chloro, $X^2$ is C—Cl, $X^3$ is hydrogen | difluoromethyl | bromo | $Y^1$ is CH, $Y^2$ is CH, $Y^3$ is CH |
| P.0122 | $X^1$ is chloro, $X^2$ is C—Cl, $X^3$ is hydrogen | difluoromethyl | chloro | $Y^1$ is CH, $Y^2$ is CH, $Y^3$ is CH |
| P.0123 | $X^1$ is chloro, $X^2$ is C—Cl, $X^3$ is hydrogen | difluoromethyl | cyano | $Y^1$ is CH, $Y^2$ is CH, $Y^3$ is CH |
| P.0124 | $X^1$ is chloro, $X^2$ is C—Cl, $X^3$ is hydrogen | difluoromethyl | cyclopropyl | $Y^1$ is CH, $Y^2$ is CH, $Y^3$ is CH |
| P.0125 | $X^1$ is chloro, $X^2$ is C—Cl, $X^3$ is hydrogen | difluoromethyl | ethyl | $Y^1$ is CH, $Y^2$ is CH, $Y^3$ is CH |
| P.0126 | $X^1$ is chloro, $X^2$ is C—Cl, $X^3$ is hydrogen | difluoromethyl | fluoro | $Y^1$ is CH, $Y^2$ is CH, $Y^3$ is CH |
| P.0127 | $X^1$ is chloro, $X^2$ is C—Cl, $X^3$ is hydrogen | difluoromethyl | hydrogen | $Y^1$ is CH, $Y^2$ is CH, $Y^3$ is CH |
| P.0128 | $X^1$ is chloro, $X^2$ is C—Cl, $X^3$ is hydrogen | difluoromethyl | methoxy | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0129 | $X^1$ is chloro, $X^2$ is C—Cl, $X^3$ is hydrogen | difluoromethyl | methyl | $Y^1$ is CH, $Y^2$ is CH, $Y^3$ is CH |
| P.0130 | $X^1$ is chloro, $X^2$ is C—Cl, $X^3$ is hydrogen | difluoromethyl | nitro | $Y^1$ is CH, $Y^2$ is CH, $Y^3$ is CH |
| P.0131 | $X^1$ is chloro, $X^2$ is C—Cl, $X^3$ is hydrogen | difluoromethyl | trifluoromethoxy | $Y^1$ is CH, $Y^2$ is CH, $Y^3$ is CH |
| P.0132 | $X^1$ is chloro, $X^2$ is C—Cl, $X^3$ is hydrogen | difluoromethyl | trifluoromethyl | $Y^1$ is CH, $Y^2$ is CH, $Y^3$ is CH |
| P.0133 | $X^1$ is chloro, $X^2$ is C—Cl, $X^3$ is hydrogen | trifluoromethyl | bromo | $Y^1$ is CH, $Y^2$ is CH, $Y^3$ is CH |
| P.0134 | $X^1$ is chloro, $X^2$ is C—Cl, $X^3$ is hydrogen | trifluoromethyl | chloro | $Y^1$ is CH, $Y^2$ is CH, $Y^3$ is CH |
| P.0135 | $X^1$ is chloro, $X^2$ is C—Cl, $X^3$ is hydrogen | trifluoromethyl | cyano | $Y^1$ is CH, $Y^2$ is CH, $Y^3$ is CH |
| P.0136 | $X^1$ is chloro, $X^2$ is C—Cl, $X^3$ is hydrogen | trifluoromethyl | cyclopropyl | $Y^1$ is CH, $Y^2$ is CH, $Y^3$ is CH |
| P.0137 | $X^1$ is chloro, $X^2$ is C—Cl, $X^3$ is hydrogen | trifluoromethyl | ethyl | $Y^1$ is CH, $Y^2$ is CH, $Y^3$ is CH |
| P.0138 | $X^1$ is chloro, $X^2$ is C—Cl, $X^3$ is hydrogen | trifluoromethyl | fluoro | $Y^1$ is CH, $Y^2$ is CH, $Y^3$ is CH |
| P.0139 | $X^1$ is chloro, $X^2$ is C—Cl, $X^3$ is hydrogen | trifluoromethyl | hydrogen | $Y^1$ is CH, $Y^2$ is CH, $Y^3$ is CH |
| P.0140 | $X^1$ is chloro, $X^2$ is C—Cl, $X^3$ is hydrogen | trifluoromethyl | methoxy | $Y^1$ is CH, $Y^2$ is CH, $Y^3$ is CH |
| P.0141 | $X^1$ is chloro, $X^2$ is C—Cl, $X^3$ is hydrogen | trifluoromethyl | methyl | $Y^1$ is CH, $Y^2$ is CH, $Y^3$ is CH |
| P.0142 | $X^1$ is chloro, $X^2$ is C—Cl, $X^3$ is hydrogen | trifluoromethyl | nitro | $Y^1$ is CH, $Y^2$ is CH, $Y^3$ is CH |
| P.0143 | $X^1$ is chloro, $X^2$ is C—Cl, $X^3$ is hydrogen | trifluoromethyl | trifluoromethoxy | $Y^1$ is CH, $Y^2$ is CH, $Y^3$ is CH |
| P.0144 | $X^1$ is chloro, $X^2$ is C—Cl, $X^3$ is hydrogen | trifluoromethyl | trifluoromethyl | $Y^1$ is CH, $Y^2$ is CH, $Y^3$ is CH |
| P.0145 | $X^1$ is chloro, $X^2$ is C—Br, $X^3$ is chloro | chlorodifluoromethyl | bromo | $Y^1$ is CH, $Y^2$ is CH, $Y^3$ is CH |
| P.0146 | $X^1$ is chloro, $X^2$ is C—Br, $X^3$ is chloro | chlorodifluoromethyl | chloro | $Y^1$ is CH, $Y^2$ is CH, $Y^3$ is CH |
| P.0147 | $X^1$ is chloro, $X^2$ is C—Br, $X^3$ is chloro | chlorodifluoromethyl | cyano | $Y^1$ is CH, $Y^2$ is CH, $Y^3$ is CH |
| P.0148 | $X^1$ is chloro, $X^2$ is C—Br, $X^3$ is chloro | chlorodifluoromethyl | cyclopropyl | $Y^1$ is CH, $Y^2$ is CH, $Y^3$ is CH |
| P.0149 | $X^1$ is chloro, $X^2$ is C—Br, $X^3$ is chloro | chlorodifluoromethyl | ethyl | $Y^1$ is CH, $Y^2$ is CH, $Y^3$ is CH |
| P.0150 | $X^1$ is chloro, $X^2$ is C—Br, $X^3$ is chloro | chlorodifluoromethyl | fluoro | $Y^1$ is CH, $Y^2$ is CH, $Y^3$ is CH |
| P.0151 | $X^1$ is chloro, $X^2$ is C—Br, $X^3$ is chloro | chlorodifluoromethyl | hydrogen | $Y^1$ is CH, $Y^2$ is CH, $Y^3$ is CH |
| P.0152 | $X^1$ is chloro, $X^2$ is C—Br, $X^3$ is chloro | chlorodifluoromethyl | methoxy | $Y^1$ is CH, $Y^2$ is CH, $Y^3$ is CH |
| P.0153 | $X^1$ is chloro, $X^2$ is C—Br, $X^3$ is chloro | chlorodifluoromethyl | methyl | $Y^1$ is CH, $Y^2$ is CH, $Y^3$ is CH |
| P.0154 | $X^1$ is chloro, $X^2$ is C—Br, $X^3$ is chloro | chlorodifluoromethyl | nitro | $Y^1$ is CH, $Y^2$ is CH, $Y^3$ is CH |
| P.0155 | $X^1$ is chloro, $X^2$ is C—Br, $X^3$ is chloro | chlorodifluoromethyl | trifluoromethoxy | $Y^1$ is CH, $Y^2$ is CH, $Y^3$ is CH |
| P.0156 | $X^1$ is chloro, $X^2$ is C—Br, $X^3$ is chloro | chlorodifluoromethyl | trifluoromethyl | $Y^1$ is CH, $Y^2$ is CH, $Y^3$ is CH |
| P.0157 | $X^1$ is chloro, $X^2$ is C—Br, $X^3$ is chloro | difluoromethyl | bromo | $Y^1$ is CH, $Y^2$ is CH, $Y^3$ is CH |
| P.0158 | $X^1$ is chloro, $X^2$ is C—Br, $X^3$ is chloro | difluoromethyl | chloro | $Y^1$ is CH, $Y^2$ is CH, $Y^3$ is CH |
| P.0159 | $X^1$ is chloro, $X^2$ is C—Br, $X^3$ is chloro | difluoromethyl | cyano | $Y^1$ is CH, $Y^2$ is CH, $Y^3$ is CH |
| P.0160 | $X^1$ is chloro, $X^2$ is C—Br, $X^3$ is chloro | difluoromethyl | cyclopropyl | $Y^1$ is CH, $Y^2$ is CH, $Y^3$ is CH |
| P.0161 | $X^1$ is chloro, $X^2$ is C—Br, $X^3$ is chloro | difluoromethyl | ethyl | $Y^1$ is CH, $Y^2$ is CH, $Y^3$ is CH |
| P.0162 | $X^1$ is chloro, $X^2$ is C—Br, $X^3$ is chloro | difluoromethyl | fluoro | $Y^1$ is CH, $Y^2$ is CH, $Y^3$ is CH |
| P.0163 | $X^1$ is chloro, $X^2$ is C—Br, $X^3$ is chloro | difluoromethyl | hydrogen | $Y^1$ is CH, $Y^2$ is CH, $Y^3$ is CH |
| P.0164 | $X^1$ is chloro, $X^2$ is C—Br, $X^3$ is chloro | difluoromethyl | methoxy | $Y^1$ is CH, $Y^2$ is CH, $Y^3$ is CH |
| P.0165 | $X^1$ is chloro, $X^2$ is C—Br, $X^3$ is chloro | difluoromethyl | methyl | $Y^1$ is CH, $Y^2$ is CH, $Y^3$ is CH |
| P.0166 | $X^1$ is chloro, $X^2$ is C—Br, $X^3$ is chloro | difluoromethyl | nitro | $Y^1$ is CH, $Y^2$ is CH, $Y^3$ is CH |
| P.0167 | $X^1$ is chloro, $X^2$ is C—Br, $X^3$ is chloro | difluoromethyl | trifluoromethoxy | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0168 | $X^1$ is chloro, $X^2$ is C—Br, $X^3$ is chloro | difluoromethyl | trifluoromethyl | $Y^1$ is CH, $Y^2$ is CH, $Y^3$ is CH |
| P.0169 | $X^1$ is chloro, $X^2$ is C—Br, $X^3$ is chloro | trifluoromethyl | bromo | $Y^1$ is CH, $Y^2$ is CH, $Y^3$ is CH |
| P.0170 | $X^1$ is chloro, $X^2$ is C—Br, $X^3$ is chloro | trifluoromethyl | chloro | $Y^1$ is CH, $Y^2$ is CH, $Y^3$ is CH |
| P.0171 | $X^1$ is chloro, $X^2$ is C—Br, $X^3$ is chloro | trifluoromethyl | cyano | $Y^1$ is CH, $Y^2$ is CH, $Y^3$ is CH |
| P.0172 | $X^1$ is chloro, $X^2$ is C—Br, $X^3$ is chloro | trifluoromethyl | cyclopropyl | $Y^1$ is CH, $Y^2$ is CH, $Y^3$ is CH |
| P.0173 | $X^1$ is chloro, $X^2$ is C—Br, $X^3$ is chloro | trifluoromethyl | ethyl | $Y^1$ is CH, $Y^2$ is CH, $Y^3$ is CH |
| P.0174 | $X^1$ is chloro, $X^2$ is C—Br, $X^3$ is chloro | trifluoromethyl | fluoro | $Y^1$ is CH, $Y^2$ is CH, $Y^3$ is CH |
| P.0175 | $X^1$ is chloro, $X^2$ is C—Br, $X^3$ is chloro | trifluoromethyl | hydrogen | $Y^1$ is CH, $Y^2$ is CH, $Y^3$ is CH |
| P.0176 | $X^1$ is chloro, $X^2$ is C—Br, $X^3$ is chloro | trifluoromethyl | methoxy | $Y^1$ is CH, $Y^2$ is CH, $Y^3$ is CH |
| P.0177 | $X^1$ is chloro, $X^2$ is C—Br, $X^3$ is chloro | trifluoromethyl | methyl | $Y^1$ is CH, $Y^2$ is CH, $Y^3$ is CH |
| P.0178 | $X^1$ is chloro, $X^2$ is C—Br, $X^3$ is chloro | trifluoromethyl | nitro | $Y^1$ is CH, $Y^2$ is CH, $Y^3$ is CH |
| P.0179 | $X^1$ is chloro, $X^2$ is C—Br, $X^3$ is chloro | trifluoromethyl | trifluoromethoxy | $Y^1$ is CH, $Y^2$ is CH, $Y^3$ is CH |
| P.0180 | $X^1$ is chloro, $X^2$ is C—Br, $X^3$ is chloro | trifluoromethyl | trifluoromethyl | $Y^1$ is CH, $Y^2$ is CH, $Y^3$ is CH |
| P.0181 | $X^1$ is chloro, $X^2$ is C—F, $X^3$ is chloro | chlorodifluoromethyl | bromo | $Y^1$ is CH, $Y^2$ is CH, $Y^3$ is CH |
| P.0182 | $X^1$ is chloro, $X^2$ is C—F, $X^3$ is chloro | chlorodifluoromethyl | chloro | $Y^1$ is CH, $Y^2$ is CH, $Y^3$ is CH |
| P.0183 | $X^1$ is chloro, $X^2$ is C—F, $X^3$ is chloro | chlorodifluoromethyl | cyano | $Y^1$ is CH, $Y^2$ is CH, $Y^3$ is CH |
| P.0184 | $X^1$ is chloro, $X^2$ is C—F, $X^3$ is chloro | chlorodifluoromethyl | cyclopropyl | $Y^1$ is CH, $Y^2$ is CH, $Y^3$ is CH |
| P.0185 | $X^1$ is chloro, $X^2$ is C—F, $X^3$ is chloro | chlorodifluoromethyl | ethyl | $Y^1$ is CH, $Y^2$ is CH, $Y^3$ is CH |
| P.0186 | $X^1$ is chloro, $X^2$ is C—F, $X^3$ is chloro | chlorodifluoromethyl | fluoro | $Y^1$ is CH, $Y^2$ is CH, $Y^3$ is CH |
| P.0187 | $X^1$ is chloro, $X^2$ is C—F, $X^3$ is chloro | chlorodifluoromethyl | hydrogen | $Y^1$ is CH, $Y^2$ is CH, $Y^3$ is CH |
| P.0188 | $X^1$ is chloro, $X^2$ is C—F, $X^3$ is chloro | chlorodifluoromethyl | methoxy | $Y^1$ is CH, $Y^2$ is CH, $Y^3$ is CH |
| P.0189 | $X^1$ is chloro, $X^2$ is C—F, $X^3$ is chloro | chlorodifluoromethyl | methyl | $Y^1$ is CH, $Y^2$ is CH, $Y^3$ is CH |
| P.0190 | $X^1$ is chloro, $X^2$ is C—F, $X^3$ is chloro | chlorodifluoromethyl | nitro | $Y^1$ is CH, $Y^2$ is CH, $Y^3$ is CH |
| P.0191 | $X^1$ is chloro, $X^2$ is C—F, $X^3$ is chloro | chlorodifluoromethyl | trifluoromethoxy | $Y^1$ is CH, $Y^2$ is CH, $Y^3$ is CH |
| P.0192 | $X^1$ is chloro, $X^2$ is C—F, $X^3$ is chloro | chlorodifluoromethyl | trifluoromethyl | $Y^1$ is CH, $Y^2$ is CH, $Y^3$ is CH |
| P.0193 | $X^1$ is chloro, $X^2$ is C—F, $X^3$ is chloro | difluoromethyl | bromo | $Y^1$ is CH, $Y^2$ is CH, $Y^3$ is CH |
| P.0194 | $X^1$ is chloro, $X^2$ is C—F, $X^3$ is chloro | difluoromethyl | chloro | $Y^1$ is CH, $Y^2$ is CH, $Y^3$ is CH |
| P.0195 | $X^1$ is chloro, $X^2$ is C—F, $X^3$ is chloro | difluoromethyl | cyano | $Y^1$ is CH, $Y^2$ is CH, $Y^3$ is CH |
| P.0196 | $X^1$ is chloro, $X^2$ is C—F, $X^3$ is chloro | difluoromethyl | cyclopropyl | $Y^1$ is CH, $Y^2$ is CH, $Y^3$ is CH |
| P.0197 | $X^1$ is chloro, $X^2$ is C—F, $X^3$ is chloro | difluoromethyl | ethyl | $Y^1$ is CH, $Y^2$ is CH, $Y^3$ is CH |
| P.0198 | $X^1$ is chloro, $X^2$ is C—F, $X^3$ is chloro | difluoromethyl | fluoro | $Y^1$ is CH, $Y^2$ is CH, $Y^3$ is CH |
| P.0199 | $X^1$ is chloro, $X^2$ is C—F, $X^3$ is chloro | difluoromethyl | hydrogen | $Y^1$ is CH, $Y^2$ is CH, $Y^3$ is CH |
| P.0200 | $X^1$ is chloro, $X^2$ is C—F, $X^3$ is chloro | difluoromethyl | methoxy | $Y^1$ is CH, $Y^2$ is CH, $Y^3$ is CH |
| P.0201 | $X^1$ is chloro, $X^2$ is C—F, $X^3$ is chloro | difluoromethyl | methyl | $Y^1$ is CH, $Y^2$ is CH, $Y^3$ is CH |
| P.0202 | $X^1$ is chloro, $X^2$ is C—F, $X^3$ is chloro | difluoromethyl | nitro | $Y^1$ is CH, $Y^2$ is CH, $Y^3$ is CH |
| P.0203 | $X^1$ is chloro, $X^2$ is C—F, $X^3$ is chloro | difluoromethyl | trifluoromethoxy | $Y^1$ is CH, $Y^2$ is CH, $Y^3$ is CH |
| P.0204 | $X^1$ is chloro, $X^2$ is C—F, $X^3$ is chloro | difluoromethyl | trifluoromethyl | $Y^1$ is CH, $Y^2$ is CH, $Y^3$ is CH |
| P.0205 | $X^1$ is chloro, $X^2$ is C—F, $X^3$ is chloro | trifluoromethyl | bromo | $Y^1$ is CH, $Y^2$ is CH, $Y^3$ is CH |
| P.0206 | $X^1$ is chloro, $X^2$ is C—F, $X^3$ is chloro | trifluoromethyl | chloro | $Y^1$ is CH, $Y^2$ is CH, $Y^3$ is CH |

TABLE P-continued

|  | X1, X2, X3 | X4 | R5 | Y1, Y2, Y3 |
| --- | --- | --- | --- | --- |
| P.0207 | $X^1$ is chloro, $X^2$ is C—F, $X^3$ is chloro | trifluoromethyl | cyano | $Y^1$ is CH, $Y^2$ is CH, $Y^3$ is CH |
| P.0208 | $X^1$ is chloro, $X^2$ is C—F, $X^3$ is chloro | trifluoromethyl | cyclopropyl | $Y^1$ is CH, $Y^2$ is CH, $Y^3$ is CH |
| P.0209 | $X^1$ is chloro, $X^2$ is C—F, $X^3$ is chloro | trifluoromethyl | ethyl | $Y^1$ is CH, $Y^2$ is CH, $Y^3$ is CH |
| P.0210 | $X^1$ is chloro, $X^2$ is C—F, $X^3$ is chloro | trifluoromethyl | fluoro | $Y^1$ is CH, $Y^2$ is CH, $Y^3$ is CH |
| P.0211 | $X^1$ is chloro, $X^2$ is C—F, $X^3$ is chloro | trifluoromethyl | hydrogen | $Y^1$ is CH, $Y^2$ is CH, $Y^3$ is CH |
| P.0212 | $X^1$ is chloro, $X^2$ is C—F, $X^3$ is chloro | trifluoromethyl | methoxy | $Y^1$ is CH, $Y^2$ is CH, $Y^3$ is CH |
| P.0213 | $X^1$ is chloro, $X^2$ is C—F, $X^3$ is chloro | trifluoromethyl | methyl | $Y^1$ is CH, $Y^2$ is CH, $Y^3$ is CH |
| P.0214 | $X^1$ is chloro, $X^2$ is C—F, $X^3$ is chloro | trifluoromethyl | nitro | $Y^1$ is CH, $Y^2$ is CH, $Y^3$ is CH |
| P.0215 | $X^1$ is chloro, $X^2$ is C—F, $X^3$ is chloro | trifluoromethyl | trifluoromethoxy | $Y^1$ is CH, $Y^2$ is CH, $Y^3$ is CH |
| P.0216 | $X^1$ is chloro, $X^2$ is C—F, $X^3$ is chloro | trifluoromethyl | trifluoromethyl | $Y^1$ is CH, $Y^2$ is CH, $Y^3$ is CH |
| P.0217 | $X^1$ is chloro, $X^2$ is C—Cl, $X^3$ is chloro | chlorodifluoromethyl | bromo | $Y^1$ is CH, $Y^2$ is CH, $Y^3$ is CH |
| P.0218 | $X^1$ is chloro, $X^2$ is C—Cl, $X^3$ is chloro | chlorodifluoromethyl | chloro | $Y^1$ is CH, $Y^2$ is CH, $Y^3$ is CH |
| P.0219 | $X^1$ is chloro, $X^2$ is C—Cl, $X^3$ is chloro | chlorodifluoromethyl | cyano | $Y^1$ is CH, $Y^2$ is CH, $Y^3$ is CH |
| P.0220 | $X^1$ is chloro, $X^2$ is C—Cl, $X^3$ is chloro | chlorodifluoromethyl | cyclopropyl | $Y^1$ is CH, $Y^2$ is CH, $Y^3$ is CH |
| P.0221 | $X^1$ is chloro, $X^2$ is C—Cl, $X^3$ is chloro | chlorodifluoromethyl | ethyl | $Y^1$ is CH, $Y^2$ is CH, $Y^3$ is CH |
| P.0222 | $X^1$ is chloro, $X^2$ is C—Cl, $X^3$ is chloro | chlorodifluoromethyl | fluoro | $Y^1$ is CH, $Y^2$ is CH, $Y^3$ is CH |
| P.0223 | $X^1$ is chloro, $X^2$ is C—Cl, $X^3$ is chloro | chlorodifluoromethyl | hydrogen | $Y^1$ is CH, $Y^2$ is CH, $Y^3$ is CH |
| P.0224 | $X^1$ is chloro, $X^2$ is C—Cl, $X^3$ is chloro | chlorodifluoromethyl | methoxy | $Y^1$ is CH, $Y^2$ is CH, $Y^3$ is CH |
| P.0225 | $X^1$ is chloro, $X^2$ is C—Cl, $X^3$ is chloro | chlorodifluoromethyl | methyl | $Y^1$ is CH, $Y^2$ is CH, $Y^3$ is CH |
| P.0226 | $X^1$ is chloro, $X^2$ is C—Cl, $X^3$ is chloro | chlorodifluoromethyl | nitro | $Y^1$ is CH, $Y^2$ is CH, $Y^3$ is CH |
| P.0227 | $X^1$ is chloro, $X^2$ is C—Cl, $X^3$ is chloro | chlorodifluoromethyl | trifluoromethoxy | $Y^1$ is CH, $Y^2$ is CH, $Y^3$ is CH |
| P.0228 | $X^1$ is chloro, $X^2$ is C—Cl, $X^3$ is chloro | chlorodifluoromethyl | trifluoromethyl | $Y^1$ is CH, $Y^2$ is CH, $Y^3$ is CH |
| P.0229 | $X^1$ is chloro, $X^2$ is C—Cl, $X^3$ is chloro | difluoromethyl | bromo | $Y^1$ is CH, $Y^2$ is CH, $Y^3$ is CH |
| P.0230 | $X^1$ is chloro, $X^2$ is C—Cl, $X^3$ is chloro | difluoromethyl | chloro | $Y^1$ is CH, $Y^2$ is CH, $Y^3$ is CH |
| P.0231 | $X^1$ is chloro, $X^2$ is C—Cl, $X^3$ is chloro | difluoromethyl | cyano | $Y^1$ is CH, $Y^2$ is CH, $Y^3$ is CH |
| P.0232 | $X^1$ is chloro, $X^2$ is C—Cl, $X^3$ is chloro | difluoromethyl | cyclopropyl | $Y^1$ is CH, $Y^2$ is CH, $Y^3$ is CH |
| P.0233 | $X^1$ is chloro, $X^2$ is C—Cl, $X^3$ is chloro | difluoromethyl | ethyl | $Y^1$ is CH, $Y^2$ is CH, $Y^3$ is CH |
| P.0234 | $X^1$ is chloro, $X^2$ is C—Cl, $X^3$ is chloro | difluoromethyl | fluoro | $Y^1$ is CH, $Y^2$ is CH, $Y^3$ is CH |
| P.0235 | $X^1$ is chloro, $X^2$ is C—Cl, $X^3$ is chloro | difluoromethyl | hydrogen | $Y^1$ is CH, $Y^2$ is CH, $Y^3$ is CH |
| P.0236 | $X^1$ is chloro, $X^2$ is C—Cl, $X^3$ is chloro | difluoromethyl | methoxy | $Y^1$ is CH, $Y^2$ is CH, $Y^3$ is CH |
| P.0237 | $X^1$ is chloro, $X^2$ is C—Cl, $X^3$ is chloro | difluoromethyl | methyl | $Y^1$ is CH, $Y^2$ is CH, $Y^3$ is CH |
| P.0238 | $X^1$ is chloro, $X^2$ is C—Cl, $X^3$ is chloro | difluoromethyl | nitro | $Y^1$ is CH, $Y^2$ is CH, $Y^3$ is CH |
| P.0239 | $X^1$ is chloro, $X^2$ is C—Cl, $X^3$ is chloro | difluoromethyl | trifluoromethoxy | $Y^1$ is CH, $Y^2$ is CH, $Y^3$ is CH |
| P.0240 | $X^1$ is chloro, $X^2$ is C—Cl, $X^3$ is chloro | difluoromethyl | trifluoromethyl | $Y^1$ is CH, $Y^2$ is CH, $Y^3$ is CH |
| P.0241 | $X^1$ is chloro, $X^2$ is C—Cl, $X^3$ is chloro | trifluoromethyl | bromo | $Y^1$ is CH, $Y^2$ is CH, $Y^3$ is CH |
| P.0242 | $X^1$ is chloro, $X^2$ is C—Cl, $X^3$ is chloro | trifluoromethyl | chloro | $Y^1$ is CH, $Y^2$ is CH, $Y^3$ is CH |
| P.0243 | $X^1$ is chloro, $X^2$ is C—Cl, $X^3$ is chloro | trifluoromethyl | cyano | $Y^1$ is CH, $Y^2$ is CH, $Y^3$ is CH |
| P.0244 | $X^1$ is chloro, $X^2$ is C—Cl, $X^3$ is chloro | trifluoromethyl | cyclopropyl | $Y^1$ is CH, $Y^2$ is CH, $Y^3$ is CH |
| P.0245 | $X^1$ is chloro, $X^2$ is C—Cl, $X^3$ is chloro | trifluoromethyl | ethyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0246 | $X^1$ is chloro, $X^2$ is C—Cl, $X^3$ is chloro | trifluoromethyl | fluoro | $Y^1$ is CH, $Y^2$ is CH, $Y^3$ is CH |
| P.0247 | $X^1$ is chloro, $X^2$ is C—Cl, $X^3$ is chloro | trifluoromethyl | hydrogen | $Y^1$ is CH, $Y^2$ is CH, $Y^3$ is CH |
| P.0248 | $X^1$ is chloro, $X^2$ is C—Cl, $X^3$ is chloro | trifluoromethyl | methoxy | $Y^1$ is CH, $Y^2$ is CH, $Y^3$ is CH |
| P.0249 | $X^1$ is chloro, $X^2$ is C—Cl, $X^3$ is chloro | trifluoromethyl | methyl | $Y^1$ is CH, $Y^2$ is CH, $Y^3$ is CH |
| P.0250 | $X^1$ is chloro, $X^2$ is C—Cl, $X^3$ is chloro | trifluoromethyl | nitro | $Y^1$ is CH, $Y^2$ is CH, $Y^3$ is CH |
| P.0251 | $X^1$ is chloro, $X^2$ is C—Cl, $X^3$ is chloro | trifluoromethyl | trifluoromethoxy | $Y^1$ is CH, $Y^2$ is CH, $Y^3$ is CH |
| P.0252 | $X^1$ is chloro, $X^2$ is C—Cl, $X^3$ is chloro | trifluoromethyl | trifluoromethyl | $Y^1$ is CH, $Y^2$ is CH, $Y^3$ is CH |
| P.0253 | $X^1$ is chloro, $X^2$ is C—I, $X^3$ is chloro | chlorodifluoromethyl | bromo | $Y^1$ is CH, $Y^2$ is CH, $Y^3$ is CH |
| P.0254 | $X^1$ is chloro, $X^2$ is C—I, $X^3$ is chloro | chlorodifluoromethyl | chloro | $Y^1$ is CH, $Y^2$ is CH, $Y^3$ is CH |
| P.0255 | $X^1$ is chloro, $X^2$ is C—I, $X^3$ is chloro | chlorodifluoromethyl | cyano | $Y^1$ is CH, $Y^2$ is CH, $Y^3$ is CH |
| P.0256 | $X^1$ is chloro, $X^2$ is C—I, $X^3$ is chloro | chlorodifluoromethyl | cyclopropyl | $Y^1$ is CH, $Y^2$ is CH, $Y^3$ is CH |
| P.0257 | $X^1$ is chloro, $X^2$ is C—I, $X^3$ is chloro | chlorodifluoromethyl | ethyl | $Y^1$ is CH, $Y^2$ is CH, $Y^3$ is CH |
| P.0258 | $X^1$ is chloro, $X^2$ is C—I, $X^3$ is chloro | chlorodifluoromethyl | fluoro | $Y^1$ is CH, $Y^2$ is CH, $Y^3$ is CH |
| P.0259 | $X^1$ is chloro, $X^2$ is C—I, $X^3$ is chloro | chlorodifluoromethyl | hydrogen | $Y^1$ is CH, $Y^2$ is CH, $Y^3$ is CH |
| P.0260 | $X^1$ is chloro, $X^2$ is C—I, $X^3$ is chloro | chlorodifluoromethyl | methoxy | $Y^1$ is CH, $Y^2$ is CH, $Y^3$ is CH |
| P.0261 | $X^1$ is chloro, $X^2$ is C—I, $X^3$ is chloro | chlorodifluoromethyl | methyl | $Y^1$ is CH, $Y^2$ is CH, $Y^3$ is CH |
| P.0262 | $X^1$ is chloro, $X^2$ is C—I, $X^3$ is chloro | chlorodifluoromethyl | nitro | $Y^1$ is CH, $Y^2$ is CH, $Y^3$ is CH |
| P.0263 | $X^1$ is chloro, $X^2$ is C—I, $X^3$ is chloro | chlorodifluoromethyl | trifluoromethoxy | $Y^1$ is CH, $Y^2$ is CH, $Y^3$ is CH |
| P.0264 | $X^1$ is chloro, $X^2$ is C—I, $X^3$ is chloro | chlorodifluoromethyl | trifluoromethyl | $Y^1$ is CH, $Y^2$ is CH, $Y^3$ is CH |
| P.0265 | $X^1$ is chloro, $X^2$ is C—I, $X^3$ is chloro | difluoromethyl | bromo | $Y^1$ is CH, $Y^2$ is CH, $Y^3$ is CH |
| P.0266 | $X^1$ is chloro, $X^2$ is C—I, $X^3$ is chloro | difluoromethyl | chloro | $Y^1$ is CH, $Y^2$ is CH, $Y^3$ is CH |
| P.0267 | $X^1$ is chloro, $X^2$ is C—I, $X^3$ is chloro | difluoromethyl | cyano | $Y^1$ is CH, $Y^2$ is CH, $Y^3$ is CH |
| P.0268 | $X^1$ is chloro, $X^2$ is C—I, $X^3$ is chloro | difluoromethyl | cyclopropyl | $Y^1$ is CH, $Y^2$ is CH, $Y^3$ is CH |
| P.0269 | $X^1$ is chloro, $X^2$ is C—I, $X^3$ is chloro | difluoromethyl | ethyl | $Y^1$ is CH, $Y^2$ is CH, $Y^3$ is CH |
| P.0270 | $X^1$ is chloro, $X^2$ is C—I, $X^3$ is chloro | difluoromethyl | fluoro | $Y^1$ is CH, $Y^2$ is CH, $Y^3$ is CH |
| P.0271 | $X^1$ is chloro, $X^2$ is C—I, $X^3$ is chloro | difluoromethyl | hydrogen | $Y^1$ is CH, $Y^2$ is CH, $Y^3$ is CH |
| P.0272 | $X^1$ is chloro, $X^2$ is C—I, $X^3$ is chloro | difluoromethyl | methoxy | $Y^1$ is CH, $Y^2$ is CH, $Y^3$ is CH |
| P.0273 | $X^1$ is chloro, $X^2$ is C—I, $X^3$ is chloro | difluoromethyl | methyl | $Y^1$ is CH, $Y^2$ is CH, $Y^3$ is CH |
| P.0274 | $X^1$ is chloro, $X^2$ is C—I, $X^3$ is chloro | difluoromethyl | nitro | $Y^1$ is CH, $Y^2$ is CH, $Y^3$ is CH |
| P.0275 | $X^1$ is chloro, $X^2$ is C—I, $X^3$ is chloro | difluoromethyl | trifluoromethoxy | $Y^1$ is CH, $Y^2$ is CH, $Y^3$ is CH |
| P.0276 | $X^1$ is chloro, $X^2$ is C—I, $X^3$ is chloro | difluoromethyl | trifluoromethyl | $Y^1$ is CH, $Y^2$ is CH, $Y^3$ is CH |
| P.0277 | $X^1$ is chloro, $X^2$ is C—I, $X^3$ is chloro | trifluoromethyl | bromo | $Y^1$ is CH, $Y^2$ is CH, $Y^3$ is CH |
| P.0278 | $X^1$ is chloro, $X^2$ is C—I, $X^3$ is chloro | trifluoromethyl | chloro | $Y^1$ is CH, $Y^2$ is CH, $Y^3$ is CH |
| P.0279 | $X^1$ is chloro, $X^2$ is C—I, $X^3$ is chloro | trifluoromethyl | cyano | $Y^1$ is CH, $Y^2$ is CH, $Y^3$ is CH |
| P.0280 | $X^1$ is chloro, $X^2$ is C—I, $X^3$ is chloro | trifluoromethyl | cyclopropyl | $Y^1$ is CH, $Y^2$ is CH, $Y^3$ is CH |
| P.0281 | $X^1$ is chloro, $X^2$ is C—I, $X^3$ is chloro | trifluoromethyl | ethyl | $Y^1$ is CH, $Y^2$ is CH, $Y^3$ is CH |
| P.0282 | $X^1$ is chloro, $X^2$ is C—I, $X^3$ is chloro | trifluoromethyl | fluoro | $Y^1$ is CH, $Y^2$ is CH, $Y^3$ is CH |
| P.0283 | $X^1$ is chloro, $X^2$ is C—I, $X^3$ is chloro | trifluoromethyl | hydrogen | $Y^1$ is CH, $Y^2$ is CH, $Y^3$ is CH |
| P.0284 | $X^1$ is chloro, $X^2$ is C—I, $X^3$ is chloro | trifluoromethyl | methoxy | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0285 | $X^1$ is chloro, $X^2$ is C—I, $X^3$ is chloro | trifluoromethyl | methyl | $Y^1$ is CH, $Y^2$ is CH, $Y^3$ is CH |
| P.0286 | $X^1$ is chloro, $X^2$ is C—I, $X^3$ is chloro | trifluoromethyl | nitro | $Y^1$ is CH, $Y^2$ is CH, $Y^3$ is CH |
| P.0287 | $X^1$ is chloro, $X^2$ is C—I, $X^3$ is chloro | trifluoromethyl | trifluoromethoxy | $Y^1$ is CH, $Y^2$ is CH, $Y^3$ is CH |
| P.0288 | $X^1$ is chloro, $X^2$ is C—I, $X^3$ is chloro | trifluoromethyl | trifluoromethyl | $Y^1$ is CH, $Y^2$ is CH, $Y^3$ is CH |
| P.0289 | $X^1$ is fluoro, $X^2$ is C—F, $X^3$ is fluoro | chlorodifluoromethyl | bromo | $Y^1$ is CH, $Y^2$ is CH, $Y^3$ is CH |
| P.0290 | $X^1$ is fluoro, $X^2$ is C—F, $X^3$ is fluoro | chlorodifluoromethyl | chloro | $Y^1$ is CH, $Y^2$ is CH, $Y^3$ is CH |
| P.0291 | $X^1$ is fluoro, $X^2$ is C—F, $X^3$ is fluoro | chlorodifluoromethyl | cyano | $Y^1$ is CH, $Y^2$ is CH, $Y^3$ is CH |
| P.0292 | $X^1$ is fluoro, $X^2$ is C—F, $X^3$ is fluoro | chlorodifluoromethyl | cyclopropyl | $Y^1$ is CH, $Y^2$ is CH, $Y^3$ is CH |
| P.0293 | $X^1$ is fluoro, $X^2$ is C—F, $X^3$ is fluoro | chlorodifluoromethyl | ethyl | $Y^1$ is CH, $Y^2$ is CH, $Y^3$ is CH |
| P.0294 | $X^1$ is fluoro, $X^2$ is C—F, $X^3$ is fluoro | chlorodifluoromethyl | fluoro | $Y^1$ is CH, $Y^2$ is CH, $Y^3$ is CH |
| P.0295 | $X^1$ is fluoro, $X^2$ is C—F, $X^3$ is fluoro | chlorodifluoromethyl | hydrogen | $Y^1$ is CH, $Y^2$ is CH, $Y^3$ is CH |
| P.0296 | $X^1$ is fluoro, $X^2$ is C—F, $X^3$ is fluoro | chlorodifluoromethyl | methoxy | $Y^1$ is CH, $Y^2$ is CH, $Y^3$ is CH |
| P.0297 | $X^1$ is fluoro, $X^2$ is C—F, $X^3$ is fluoro | chlorodifluoromethyl | methyl | $Y^1$ is CH, $Y^2$ is CH, $Y^3$ is CH |
| P.0298 | $X^1$ is fluoro, $X^2$ is C—F, $X^3$ is fluoro | chlorodifluoromethyl | nitro | $Y^1$ is CH, $Y^2$ is CH, $Y^3$ is CH |
| P.0299 | $X^1$ is fluoro, $X^2$ is C—F, $X^3$ is fluoro | chlorodifluoromethyl | trifluoromethoxy | $Y^1$ is CH, $Y^2$ is CH, $Y^3$ is CH |
| P.0300 | $X^1$ is fluoro, $X^2$ is C—F, $X^3$ is fluoro | chlorodifluoromethyl | trifluoromethyl | $Y^1$ is CH, $Y^2$ is CH, $Y^3$ is CH |
| P.0301 | $X^1$ is fluoro, $X^2$ is C—F, $X^3$ is fluoro | difluoromethyl | bromo | $Y^1$ is CH, $Y^2$ is CH, $Y^3$ is CH |
| P.0302 | $X^1$ is fluoro, $X^2$ is C—F, $X^3$ is fluoro | difluoromethyl | chloro | $Y^1$ is CH, $Y^2$ is CH, $Y^3$ is CH |
| P.0303 | $X^1$ is fluoro, $X^2$ is C—F, $X^3$ is fluoro | difluoromethyl | cyano | $Y^1$ is CH, $Y^2$ is CH, $Y^3$ is CH |
| P.0304 | $X^1$ is fluoro, $X^2$ is C—F, $X^3$ is fluoro | difluoromethyl | cyclopropyl | $Y^1$ is CH, $Y^2$ is CH, $Y^3$ is CH |
| P.0305 | $X^1$ is fluoro, $X^2$ is C—F, $X^3$ is fluoro | difluoromethyl | ethyl | $Y^1$ is CH, $Y^2$ is CH, $Y^3$ is CH |
| P.0306 | $X^1$ is fluoro, $X^2$ is C—F, $X^3$ is fluoro | difluoromethyl | fluoro | $Y^1$ is CH, $Y^2$ is CH, $Y^3$ is CH |
| P.0307 | $X^1$ is fluoro, $X^2$ is C—F, $X^3$ is fluoro | difluoromethyl | hydrogen | $Y^1$ is CH, $Y^2$ is CH, $Y^3$ is CH |
| P.0308 | $X^1$ is fluoro, $X^2$ is C—F, $X^3$ is fluoro | difluoromethyl | methoxy | $Y^1$ is CH, $Y^2$ is CH, $Y^3$ is CH |
| P.0309 | $X^1$ is fluoro, $X^2$ is C—F, $X^3$ is fluoro | difluoromethyl | methyl | $Y^1$ is CH, $Y^2$ is CH, $Y^3$ is CH |
| P.0310 | $X^1$ is fluoro, $X^2$ is C—F, $X^3$ is fluoro | difluoromethyl | nitro | $Y^1$ is CH, $Y^2$ is CH, $Y^3$ is CH |
| P.0311 | $X^1$ is fluoro, $X^2$ is C—F, $X^3$ is fluoro | difluoromethyl | trifluoromethoxy | $Y^1$ is CH, $Y^2$ is CH, $Y^3$ is CH |
| P.0312 | $X^1$ is fluoro, $X^2$ is C—F, $X^3$ is fluoro | difluoromethyl | trifluoromethyl | $Y^1$ is CH, $Y^2$ is CH, $Y^3$ is CH |
| P.0313 | $X^1$ is fluoro, $X^2$ is C—F, $X^3$ is fluoro | trifluoromethyl | bromo | $Y^1$ is CH, $Y^2$ is CH, $Y^3$ is CH |
| P.0314 | $X^1$ is fluoro, $X^2$ is C—F, $X^3$ is fluoro | trifluoromethyl | chloro | $Y^1$ is CH, $Y^2$ is CH, $Y^3$ is CH |
| P.0315 | $X^1$ is fluoro, $X^2$ is C—F, $X^3$ is fluoro | trifluoromethyl | cyano | $Y^1$ is CH, $Y^2$ is CH, $Y^3$ is CH |
| P.0316 | $X^1$ is fluoro, $X^2$ is C—F, $X^3$ is fluoro | trifluoromethyl | cyclopropyl | $Y^1$ is CH, $Y^2$ is CH, $Y^3$ is CH |
| P.0317 | $X^1$ is fluoro, $X^2$ is C—F, $X^3$ is fluoro | trifluoromethyl | ethyl | $Y^1$ is CH, $Y^2$ is CH, $Y^3$ is CH |
| P.0318 | $X^1$ is fluoro, $X^2$ is C—F, $X^3$ is fluoro | trifluoromethyl | fluoro | $Y^1$ is CH, $Y^2$ is CH, $Y^3$ is CH |
| P.0319 | $X^1$ is fluoro, $X^2$ is C—F, $X^3$ is fluoro | trifluoromethyl | hydrogen | $Y^1$ is CH, $Y^2$ is CH, $Y^3$ is CH |
| P.0320 | $X^1$ is fluoro, $X^2$ is C—F, $X^3$ is fluoro | trifluoromethyl | methoxy | $Y^1$ is CH, $Y^2$ is CH, $Y^3$ is CH |
| P.0321 | $X^1$ is fluoro, $X^2$ is C—F, $X^3$ is fluoro | trifluoromethyl | methyl | $Y^1$ is CH, $Y^2$ is CH, $Y^3$ is CH |
| P.0322 | $X^1$ is fluoro, $X^2$ is C—F, $X^3$ is fluoro | trifluoromethyl | nitro | $Y^1$ is CH, $Y^2$ is CH, $Y^3$ is CH |
| P.0323 | $X^1$ is fluoro, $X^2$ is C—F, $X^3$ is fluoro | trifluoromethyl | trifluoromethoxy | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0324 | $X^1$ is fluoro, $X^2$ is C—F, $X^3$ is fluoro | trifluoromethyl | trifluoromethyl | $Y^1$ is CH, $Y^2$ is CH, $Y^3$ is CH |
| P.0325 | $X^1$ is chloro, $X^2$ is CH, $X^3$ is bromo | chlorodifluoromethyl | bromo | $Y^1$ is CH, $Y^2$ is CH, $Y^3$ is CH |
| P.0326 | $X^1$ is chloro, $X^2$ is CH, $X^3$ is bromo | chlorodifluoromethyl | chloro | $Y^1$ is CH, $Y^2$ is CH, $Y^3$ is CH |
| P.0327 | $X^1$ is chloro, $X^2$ is CH, $X^3$ is bromo | chlorodifluoromethyl | cyano | $Y^1$ is CH, $Y^2$ is CH, $Y^3$ is CH |
| P.0328 | $X^1$ is chloro, $X^2$ is CH, $X^3$ is bromo | chlorodifluoromethyl | cyclopropyl | $Y^1$ is CH, $Y^2$ is CH, $Y^3$ is CH |
| P.0329 | $X^1$ is chloro, $X^2$ is CH, $X^3$ is bromo | chlorodifluoromethyl | ethyl | $Y^1$ is CH, $Y^2$ is CH, $Y^3$ is CH |
| P.0330 | $X^1$ is chloro, $X^2$ is CH, $X^3$ is bromo | chlorodifluoromethyl | fluoro | $Y^1$ is CH, $Y^2$ is CH, $Y^3$ is CH |
| P.0331 | $X^1$ is chloro, $X^2$ is CH, $X^3$ is bromo | chlorodifluoromethyl | hydrogen | $Y^1$ is CH, $Y^2$ is CH, $Y^3$ is CH |
| P.0332 | $X^1$ is chloro, $X^2$ is CH, $X^3$ is bromo | chlorodifluoromethyl | methoxy | $Y^1$ is CH, $Y^2$ is CH, $Y^3$ is CH |
| P.0333 | $X^1$ is chloro, $X^2$ is CH, $X^3$ is bromo | chlorodifluoromethyl | methyl | $Y^1$ is CH, $Y^2$ is CH, $Y^3$ is CH |
| P.0334 | $X^1$ is chloro, $X^2$ is CH, $X^3$ is bromo | chlorodifluoromethyl | nitro | $Y^1$ is CH, $Y^2$ is CH, $Y^3$ is CH |
| P.0335 | $X^1$ is chloro, $X^2$ is CH, $X^3$ is bromo | chlorodifluoromethyl | trifluoromethoxy | $Y^1$ is CH, $Y^2$ is CH, $Y^3$ is CH |
| P.0336 | $X^1$ is chloro, $X^2$ is CH, $X^3$ is bromo | chlorodifluoromethyl | trifluoromethyl | $Y^1$ is CH, $Y^2$ is CH, $Y^3$ is CH |
| P.0337 | $X^1$ is chloro, $X^2$ is CH, $X^3$ is bromo | difluoromethyl | bromo | $Y^1$ is CH, $Y^2$ is CH, $Y^3$ is CH |
| P.0338 | $X^1$ is chloro, $X^2$ is CH, $X^3$ is bromo | difluoromethyl | chloro | $Y^1$ is CH, $Y^2$ is CH, $Y^3$ is CH |
| P.0339 | $X^1$ is chloro, $X^2$ is CH, $X^3$ is bromo | difluoromethyl | cyano | $Y^1$ is CH, $Y^2$ is CH, $Y^3$ is CH |
| P.0340 | $X^1$ is chloro, $X^2$ is CH, $X^3$ is bromo | difluoromethyl | cyclopropyl | $Y^1$ is CH, $Y^2$ is CH, $Y^3$ is CH |
| P.0341 | $X^1$ is chloro, $X^2$ is CH, $X^3$ is bromo | difluoromethyl | ethyl | $Y^1$ is CH, $Y^2$ is CH, $Y^3$ is CH |
| P.0342 | $X^1$ is chloro, $X^2$ is CH, $X^3$ is bromo | difluoromethyl | fluoro | $Y^1$ is CH, $Y^2$ is CH, $Y^3$ is CH |
| P.0343 | $X^1$ is chloro, $X^2$ is CH, $X^3$ is bromo | difluoromethyl | hydrogen | $Y^1$ is CH, $Y^2$ is CH, $Y^3$ is CH |
| P.0344 | $X^1$ is chloro, $X^2$ is CH, $X^3$ is bromo | difluoromethyl | methoxy | $Y^1$ is CH, $Y^2$ is CH, $Y^3$ is CH |
| P.0345 | $X^1$ is chloro, $X^2$ is CH, $X^3$ is bromo | difluoromethyl | methyl | $Y^1$ is CH, $Y^2$ is CH, $Y^3$ is CH |
| P.0346 | $X^1$ is chloro, $X^2$ is CH, $X^3$ is bromo | difluoromethyl | nitro | $Y^1$ is CH, $Y^2$ is CH, $Y^3$ is CH |
| P.0347 | $X^1$ is chloro, $X^2$ is CH, $X^3$ is bromo | difluoromethyl | trifluoromethoxy | $Y^1$ is CH, $Y^2$ is CH, $Y^3$ is CH |
| P.0348 | $X^1$ is chloro, $X^2$ is CH, $X^3$ is bromo | difluoromethyl | trifluoromethyl | $Y^1$ is CH, $Y^2$ is CH, $Y^3$ is CH |
| P.0349 | $X^1$ is chloro, $X^2$ is CH, $X^3$ is bromo | trifluoromethyl | bromo | $Y^1$ is CH, $Y^2$ is CH, $Y^3$ is CH |
| P.0350 | $X^1$ is chloro, $X^2$ is CH, $X^3$ is bromo | trifluoromethyl | chloro | $Y^1$ is CH, $Y^2$ is CH, $Y^3$ is CH |
| P.0351 | $X^1$ is chloro, $X^2$ is CH, $X^3$ is fluoro | trifluoromethyl | cyano | $Y^1$ is CH, $Y^2$ is CH, $Y^3$ is CH |
| P.0352 | $X^1$ is chloro, $X^2$ is CH, $X^3$ is bromo | trifluoromethyl | cyclopropyl | $Y^1$ is CH, $Y^2$ is CH, $Y^3$ is CH |
| P.0353 | $X^1$ is chloro, $X^2$ is CH, $X^3$ is bromo | trifluoromethyl | ethyl | $Y^1$ is CH, $Y^2$ is CH, $Y^3$ is CH |
| P.0354 | $X^1$ is chloro, $X^2$ is CH, $X^3$ is bromo | trifluoromethyl | fluoro | $Y^1$ is CH, $Y^2$ is CH, $Y^3$ is CH |
| P.0355 | $X^1$ is chloro, $X^2$ is CH, $X^3$ is bromo | trifluoromethyl | hydrogen | $Y^1$ is CH, $Y^2$ is CH, $Y^3$ is CH |
| P.0356 | $X^1$ is chloro, $X^2$ is CH, $X^3$ is bromo | trifluoromethyl | methoxy | $Y^1$ is CH, $Y^2$ is CH, $Y^3$ is CH |
| P.0357 | $X^1$ is chloro, $X^2$ is CH, $X^3$ is bromo | trifluoromethyl | methyl | $Y^1$ is CH, $Y^2$ is CH, $Y^3$ is CH |
| P.0358 | $X^1$ is chloro, $X^2$ is CH, $X^3$ is bromo | trifluoromethyl | nitro | $Y^1$ is CH, $Y^2$ is CH, $Y^3$ is CH |
| P.0359 | $X^1$ is chloro, $X^2$ is CH, $X^3$ is bromo | trifluoromethyl | trifluoromethoxy | $Y^1$ is CH, $Y^2$ is CH, $Y^3$ is CH |
| P.0360 | $X^1$ is chloro, $X^2$ is CH, $X^3$ is bromo | trifluoromethyl | trifluoromethyl | $Y^1$ is CH, $Y^2$ is CH, $Y^3$ is CH |
| P.0361 | $X^1$ is chloro, $X^2$ is CH, $X^3$ is bromo | chlorodifluoromethyl | bromo | $Y^1$ is CH, $Y^2$ is CH, $Y^3$ is CH |
| P.0362 | $X^1$ is chloro, $X^2$ is CH, $X^3$ is bromo | chlorodifluoromethyl | chloro | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0363 | $X^1$ is chloro, $X^2$ is CH, $X^3$ is bromo | chlorodifluoromethyl | cyano | $Y^1$ is CH, $Y^2$ is CH, $Y^3$ is CH |
| P.0364 | $X^1$ is chloro, $X^2$ is CH, $X^3$ is bromo | chlorodifluoromethyl | cyclopropyl | $Y^1$ is CH, $Y^2$ is CH, $Y^3$ is CH |
| P.0365 | $X^1$ is chloro, $X^2$ is CH, $X^3$ is bromo | chlorodifluoromethyl | ethyl | $Y^1$ is CH, $Y^2$ is CH, $Y^3$ is CH |
| P.0366 | $X^1$ is chloro, $X^2$ is CH, $X^3$ is bromo | chlorodifluoromethyl | fluoro | $Y^1$ is CH, $Y^2$ is CH, $Y^3$ is CH |
| P.0367 | $X^1$ is chloro, $X^2$ is CH, $X^3$ is bromo | chlorodifluoromethyl | hydrogen | $Y^1$ is CH, $Y^2$ is CH, $Y^3$ is CH |
| P.0368 | $X^1$ is chloro, $X^2$ is CH, $X^3$ is bromo | chlorodifluoromethyl | methoxy | $Y^1$ is CH, $Y^2$ is CH, $Y^3$ is CH |
| P.0369 | $X^1$ is chloro, $X^2$ is CH, $X^3$ is bromo | chlorodifluoromethyl | methyl | $Y^1$ is CH, $Y^2$ is CH, $Y^3$ is CH |
| P.0370 | $X^1$ is chloro, $X^2$ is CH, $X^3$ is bromo | chlorodifluoromethyl | nitro | $Y^1$ is CH, $Y^2$ is CH, $Y^3$ is CH |
| P.0371 | $X^1$ is chloro, $X^2$ is CH, $X^3$ is bromo | chlorodifluoromethyl | trifluoromethoxy | $Y^1$ is CH, $Y^2$ is CH, $Y^3$ is CH |
| P.0372 | $X^1$ is chloro, $X^2$ is CH, $X^3$ is bromo | chlorodifluoromethyl | trifluoromethyl | $Y^1$ is CH, $Y^2$ is CH, $Y^3$ is CH |
| P.0373 | $X^1$ is chloro, $X^2$ is CH, $X^3$ is bromo | difluoromethyl | bromo | $Y^1$ is CH, $Y^2$ is CH, $Y^3$ is CH |
| P.0374 | $X^1$ is chloro, $X^2$ is CH, $X^3$ is bromo | difluoromethyl | chloro | $Y^1$ is CH, $Y^2$ is CH, $Y^3$ is CH |
| P.0375 | $X^1$ is chloro, $X^2$ is CH, $X^3$ is bromo | difluoromethyl | cyano | $Y^1$ is CH, $Y^2$ is CH, $Y^3$ is CH |
| P.0376 | $X^1$ is chloro, $X^2$ is CH, $X^3$ is bromo | difluoromethyl | cyclopropyl | $Y^1$ is CH, $Y^2$ is CH, $Y^3$ is CH |
| P.0377 | $X^1$ is chloro, $X^2$ is CH, $X^3$ is bromo | difluoromethyl | ethyl | $Y^1$ is CH, $Y^2$ is CH, $Y^3$ is CH |
| P.0378 | $X^1$ is chloro, $X^2$ is CH, $X^3$ is bromo | difluoromethyl | fluoro | $Y^1$ is CH, $Y^2$ is CH, $Y^3$ is CH |
| P.0379 | $X^1$ is chloro, $X^2$ is CH, $X^3$ is bromo | difluoromethyl | hydrogen | $Y^1$ is CH, $Y^2$ is CH, $Y^3$ is CH |
| P.0380 | $X^1$ is chloro, $X^2$ is CH, $X^3$ is bromo | difluoromethyl | methoxy | $Y^1$ is CH, $Y^2$ is CH, $Y^3$ is CH |
| P.0381 | $X^1$ is chloro, $X^2$ is CH, $X^3$ is bromo | difluoromethyl | methyl | $Y^1$ is CH, $Y^2$ is CH, $Y^3$ is CH |
| P.0382 | $X^1$ is chloro, $X^2$ is CH, $X^3$ is bromo | difluoromethyl | nitro | $Y^1$ is CH, $Y^2$ is CH, $Y^3$ is CH |
| P.0383 | $X^1$ is chloro, $X^2$ is CH, $X^3$ is bromo | difluoromethyl | trifluoromethoxy | $Y^1$ is CH, $Y^2$ is CH, $Y^3$ is CH |
| P.0384 | $X^1$ is chloro, $X^2$ is CH, $X^3$ is bromo | difluoromethyl | trifluoromethyl | $Y^1$ is CH, $Y^2$ is CH, $Y^3$ is CH |
| P.0385 | $X^1$ is chloro, $X^2$ is CH, $X^3$ is bromo | trifluoromethyl | bromo | $Y^1$ is CH, $Y^2$ is CH, $Y^3$ is CH |
| P.0386 | $X^1$ is chloro, $X^2$ is CH, $X^3$ is bromo | trifluoromethyl | chloro | $Y^1$ is CH, $Y^2$ is CH, $Y^3$ is CH |
| P.0387 | $X^1$ is chloro, $X^2$ is CH, $X^3$ is bromo | trifluoromethyl | cyano | $Y^1$ is CH, $Y^2$ is CH, $Y^3$ is CH |
| P.0388 | $X^1$ is chloro, $X^2$ is CH, $X^3$ is bromo | trifluoromethyl | cyclopropyl | $Y^1$ is CH, $Y^2$ is CH, $Y^3$ is CH |
| P.0389 | $X^1$ is chloro, $X^2$ is CH, $X^3$ is bromo | trifluoromethyl | ethyl | $Y^1$ is CH, $Y^2$ is CH, $Y^3$ is CH |
| P.0390 | $X^1$ is chloro, $X^2$ is CH, $X^3$ is bromo | trifluoromethyl | fluoro | $Y^1$ is CH, $Y^2$ is CH, $Y^3$ is CH |
| P.0391 | $X^1$ is chloro, $X^2$ is CH, $X^3$ is bromo | trifluoromethyl | hydrogen | $Y^1$ is CH, $Y^2$ is CH, $Y^3$ is CH |
| P.0392 | $X^1$ is chloro, $X^2$ is CH, $X^3$ is bromo | trifluoromethyl | methoxy | $Y^1$ is CH, $Y^2$ is CH, $Y^3$ is CH |
| P.0393 | $X^1$ is chloro, $X^2$ is CH, $X^3$ is bromo | trifluoromethyl | methyl | $Y^1$ is CH, $Y^2$ is CH, $Y^3$ is CH |
| P.0394 | $X^1$ is chloro, $X^2$ is CH, $X^3$ is bromo | trifluoromethyl | nitro | $Y^1$ is CH, $Y^2$ is CH, $Y^3$ is CH |
| P.0395 | $X^1$ is chloro, $X^2$ is CH, $X^3$ is bromo | trifluoromethyl | trifluoromethoxy | $Y^1$ is CH, $Y^2$ is CH, $Y^3$ is CH |
| P.0396 | $X^1$ is chloro, $X^2$ is CH, $X^3$ is bromo | trifluoromethyl | trifluoromethyl | $Y^1$ is CH, $Y^2$ is CH, $Y^3$ is CH |
| P.0397 | $X^1$ is chloro, $X^2$ is CH, $X^3$ is bromo | chlorodifluoromethyl | bromo | $Y^1$ is CH, $Y^2$ is CH, $Y^3$ is CH |
| P.0398 | $X^1$ is chloro, $X^2$ is CH, $X^3$ is bromo | chlorodifluoromethyl | chloro | $Y^1$ is CH, $Y^2$ is CH, $Y^3$ is CH |
| P.0399 | $X^1$ is chloro, $X^2$ is CH, $X^3$ is bromo | chlorodifluoromethyl | cyano | $Y^1$ is CH, $Y^2$ is CH, $Y^3$ is CH |
| P.0400 | $X^1$ is chloro, $X^2$ is CH, $X^3$ is bromo | chlorodifluoromethyl | cyclopropyl | $Y^1$ is CH, $Y^2$ is CH, $Y^3$ is CH |
| P.0401 | $X^1$ is chloro, $X^2$ is CH, $X^3$ is bromo | chlorodifluoromethyl | ethyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0402 | $X^1$ is chloro, $X^2$ is CH, $X^3$ is bromo | chlorodifluoromethyl | fluoro | $Y^1$ is CH, $Y^2$ is CH, $Y^3$ is CH |
| P.0403 | $X^1$ is chloro, $X^2$ is CH, $X^3$ is bromo | chlorodifluoromethyl | hydrogen | $Y^1$ is CH, $Y^2$ is CH, $Y^3$ is CH |
| P.0404 | $X^1$ is chloro, $X^2$ is CH, $X^3$ is bromo | chlorodifluoromethyl | methoxy | $Y^1$ is CH, $Y^2$ is CH, $Y^3$ is CH |
| P.0405 | $X^1$ is chloro, $X^2$ is CH, $X^3$ is bromo | chlorodifluoromethyl | methyl | $Y^1$ is CH, $Y^2$ is CH, $Y^3$ is CH |
| P.0406 | $X^1$ is chloro, $X^2$ is CH, $X^3$ is bromo | chlorodifluoromethyl | nitro | $Y^1$ is CH, $Y^2$ is CH, $Y^3$ is CH |
| P.0407 | $X^1$ is chloro, $X^2$ is CH, $X^3$ is bromo | chlorodifluoromethyl | trifluoromethoxy | $Y^1$ is CH, $Y^2$ is CH, $Y^3$ is CH |
| P.0408 | $X^1$ is chloro, $X^2$ is CH, $X^3$ is bromo | chlorodifluoromethyl | trifluoromethyl | $Y^1$ is CH, $Y^2$ is CH, $Y^3$ is CH |
| P.0409 | $X^1$ is chloro, $X^2$ is CH, $X^3$ is bromo | difluoromethyl | bromo | $Y^1$ is CH, $Y^2$ is CH, $Y^3$ is CH |
| P.0410 | $X^1$ is chloro, $X^2$ is CH, $X^3$ is bromo | difluoromethyl | chloro | $Y^1$ is CH, $Y^2$ is CH, $Y^3$ is CH |
| P.0411 | $X^1$ is chloro, $X^2$ is CH, $X^3$ is bromo | difluoromethyl | cyano | $Y^1$ is CH, $Y^2$ is CH, $Y^3$ is CH |
| P.0412 | $X^1$ is chloro, $X^2$ is CH, $X^3$ is bromo | difluoromethyl | cyclopropyl | $Y^1$ is CH, $Y^2$ is CH, $Y^3$ is CH |
| P.0413 | $X^1$ is chloro, $X^2$ is CH, $X^3$ is bromo | difluoromethyl | ethyl | $Y^1$ is CH, $Y^2$ is CH, $Y^3$ is CH |
| P.0414 | $X^1$ is chloro, $X^2$ is CH, $X^3$ is bromo | difluoromethyl | fluoro | $Y^1$ is CH, $Y^2$ is CH, $Y^3$ is CH |
| P.0415 | $X^1$ is chloro, $X^2$ is CH, $X^3$ is bromo | difluoromethyl | hydrogen | $Y^1$ is CH, $Y^2$ is CH, $Y^3$ is CH |
| P.0416 | $X^1$ is chloro, $X^2$ is CH, $X^3$ is bromo | difluoromethyl | methoxy | $Y^1$ is CH, $Y^2$ is CH, $Y^3$ is CH |
| P.0417 | $X^1$ is chloro, $X^2$ is CH, $X^3$ is bromo | difluoromethyl | methyl | $Y^1$ is CH, $Y^2$ is CH, $Y^3$ is CH |
| P.0418 | $X^1$ is chloro, $X^2$ is CH, $X^3$ is bromo | difluoromethyl | nitro | $Y^1$ is CH, $Y^2$ is CH, $Y^3$ is CH |
| P.0419 | $X^1$ is chloro, $X^2$ is CH, $X^3$ is bromo | difluoromethyl | trifluoromethoxy | $Y^1$ is CH, $Y^2$ is CH, $Y^3$ is CH |
| P.0420 | $X^1$ is chloro, $X^2$ is CH, $X^3$ is bromo | difluoromethyl | trifluoromethyl | $Y^1$ is CH, $Y^2$ is CH, $Y^3$ is CH |
| P.0421 | $X^1$ is chloro, $X^2$ is CH, $X^3$ is bromo | trifluoromethyl | bromo | $Y^1$ is CH, $Y^2$ is CH, $Y^3$ is CH |
| P.0422 | $X^1$ is chloro, $X^2$ is CH, $X^3$ is bromo | trifluoromethyl | chloro | $Y^1$ is CH, $Y^2$ is CH, $Y^3$ is CH |
| P.0423 | $X^1$ is chloro, $X^2$ is CH, $X^3$ is bromo | trifluoromethyl | cyano | $Y^1$ is CH, $Y^2$ is CH, $Y^3$ is CH |
| P.0424 | $X^1$ is chloro, $X^2$ is CH, $X^3$ is bromo | trifluoromethyl | cyclopropyl | $Y^1$ is CH, $Y^2$ is CH, $Y^3$ is CH |
| P.0425 | $X^1$ is chloro, $X^2$ is CH, $X^3$ is bromo | trifluoromethyl | ethyl | $Y^1$ is CH, $Y^2$ is CH, $Y^3$ is CH |
| P.0426 | $X^1$ is chloro, $X^2$ is CH, $X^3$ is bromo | trifluoromethyl | fluoro | $Y^1$ is CH, $Y^2$ is CH, $Y^3$ is CH |
| P.0427 | $X^1$ is chloro, $X^2$ is CH, $X^3$ is bromo | trifluoromethyl | hydrogen | $Y^1$ is CH, $Y^2$ is CH, $Y^3$ is CH |
| P.0428 | $X^1$ is chloro, $X^2$ is CH, $X^3$ is bromo | trifluoromethyl | methoxy | $Y^1$ is CH, $Y^2$ is CH, $Y^3$ is CH |
| P.0429 | $X^1$ is chloro, $X^2$ is CH, $X^3$ is bromo | trifluoromethyl | methyl | $Y^1$ is CH, $Y^2$ is CH, $Y^3$ is CH |
| P.0430 | $X^1$ is chloro, $X^2$ is CH, $X^3$ is bromo | trifluoromethyl | nitro | $Y^1$ is CH, $Y^2$ is CH, $Y^3$ is CH |
| P.0431 | $X^1$ is chloro, $X^2$ is CH, $X^3$ is bromo | trifluoromethyl | trifluoromethoxy | $Y^1$ is CH, $Y^2$ is CH, $Y^3$ is CH |
| P.0432 | $X^1$ is chloro, $X^2$ is CH, $X^3$ is bromo | trifluoromethyl | trifluoromethyl | $Y^1$ is CH, $Y^2$ is CH, $Y^3$ is CH |
| P.0433 | $X^1$ is chloro, $X^2$ is C—Cl, $X^3$ is trifluoromethyl | chlorodifluoromethyl | bromo | $Y^1$ is CH, $Y^2$ is CH, $Y^3$ is CH |
| P.0434 | $X^1$ is chloro, $X^2$ is C—Cl, $X^3$ is trifluoromethyl | chlorodifluoromethyl | chloro | $Y^1$ is CH, $Y^2$ is CH, $Y^3$ is CH |
| P.0435 | $X^1$ is chloro, $X^2$ is C—Cl, $X^3$ is trifluoromethyl | chlorodifluoromethyl | cyano | $Y^1$ is CH, $Y^2$ is CH, $Y^3$ is CH |
| P.0436 | $X^1$ is chloro, $X^2$ is C—Cl, $X^3$ is trifluoromethyl | chlorodifluoromethyl | cyclopropyl | $Y^1$ is CH, $Y^2$ is CH, $Y^3$ is CH |
| P.0437 | $X^1$ is chloro, $X^2$ is C—Cl, $X^3$ is trifluoromethyl | chlorodifluoromethyl | ethyl | $Y^1$ is CH, $Y^2$ is CH, $Y^3$ is CH |
| P.0438 | $X^1$ is chloro, $X^2$ is C—Cl, $X^3$ is trifluoromethyl | chlorodifluoromethyl | fluoro | $Y^1$ is CH, $Y^2$ is CH, $Y^3$ is CH |
| P.0439 | $X^1$ is chloro, $X^2$ is C—Cl, $X^3$ is trifluoromethyl | chlorodifluoromethyl | hydrogen | $Y^1$ is CH, $Y^2$ is CH, $Y^3$ is CH |
| P.0440 | $X^1$ is chloro, $X^2$ is C—Cl, $X^3$ is trifluoromethyl | chlorodifluoromethyl | methoxy | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0441 | X¹ is chloro, X² is C—Cl, X³ is trifluoromethyl | chlorodifluoromethyl | methyl | Y¹ is CH, Y² is CH, Y³ is CH |
| P.0442 | X¹ is chloro, X² is C—Cl, X³ is trifluoromethyl | chlorodifluoromethyl | nitro | Y¹ is CH, Y² is CH, Y³ is CH |
| P.0443 | X¹ is chloro, X² is C—Cl, X³ is trifluoromethyl | chlorodifluoromethyl | trifluoromethoxy | Y¹ is CH, Y² is CH, Y³ is CH |
| P.0444 | X¹ is chloro, X² is C—Cl, X³ is trifluoromethyl | chlorodifluoromethyl | trifluoromethyl | Y¹ is CH, Y² is CH, Y³ is CH |
| P.0445 | X¹ is chloro, X² is C—Cl, X³ is trifluoromethyl | difluoromethyl | bromo | Y¹ is CH, Y² is CH, Y³ is CH |
| P.0446 | X¹ is chloro, X² is C—Cl, X³ is trifluoromethyl | difluoromethyl | chloro | Y¹ is CH, Y² is CH, Y³ is CH |
| P.0447 | X¹ is chloro, X² is C—Cl, X³ is trifluoromethyl | difluoromethyl | cyano | Y¹ is CH, Y² is CH, Y³ is CH |
| P.0448 | X¹ is chloro, X² is C—Cl, X³ is trifluoromethyl | difluoromethyl | cyclopropyl | Y¹ is CH, Y² is CH, Y³ is CH |
| P.0449 | X¹ is chloro, X² is C—Cl, X³ is trifluoromethyl | difluoromethyl | ethyl | Y¹ is CH, Y² is CH, Y³ is CH |
| P.0450 | X¹ is chloro, X² is C—Cl, X³ is trifluoromethyl | difluoromethyl | fluoro | Y¹ is CH, Y² is CH, Y³ is CH |
| P.0451 | X¹ is chloro, X² is C—Cl, X³ is trifluoromethyl | difluoromethyl | hydrogen | Y¹ is CH, Y² is CH, Y³ is CH |
| P.0452 | X¹ is chloro, X² is C—Cl, X³ is trifluoromethyl | difluoromethyl | methoxy | Y¹ is CH, Y² is CH, Y³ is CH |
| P.0453 | X¹ is chloro, X² is C—Cl, X³ is trifluoromethyl | difluoromethyl | methyl | Y¹ is CH, Y² is CH, Y³ is CH |
| P.0454 | X¹ is chloro, X² is C—Cl, X³ is trifluoromethyl | difluoromethyl | nitro | Y¹ is CH, Y² is CH, Y³ is CH |
| P.0455 | X¹ is chloro, X² is C—Cl, X³ is trifluoromethyl | difluoromethyl | trifluoromethoxy | Y¹ is CH, Y² is CH, Y³ is CH |
| P.0456 | X¹ is chloro, X² is C—Cl, X³ is trifluoromethyl | difluoromethyl | trifluoromethyl | Y¹ is CH, Y² is CH, Y³ is CH |
| P.0457 | X¹ is chloro, X² is C—Cl, X³ is trifluoromethyl | trifluoromethyl | bromo | Y¹ is CH, Y² is CH, Y³ is CH |
| P.0458 | X¹ is chloro, X² is C—Cl, X³ is trifluoromethyl | trifluoromethyl | chloro | Y¹ is CH, Y² is CH, Y³ is CH |
| P.0459 | X¹ is chloro, X² is C—Cl, X³ is trifluoromethyl | trifluoromethyl | cyano | Y¹ is CH, Y² is CH, Y³ is CH |
| P.0460 | X¹ is chloro, X² is C—Cl, X³ is trifluoromethyl | trifluoromethyl | cyclopropyl | Y¹ is CH, Y² is CH, Y³ is CH |
| P.0461 | X¹ is chloro, X² is C—Cl, X³ is trifluoromethyl | trifluoromethyl | ethyl | Y¹ is CH, Y² is CH, Y³ is CH |
| P.0462 | X¹ is chloro, X² is C—Cl, X³ is trifluoromethyl | trifluoromethyl | fluoro | Y¹ is CH, Y² is CH, Y³ is CH |
| P.0463 | X¹ is chloro, X² is C—Cl, X³ is trifluoromethyl | trifluoromethyl | hydrogen | Y¹ is CH, Y² is CH, Y³ is CH |
| P.0464 | X¹ is chloro, X² is C—Cl, X³ is trifluoromethyl | trifluoromethyl | methoxy | Y¹ is CH, Y² is CH, Y³ is CH |
| P.0465 | X¹ is chloro, X² is C—Cl, X³ is trifluoromethyl | trifluoromethyl | methyl | Y¹ is CH, Y² is CH, Y³ is CH |
| P.0466 | X¹ is chloro, X² is C—Cl, X³ is trifluoromethyl | trifluoromethyl | nitro | Y¹ is CH, Y² is CH, Y³ is CH |
| P.0467 | X¹ is chloro, X² is C—Cl, X³ is trifluoromethyl | trifluoromethyl | trifluoromethoxy | Y¹ is CH, Y² is CH, Y³ is CH |
| P.0468 | X¹ is chloro, X² is C—Cl, X³ is trifluoromethyl | trifluoromethyl | trifluoromethyl | Y¹ is CH, Y² is CH, Y³ is CH |
| P.0469 | X¹ is trifluoromethyl, X² is CH, X³ is trifluoromethyl | chlorodifluoromethyl | bromo | Y¹ is CH, Y² is CH, Y³ is CH |
| P.0470 | X¹ is trifluoromethyl, X² is CH, X³ is trifluoromethyl | chlorodifluoromethyl | chloro | Y¹ is CH, Y² is CH, Y³ is CH |
| P.0471 | X¹ is trifluoromethyl, X² is CH, X³ is trifluoromethyl | chlorodifluoromethyl | cyano | Y¹ is CH, Y² is CH, Y³ is CH |
| P.0472 | X¹ is trifluoromethyl, X² is CH, X³ is trifluoromethyl | chlorodifluoromethyl | cyclopropyl | Y¹ is CH, Y² is CH, Y³ is CH |
| P.0473 | X¹ is trifluoromethyl, X² is CH, X³ is trifluoromethyl | chlorodifluoromethyl | ethyl | Y¹ is CH, Y² is CH, Y³ is CH |
| P.0474 | X¹ is trifluoromethyl, X² is CH, X³ is trifluoromethyl | chlorodifluoromethyl | fluoro | Y¹ is CH, Y² is CH, Y³ is CH |
| P.0475 | X¹ is trifluoromethyl, X² is CH, X³ is trifluoromethyl | chlorodifluoromethyl | hydrogen | Y¹ is CH, Y² is CH, Y³ is CH |
| P.0476 | X¹ is trifluoromethyl, X² is CH, X³ is trifluoromethyl | chlorodifluoromethyl | methoxy | Y¹ is CH, Y² is CH, Y³ is CH |
| P.0477 | X¹ is trifluoromethyl, X² is CH, X³ is trifluoromethyl | chlorodifluoromethyl | methyl | Y¹ is CH, Y² is CH, Y³ is CH |
| P.0478 | X¹ is trifluoromethyl, X² is CH, X³ is trifluoromethyl | chlorodifluoromethyl | nitro | Y¹ is CH, Y² is CH, Y³ is CH |
| P.0479 | X¹ is trifluoromethyl, X² is CH, X³ is trifluoromethyl | chlorodifluoromethyl | trifluoromethoxy | Y¹ is CH, Y² is CH, Y³ is CH |

TABLE P-continued

| | X1, X2, X3 | X4 | R5 | Y1, Y2, Y3 |
|---|---|---|---|---|
| P.0480 | $X^1$ is trifluoromethyl, $X^2$ is CH, $X^3$ is trifluoromethyl | chlorodifluoromethyl | trifluoromethyl | $Y^1$ is CH, $Y^2$ is CH, $Y^3$ is CH |
| P.0481 | $X^1$ is trifluoromethyl, $X^2$ is CH, $X^3$ is trifluoromethyl | difluoromethyl | bromo | $Y^1$ is CH, $Y^2$ is CH, $Y^3$ is CH |
| P.0482 | $X^1$ is trifluoromethyl, $X^2$ is CH, $X^3$ is trifluoromethyl | difluoromethyl | chloro | $Y^1$ is CH, $Y^2$ is CH, $Y^3$ is CH |
| P.0483 | $X^1$ is trifluoromethyl, $X^2$ is CH, $X^3$ is trifluoromethyl | difluoromethyl | cyano | $Y^1$ is CH, $Y^2$ is CH, $Y^3$ is CH |
| P.0484 | $X^1$ is trifluoromethyl, $X^2$ is CH, $X^3$ is trifluoromethyl | difluoromethyl | cyclopropyl | $Y^1$ is CH, $Y^2$ is CH, $Y^3$ is CH |
| P.0485 | $X^1$ is trifluoromethyl, $X^2$ is CH, $X^3$ is trifluoromethyl | difluoromethyl | ethyl | $Y^1$ is CH, $Y^2$ is CH, $Y^3$ is CH |
| P.0486 | $X^1$ is trifluoromethyl, $X^2$ is CH, $X^3$ is trifluoromethyl | difluoromethyl | fluoro | $Y^1$ is CH, $Y^2$ is CH, $Y^3$ is CH |
| P.0487 | $X^1$ is trifluoromethyl, $X^2$ is CH, $X^3$ is trifluoromethyl | difluoromethyl | hydrogen | $Y^1$ is CH, $Y^2$ is CH, $Y^3$ is CH |
| P.0488 | $X^1$ is trifluoromethyl, $X^2$ is CH, $X^3$ is trifluoromethyl | difluoromethyl | methoxy | $Y^1$ is CH, $Y^2$ is CH, $Y^3$ is CH |
| P.0489 | $X^1$ is trifluoromethyl, $X^2$ is CH, $X^3$ is trifluoromethyl | difluoromethyl | methyl | $Y^1$ is CH, $Y^2$ is CH, $Y^3$ is CH |
| P.0490 | $X^1$ is trifluoromethyl, $X^2$ is CH, $X^3$ is trifluoromethyl | difluoromethyl | nitro | $Y^1$ is CH, $Y^2$ is CH, $Y^3$ is CH |
| P.0491 | $X^1$ is trifluoromethyl, $X^2$ is CH, $X^3$ is trifluoromethyl | difluoromethyl | trifluoromethoxy | $Y^1$ is CH, $Y^2$ is CH, $Y^3$ is CH |
| P.0492 | $X^1$ is trifluoromethyl, $X^2$ is CH, $X^3$ is trifluoromethyl | difluoromethyl | trifluoromethyl | $Y^1$ is CH, $Y^2$ is CH, $Y^3$ is CH |
| P.0493 | $X^1$ is trifluoromethyl, $X^2$ is CH, $X^3$ is trifluoromethyl | trifluoromethyl | bromo | $Y^1$ is CH, $Y^2$ is CH, $Y^3$ is CH |
| P.0494 | $X^1$ is trifluoromethyl, $X^2$ is CH, $X^3$ is trifluoromethyl | trifluoromethyl | chloro | $Y^1$ is CH, $Y^2$ is CH, $Y^3$ is CH |
| P.0495 | $X^1$ is trifluoromethyl, $X^2$ is CH, $X^3$ is trifluoromethyl | trifluoromethyl | cyano | $Y^1$ is CH, $Y^2$ is CH, $Y^3$ is CH |
| P.0496 | $X^1$ is trifluoromethyl, $X^2$ is CH, $X^3$ is trifluoromethyl | trifluoromethyl | cyclopropyl | $Y^1$ is CH, $Y^2$ is CH, $Y^3$ is CH |
| P.0497 | $X^1$ is trifluoromethyl, $X^2$ is CH, $X^3$ is trifluoromethyl | trifluoromethyl | ethyl | $Y^1$ is CH, $Y^2$ is CH, $Y^3$ is CH |
| P.0498 | $X^1$ is trifluoromethyl, $X^2$ is CH, $X^3$ is trifluoromethyl | trifluoromethyl | fluoro | $Y^1$ is CH, $Y^2$ is CH, $Y^3$ is CH |
| P.0499 | $X^1$ is trifluoromethyl, $X^2$ is CH, $X^3$ is trifluoromethyl | trifluoromethyl | hydrogen | $Y^1$ is CH, $Y^2$ is CH, $Y^3$ is CH |
| P.0500 | $X^1$ is trifluoromethyl, $X^2$ is CH, $X^3$ is trifluoromethyl | trifluoromethyl | methoxy | $Y^1$ is CH, $Y^2$ is CH, $Y^3$ is CH |
| P.0501 | $X^1$ is trifluoromethyl, $X^2$ is CH, $X^3$ is trifluoromethyl | trifluoromethyl | methyl | $Y^1$ is CH, $Y^2$ is CH, $Y^3$ is CH |
| P.0502 | $X^1$ is trifluoromethyl, $X^2$ is CH, $X^3$ is trifluoromethyl | trifluoromethyl | nitro | $Y^1$ is CH, $Y^2$ is CH, $Y^3$ is CH |
| P.0503 | $X^1$ is trifluoromethyl, $X^2$ is CH, $X^3$ is trifluoromethyl | trifluoromethyl | trifluoromethoxy | $Y^1$ is CH, $Y^2$ is CH, $Y^3$ is CH |
| P.0504 | $X^1$ is trifluoromethyl, $X^2$ is CH, $X^3$ is trifluoromethyl | trifluoromethyl | trifluoromethyl | $Y^1$ is CH, $Y^2$ is CH, $Y^3$ is CH |
| P.0505 | $X^1$ is trifluoromethyl, $X^2$ is CH, $X^3$ is trifluoromethyl | chlorodifluoromethyl | bromo | $Y^1$ is CH, $Y^2$ is CH, $Y^3$ is CH |
| P.0506 | $X^1$ is trifluoromethyl, $X^2$ is CH, $X^3$ is trifluoromethyl | chlorodifluoromethyl | chloro | $Y^1$ is CH, $Y^2$ is CH, $Y^3$ is CH |
| P.0507 | $X^1$ is trifluoromethyl, $X^2$ is CH, $X^3$ is trifluoromethyl | chlorodifluoromethyl | cyano | $Y^1$ is CH, $Y^2$ is CH, $Y^3$ is CH |
| P.0508 | $X^1$ is trifluoromethyl, $X^2$ is CH, $X^3$ is trifluoromethyl | chlorodifluoromethyl | cyclopropyl | $Y^1$ is CH, $Y^2$ is CH, $Y^3$ is CH |
| P.0509 | $X^1$ is trifluoromethyl, $X^2$ is CH, $X^3$ is trifluoromethyl | chlorodifluoromethyl | ethyl | $Y^1$ is CH, $Y^2$ is CH, $Y^3$ is CH |
| P.0510 | $X^1$ is trifluoromethyl, $X^2$ is CH, $X^3$ is trifluoromethyl | chlorodifluoromethyl | fluoro | $Y^1$ is CH, $Y^2$ is CH, $Y^3$ is CH |
| P.0511 | $X^1$ is trifluoromethyl, $X^2$ is CH, $X^3$ is trifluoromethyl | chlorodifluoromethyl | hydrogen | $Y^1$ is CH, $Y^2$ is CH, $Y^3$ is CH |
| P.0512 | $X^1$ is trifluoromethyl, $X^2$ is CH, $X^3$ is trifluoromethyl | chlorodifluoromethyl | methoxy | $Y^1$ is CH, $Y^2$ is CH, $Y^3$ is CH |
| P.0513 | $X^1$ is trifluoromethyl, $X^2$ is CH, $X^3$ is trifluoromethyl | chlorodifluoromethyl | methyl | $Y^1$ is CH, $Y^2$ is CH, $Y^3$ is CH |
| P.0514 | $X^1$ is trifluoromethyl, $X^2$ is CH, $X^3$ is trifluoromethyl | chlorodifluoromethyl | nitro | $Y^1$ is CH, $Y^2$ is CH, $Y^3$ is CH |
| P.0515 | $X^1$ is trifluoromethyl, $X^2$ is CH, $X^3$ is trifluoromethyl | chlorodifluoromethyl | trifluoromethoxy | $Y^1$ is CH, $Y^2$ is CH, $Y^3$ is CH |
| P.0516 | $X^1$ is trifluoromethyl, $X^2$ is CH, $X^3$ is trifluoromethyl | chlorodifluoromethyl | trifluoromethyl | $Y^1$ is CH, $Y^2$ is CH, $Y^3$ is CH |
| P.0517 | $X^1$ is trifluoromethyl, $X^2$ is CH, $X^3$ is trifluoromethyl | difluoromethyl | bromo | $Y^1$ is CH, $Y^2$ is CH, $Y^3$ is CH |
| P.0518 | $X^1$ is trifluoromethyl, $X^2$ is CH, $X^3$ is trifluoromethyl | difluoromethyl | chloro | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0519 | $X^1$ is trifluoromethyl, $X^2$ is CH, $X^3$ is trifluoromethyl | difluoromethyl | cyano | $Y^1$ is CH, $Y^2$ is CH, $Y^3$ is CH |
| P.0520 | $X^1$ is trifluoromethyl, $X^2$ is CH, $X^3$ is trifluoromethyl | difluoromethyl | cyclopropyl | $Y^1$ is CH, $Y^2$ is CH, $Y^3$ is CH |
| P.0521 | $X^1$ is trifluoromethyl, $X^2$ is CH, $X^3$ is trifluoromethyl | difluoromethyl | ethyl | $Y^1$ is CH, $Y^2$ is CH, $Y^3$ is CH |
| P.0522 | $X^1$ is trifluoromethyl, $X^2$ is CH, $X^3$ is trifluoromethyl | difluoromethyl | fluoro | $Y^1$ is CH, $Y^2$ is CH, $Y^3$ is CH |
| P.0523 | $X^1$ is trifluoromethyl, $X^2$ is CH, $X^3$ is trifluoromethyl | difluoromethyl | hydrogen | $Y^1$ is CH, $Y^2$ is CH, $Y^3$ is CH |
| P.0524 | $X^1$ is trifluoromethyl, $X^2$ is CH, $X^3$ is trifluoromethyl | difluoromethyl | methoxy | $Y^1$ is CH, $Y^2$ is CH, $Y^3$ is CH |
| P.0525 | $X^1$ is trifluoromethyl, $X^2$ is CH, $X^3$ is trifluoromethyl | difluoromethyl | methyl | $Y^1$ is CH, $Y^2$ is CH, $Y^3$ is CH |
| P.0526 | $X^1$ is trifluoromethyl, $X^2$ is CH, $X^3$ is trifluoromethyl | difluoromethyl | nitro | $Y^1$ is CH, $Y^2$ is CH, $Y^3$ is CH |
| P.0527 | $X^1$ is trifluoromethyl, $X^2$ is CH, $X^3$ is trifluoromethyl | difluoromethyl | trifluoromethoxy | $Y^1$ is CH, $Y^2$ is CH, $Y^3$ is CH |
| P.0528 | $X^1$ is trifluoromethyl, $X^2$ is CH, $X^3$ is trifluoromethyl | difluoromethyl | trifluoromethyl | $Y^1$ is CH, $Y^2$ is CH, $Y^3$ is CH |
| P.0529 | $X^1$ is trifluoromethyl, $X^2$ is CH, $X^3$ is trifluoromethyl | trifluoromethyl | bromo | $Y^1$ is CH, $Y^2$ is CH, $Y^3$ is CH |
| P.0530 | $X^1$ is trifluoromethyl, $X^2$ is CH, $X^3$ is trifluoromethyl | trifluoromethyl | chloro | $Y^1$ is CH, $Y^2$ is CH, $Y^3$ is CH |
| P.0531 | $X^1$ is trifluoromethyl, $X^2$ is CH, $X^3$ is trifluoromethyl | trifluoromethyl | cyano | $Y^1$ is CH, $Y^2$ is CH, $Y^3$ is CH |
| P.0532 | $X^1$ is trifluoromethyl, $X^2$ is CH, $X^3$ is trifluoromethyl | trifluoromethyl | cyclopropyl | $Y^1$ is CH, $Y^2$ is CH, $Y^3$ is CH |
| P.0533 | $X^1$ is trifluoromethyl, $X^2$ is CH, $X^3$ is trifluoromethyl | trifluoromethyl | ethyl | $Y^1$ is CH, $Y^2$ is CH, $Y^3$ is CH |
| P.0534 | $X^1$ is trifluoromethyl, $X^2$ is CH, $X^3$ is trifluoromethyl | trifluoromethyl | fluoro | $Y^1$ is CH, $Y^2$ is CH, $Y^3$ is CH |
| P.0535 | $X^1$ is trifluoromethyl, $X^2$ is CH, $X^3$ is trifluoromethyl | trifluoromethyl | hydrogen | $Y^1$ is CH, $Y^2$ is CH, $Y^3$ is CH |
| P.0536 | $X^1$ is trifluoromethyl, $X^2$ is CH, $X^3$ is trifluoromethyl | trifluoromethyl | methoxy | $Y^1$ is CH, $Y^2$ is CH, $Y^3$ is CH |
| P.0537 | $X^1$ is trifluoromethyl, $X^2$ is CH, $X^3$ is trifluoromethyl | trifluoromethyl | methyl | $Y^1$ is CH, $Y^2$ is CH, $Y^3$ is CH |
| P.0538 | $X^1$ is trifluoromethyl, $X^2$ is CH, $X^3$ is trifluoromethyl | trifluoromethyl | nitro | $Y^1$ is CH, $Y^2$ is CH, $Y^3$ is CH |
| P.0539 | $X^1$ is trifluoromethyl, $X^2$ is CH, $X^3$ is trifluoromethyl | trifluoromethyl | trifluoromethoxy | $Y^1$ is CH, $Y^2$ is CH, $Y^3$ is CH |
| P.0540 | $X^1$ is trifluoromethyl, $X^2$ is CH, $X^3$ is trifluoromethyl | trifluoromethyl | trifluoromethyl | $Y^1$ is CH, $Y^2$ is CH, $Y^3$ is CH |
| P.0541 | $X^1$ is trifluoromethyl, $X^2$ is CH, $X^3$ is hydrogen | chlorodifluoromethyl | bromo | $Y^1$ is CH, $Y^2$ is CH, $Y^3$ is CH |
| P.0542 | $X^1$ is trifluoromethyl, $X^2$ is CH, $X^3$ is hydrogen | chlorodifluoromethyl | chloro | $Y^1$ is CH, $Y^2$ is CH, $Y^3$ is CH |
| P.0543 | $X^1$ is trifluoromethyl, $X^2$ is CH, $X^3$ is hydrogen | chlorodifluoromethyl | cyano | $Y^1$ is CH, $Y^2$ is CH, $Y^3$ is CH |
| P.0544 | $X^1$ is trifluoromethyl, $X^2$ is CH, $X^3$ is hydrogen | chlorodifluoromethyl | cyclopropyl | $Y^1$ is CH, $Y^2$ is CH, $Y^3$ is CH |
| P.0545 | $X^1$ is trifluoromethyl, $X^2$ is CH, $X^3$ is hydrogen | chlorodifluoromethyl | ethyl | $Y^1$ is CH, $Y^2$ is CH, $Y^3$ is CH |
| P.0546 | $X^1$ is trifluoromethyl, $X^2$ is CH, $X^3$ is hydrogen | chlorodifluoromethyl | fluoro | $Y^1$ is CH, $Y^2$ is CH, $Y^3$ is CH |
| P.0547 | $X^1$ is trifluoromethyl, $X^2$ is CH, $X^3$ is hydrogen | chlorodifluoromethyl | hydrogen | $Y^1$ is CH, $Y^2$ is CH, $Y^3$ is CH |
| P.0548 | $X^1$ is trifluoromethyl, $X^2$ is CH, $X^3$ is hydrogen | chlorodifluoromethyl | methoxy | $Y^1$ is CH, $Y^2$ is CH, $Y^3$ is CH |
| P.0549 | $X^1$ is trifluoromethyl, $X^2$ is CH, $X^3$ is hydrogen | chlorodifluoromethyl | methyl | $Y^1$ is CH, $Y^2$ is CH, $Y^3$ is CH |
| P.0550 | $X^1$ is trifluoromethyl, $X^2$ is CH, $X^3$ is hydrogen | chlorodifluoromethyl | nitro | $Y^1$ is CH, $Y^2$ is CH, $Y^3$ is CH |
| P.0551 | $X^1$ is trifluoromethyl, $X^2$ is CH, $X^3$ is hydrogen | chlorodifluoromethyl | trifluoromethoxy | $Y^1$ is CH, $Y^2$ is CH, $Y^3$ is CH |
| P.0552 | $X^1$ is trifluoromethyl, $X^2$ is CH, $X^3$ is hydrogen | chlorodifluoromethyl | trifluoromethyl | $Y^1$ is CH, $Y^2$ is CH, $Y^3$ is CH |
| P.0553 | $X^1$ is trifluoromethyl, $X^2$ is CH, $X^3$ is hydrogen | difluoromethyl | bromo | $Y^1$ is CH, $Y^2$ is CH, $Y^3$ is CH |
| P.0554 | $X^1$ is trifluoromethyl, $X^2$ is CH, $X^3$ is hydrogen | difluoromethyl | chloro | $Y^1$ is CH, $Y^2$ is CH, $Y^3$ is CH |
| P.0555 | $X^1$ is trifluoromethyl, $X^2$ is CH, $X^3$ is hydrogen | difluoromethyl | cyano | $Y^1$ is CH, $Y^2$ is CH, $Y^3$ is CH |
| P.0556 | $X^1$ is trifluoromethyl, $X^2$ is CH, $X^3$ is hydrogen | difluoromethyl | cyclopropyl | $Y^1$ is CH, $Y^2$ is CH, $Y^3$ is CH |
| P.0557 | $X^1$ is trifluoromethyl, $X^2$ is CH, $X^3$ is hydrogen | difluoromethyl | ethyl | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0558 | $X^1$ is trifluoromethyl, $X^2$ is CH, $X^3$ is hydrogen | difluoromethyl | fluoro | $Y^1$ is CH, $Y^2$ is CH, $Y^3$ is CH |
| P.0559 | $X^1$ is trifluoromethyl, $X^2$ is CH, $X^3$ is hydrogen | difluoromethyl | hydrogen | $Y^1$ is CH, $Y^2$ is CH, $Y^3$ is CH |
| P.0560 | $X^1$ is trifluoromethyl, $X^2$ is CH, $X^3$ is hydrogen | difluoromethyl | methoxy | $Y^1$ is CH, $Y^2$ is CH, $Y^3$ is CH |
| P.0561 | $X^1$ is trifluoromethyl, $X^2$ is CH, $X^3$ is hydrogen | difluoromethyl | methyl | $Y^1$ is CH, $Y^2$ is CH, $Y^3$ is CH |
| P.0562 | $X^1$ is trifluoromethyl, $X^2$ is CH, $X^3$ is hydrogen | difluoromethyl | nitro | $Y^1$ is CH, $Y^2$ is CH, $Y^3$ is CH |
| P.0563 | $X^1$ is trifluoromethyl, $X^2$ is CH, $X^3$ is hydrogen | difluoromethyl | trifluoromethoxy | $Y^1$ is CH, $Y^2$ is CH, $Y^3$ is CH |
| P.0564 | $X^1$ is trifluoromethyl, $X^2$ is CH, $X^3$ is hydrogen | difluoromethyl | trifluoromethyl | $Y^1$ is CH, $Y^2$ is CH, $Y^3$ is CH |
| P.0565 | $X^1$ is trifluoromethyl, $X^2$ is CH, $X^3$ is hydrogen | trifluoromethyl | bromo | $Y^1$ is CH, $Y^2$ is CH, $Y^3$ is CH |
| P.0566 | $X^1$ is trifluoromethyl, $X^2$ is CH, $X^3$ is hydrogen | trifluoromethyl | chloro | $Y^1$ is CH, $Y^2$ is CH, $Y^3$ is CH |
| P.0567 | $X^1$ is trifluoromethyl, $X^2$ is CH, $X^3$ is hydrogen | trifluoromethyl | cyano | $Y^1$ is CH, $Y^2$ is CH, $Y^3$ is CH |
| P.0568 | $X^1$ is trifluoromethyl, $X^2$ is CH, $X^3$ is hydrogen | trifluoromethyl | cyclopropyl | $Y^1$ is CH, $Y^2$ is CH, $Y^3$ is CH |
| P.0569 | $X^1$ is trifluoromethyl, $X^2$ is CH, $X^3$ is hydrogen | trifluoromethyl | ethyl | $Y^1$ is CH, $Y^2$ is CH, $Y^3$ is CH |
| P.0570 | $X^1$ is trifluoromethyl, $X^2$ is CH, $X^3$ is hydrogen | trifluoromethyl | fluoro | $Y^1$ is CH, $Y^2$ is CH, $Y^3$ is CH |
| P.0571 | $X^1$ is trifluoromethyl, $X^2$ is CH, $X^3$ is hydrogen | trifluoromethyl | hydrogen | $Y^1$ is CH, $Y^2$ is CH, $Y^3$ is CH |
| P.0572 | $X^1$ is trifluoromethyl, $X^2$ is CH, $X^3$ is hydrogen | trifluoromethyl | methoxy | $Y^1$ is CH, $Y^2$ is CH, $Y^3$ is CH |
| P.0573 | $X^1$ is trifluoromethyl, $X^2$ is CH, $X^3$ is hydrogen | trifluoromethyl | methyl | $Y^1$ is CH, $Y^2$ is CH, $Y^3$ is CH |
| P.0574 | $X^1$ is trifluoromethyl, $X^2$ is CH, $X^3$ is hydrogen | trifluoromethyl | nitro | $Y^1$ is CH, $Y^2$ is CH, $Y^3$ is CH |
| P.0575 | $X^1$ is trifluoromethyl, $X^2$ is CH, $X^3$ is hydrogen | trifluoromethyl | trifluoromethoxy | $Y^1$ is CH, $Y^2$ is CH, $Y^3$ is CH |
| P.0576 | $X^1$ is trifluoromethyl, $X^2$ is CH, $X^3$ is hydrogen | trifluoromethyl | trifluoromethyl | $Y^1$ is CH, $Y^2$ is CH, $Y^3$ is CH |
| P.0577 | $X^1$ is chloro, $X^2$ is N, $X^3$ is chloro | chlorodifluoromethyl | bromo | $Y^1$ is CH, $Y^2$ is CH, $Y^3$ is CH |
| P.0578 | $X^1$ is chloro, $X^2$ is N, $X^3$ is chloro | chlorodifluoromethyl | chloro | $Y^1$ is CH, $Y^2$ is CH, $Y^3$ is CH |
| P.0579 | $X^1$ is chloro, $X^2$ is N, $X^3$ is chloro | chlorodifluoromethyl | cyano | $Y^1$ is CH, $Y^2$ is CH, $Y^3$ is CH |
| P.0580 | $X^1$ is chloro, $X^2$ is N, $X^3$ is chloro | chlorodifluoromethyl | cyclopropyl | $Y^1$ is CH, $Y^2$ is CH, $Y^3$ is CH |
| P.0581 | $X^1$ is chloro, $X^2$ is N, $X^3$ is chloro | chlorodifluoromethyl | ethyl | $Y^1$ is CH, $Y^2$ is CH, $Y^3$ is CH |
| P.0582 | $X^1$ is chloro, $X^2$ is N, $X^3$ is chloro | chlorodifluoromethyl | fluoro | $Y^1$ is CH, $Y^2$ is CH, $Y^3$ is CH |
| P.0583 | $X^1$ is chloro, $X^2$ is N, $X^3$ is chloro | chlorodifluoromethyl | hydrogen | $Y^1$ is CH, $Y^2$ is CH, $Y^3$ is CH |
| P.0584 | $X^1$ is chloro, $X^2$ is N, $X^3$ is chloro | chlorodifluoromethyl | methoxy | $Y^1$ is CH, $Y^2$ is CH, $Y^3$ is CH |
| P.0585 | $X^1$ is chloro, $X^2$ is N, $X^3$ is chloro | chlorodifluoromethyl | methyl | $Y^1$ is CH, $Y^2$ is CH, $Y^3$ is CH |
| P.0586 | $X^1$ is chloro, $X^2$ is N, $X^3$ is chloro | chlorodifluoromethyl | nitro | $Y^1$ is CH, $Y^2$ is CH, $Y^3$ is CH |
| P.0587 | $X^1$ is chloro, $X^2$ is N, $X^3$ is chloro | chlorodifluoromethyl | trifluoromethoxy | $Y^1$ is CH, $Y^2$ is CH, $Y^3$ is CH |
| P.0588 | $X^1$ is chloro, $X^2$ is N, $X^3$ is chloro | chlorodifluoromethyl | trifluoromethyl | $Y^1$ is CH, $Y^2$ is CH, $Y^3$ is CH |
| P.0589 | $X^1$ is chloro, $X^2$ is N, $X^3$ is chloro | difluoromethyl | bromo | $Y^1$ is CH, $Y^2$ is CH, $Y^3$ is CH |
| P.0590 | $X^1$ is chloro, $X^2$ is N, $X^3$ is chloro | difluoromethyl | chloro | $Y^1$ is CH, $Y^2$ is CH, $Y^3$ is CH |
| P.0591 | $X^1$ is chloro, $X^2$ is N, $X^3$ is chloro | difluoromethyl | cyano | $Y^1$ is CH, $Y^2$ is CH, $Y^3$ is CH |
| P.0592 | $X^1$ is chloro, $X^2$ is N, $X^3$ is chloro | difluoromethyl | cyclopropyl | $Y^1$ is CH, $Y^2$ is CH, $Y^3$ is CH |
| P.0593 | $X^1$ is chloro, $X^2$ is N, $X^3$ is chloro | difluoromethyl | ethyl | $Y^1$ is CH, $Y^2$ is CH, $Y^3$ is CH |
| P.0594 | $X^1$ is chloro, $X^2$ is N, $X^3$ is chloro | difluoromethyl | fluoro | $Y^1$ is CH, $Y^2$ is CH, $Y^3$ is CH |
| P.0595 | $X^1$ is chloro, $X^2$ is N, $X^3$ is chloro | difluoromethyl | hydrogen | $Y^1$ is CH, $Y^2$ is CH, $Y^3$ is CH |
| P.0596 | $X^1$ is chloro, $X^2$ is N, $X^3$ is chloro | difluoromethyl | methoxy | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0597 | $X^1$ is chloro, $X^2$ is N, $X^3$ is chloro | difluoromethyl | methyl | $Y^1$ is CH, $Y^2$ is CH, $Y^3$ is CH |
| P.0598 | $X^1$ is chloro, $X^2$ is N, $X^3$ is chloro | difluoromethyl | nitro | $Y^1$ is CH, $Y^2$ is CH, $Y^3$ is CH |
| P.0599 | $X^1$ is chloro, $X^2$ is N, $X^3$ is chloro | difluoromethyl | trifluoromethoxy | $Y^1$ is CH, $Y^2$ is CH, $Y^3$ is CH |
| P.0600 | $X^1$ is chloro, $X^2$ is N, $X^3$ is chloro | difluoromethyl | trifluoromethyl | $Y^1$ is CH, $Y^2$ is CH, $Y^3$ is CH |
| P.0601 | $X^1$ is chloro, $X^2$ is N, $X^3$ is chloro | trifluoromethyl | bromo | $Y^1$ is CH, $Y^2$ is CH, $Y^3$ is CH |
| P.0602 | $X^1$ is chloro, $X^2$ is N, $X^3$ is chloro | trifluoromethyl | chloro | $Y^1$ is CH, $Y^2$ is CH, $Y^3$ is CH |
| P.0603 | $X^1$ is chloro, $X^2$ is N, $X^3$ is chloro | trifluoromethyl | cyano | $Y^1$ is CH, $Y^2$ is CH, $Y^3$ is CH |
| P.0604 | $X^1$ is chloro, $X^2$ is N, $X^3$ is chloro | trifluoromethyl | cyclopropyl | $Y^1$ is CH, $Y^2$ is CH, $Y^3$ is CH |
| P.0605 | $X^1$ is chloro, $X^2$ is N, $X^3$ is chloro | trifluoromethyl | ethyl | $Y^1$ is CH, $Y^2$ is CH, $Y^3$ is CH |
| P.0606 | $X^1$ is chloro, $X^2$ is N, $X^3$ is chloro | trifluoromethyl | fluoro | $Y^1$ is CH, $Y^2$ is CH, $Y^3$ is CH |
| P.0607 | $X^1$ is chloro, $X^2$ is N, $X^3$ is chloro | trifluoromethyl | hydrogen | $Y^1$ is CH, $Y^2$ is CH, $Y^3$ is CH |
| P.0608 | $X^1$ is chloro, $X^2$ is N, $X^3$ is chloro | trifluoromethyl | methoxy | $Y^1$ is CH, $Y^2$ is CH, $Y^3$ is CH |
| P.0609 | $X^1$ is chloro, $X^2$ is N, $X^3$ is chloro | trifluoromethyl | methyl | $Y^1$ is CH, $Y^2$ is CH, $Y^3$ is CH |
| P.0610 | $X^1$ is chloro, $X^2$ is N, $X^3$ is chloro | trifluoromethyl | nitro | $Y^1$ is CH, $Y^2$ is CH, $Y^3$ is CH |
| P.0611 | $X^1$ is chloro, $X^2$ is N, $X^3$ is chloro | trifluoromethyl | trifluoromethoxy | $Y^1$ is CH, $Y^2$ is CH, $Y^3$ is CH |
| P.0612 | $X^1$ is chloro, $X^2$ is N, $X^3$ is chloro | trifluoromethyl | trifluoromethyl | $Y^1$ is CH, $Y^2$ is CH, $Y^3$ is CH |
| P.0613 | $X^1$ is trifluoromethyl, $X^2$ is N, $X^3$ is trifluoromethyl | chlorodifluoromethyl | bromo | $Y^1$ is CH, $Y^2$ is CH, $Y^3$ is CH |
| P.0614 | $X^1$ is trifluoromethyl, $X^2$ is N, $X^3$ is trifluoromethyl | chlorodifluoromethyl | chloro | $Y^1$ is CH, $Y^2$ is CH, $Y^3$ is CH |
| P.0615 | $X^1$ is trifluoromethyl, $X^2$ is N, $X^3$ is trifluoromethyl | chlorodifluoromethyl | cyano | $Y^1$ is CH, $Y^2$ is CH, $Y^3$ is CH |
| P.0616 | $X^1$ is trifluoromethyl, $X^2$ is N, $X^3$ is trifluoromethyl | chlorodifluoromethyl | cyclopropyl | $Y^1$ is CH, $Y^2$ is CH, $Y^3$ is CH |
| P.0617 | $X^1$ is trifluoromethyl, $X^2$ is N, $X^3$ is trifluoromethyl | chlorodifluoromethyl | ethyl | $Y^1$ is CH, $Y^2$ is CH, $Y^3$ is CH |
| P.0618 | $X^1$ is trifluoromethyl, $X^2$ is N, $X^3$ is trifluoromethyl | chlorodifluoromethyl | fluoro | $Y^1$ is CH, $Y^2$ is CH, $Y^3$ is CH |
| P.0619 | $X^1$ is trifluoromethyl, $X^2$ is N, $X^3$ is trifluoromethyl | chlorodifluoromethyl | hydrogen | $Y^1$ is CH, $Y^2$ is CH, $Y^3$ is CH |
| P.0620 | $X^1$ is trifluoromethyl, $X^2$ is N, $X^3$ is trifluoromethyl | chlorodifluoromethyl | methoxy | $Y^1$ is CH, $Y^2$ is CH, $Y^3$ is CH |
| P.0621 | $X^1$ is trifluoromethyl, $X^2$ is N, $X^3$ is trifluoromethyl | chlorodifluoromethyl | methyl | $Y^1$ is CH, $Y^2$ is CH, $Y^3$ is CH |
| P.0622 | $X^1$ is trifluoromethyl, $X^2$ is N, $X^3$ is trifluoromethyl | chlorodifluoromethyl | nitro | $Y^1$ is CH, $Y^2$ is CH, $Y^3$ is CH |
| P.0623 | $X^1$ is trifluoromethyl, $X^2$ is N, $X^3$ is trifluoromethyl | chlorodifluoromethyl | trifluoromethoxy | $Y^1$ is CH, $Y^2$ is CH, $Y^3$ is CH |
| P.0624 | $X^1$ is trifluoromethyl, $X^2$ is N, $X^3$ is trifluoromethyl | chlorodifluoromethyl | trifluoromethyl | $Y^1$ is CH, $Y^2$ is CH, $Y^3$ is CH |
| P.0625 | $X^1$ is trifluoromethyl, $X^2$ is N, $X^3$ is trifluoromethyl | difluoromethyl | bromo | $Y^1$ is CH, $Y^2$ is CH, $Y^3$ is CH |
| P.0626 | $X^1$ is trifluoromethyl, $X^2$ is N, $X^3$ is trifluoromethyl | difluoromethyl | chloro | $Y^1$ is CH, $Y^2$ is CH, $Y^3$ is CH |
| P.0627 | $X^1$ is trifluoromethyl, $X^2$ is N, $X^3$ is trifluoromethyl | difluoromethyl | cyano | $Y^1$ is CH, $Y^2$ is CH, $Y^3$ is CH |
| P.0628 | $X^1$ is trifluoromethyl, $X^2$ is N, $X^3$ is trifluoromethyl | difluoromethyl | cyclopropyl | $Y^1$ is CH, $Y^2$ is CH, $Y^3$ is CH |
| P.0629 | $X^1$ is trifluoromethyl, $X^2$ is N, $X^3$ is trifluoromethyl | difluoromethyl | ethyl | $Y^1$ is CH, $Y^2$ is CH, $Y^3$ is CH |
| P.0630 | $X^1$ is trifluoromethyl, $X^2$ is N, $X^3$ is trifluoromethyl | difluoromethyl | fluoro | $Y^1$ is CH, $Y^2$ is CH, $Y^3$ is CH |
| P.0631 | $X^1$ is trifluoromethyl, $X^2$ is N, $X^3$ is trifluoromethyl | difluoromethyl | hydrogen | $Y^1$ is CH, $Y^2$ is CH, $Y^3$ is CH |
| P.0632 | $X^1$ is trifluoromethyl, $X^2$ is N, $X^3$ is trifluoromethyl | difluoromethyl | methoxy | $Y^1$ is CH, $Y^2$ is CH, $Y^3$ is CH |
| P.0633 | $X^1$ is trifluoromethyl, $X^2$ is N, $X^3$ is trifluoromethyl | difluoromethyl | methyl | $Y^1$ is CH, $Y^2$ is CH, $Y^3$ is CH |
| P.0634 | $X^1$ is trifluoromethyl, $X^2$ is N, $X^3$ is trifluoromethyl | difluoromethyl | nitro | $Y^1$ is CH, $Y^2$ is CH, $Y^3$ is CH |
| P.0635 | $X^1$ is trifluoromethyl, $X^2$ is N, $X^3$ is trifluoromethyl | difluoromethyl | trifluoromethoxy | $Y^1$ is CH, $Y^2$ is CH, $Y^3$ is CH |

TABLE P-continued

| | X1, X2, X3 | X4 | R5 | Y1, Y2, Y3 |
|---|---|---|---|---|
| P.0636 | $X^1$ is trifluoromethyl, $X^2$ is N, $X^3$ is trifluoromethyl | difluoromethyl | trifluoromethyl | $Y^1$ is CH, $Y^2$ is CH, $Y^3$ is CH |
| P.0637 | $X^1$ is trifluoromethyl, $X^2$ is N, $X^3$ is trifluoromethyl | trifluoromethyl | bromo | $Y^1$ is CH, $Y^2$ is CH, $Y^3$ is CH |
| P.0638 | $X^1$ is trifluoromethyl, $X^2$ is N, $X^3$ is trifluoromethyl | trifluoromethyl | chloro | $Y^1$ is CH, $Y^2$ is CH, $Y^3$ is CH |
| P.0639 | $X^1$ is trifluoromethyl, $X^2$ is N, $X^3$ is trifluoromethyl | trifluoromethyl | cyano | $Y^1$ is CH, $Y^2$ is CH, $Y^3$ is CH |
| P.0640 | $X^1$ is trifluoromethyl, $X^2$ is N, $X^3$ is trifluoromethyl | trifluoromethyl | cyclopropyl | $Y^1$ is CH, $Y^2$ is CH, $Y^3$ is CH |
| P.0641 | $X^1$ is trifluoromethyl, $X^2$ is N, $X^3$ is trifluoromethyl | trifluoromethyl | ethyl | $Y^1$ is CH, $Y^2$ is CH, $Y^3$ is CH |
| P.0642 | $X^1$ is trifluoromethyl, $X^2$ is N, $X^3$ is trifluoromethyl | trifluoromethyl | fluoro | $Y^1$ is CH, $Y^2$ is CH, $Y^3$ is CH |
| P.0643 | $X^1$ is trifluoromethyl, $X^2$ is N, $X^3$ is trifluoromethyl | trifluoromethyl | hydrogen | $Y^1$ is CH, $Y^2$ is CH, $Y^3$ is CH |
| P.0644 | $X^1$ is trifluoromethyl, $X^2$ is N, $X^3$ is trifluoromethyl | trifluoromethyl | methoxy | $Y^1$ is CH, $Y^2$ is CH, $Y^3$ is CH |
| P.0645 | $X^1$ is trifluoromethyl, $X^2$ is N, $X^3$ is trifluoromethyl | trifluoromethyl | methyl | $Y^1$ is CH, $Y^2$ is CH, $Y^3$ is CH |
| P.0646 | $X^1$ is trifluoromethyl, $X^2$ is N, $X^3$ is trifluoromethyl | trifluoromethyl | nitro | $Y^1$ is CH, $Y^2$ is CH, $Y^3$ is CH |
| P.0647 | $X^1$ is trifluoromethyl, $X^2$ is N, $X^3$ is trifluoromethyl | trifluoromethyl | trifluoromethoxy | $Y^1$ is CH, $Y^2$ is CH, $Y^3$ is CH |
| P.0648 | $X^1$ is trifluoromethyl, $X^2$ is N, $X^3$ is trifluoromethyl | trifluoromethyl | trifluoromethyl | $Y^1$ is CH, $Y^2$ is CH, $Y^3$ is CH |

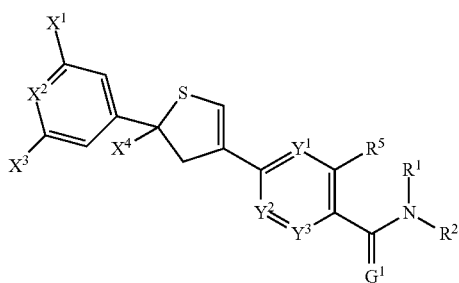

(I-A)

Table 1P:
Table 1P provides 648 compounds of formula (I-A) wherein $G^1$ is oxygen, $R^1$ is hydrogen, $R^2$ is G.001, $X^1$, $X^2$, $X^3$, $Y^1$, $Y^2$, $Y^3$, $X^4$ and $R^5$ have the values listed in the table P.

Table 2P:
Table 2P provides 648 compounds of formula (I-A) wherein $G^1$ is oxygen, $R^1$ is hydrogen, $R^2$ is G.002, $X^1$, $X^2$, $X^3$, $Y^1$, $Y^2$, $Y^3$, $X^4$ and $R^5$ have the values listed in the table P.

Table 3P:
Table 3P provides 648 compounds of formula (I-A) wherein $G^1$ is oxygen, $R^1$ is hydrogen, $R^2$ is G.003, $X^1$, $X^2$, $X^3$, $Y^1$, $Y^2$, $Y^3$, $X^4$ and $R^5$ have the values listed in the table P.

Table 4P:
Table 4P provides 648 compounds of formula (I-A) wherein $G^1$ is oxygen, $R^1$ is hydrogen, $R^2$ is G.004, $X^1$, $X^2$, $X^3$, $Y^1$, $Y^2$, $Y^3$, $X^4$ and $R^5$ have the values listed in the table P.

Table 5P:
Table 5P provides 648 compounds of formula (I-A) wherein $G^1$ is oxygen, $R^1$ is hydrogen, $R^2$ is G.005, $X^1$, $X^2$, $X^3$, $Y^1$, $Y^2$, $Y^3$, $X^4$ and $R^5$ have the values listed in the table P.

Table 6P:
Table 6P provides 648 compounds of formula (I-A) wherein $G^1$ is oxygen, $R^1$ is hydrogen, $R^2$ is G.006, $X^1$, $X^2$, $X^3$, $Y^1$, $Y^2$, $Y^3$, $X^4$ and $R^5$ have the values listed in the table P.

Table 7P:
Table 7P provides 648 compounds of formula (I-A) wherein $G^1$ is oxygen, $R^1$ is hydrogen, $R^2$ is G.007, $X^1$, $X^2$, $X^3$, $Y^1$, $Y^2$, $Y^3$, $X^4$ and $R^5$ have the values listed in the table P.

Table 8P:
Table 8P provides 648 compounds of formula (I-A) wherein $G^1$ is oxygen, $R^1$ is hydrogen, $R^2$ is G.008, $X^1$, $X^2$, $X^3$, $Y^1$, $Y^2$, $Y^3$, $X^4$ and $R^5$ have the values listed in the table P.

Table 9P:
Table 9P provides 648 compounds of formula (I-A) wherein $G^1$ is oxygen, $R^1$ is hydrogen, $R^2$ is G.009, $X^1$, $X^2$, $X^3$, $Y^1$, $Y^2$, $Y^3$, $X^4$ and $R^5$ have the values listed in the table P.

Table 10P:
Table 10P provides 648 compounds of formula (I-A) wherein $G^1$ is oxygen, $R^1$ is hydrogen, $R^2$ is G.010, $X^1$, $X^2$, $X^3$, $Y^1$, $Y^2$, $Y^3$, $X^4$ and $R^5$ have the values listed in the table P.

Table 11P:
Table 11P provides 648 compounds of formula (I-A) wherein $G^1$ is oxygen, $R^1$ is hydrogen, $R^2$ is G.011, $X^1$, $X^2$, $X^3$, $Y^1$, $Y^2$, $Y^3$, $X^4$ and $R^5$ have the values listed in the table P.

Table 12P:
Table 12P provides 648 compounds of formula (I-A) wherein $G^1$ is oxygen, $R^1$ is hydrogen, $R^2$ is G.012, $X^1$, $X^2$, $X^3$, $Y^1$, $Y^2$, $Y^3$, $X^4$ and $R^5$ have the values listed in the table P.

Table 13P:
Table 13P provides 648 compounds of formula (I-A) wherein $G^1$ is oxygen, $R^1$ is hydrogen, $R^2$ is G.013, $X^1$, $X^2$, $X^3$, $Y^1$, $Y^2$, $Y^3$, $X^4$ and $R^5$ have the values listed in the table P.

Table 14P:
Table 14P provides 648 compounds of formula (I-A) wherein $G^1$ is oxygen, $R^1$ is hydrogen, $R^2$ is G.014, $X^1$, $X^2$, $X^3$, $Y^1$, $Y^2$, $Y^3$, $X^4$ and $R^5$ have the values listed in the table P.

Table 15P:
Table 15P provides 648 compounds of formula (I-A) wherein $G^1$ is oxygen, $R^1$ is hydrogen, $R^2$ is G.015, $X^1$, $X^2$, $X^3$, $Y^1$, $Y^2$, $Y^3$, $X^4$ and $R^5$ have the values listed in the table P.

Table 16P:
Table 16P provides 648 compounds of formula (I-A) wherein $G^1$ is oxygen, $R^1$ is hydrogen, $R^2$ is G.016, $X^1$, $X^2$, $X^3$, $Y^1$, $Y^2$, $Y^3$, $X^4$ and $R^5$ have the values listed in the table P.

Table 17P:
Table 17P provides 648 compounds of formula (I-A) wherein $G^1$ is oxygen, $R^1$ is hydrogen, $R^2$ is G.017, $X^1$, $X^2$, $X^3$, $Y^1$, $Y^2$, $Y^3$, $X^4$ and $R^5$ have the values listed in the table P.

Table 18P:
Table 18P provides 648 compounds of formula (I-A) wherein $G^1$ is oxygen, $R^1$ is hydrogen, $R^2$ is G.018, $X^1$, $X^2$, $X^3$, $Y^1$, $Y^2$, $Y^3$, $X^4$ and $R^5$ have the values listed in the table P.

Table 19P:
Table 19P provides 648 compounds of formula (I-A) wherein $G^1$ is oxygen, $R^1$ is hydrogen, $R^2$ is G.019, $X^1$, $X^2$, $X^3$, $Y^1$, $Y^2$, $Y^3$, $X^4$ and $R^5$ have the values listed in the table P.

Table 20P:
Table 20P provides 648 compounds of formula (I-A) wherein $G^1$ is oxygen, $R^1$ is hydrogen, $R^2$ is G.020, $X^1$, $X^2$, $X^3$, $Y^1$, $Y^2$, $Y^3$, $X^4$ and $R^5$ have the values listed in the table P.

Table 21P:
Table 21P provides 648 compounds of formula (I-A) wherein $G^1$ is oxygen, $R^1$ is hydrogen, $R^2$ is G.021, $X^1$, $X^2$, $X^3$, $Y^1$, $Y^2$, $Y^3$, $X^4$ and $R^5$ have the values listed in the table P.

Table 22P:
Table 22P provides 648 compounds of formula (I-A) wherein $G^1$ is oxygen, $R^1$ is hydrogen, $R^2$ is G.022, $X^1$, $X^2$, $X^3$, $Y^1$, $Y^2$, $Y^3$, $X^4$ and $R^5$ have the values listed in the table P.

Table 23P:
Table 23P provides 648 compounds of formula (I-A) wherein $G^1$ is oxygen, $R^1$ is hydrogen, $R^2$ is G.023, $X^1$, $X^2$, $X^3$, $Y^1$, $Y^2$, $Y^3$, $X^4$ and $R^5$ have the values listed in the table P.

Table 24P:
Table 24P provides 648 compounds of formula (I-A) wherein $G^1$ is oxygen, $R^1$ is hydrogen, $R^2$ is G.024, $X^1$, $X^2$, $X^3$, $Y^1$, $Y^2$, $Y^3$, $X^4$ and $R^5$ have the values listed in the table P.

Table 25P:
Table 25P provides 648 compounds of formula (I-A) wherein $G^1$ is oxygen, $R^1$ is hydrogen, $R^2$ is G.025, $X^1$, $X^2$, $X^3$, $Y^1$, $Y^2$, $Y^3$, $X^4$ and $R^5$ have the values listed in the table P.

Table 26P:
Table 26P provides 648 compounds of formula (I-A) wherein $G^1$ is oxygen, $R^1$ is hydrogen, $R^2$ is G.026, $X^1$, $X^2$, $X^3$, $Y^1$, $Y^2$, $Y^3$, $X^4$ and $R^5$ have the values listed in the table P.

Table 27P:
Table 27P provides 648 compounds of formula (I-A) wherein $G^1$ is oxygen, $R^1$ is hydrogen, $R^2$ is G.027, $X^1$, $X^2$, $X^3$, $Y^1$, $Y^2$, $Y^3$, $X^4$ and $R^5$ have the values listed in the table P.

Table 28P:
Table 28P provides 648 compounds of formula (I-A) wherein $G^1$ is oxygen, $R^1$ is hydrogen, $R^2$ is G.028, $X^1$, $X^2$, $X^3$, $Y^1$, $Y^2$, $Y^3$, $X^4$ and $R^5$ have the values listed in the table P.

Table 29P:
Table 29P provides 648 compounds of formula (I-A) wherein $G^1$ is oxygen, $R^1$ is hydrogen, $R^2$ is G.029, $X^1$, $X^2$, $X^3$, $Y^1$, $Y^2$, $Y^3$, $X^4$ and $R^5$ have the values listed in the table P.

Table 30P:
Table 30P provides 648 compounds of formula (I-A) wherein $G^1$ is oxygen, $R^1$ is hydrogen, $R^2$ is G.030, $X^1$, $X^2$, $X^3$, $Y^1$, $Y^2$, $Y^3$, $X^4$ and $R^5$ have the values listed in the table P.

Table 31P:
Table 31P provides 648 compounds of formula (I-A) wherein $G^1$ is oxygen, $R^1$ is hydrogen, $R^2$ is G.031, $X^1$, $X^2$, $X^3$, $Y^1$, $Y^2$, $Y^3$, $X^4$ and $R^5$ have the values listed in the table P.

Table 32P:
Table 32P provides 648 compounds of formula (I-A) wherein $G^1$ is oxygen, $R^1$ is hydrogen, $R^2$ is G.032, $X^1$, $X^2$, $X^3$, $Y^1$, $Y^2$, $Y^3$, $X^4$ and $R^5$ have the values listed in the table P.

Table 33P:
Table 33P provides 648 compounds of formula (I-A) wherein $G^1$ is oxygen, $R^1$ is hydrogen, $R^2$ is G.033, $X^1$, $X^2$, $X^3$, $Y^1$, $Y^2$, $Y^3$, $X^4$ and $R^5$ have the values listed in the table P.

Table 34P:
Table 34P provides 648 compounds of formula (I-A) wherein $G^1$ is oxygen, $R^1$ is hydrogen, $R^2$ is G.034, $X^1$, $X^2$, $X^3$, $Y^1$, $Y^2$, $Y^3$, $X^4$ and $R^5$ have the values listed in the table P.

Table 35P:
Table 35P provides 648 compounds of formula (I-A) wherein $G^1$ is oxygen, $R^1$ is hydrogen, $R^2$ is G.035, $X^1$, $X^2$, $X^3$, $Y^1$, $Y^2$, $Y^3$, $X^4$ and $R^5$ have the values listed in the table P.

Table 36P:
Table 36P provides 648 compounds of formula (I-A) wherein $G^1$ is oxygen, $R^1$ is hydrogen, $R^2$ is G.036, $X^1$, $X^2$, $X^3$, $Y^1$, $Y^2$, $Y^3$, $X^4$ and $R^5$ have the values listed in the table P.

Table 37P:
Table 37P provides 648 compounds of formula (I-A) wherein $G^1$ is oxygen, $R^1$ is hydrogen, $R^2$ is G.037, $X^1$, $X^2$, $X^3$, $Y^1$, $Y^2$, $Y^3$, $X^4$ and $R^5$ have the values listed in the table P.

Table 38P:
Table 38P provides 648 compounds of formula (I-A) wherein $G^1$ is oxygen, $R^1$ is hydrogen, $R^2$ is G.038, $X^1$, $X^2$, $X^3$, $Y^1$, $Y^2$, $Y^3$, $X^4$ and $R^5$ have the values listed in the table P.

Table 39P:
Table 39P provides 648 compounds of formula (I-A) wherein $G^1$ is oxygen, $R^1$ is hydrogen, $R^2$ is G.039, $X^1$, $X^2$, $X^3$, $Y^1$, $Y^2$, $Y^3$, $X^4$ and $R^5$ have the values listed in the table P.

Table 40P:
Table 40P provides 648 compounds of formula (I-A) wherein $G^1$ is oxygen, $R^1$ is hydrogen, $R^2$ is G.040, $X^1$, $X^2$, $X^3$, $Y^1$, $Y^2$, $Y^3$, $X^4$ and $R^5$ have the values listed in the table P.

Table 41P:
Table 41P provides 648 compounds of formula (I-A) wherein $G^1$ is oxygen, $R^1$ is hydrogen, $R^2$ is G.041, $X^1$, $X^2$, $X^3$, $Y^1$, $Y^2$, $Y^3$, $X^4$ and $R^5$ have the values listed in the table P.

Table 42P:
Table 42P provides 648 compounds of formula (I-A) wherein $G^1$ is oxygen, $R^1$ is hydrogen, $R^2$ is G.042, $X^1$, $X^2$, $X^3$, $Y^1$, $Y^2$, $Y^3$, $X^4$ and $R^5$ have the values listed in the table P.

Table 43P:
Table 43P provides 648 compounds of formula (I-A) wherein $G^1$ is oxygen, $R^1$ is hydrogen, $R^2$ is G.043, $X^1$, $X^2$, $X^3$, $Y^1$, $Y^2$, $Y^3$, $X^4$ and $R^5$ have the values listed in the table P.

Table 44P:
Table 44P provides 648 compounds of formula (I-A) wherein $G^1$ is oxygen, $R^1$ is hydrogen, $R^2$ is G.044, $X^1$, $X^2$, $X^3$, $Y^1$, $Y^2$, $Y^3$, $X^4$ and $R^5$ have the values listed in the table P.

Table 45P:
Table 45P provides 648 compounds of formula (I-A) wherein $G^1$ is oxygen, $R^1$ is hydrogen, $R^2$ is G.045, $X^1$, $X^2$, $X^3$, $Y^1$, $Y^2$, $Y^3$, $X^4$ and $R^5$ have the values listed in the table P.

Table 46P:
Table 46P provides 648 compounds of formula (I-A) wherein $G^1$ is oxygen, $R^1$ is hydrogen, $R^2$ is G.046, $X^1$, $X^2$, $X^3$, $Y^1$, $Y^2$, $Y^3$, $X^4$ and $R^5$ have the values listed in the table P.

Table 47P:
Table 47P provides 648 compounds of formula (I-A) wherein $G^1$ is oxygen, $R^1$ is hydrogen, $R^2$ is G.047, $X^1$, $X^2$, $X^3$, $Y^1$, $Y^2$, $Y^3$, $X^4$ and $R^5$ have the values listed in the table P.

Table 48P:
Table 48P provides 648 compounds of formula (I-A) wherein $G^1$ is oxygen, $R^1$ is hydrogen, $R^2$ is G.048, $X^1$, $X^2$, $X^3$, $Y^1$, $Y^2$, $Y^3$, $X^4$ and $R^5$ have the values listed in the table P.

Table 49P:
Table 49P provides 648 compounds of formula (I-A) wherein $G^1$ is oxygen, $R^1$ is hydrogen, $R^2$ is G.049, $X^1$, $X^2$, $X^3$, $Y^1$, $Y^2$, $Y^3$, $X^4$ and $R^5$ have the values listed in the table P.

Table 50P:
Table 50P provides 648 compounds of formula (I-A) wherein $G^1$ is oxygen, $R^1$ is hydrogen, $R^2$ is G.050, $X^1$, $X^2$, $X^3$, $Y^1$, $Y^2$, $Y^3$, $X^4$ and $R^5$ have the values listed in the table P.

Table 51P:
Table 51P provides 648 compounds of formula (I-A) wherein $G^1$ is oxygen, $R^1$ is hydrogen, $R^2$ is G.051, $X^1$, $X^2$, $X^3$, $Y^1$, $Y^2$, $Y^3$, $X^4$ and $R^5$ have the values listed in the table P.

Table 52P:
Table 52P provides 648 compounds of formula (I-A) wherein $G^1$ is oxygen, $R^1$ is hydrogen, $R^2$ is G.052, $X^1$, $X^2$, $X^3$, $Y^1$, $Y^2$, $Y^3$, $X^4$ and $R^5$ have the values listed in the table P.

Table 53P:
Table 53P provides 648 compounds of formula (I-A) wherein $G^1$ is oxygen, $R^1$ is hydrogen, $R^2$ is G.053, $X^1$, $X^2$, $X^3$, $Y^1$, $Y^2$, $Y^3$, $X^4$ and $R^5$ have the values listed in the table P.

Table 54P:
Table 54P provides 648 compounds of formula (I-A) wherein $G^1$ is oxygen, $R^1$ is hydrogen, $R^2$ is G.054, $X^1$, $X^2$, $X^3$, $Y^1$, $Y^2$, $Y^3$, $X^4$ and $R^5$ have the values listed in the table P.

Table 55P:
Table 55P provides 648 compounds of formula (I-A) wherein $G^1$ is oxygen, $R^1$ is hydrogen, $R^2$ is G.055, $X^1$, $X^2$, $X^3$, $Y^1$, $Y^2$, $Y^3$, $X^4$ and $R^5$ have the values listed in the table P.

Table 56P:
Table 56P provides 648 compounds of formula (I-A) wherein $G^1$ is oxygen, $R^1$ is hydrogen, $R^2$ is G.056, $X^1$, $X^2$, $X^3$, $Y^1$, $Y^2$, $Y^3$, $X^4$ and $R^5$ have the values listed in the table P.

Table 57P:
Table 57P provides 648 compounds of formula (I-A) wherein $G^1$ is oxygen, $R^1$ is hydrogen, $R^2$ is G.057, $X^1$, $X^2$, $X^3$, $Y^1$, $Y^2$, $Y^3$, $X^4$ and $R^5$ have the values listed in the table P.

Table 58P:
Table 58P provides 648 compounds of formula (I-A) wherein $G^1$ is oxygen, $R^1$ is hydrogen, $R^2$ is G.058, $X^1$, $X^2$, $X^3$, $Y^1$, $Y^2$, $Y^3$, $X^4$ and $R^5$ have the values listed in the table P.

Table 59P:
Table 59P provides 648 compounds of formula (I-A) wherein $G^1$ is oxygen, $R^1$ is hydrogen, $R^2$ is G.059, $X^1$, $X^2$, $X^3$, $Y^1$, $Y^2$, $Y^3$, $X^4$ and $R^5$ have the values listed in the table P.

Table 60P:
Table 60P provides 648 compounds of formula (I-A) wherein $G^1$ is oxygen, $R^1$ is hydrogen, $R^2$ is G.060, $X^1$, $X^2$, $X^3$, $Y^1$, $Y^2$, $Y^3$, $X^4$ and $R^5$ have the values listed in the table P.

Table 61P:
Table 61P provides 648 compounds of formula (I-A) wherein $G^1$ is oxygen, $R^1$ is hydrogen, $R^2$ is G.061, $X^1$, $X^2$, $X^3$, $Y^1$, $Y^2$, $Y^3$, $X^4$ and $R^5$ have the values listed in the table P.

Table 62P:
Table 62P provides 648 compounds of formula (I-A) wherein $G^1$ is oxygen, $R^1$ is hydrogen, $R^2$ is G.062, $X^1$, $X^2$, $X^3$, $Y^1$, $Y^2$, $Y^3$, $X^4$ and $R^5$ have the values listed in the table P.

Table 63P:
Table 63P provides 648 compounds of formula (I-A) wherein $G^1$ is oxygen, $R^1$ is hydrogen, $R^2$ is G.063, $X^1$, $X^2$, $X^3$, $Y^1$, $Y^2$, $Y^3$, $X^4$ and $R^5$ have the values listed in the table P.

Table 64P:
Table 64P provides 648 compounds of formula (I-A) wherein $G^1$ is oxygen, $R^1$ is hydrogen, $R^2$ is G.064, $X^1$, $X^2$, $X^3$, $Y^1$, $Y^2$, $Y^3$, $X^4$ and $R^5$ have the values listed in the table P.

Table 65P:
Table 65P provides 648 compounds of formula (I-A) wherein $G^1$ is oxygen, $R^1$ is hydrogen, $R^2$ is G.065, $X^1$, $X^2$, $X^3$, $Y^1$, $Y^2$, $Y^3$, $X^4$ and $R^5$ have the values listed in the table P.

Table 66P:
Table 66P provides 648 compounds of formula (I-A) wherein $G^1$ is oxygen, $R^1$ is hydrogen, $R^2$ is G.066, $X^1$, $X^2$, $X^3$, $Y^1$, $Y^2$, $Y^3$, $X^4$ and $R^5$ have the values listed in the table P.

Table 67P:
Table 67P provides 648 compounds of formula (I-A) wherein $G^1$ is oxygen, $R^1$ is hydrogen, $R^2$ is G.067, $X^1$, $X^2$, $X^3$, $Y^1$, $Y^2$, $Y^3$, $X^4$ and $R^5$ have the values listed in the table P.

Table 68P:
Table 68P provides 648 compounds of formula (I-A) wherein $G^1$ is oxygen, $R^1$ is hydrogen, $R^2$ is G.068, $X^1$, $X^2$, $X^3$, $Y^1$, $Y^2$, $Y^3$, $X^4$ and $R^5$ have the values listed in the table P.

Table 69P:
Table 69P provides 648 compounds of formula (I-A) wherein $G^1$ is oxygen, $R^1$ is hydrogen, $R^2$ is G.069, $X^1$, $X^2$, $X^3$, $Y^1$, $Y^2$, $Y^3$, $X^4$ and $R^5$ have the values listed in the table P.

Table 70P:
Table 70P provides 648 compounds of formula (I-A) wherein $G^1$ is oxygen, $R^1$ is hydrogen, $R^2$ is G.070, $X^1$, $X^2$, $X^3$, $Y^1$, $Y^2$, $Y^3$, $X^4$ and $R^5$ have the values listed in the table P.

Table 71P:
Table 71P provides 648 compounds of formula (I-A) wherein $G^1$ is oxygen, $R^1$ is hydrogen, $R^2$ is G.071, $X^1$, $X^2$, $X^3$, $Y^1$, $Y^2$, $Y^3$, $X^4$ and $R^5$ have the values listed in the table P.

Table 72P:
Table 72P provides 648 compounds of formula (I-A) wherein $G^1$ is oxygen, $R^1$ is hydrogen, $R^2$ is G.072, $X^1$, $X^2$, $X^3$, $Y^1$, $Y^2$, $Y^3$, $X^4$ and $R^5$ have the values listed in the table P.

Table 73P:
Table 73P provides 648 compounds of formula (I-A) wherein $G^1$ is oxygen, $R^1$ is hydrogen, $R^2$ is G.073, $X^1$, $X^2$, $X^3$, $Y^1$, $Y^2$, $Y^3$, $X^4$ and $R^5$ have the values listed in the table P.

Table 74P:
Table 74P provides 648 compounds of formula (I-A) wherein $G^1$ is oxygen, $R^1$ is hydrogen, $R^2$ is G.074, $X^1$, $X^2$, $X^3$, $Y^1$, $Y^2$, $Y^3$, $X^4$ and $R^5$ have the values listed in the table P.

Table 75P:
Table 75P provides 648 compounds of formula (I-A) wherein $G^1$ is oxygen, $R^1$ is hydrogen, $R^2$ is G.075, $X^1$, $X^2$, $X^3$, $Y^1$, $Y^2$, $Y^3$, $X^4$ and $R^5$ have the values listed in the table P.

Table 76P:
Table 76P provides 648 compounds of formula (I-A) wherein $G^1$ is oxygen, $R^1$ is hydrogen, $R^2$ is G.076, $X^1$, $X^2$, $X^3$, $Y^1$, $Y^2$, $Y^3$, $X^4$ and $R^5$ have the values listed in the table P.

Table 77P:
Table 77P provides 648 compounds of formula (I-A) wherein $G^1$ is oxygen, $R^1$ is hydrogen, $R^2$ is G.077, $X^1$, $X^2$, $X^3$, $Y^1$, $Y^2$, $Y^3$, $X^4$ and $R^5$ have the values listed in the table P.

Table 78P:
Table 78P provides 648 compounds of formula (I-A) wherein $G^1$ is oxygen, $R^1$ is hydrogen, $R^2$ is G.078, $X^1$, $X^2$, $X^3$, $Y^1$, $Y^2$, $Y^3$, $X^4$ and $R^5$ have the values listed in the table P.

Table 79P:
Table 79P provides 648 compounds of formula (I-A) wherein $G^1$ is oxygen, $R^1$ is hydrogen, $R^2$ is G.079, $X^1$, $X^2$, $X^3$, $Y^1$, $Y^2$, $Y^3$, $X^4$ and $R^5$ have the values listed in the table P.

Table 80P:
Table 80P provides 648 compounds of formula (I-A) wherein $G^1$ is oxygen, $R^1$ is hydrogen, $R^2$ is G.080, $X^1$, $X^2$, $X^3$, $Y^1$, $Y^2$, $Y^3$, $X^4$ and $R^5$ have the values listed in the table P.

Table 81P:
Table 81P provides 648 compounds of formula (I-A) wherein $G^1$ is oxygen, $R^1$ is hydrogen, $R^2$ is G.081, $X^1$, $X^2$, $X^3$, $Y^1$, $Y^2$, $Y^3$, $X^4$ and $R^5$ have the values listed in the table P.

Table 82P:
Table 82P provides 648 compounds of formula (I-A) wherein $G^1$ is oxygen, $R^1$ is hydrogen, $R^2$ is G.082, $X^1$, $X^2$, $X^3$, $Y^1$, $Y^2$, $Y^3$, $X^4$ and $R^5$ have the values listed in the table P.

Table 83P:
Table 83P provides 648 compounds of formula (I-A) wherein $G^1$ is oxygen, $R^1$ is hydrogen, $R^2$ is G.083, $X^1$, $X^2$, $X^3$, $Y^1$, $Y^2$, $Y^3$, $X^4$ and $R^5$ have the values listed in the table P.

Table 84P:
Table 84P provides 648 compounds of formula (I-A) wherein $G^1$ is oxygen, $R^1$ is hydrogen, $R^2$ is G.084, $X^1$, $X^2$, $X^3$, $Y^1$, $Y^2$, $Y^3$, $X^4$ and $R^5$ have the values listed in the table P.

Table 85P:
Table 85P provides 648 compounds of formula (I-A) wherein $G^1$ is oxygen, $R^1$ is hydrogen, $R^2$ is G.085, $X^1$, $X^2$, $X^3$, $Y^1$, $Y^2$, $Y^3$, $X^4$ and $R^5$ have the values listed in the table P.

Table 86P:
Table 86P provides 648 compounds of formula (I-A) wherein $G^1$ is oxygen, $R^1$ is hydrogen, $R^2$ is G.086, $X^1$, $X^2$, $X^3$, $Y^1$, $Y^2$, $Y^3$, $X^4$ and $R^5$ have the values listed in the table P.

Table 87P:
Table 87P provides 648 compounds of formula (I-A) wherein $G^1$ is oxygen, $R^1$ is hydrogen, $R^2$ is G.087, $X^1$, $X^2$, $X^3$, $Y^1$, $Y^2$, $Y^3$, $X^4$ and $R^5$ have the values listed in the table P.

Table 88P:
Table 88P provides 648 compounds of formula (I-A) wherein $G^1$ is oxygen, $R^1$ is hydrogen, $R^2$ is G.088, $X^1$, $X^2$, $X^3$, $Y^1$, $Y^2$, $Y^3$, $X^4$ and $R^5$ have the values listed in the table P.

Table 89P:
Table 89P provides 648 compounds of formula (I-A) wherein $G^1$ is oxygen, $R^1$ is hydrogen, $R^2$ is G.089, $X^1$, $X^2$, $X^3$, $Y^1$, $Y^2$, $Y^3$, $X^4$ and $R^5$ have the values listed in the table P.

Table 90P:
Table 90P provides 648 compounds of formula (I-A) wherein $G^1$ is oxygen, $R^1$ is hydrogen, $R^2$ is G.090, $X^1$, $X^2$, $X^3$, $Y^1$, $Y^2$, $Y^3$, $X^4$ and $R^5$ have the values listed in the table P.

Table 91P
Table 91P provides 648 compounds of formula (I-A) wherein $G^1$ is oxygen, $R^1$ is hydrogen, $R^2$ is G.091, $X^1$, $X^2$, $X^3$, $Y^1$, $Y^2$, $Y^3$, $X^4$ and $R^5$ have the values listed in the table P.

Table 92P
Table 92P provides 648 compounds of formula (I-A) wherein $G^1$ is oxygen, $R^1$ is hydrogen, $R^2$ is G.092, $X^1$, $X^2$, $X^3$, $Y^1$, $Y^2$, $Y^3$, $X^4$ and $R^5$ have the values listed in the table P.

Table 93P
Table 93P provides 648 compounds of formula (I-A) wherein $G^1$ is oxygen, $R^1$ is hydrogen, $R^2$ is G.093, $X^1$, $X^2$, $X^3$, $Y^1$, $Y^2$, $Y^3$, $X^4$ and $R^5$ have the values listed in the table P.

Table 94P
Table 94P provides 648 compounds of formula (I-A) wherein $G^1$ is oxygen, $R^1$ is hydrogen, $R^2$ is G.094, $X^1$, $X^2$, $X^3$, $Y^1$, $Y^2$, $Y^3$, $X^4$ and $R^5$ have the values listed in the table P.

Table 95P
Table 95P provides 648 compounds of formula (I-A) wherein $G^1$ is oxygen, $R^1$ is hydrogen, $R^2$ is G.095, $X^1$, $X^2$, $X^3$, $Y^1$, $Y^2$, $Y^3$, $X^4$ and $R^5$ have the values listed in the table P.

Table 96P
Table 96P provides 648 compounds of formula (I-A) wherein $G^1$ is oxygen, $R^1$ is hydrogen, $R^2$ is G.096, $X^1$, $X^2$, $X^3$, $Y^1$, $Y^2$, $Y^3$, $X^4$ and $R^5$ have the values listed in the table P.

Table 97P
Table 97P provides 648 compounds of formula (I-A) wherein $G^1$ is oxygen, $R^1$ is hydrogen, $R^2$ is G.097, $X^1$, $X^2$, $X^3$, $Y^1$, $Y^2$, $Y^3$, $X^4$ and $R^5$ have the values listed in the table P.

Table 98P
Table 98P provides 648 compounds of formula (I-A) wherein $G^1$ is oxygen, $R^1$ is hydrogen, $R^2$ is G.098, $X^1$, $X^2$, $X^3$, $Y^1$, $Y^2$, $Y^3$, $X^4$ and $R^5$ have the values listed in the table P.

Table 99P
Table 99P provides 648 compounds of formula (I-A) wherein $G^1$ is oxygen, $R^1$ is hydrogen, $R^2$ is G.099, $X^1$, $X^2$, $X^3$, $Y^1$, $Y^2$, $Y^3$, $X^4$ and $R^5$ have the values listed in the table P.

Table 100P
Table 100P provides 648 compounds of formula (I-A) wherein $G^1$ is oxygen, $R^1$ is hydrogen, $R^2$ is G.100, $X^1$, $X^2$, $X^3$, $Y^1$, $Y^2$, $Y^3$, $X^4$ and $R^5$ have the values listed in the table P.

Table 101P
Table 101P provides 648 compounds of formula (I-A) wherein $G^1$ is oxygen, $R^1$ is hydrogen, $R^2$ is G.101, $X^1$, $X^2$, $X^3$, $Y^1$, $Y^2$, $Y^3$, $X^4$ and $R^5$ have the values listed in the table P.

Table 102P
Table 102P provides 648 compounds of formula (I-A) wherein $G^1$ is oxygen, $R^1$ is hydrogen, $R^2$ is G.102, $X^1$, $X^2$, $X^3$, $Y^1$, $Y^2$, $Y^3$, $X^4$ and $R^5$ have the values listed in the table P.

Table 103P
Table 103P provides 648 compounds of formula (I-A) wherein $G^1$ is oxygen, $R^1$ is hydrogen, $R^2$ is G.103, $X^1$, $X^2$, $X^3$, $Y^1$, $Y^2$, $Y^3$, $X^4$ and $R^5$ have the values listed in the table P.

Table 104P
Table 104P provides 648 compounds of formula (I-A) wherein $G^1$ is oxygen, $R^1$ is hydrogen, $R^2$ is G.104, $X^1$, $X^2$, $X^3$, $Y^1$, $Y^2$, $Y^3$, $X^4$ and $R^5$ have the values listed in the table P.

Table 105P
Table 105P provides 648 compounds of formula (I-A) wherein $G^1$ is oxygen, $R^1$ is hydrogen, $R^2$ is G.105, $X^1$, $X^2$, $X^3$, $Y^1$, $Y^2$, $Y^3$, $X^4$ and $R^5$ have the values listed in the table P.

Table 106P
Table 106P provides 648 compounds of formula (I-A) wherein $G^1$ is oxygen, $R^1$ is hydrogen, $R^2$ is G.106, $X^1$, $X^2$, $X^3$, $Y^1$, $Y^2$, $Y^3$, $X^4$ and $R^5$ have the values listed in the table P.

Table 107P
Table 107P provides 648 compounds of formula (I-A) wherein $G^1$ is oxygen, $R^1$ is hydrogen, $R^2$ is G.107, $X^1$, $X^2$, $X^3$, $Y^1$, $Y^2$, $Y^3$, $X^4$ and $R^5$ have the values listed in the table P.

Table 108P
Table 108P provides 648 compounds of formula (I-A) wherein $G^1$ is oxygen, $R^1$ is hydrogen, $R^2$ is G.108, $X^1$, $X^2$, $X^3$, $Y^1$, $Y^2$, $Y^3$, $X^4$ and $R^5$ have the values listed in the table P.

Table 109P
Table 109P provides 648 compounds of formula (I-A) wherein $G^1$ is oxygen, $R^1$ is hydrogen, $R^2$ is G.109, $X^1$, $X^2$, $X^3$, $Y^1$, $Y^2$, $Y^3$, $X^4$ and $R^5$ have the values listed in the table P.

Table 110P
Table 110P provides 648 compounds of formula (I-A) wherein $G^1$ is oxygen, $R^1$ is hydrogen, $R^2$ is G.110, $X^1$, $X^2$, $X^3$, $Y^1$, $Y^2$, $Y^3$, $X^4$ and $R^5$ have the values listed in the table P.

Table 111P:
Table 111P provides 648 compounds of formula (I-A) wherein $G^1$ is oxygen, $R^1$ is hydrogen, $R^2$ is G.111, $X^1$, $X^2$, $X^3$, $Y^1$, $Y^2$, $Y^3$, $X^4$ and $R^5$ have the values listed in the table P.

Table 112P
Table 112P provides 648 compounds of formula (I-A) wherein $G^1$ is oxygen, $R^1$ is hydrogen, $R^2$ is G.112, $X^1$, $X^2$, $X^3$, $Y^1$, $Y^2$, $Y^3$, $X^4$ and $R^5$ have the values listed in the table P.

Table 113P
Table 113P provides 648 compounds of formula (I-A) wherein $G^1$ is oxygen, $R^1$ is hydrogen, $R^2$ is G.113, $X^1$, $X^2$, $X^3$, $Y^1$, $Y^2$, $Y^3$, $X^4$ and $R^5$ have the values listed in the table P.

Table 114P
Table 114P provides 648 compounds of formula (I-A) wherein $G^1$ is oxygen, $R^1$ is hydrogen, $R^2$ is G.114, $X^1$, $X^2$, $X^3$, $Y^1$, $Y^2$, $Y^3$, $X^4$ and $R^5$ have the values listed in the table P.

Table 115P
Table 115P provides 648 compounds of formula (I-A) wherein $G^1$ is oxygen, $R^1$ is hydrogen, $R^2$ is G.115, $X^1$, $X^2$, $X^3$, $Y^1$, $Y^2$, $Y^3$, $X^4$ and $R^5$ have the values listed in the table P.

Table 116P
Table 116P provides 648 compounds of formula (I-A) wherein $G^1$ is oxygen, $R^1$ is hydrogen, $R^2$ is G.116, $X^1$, $X^2$, $X^3$, $Y^1$, $Y^2$, $Y^3$, $X^4$ and $R^5$ have the values listed in the table P.

TABLE Het

| Het | Chemical structure |
| --- | --- |
| Het.01 | (triazole structure) |
| Het.03 | (pyrazole with CN structure) |
| Het.03 | (pyrazole with F structure) |

TABLE Het-continued

| Het | Chemical structure |
|---|---|
| Het.04 | 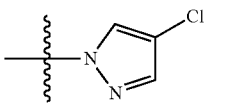 |

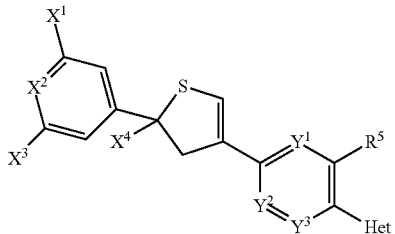

(I-D)

Table 117P
Table 117P provides 648 compounds of formula (I-D) wherein Het is Het.01 and $X^1$, $X^2$, $X^3$, $Y^1$, $Y^2$, $Y^3$, $X^4$ and $R^5$ have the values listed in the table P.
Table 118P
Table 118P provides 648 compounds of formula (I-D) wherein Het is Het.02 and $X^1$, $X^2$, $X^3$, $Y^1$, $Y^2$, $Y^3$, $X^4$ and $R^5$ have the values listed in the table P.
Table 119P
Table 119P provides 648 compounds of formula (I-D) wherein Het is Het.03 and $X^1$, $X^2$, $X^3$, $Y^1$, $Y^2$, $Y^3$, $X^4$ and $R^5$ have the values listed in the table P.
Table 120P
Table 120P provides 648 compounds of formula (I-D) wherein Het is Het.04 and $X^1$, $X^2$, $X^3$, $Y^1$, $Y^2$, $Y^3$, $X^4$ and $R^5$ have the values listed in the table P.

TABLE Gi

| Gi | Chemical structure |
|---|---|
| Gi01 | 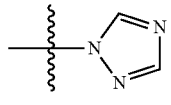 |
| Gi02 | 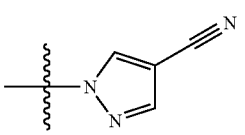 [SMILES: *n1cc(C#N)cn1] |
| Gi03 | 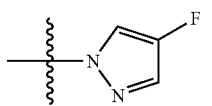 [SMILES: *n1cc(F)cn1] |
| Gi04 | 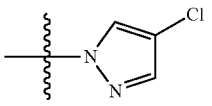 [SMILES: *n1cc(Cl)cn1] |
| Gi05 | CN |
| Gi06 | F |
| Gi07 | Br |
| Gi08 | I |
| Gi09 | Cl |

TABLE Gi-continued

| Gi | Chemical structure |
|---|---|
| Gi10 | $NO_2$ |
| Gi11 | OH |
| Gi12 | $NH_2$ |
| Gi13 | COOH |
| Gi14 | COOMe |
| Gi15 | COOEt |
| Gi16 | COOPr |
| Gi17 | COOBu |
| Gi18 | COOtBu |
| Gi19 | COOPh |
| Gi20 | $CH_3$ |

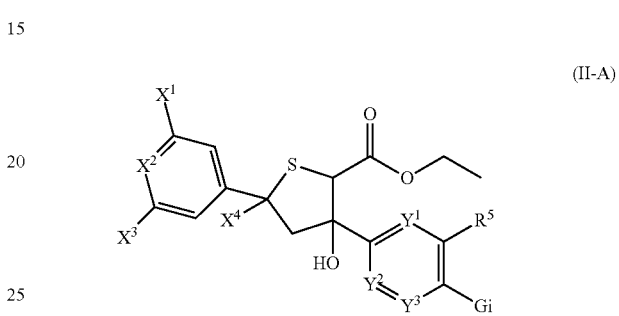

(II-A)

Table 121P
Table 121P provides 648 compounds of formula (II-A) wherein Gi is Gi01 and $X^1$, $X^2$, $X^3$, $Y^1$, $Y^2$, $Y^3$, $X^4$ and $R^5$ have the values listed in the table P.
Table 122P
Table 122P provides 648 compounds of formula (II-A) wherein Gi is Gi02 and $X^1$, $X^2$, $X^3$, $Y^1$, $Y^2$, $Y^3$, $X^4$ and $R^5$ have the values listed in the table P.
Table 123P
Table 123P provides 648 compounds of formula (II-A) wherein Gi is Gi03 and $X^1$, $X^2$, $X^3$, $Y^1$, $Y^2$, $Y^3$, $X^4$ and $R^5$ have the values listed in the table P.
Table 124P
Table 124P provides 648 compounds of formula (II-A) wherein Gi is Gi04 and $X^1$, $X^2$, $X^3$, $Y^1$, $Y^2$, $Y^3$, $X^4$ and $R^5$ have the values listed in the table P.
Table 125P
Table 125P provides 648 compounds of formula (II-A) wherein Gi is Gi05 and $X^1$, $X^2$, $X^3$, $Y^1$, $Y^2$, $Y^3$, $X^4$ and $R^5$ have the values listed in the table P.
Table 126P
Table 126P provides 648 compounds of formula (II-A) wherein Gi is Gi06 and $X^1$, $X^2$, $X^3$, $Y^1$, $Y^2$, $Y^3$, $X^4$ and $R^5$ have the values listed in the table P.
Table 127P
Table 127P provides 648 compounds of formula (II-A) wherein Gi is Gi07 and $X^1$, $X^2$, $X^3$, $Y^1$, $Y^2$, $Y^3$, $X^4$ and $R^5$ have the values listed in the table P.
Table 128P
Table 128P provides 648 compounds of formula (II-A) wherein Gi is Gi08 and $X^1$, $X^2$, $X^3$, $Y^1$, $Y^2$, $Y^3$, $X^4$ and $R^5$ have the values listed in the table P.
Table 129P
Table 129P provides 648 compounds of formula (II-A) wherein Gi is Gi09 and $X^1$, $X^2$, $X^3$, $Y^1$, $Y^2$, $Y^3$, $X^4$ and $R^5$ have the values listed in the table P.
Table 130P
Table 130P provides 648 compounds of formula (II-A) wherein Gi is Gi10 and $X^1$, $X^2$, $X^3$, $Y^1$, $Y^2$, $Y^3$, $X^4$ and $R^5$ have the values listed in the table P.

Table 131P
Table 131P provides 648 compounds of formula (II-A) wherein Gi is Gi11 and $X^1$, $X^2$, $X^3$, $Y^1$, $Y^2$, $Y^3$, $X^4$ and $R^5$ have the values listed in the table P.
Table 132P
Table 132P provides 648 compounds of formula (II-A) wherein Gi is Gi12 and $X^1$, $X^2$, $X^3$, $Y^1$, $Y^2$, $Y^3$, $X^4$ and $R^5$ have the values listed in the table P.
Table 133P
Table 133P provides 648 compounds of formula (II-A) wherein Gi is Gi13 and $X^1$, $X^2$, $X^3$, $Y^1$, $Y^2$, $Y^3$, $X^4$ and $R^5$ have the values listed in the table P.
Table 134P
Table 134P provides 648 compounds of formula (II-A) wherein Gi is Gi14 and $X^1$, $X^2$, $X^3$, $Y^1$, $Y^2$, $Y^3$, $X^4$ and $R^5$ have the values listed in the table P.
Table 135P
Table 135P provides 648 compounds of formula (II-A) wherein Gi is Gi15 and $X^1$, $X^2$, $X^3$, $Y^1$, $Y^2$, $Y^3$, $X^4$ and $R^5$ have the values listed in the table P.
Table 136P
Table 136P provides 648 compounds of formula (II-A) wherein Gi is Gi16 and $X^1$, $X^2$, $X^3$, $Y^1$, $Y^2$, $Y^3$, $X^4$ and $R^5$ have the values listed in the table P.
Table 137P
Table 137P provides 648 compounds of formula (II-A) wherein Gi is Gi17 and $X^1$, $X^2$, $X^3$, $Y^1$, $Y^2$, $Y^3$, $X^4$ and $R^5$ have the values listed in the table P.
Table 138P
Table 138P provides 648 compounds of formula (II-A) wherein Gi is Gi18 and $X^1$, $X^2$, $X^3$, $Y^1$, $Y^2$, $Y^3$, $X^4$ and $R^5$ have the values listed in the table P.
Table 139P
Table 139P provides 648 compounds of formula (II-A) wherein Gi is Gi19 and $X^1$, $X^2$, $X^3$, $Y^1$, $Y^2$, $Y^3$, $X^4$ and $R^5$ have the values listed in the table P.
Table 140P
Table 140P provides 648 compounds of formula (II-A) wherein Gi is Gi20 and $X^1$, $X^2$, $X^3$, $Y^1$, $Y^2$, $Y^3$, $X^4$ and $R^5$ have the values listed in the table P.

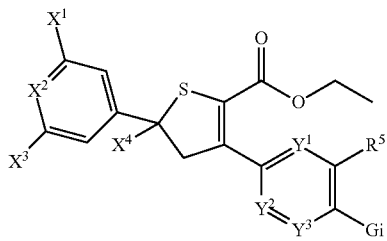

(II-B)

Table 141P
Table 141P provides 648 compounds of formula (II-B) wherein Gi is Gi01 and $X^1$, $X^2$, $X^3$, $Y^1$, $Y^2$, $Y^3$, $X^4$ and $R^5$ have the values listed in the table P.
Table 142P
Table 142P provides 648 compounds of formula (II-B) wherein Gi is Gi02 and $X^1$, $X^2$, $X^3$, $Y^1$, $Y^2$, $Y^3$, $X^4$ and $R^5$ have the values listed in the table P.
Table 143P
Table 143P provides 648 compounds of formula (II-B) wherein Gi is Gi03 and $X^1$, $X^2$, $X^3$, $Y^1$, $Y^2$, $Y^3$, $X^4$ and $R^5$ have the values listed in the table P.
Table 144P
Table 144P provides 648 compounds of formula (II-B) wherein Gi is Gi04 and $X^1$, $X^2$, $X^3$, $Y^1$, $Y^2$, $Y^3$, $X^4$ and $R^5$ have the values listed in the table P.
Table 145P
Table 145P provides 648 compounds of formula (II-B) wherein Gi is Gi05 and $X^1$, $X^2$, $X^3$, $Y^1$, $Y^2$, $Y^3$, $X^4$ and $R^5$ have the values listed in the table P.
Table 146P
Table 146P provides 648 compounds of formula (II-B) wherein Gi is Gi06 and $X^1$, $X^2$, $X^3$, $Y^1$, $Y^2$, $Y^3$, $X^4$ and $R^5$ have the values listed in the table P.
Table 147P
Table 147P provides 648 compounds of formula (II-B) wherein Gi is Gi07 and $X^1$, $X^2$, $X^3$, $Y^1$, $Y^2$, $Y^3$, $X^4$ and $R^5$ have the values listed in the table P.
Table 148P
Table 148P provides 648 compounds of formula (II-B) wherein Gi is Gi08 and $X^1$, $X^2$, $X^3$, $Y^1$, $Y^2$, $Y^3$, $X^4$ and $R^5$ have the values listed in the table P.
Table 149P
Table 149P provides 648 compounds of formula (II-B) wherein Gi is Gi09 and $X^1$, $X^2$, $X^3$, $Y^1$, $Y^2$, $Y^3$, $X^4$ and $R^5$ have the values listed in the table P.
Table 150P
Table 150P provides 648 compounds of formula (II-B) wherein Gi is Gi10 and $X^1$, $X^2$, $X^3$, $Y^1$, $Y^2$, $Y^3$, $X^4$ and $R^5$ have the values listed in the table P.
Table 151P
Table 151P provides 648 compounds of formula (II-B) wherein Gi is Gi11 and $X^1$, $X^2$, $X^3$, $Y^1$, $Y^2$, $Y^3$, $X^4$ and $R^5$ have the values listed in the table P.
Table 152P
Table 152P provides 648 compounds of formula (II-B) wherein Gi is Gi12 and $X^1$, $X^2$, $X^3$, $Y^1$, $Y^2$, $Y^3$, $X^4$ and $R^5$ have the values listed in the table P.
Table 153P
Table 153P provides 648 compounds of formula (II-B) wherein Gi is Gi13 and $X^1$, $X^2$, $X^3$, $Y^1$, $Y^2$, $Y^3$, $X^4$ and $R^5$ have the values listed in the table P.
Table 154P
Table 154P provides 648 compounds of formula (II-B) wherein Gi is Gi14 and $X^1$, $X^2$, $X^3$, $Y^1$, $Y^2$, $Y^3$, $X^4$ and $R^5$ have the values listed in the table P.
Table 155P
Table 155P provides 648 compounds of formula (II-B) wherein Gi is Gi15 and $X^1$, $X^2$, $X^3$, $Y^1$, $Y^2$, $Y^3$, $X^4$ and $R^5$ have the values listed in the table P.
Table 156P
Table 156P provides 648 compounds of formula (II-B) wherein Gi is Gi16 and $X^1$, $X^2$, $X^3$, $Y^1$, $Y^2$, $Y^3$, $X^4$ and $R^5$ have the values listed in the table P.
Table 157P
Table 157P provides 648 compounds of formula (II-B) wherein Gi is Gi17 and $X^1$, $X^2$, $X^3$, $Y^1$, $Y^2$, $Y^3$, $X^4$ and $R^5$ have the values listed in the table P.
Table 158P
Table 158P provides 648 compounds of formula (II-B) wherein Gi is Gi18 and $X^1$, $X^2$, $X^3$, $Y^1$, $Y^2$, $Y^3$, $X^4$ and $R^5$ have the values listed in the table P.
Table 159P
Table 159P provides 648 compounds of formula (II-B) wherein Gi is Gi19 and $X^1$, $X^2$, $X^3$, $Y^1$, $Y^2$, $Y^3$, $X^4$ and $R^5$ have the values listed in the table P.
Table 160P
Table 160P provides 648 compounds of formula (II-B) wherein Gi is Gi20 and $X^1$, $X^2$, $X^3$, $Y^1$, $Y^2$, $Y^3$, $X^4$ and $R^5$ have the values listed in the table P.

(Structure II-C shown)

Table 161P
Table 161P provides 648 compounds of formula (II-C) wherein Gi is Gi01 and $X^1$, $X^2$, $X^3$, $Y^1$, $Y^2$, $Y^3$, $X^4$ and $R^5$ have the values listed in the table P.
Table 162P
Table 162P provides 648 compounds of formula (II-C) wherein Gi is Gi02 and $X^1$, $X^2$, $X^3$, $Y^1$, $Y^2$, $Y^3$, $X^4$ and $R^5$ have the values listed in the table P.
Table 163P
Table 163P provides 648 compounds of formula (II-C) wherein Gi is Gi03 and $X^1$, $X^2$, $Y^1$, $Y^2$, $Y^3$, $X^4$ and $R^5$ have the values listed in the table P.
Table 164P
Table 164P provides 648 compounds of formula (II-C) wherein Gi is Gi04 and $X^1$, $X^2$, $X^3$, $Y^1$, $Y^2$, $Y^3$, $X^4$ and $R^5$ have the values listed in the table P.
Table 165P
Table 165P provides 648 compounds of formula (II-C) wherein Gi is Gi05 and $X^1$, $X^2$, $X^3$, $Y^1$, $Y^2$, $Y^3$, $X^4$ and $R^5$ have the values listed in the table P.
Table 166P
Table 166P provides 648 compounds of formula (II-C) wherein Gi is Gi06 and $X^1$, $X^2$, $X^3$, $Y^1$, $Y^2$, $Y^3$, $X^4$ and $R^5$ have the values listed in the table P.
Table 167P
Table 167P provides 648 compounds of formula (II-C) wherein Gi is Gi07 and $X^1$, $X^2$, $X^3$, $Y^1$, $Y^2$, $Y^3$, $X^4$ and $R^5$ have the values listed in the table P.
Table 168P
Table 168P provides 648 compounds of formula (II-C) wherein Gi is Gi08 and $X^1$, $X^2$, $X^3$, $Y^1$, $Y^2$, $Y^3$, $X^4$ and $R^5$ have the values listed in the table P.
Table 169P
Table 169P provides 648 compounds of formula (II-C) wherein Gi is Gi09 and $X^1$, $X^2$, $X^3$, $Y^1$, $Y^2$, $Y^3$, $X^4$ and $R^5$ have the values listed in the table P.
Table 170P
Table 170P provides 648 compounds of formula (II-C) wherein Gi is Gi10 and $X^1$, $Y^2$, $X^3$, $Y^1$, $Y^2$, $Y^3$, $X^4$ and $R^5$ have the values listed in the table P.
Table 171P
Table 171P provides 648 compounds of formula (II-C) wherein Gi is Gi11 and $X^1$, $X^2$, $X^3$, $Y^1$, $Y^2$, $Y^3$, $X^4$ and $R^5$ have the values listed in the table P.
Table 172P
Table 172P provides 648 compounds of formula (II-C) wherein Gi is Gi12 and $X^1$, $X^2$, $X^3$, $Y^1$, $Y^2$, $Y^3$, $X^4$ and $R^5$ have the values listed in the table P.
Table 173P
Table 173P provides 648 compounds of formula (II-C) wherein Gi is Gi13 and $X^1$, $X^2$, $X^3$, $Y^1$, $Y^2$, $Y^3$, $X^4$ and $R^5$ have the values listed in the table P.
Table 174P
Table 174P provides 648 compounds of formula (II-C) wherein Gi is Gi14 and $X^1$, $X^2$, $X^3$, $Y^1$, $Y^2$, $Y^3$, $X^4$ and $R^5$ have the values listed in the table P.
Table 175P
Table 175P provides 648 compounds of formula (II-C) wherein Gi is Gi15 and $X^1$, $X^2$, $X^3$, $Y^1$, $Y^2$, $Y^3$, $X^4$ and $R^5$ have the values listed in the table P.
Table 176P
Table 176P provides 648 compounds of formula (II-C) wherein Gi is Gi16 and $X^1$, $X^2$, $X^3$, $Y^1$, $Y^2$, $Y^3$, $X^4$ and $R^5$ have the values listed in the table P.
Table 177P
Table 177P provides 648 compounds of formula (II-C) wherein Gi is Gi17 and $X^1$, $X^2$, $X^3$, $Y^1$, $Y^2$, $Y^3$, $X^4$ and $R^5$ have the values listed in the table P.
Table 178P
Table 178P provides 648 compounds of formula (II-C) wherein Gi is Gi18 and $X^1$, $X^2$, $X^3$, $Y^1$, $Y^2$, $Y^3$, $X^4$ and $R^5$ have the values listed in the table P.
Table 179P
Table 179P provides 648 compounds of formula (II-C) wherein Gi is Gi19 and $X^1$, $X^2$, $X^3$, $Y^1$, $Y^2$, $Y^3$, $X^4$ and $R^5$ have the values listed in the table P.
Table 180P
Table 180P provides 648 compounds of formula (II-C) wherein Gi is Gi20 and $X^1$, $X^2$, $X^3$, $Y^1$, $Y^2$, $Y^3$, $X^4$ and $R^5$ have the values listed in the table P.

(II-D)

Table 181P
Table 181P provides 648 compounds of formula (II-D) wherein Gi is Gi01 and $X^1$, $X^2$, $X^3$, $Y^1$, $Y^2$, $Y^3$, $X^4$ and $R^5$ have the values listed in the table P.
Table 182P
Table 182P provides 648 compounds of formula (II-D) wherein Gi is Gi02 and $X^1$, $X^2$, $X^3$, $Y^1$, $Y^2$, $Y^3$, $X^4$ and $R^5$ have the values listed in the table P.
Table 183P
Table 183P provides 648 compounds of formula (II-D) wherein Gi is Gi03 and $X^1$, $X^2$, $X^3$, $Y^1$, $Y^2$, $Y^3$, $X^4$ and $R^5$ have the values listed in the table P.
Table 184P
Table 184P provides 648 compounds of formula (II-D) wherein Gi is Gi04 and $X^1$, $X^2$, $X^3$, $Y^1$, $Y^2$, $Y^3$, $X^4$ and $R^5$ have the values listed in the table P.
Table 185P
Table 185P provides 648 compounds of formula (II-D) wherein Gi is Gi05 and $X^1$, $X^2$, $X^3$, $Y^1$, $Y^2$, $Y^3$, $X^4$ and $R^5$ have the values listed in the table P.
Table 186P
Table 186P provides 648 compounds of formula (II-D) wherein Gi is Gi06 and $X^1$, $X^2$, $X^3$, $Y^1$, $Y^2$, $Y^3$, $X^4$ and $R^5$ have the values listed in the table P.
Table 187P
Table 187P provides 648 compounds of formula (II-D) wherein Gi is Gi07 and $X^1$, $X^2$, $X^3$, $Y^1$, $Y^2$, $Y^3$, $X^4$ and $R^5$ have the values listed in the table P.

Table 188P
Table 188P provides 648 compounds of formula (II-D) wherein Gi is Gi08 and $X^1$, $X^2$, $X^3$, $Y^1$, $Y^2$, $Y^3$, $X^4$ and $R^5$ have the values listed in the table P.
Table 189P
Table 189P provides 648 compounds of formula (II-D) wherein Gi is Gi09 and $X^1$, $X^2$, $X^3$, $Y^1$, $Y^2$, $Y^3$, $X^4$ and $R^5$ have the values listed in the table P.
Table 190P
Table 190P provides 648 compounds of formula (II-D) wherein Gi is Gi10 and $X^1$, $X^2$, $X^3$, $Y^1$, $Y^2$, $Y^3$, $X^4$ and $R^5$ have the values listed in the table P.
Table 191P
Table 191P provides 648 compounds of formula (II-D) wherein Gi is Gi11 and $X^1$, $X^2$, $X^3$, $Y^1$, $Y^2$, $Y^3$, $X^4$ and $R^5$ have the values listed in the table P.
Table 192P
Table 192P provides 648 compounds of formula (II-D) wherein Gi is Gi12 and $X^1$, $X^2$, $X^3$, $Y^1$, $Y^2$, $Y^3$, $X^4$ and $R^5$ have the values listed in the table P.
Table 193P
Table 193P provides 648 compounds of formula (II-D) wherein Gi is Gi13 and $X^1$, $X^2$, $X^3$, $Y^1$, $Y^2$, $Y^3$, $X^4$ and $R^5$ have the values listed in the table P.
Table 194P
Table 194P provides 648 compounds of formula (II-D) wherein Gi is Gi14 and $X^1$, $X^2$, $X^3$, $Y^1$, $Y^2$, $Y^3$, $X^4$ and $R^5$ have the values listed in the table P.
Table 195P
Table 195P provides 648 compounds of formula (II-D) wherein Gi is Gi15 and $X^1$, $X^2$, $X^3$, $Y^1$, $Y^2$, $Y^3$, $X^4$ and $R^5$ have the values listed in the table P.
Table 196P
Table 196P provides 648 compounds of formula (II-D) wherein Gi is Gi16 and $X^1$, $X^2$, $X^3$, $Y^1$, $Y^2$, $Y^3$, $X^4$ and $R^5$ have the values listed in the table P.
Table 197P
Table 197P provides 648 compounds of formula (II-D) wherein Gi is Gi17 and $X^1$, $X^2$, $X^3$, $Y^1$, $Y^2$, $Y^3$, $X^4$ and $R^5$ have the values listed in the table P.
Table 198P
Table 198P provides 648 compounds of formula (II-D) wherein Gi is Gi18 and $X^1$, $X^2$, $X^3$, $Y^1$, $Y^2$, $Y^3$, $X^4$ and $R^5$ have the values listed in the table P.
Table 199P
Table 199P provides 648 compounds of formula (II-D) wherein Gi is Gi19 and $X^1$, $X^2$, $X^3$, $Y^1$, $Y^2$, $Y^3$, $X^4$ and $R^5$ have the values listed in the table P.
Table 200P
Table 200P provides 648 compounds of formula (II-D) wherein Gi is Gi20 and $X^1$, $X^2$, $X^3$, $Y^1$, $Y^2$, $Y^3$, $X^4$ and $R^5$ have the values listed in the table P.

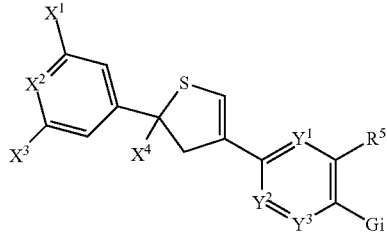

(II-E)

Table 201P
Table 201P provides 648 compounds of formula (II-E) wherein Gi is Gi05 and $X^1$, $X^2$, $X^3$, $Y^1$, $Y^2$, $Y^3$, $X^4$ and $R^5$ have the values listed in the table P.
Table 202P
Table 202P provides 648 compounds of formula (II-E) wherein Gi is Gi06 and $X^1$, $X^2$, $X^3$, $Y^1$, $Y^2$, $Y^3$, $X^4$ and $R^5$ have the values listed in the table P.
Table 203P
Table 203P provides 648 compounds of formula (II-B) wherein Gi is Gi07 and $X^1$, $X^2$, $X^3$, $Y^1$, $Y^2$, $Y^3$, $X^4$ and $R^5$ have the values listed in the table P.
Table 204P
Table 204P provides 648 compounds of formula (II-B) wherein Gi is Gi08 and $X^1$, $X^2$, $X^3$, $Y^1$, $Y^2$, $Y^3$, $X^4$ and $R^5$ have the values listed in the table P.
Table 205P
Table 205P provides 648 compounds of formula (II-B) wherein Gi is Gi09 and $X^1$, $X^2$, $X^3$, $Y^1$, $Y^2$, $Y^3$, $X^4$ and $R^5$ have the values listed in the table P.
Table 206P
Table 206P provides 648 compounds of formula (II-B) wherein Gi is Gi10 and $X^1$, $X^2$, $X^3$, $Y^1$, $Y^2$, $Y^3$, $X^4$ and $R^5$ have the values listed in the table P.
Table 207P
Table 207P provides 648 compounds of formula (II-B) wherein Gi is Gi11 and $X^1$, $X^2$, $X^3$, $Y^1$, $Y^2$, $Y^3$, $X^4$ and $R^5$ have the values listed in the table P.
Table 208P
Table 208P provides 648 compounds of formula (II-B) wherein Gi is Gi12 and $X^1$, $X^2$, $X^3$, $Y^1$, $Y^2$, $Y^3$, $X^4$ and $R^5$ have the values listed in the table P.
Table 209P
Table 209P provides 648 compounds of formula (II-B) wherein Gi is Gi13 and $X^1$, $X^2$, $X^3$, $Y^1$, $Y^2$, $Y^3$, $X^4$ and $R^5$ have the values listed in the table P.
Table 210P
Table 210P provides 648 compounds of formula (II-B) wherein Gi is Gi14 and $X^1$, $X^2$, $X^3$, $Y^1$, $Y^2$, $Y^3$, $X^4$ and $R^5$ have the values listed in the table P.
Table 211P
Table 211P provides 648 compounds of formula (II-B) wherein Gi is Gi15 and $X^1$, $X^2$, $X^3$, $Y^1$, $Y^2$, $Y^3$, $X^4$ and $R^5$ have the values listed in the table P.
Table 212P
Table 212P provides 648 compounds of formula (II-B) wherein Gi is Gi16 and $X^1$, $X^2$, $X^3$, $Y^1$, $Y^2$, $Y^3$, $X^4$ and $R^5$ have the values listed in the table P.
Table 213P
Table 213P provides 648 compounds of formula (II-B) wherein Gi is Gi17 and $X^1$, $X^2$, $X^3$, $Y^1$, $Y^2$, $Y^3$, $X^4$ and $R^5$ have the values listed in the table P.
Table 214P
Table 214P provides 648 compounds of formula (II-B) wherein Gi is Gi18 and $X^1$, $X^2$, $X^3$, $Y^1$, $Y^2$, $Y^3$, $X^4$ and $R^5$ have the values listed in the table P.
Table 215P
Table 215P provides 648 compounds of formula (II-B) wherein Gi is Gi19 and $X^1$, $X^2$, $X^3$, $Y^1$, $Y^2$, $Y^3$, $X^4$ and $R^5$ have the values listed in the table P.
Table 216P
Table 216P provides 648 compounds of formula (II-B) wherein Gi is Gi20 and $X^2$, $X^2$, $X^3$, $Y^1$, $Y^1$, $Y^2$, $Y^3$, $X^4$ and $R^5$ have the values listed in the table P.

In one embodiment the invention provides a compound selected from Tables 1P to 120P for use in controlling and/or preventing insects of the family Curculionidae, preferably in for use in controlling and/or preventing *Anthonomus grandis*.

Additional examples of insects from the family of Curculionidae. are *Anthonomus corvulus, Anthonomus elutus, Anthonomus elongatus, Anthonomus eugenii, Anthonomus consors, Anthonomus haematopus, Anthonomus lecontei, Anthonomus molochinus, Anthonomus morticinus, Anthonomus musculus, Anthonomus nigrinus, Anthonomus phyllocola, Anthonomus pictus, Anthonomus pomorum, Anthonomus quadrigibbus, Anthonomus rectirostris, Anthonomus rubi, Anthonomus santacruzi, Anthonomus signatus, Anthonomus subfasciatus*, and *Anthonomus tenebrosus*.

In one embodiment the invention provides a compound selected from Tables 1P to 120P for use against *Anthonomus grandis* in cotton.

In one embodiment the invention provides a compound selected from Tables 1P to 120P for use in controlling and/or preventing soil pests.

In one embodiment the invention provides a compound selected from Tables 1P to 120P for use in controlling and/or preventing corn rootworm, in particular for use against corn root worm from the genus *Diabrotica*.

In one embodiment the invention provides a compound selected from Tables 1P to 120P for use in controlling and/or preventing corn *Diabrotica virgifera*.

In one embodiment the invention provides a compound selected from Tables 1P to 120P for use in controlling and/or preventing corn *Diabrotica barberi*.

In one embodiment the invention provides a compound selected from Tables 1P to 120P for use in controlling and/or preventing corn *Diabrotica undecimpunctata howardi*.

In one embodiment the invention provides a compound selected from Tables 1P to 120P for use in controlling and/or preventing wireworms, in particular *Agriotes* spp.

In one embodiment the invention provides a compound selected from Tables 1P to 120P for use in controlling and/or preventing *Agriotes* spp. in cereals, potato or corn.

Additional examples of *Agriotes* spp. include *Agriotes lineatus, Agriotes obscurus, Agriotes brevis, Agriotes gurgistanus, Agriotes sputator, Agriotes ustulatus, Ctenicera destructor*, and *Limonius californicus*.

In one embodiment the invention provides a compound selected from Tables 1P to 120P for use in controlling and/or preventing grubs, in particular white grubs.

In one embodiment the invention provides a compound selected from Tables 1P to 120P for use in controlling and/or preventing *Phyllophaga* spp., particularly on corn, soybean or cotton.

In one embodiment the invention provides a compound selected from Tables 1P to 120P for use in controlling and/or preventing *Diloboderus* spp. particularly on corn, soybean or cotton.

In one embodiment the invention provides a compound selected from Tables 1P to 120P for use in controlling and/or preventing *Popillia japonica*, particularly on corn, soybean or cotton.

Additional examples of white grubs include *Phyllophaga anxia, Phyllophaga crinite, Phyllophaga subnitida, Diloboderus abderus*.

In one embodiment the invention provides a compound selected from Tables 1P to 120P for use in controlling and/or preventing termites, e.g. on sugarcane.

Examples of termites include *Reticulitermes, Coptotermes, Macrotermes, Microtermes, Globitermes*. Specific of subterranean termites include *Reticulitermes flavipes, Reticulitermes hesperus, Reticulitermes verginicus, Reticulitermes hageni, Reticulitermes speratus, Reticulitermes lucifugus, Heterotermes aureus, Coptotermes formosanus, Coptotermes acinaciformis, Coptotermes curvignathus, Nasutitermes exitiosus, Nasutitermes walkeri, Mastotermes darwiniensis, Schedorhinotermes* spp, *Macrotermes bellicosus, Macrotermes* spp., *Globitermes sulphureus, Odontotermes* spp. Specific examples of dry wood termites include *Incisitermes minor, Marginitermes hubbardi, Cryptotermes brevis, Kalotermes flavicollis*. Additional examples of termites include *procornitermes* spp. and *procornitermes araujoi*

In one embodiment the invention provides a compound selected from Tables 1P to 120P for use in controlling and/or preventing subterraneous stinkbugs, e.g. *Scaptocoris* spp.

In one embodiment the invention provides a compound selected from Tables 1P to 120P for use in controlling and/or preventing *Scaptocoris castaneus*, in particular on cereals, soybean or corn.

In one embodiment the invention provides a compound selected from Tables 1P to 120P for use in controlling and/or preventing cutworms, e.g. *agrotis* spp.

In one embodiment the invention provides a compound selected from Tables 1P to 120P for use in controlling and/or preventing *Agrotis ipsilon*, particularly on cereals, canola, soybean or corn.

In one embodiment the invention provides a compound selected from Tables 1P to 120P for use in controlling and/or preventing millipedes, e.g. *Julus* spp.

In one embodiment the invention provides a compound selected from Tables 1P to 120P for use in controlling and/or preventing *Julus* spp., particularly on cereals, canola, soybean & corn.

In one embodiment the invention provides a compound selected from Tables 1P to 120P for use in controlling and/or preventing broca gigante, e.g. *Telchin licus*, particularly on sugarcane.

In one embodiment the invention provides a compound selected from Tables 1P to 120P for use in controlling and/or preventing whitefly.

In one embodiment the invention provides a compound selected from Tables 1P to 120P for use in controlling and/or preventing *Bemisia tabaci*, particularly on vegetables, cotton, soybean, or potatoes.

In one embodiment the invention provides a compound selected from Tables 1P to 120P for use in controlling and/or preventing *Trialeurodes vaporariorum*, particularly on vegetables, cotton, soybean, or potatoes.

In one embodiment the invention provides a compound selected from Tables 1P to 120P for use in controlling and/or preventing stinkbugs, in particular *Euschistus* spp.

In one embodiment the invention provides a compound selected from Tables 1P to 120P for use in controlling and/or preventing *Euschistus* spp., particularly in soybean.

Examples of stinkbugs include *Nezara* spp. (e.g. *Nezara viridula, Nezara antennata, Nezara hilare*), *Piezodorus* spp. (e.g. *Piezodorus guildinii*), *Acrosternum* spp. *Euchistus* spp. (e.g. *Euchistus heros, Euschistus servus*), *Halyomorpha halys, Plautia crossota, Riptortus clavatus, Rhopalus msculatus, Antestiopsis orbitalus, Dichelops* spp. (e.g. *Dichelopsfurcatus, Dichelops melacanthus*), *Eurygaster* spp. (e.g. *Eurygaster intergriceps, Eurygaster maura*), *Oebalus* spp. (e.g. *Oebalus mexicana, Oebalus poecilus, Oebalus pugnase, Scotinophara* spp. (e.g. *Scotinophara lurida, Scotinophara coarctata*). Preferred targets include *Antestiopsis orbitalus, Dichelops furcatus, Dichelops melacanthus, Euchistus heros, Euschistus servus, Nezara viridula, Nezara hilare, Piezodorus guildinii, Halyomorpha halys*. In one embodiment the stinkbug target is *Nezara viridula, Piezodorus* spp., *Acrosternum* spp, *Euchistus heros*.

In one embodiment the invention provides a compound selected from Tables 1P to 120P for use against rice pests.

In one embodiment the invention provides a compound selected from Tables 1P to 120P for use against stemborer, particularly in rice.

Examples of stemborers include *Chilo* sp, *Chilo suppressalis*, *Chilo polychrysus*, *Chilo auricilius*, *Scirpophaga* spp., *Scirpophaga incertulas*, *Scirpophaga innotata*, *Scirpophaga nivella Sesamia* sp, *Sesamia inferens*.

In one embodiment the invention provides a compound selected from Tables 1P to 120P for use against leaffolder, particularly in rice.

Examples of leaffolders include *Cnaphalocrocis* spp., *Cnaphalocrocis medinalis*, *Marasmia* spp., *Marasmia patnalis*, *Marasmia exigua*.

In one embodiment the invention provides a compound selected from Tables 1P to 120P for use against hoppers, particularly in rice.

Examples of Hoppers include *Nephotettix* spp., *Nephotettix virescens*, *Nephotettix nigropictus*, *Nephotettix malayanus*, *Nephotettix cincticeps*, *Nilaparvata lugens*, *Sogatella furcifera*.

In one embodiment the invention provides a compound selected from Tables 1P to 120P for use against gallmidge, particularly in rice.

Examples of Gall midge include *Orseolia* sp, *Orseolia oryzae*.

In one embodiment the invention provides a compound selected from Tables 1P to 120P for use against whorl maggot, particularly in rice.

Examples of whorl maggots include *Hydrellia* sp, *Hydrellia philippina*.

In one embodiment the invention provides a compound selected from Tables 1P to 120P for use against Rice bugs, particularly in rice.

Examples of rice bugs include *Leptocorisa* sp, *Leptocorisa oratorius*, *Leptocorisa chinensis*, *Leptocorisa acuta*.

In one embodiment the invention provides a compound selected from Tables 1P to 120P for use against Black bugs, particularly in rice.

Examples of Black bugs include *Scotinophara* sp, *Scotinophara coarctata*, *Scotinophara lurida*, *Scotinophara latiuscula*.

In one embodiment the invention provides a compound selected from Tables 1P to 120P for use against *plutella* spp.

In one embodiment the invention provides a compound selected from Tables 1P to 120P for use against *Plutella xylostella*, particularly in *brassica* crops.

The compounds of the invention may be made by a variety of methods as shown in the following Schemes. In all compounds shown in the schemes below Q, $X^4$, $Y^1$, $Y^2$, $Y^4$ and $R^4$ are as defined in the claims, unless otherwise stated.

Scheme 1

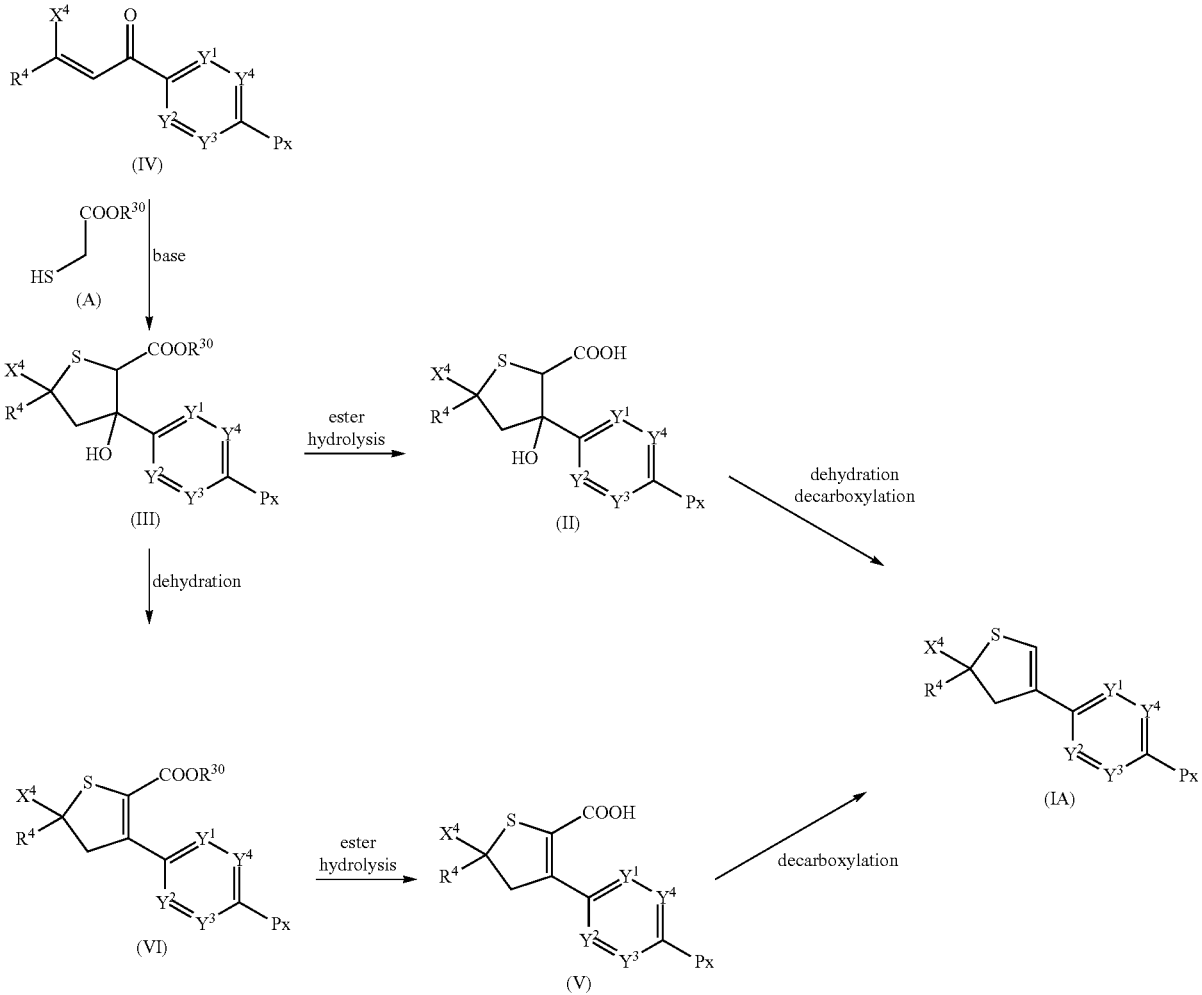

1) Compounds of formula IA, wherein Px is P as defined in the claims, a leaving group for example a halogen, such as bromo, a cyano or C(O)R wherein R is halogen, OH or $C_1$-$C_{15}$ alkoxy, can be prepared by reacting compounds of formula II with reagents such as N,N-dimethyldialkylacetal in a suitable solvent such as dimethylsulfoxide, N, N-dimethylformamide, or N-methylpyrrolidinone. The reaction is carried out at a temperature of from 25° C. to 160° C.

5) Compounds of formula III can be prepared by reacting chalcones of formula IV with alkylthioglycolates of formula A, wherein $R^{30}$ is $C_1$-$C_{15}$ alkyl in presence of organic bases such as triethyl amine, pyridine, diisopropylamine, piperidine, or inorganic bases such as alkaline salts, such as carbonates and hydroxides, in a suitable solvent such as tetrahydrofuran, dioxane or toluene. The reaction is carried out at a temperature of from 0° C. to 100° C. (See *Tetrahedron Lett.* 1964, (23-4), 1609)

Scheme 2

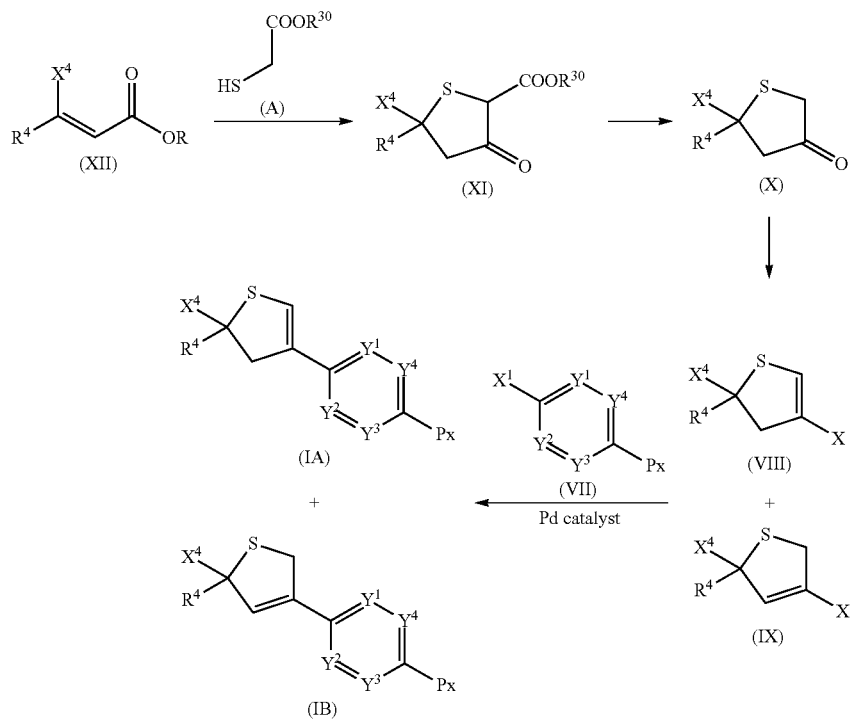

2) Compounds of formula II can be prepared from compounds of formula III, wherein $R^{30}$ is $C_1$-$C_{15}$ alkyl by hydrolysis of the ester moiety. For example, in the case where $R^{30}$ is methyl or ethyl, the hydrolysis can be done with water and a base, such as potassium hydroxide, in the absence or in the presence of a solvent, such as, for instance, tetrahydrofuran, dioxane or methanol. In the case where $R^{30}$ is, for example, tert-butyl, the hydrolysis can be done in the presence of acid, such as trifluoroacetic acid or hydrochloric acid. The reaction is carried out at a temperature of from −120° C. to +130° C., preferably from −100° C. to 100° C.
3) Alternatively compounds of formula IA can be prepared by reacting compounds of formula V with silver salts such as silver carbonate or silver oxide in a suitable solvent such as dimethylsulfoxide, N, N-dimethylformamide, or N-methylpyrrolidinone. The reaction is carried out at a temperature of from 25° C. to 160° C.
4) Compounds of formula V can be prepared from compounds of formula III by a two-step procedure. Compounds of formula III can be converted to compounds of formula VI by dehydration using reagents such as thionyl chloride, phosphorus trichloride or methanesulfonylchloride in the presence of organic bases such as triethylamine, pyridine or di-isopropylamine. Compounds of formula VI can then be converted to compound of formula V as described in 2).

6) Compounds of formula IA (and compounds of formula IB) wherein Px is P as defined in the claims, a leaving group for example a halogen, such as bromo, a cyano or C(O)R wherein R is halogen, OH or $C_1$-$C_{15}$ alkoxy, can be prepared by reacting compounds of formula VIII (and respectively compounds of formula IX) wherein X is a leaving group, for example a halogen, such as bromo, or a triflate, with a compound of formula VII wherein Px is P as defined in the claims, a leaving group for example a halogen, such as bromo, a cyano or C(O)R wherein R is halogen, OH or $C_1$-$C_{15}$ alkoxy, wherein $X^1$ is a boron derivative, such as a boronic acid, a pinacolboronate, or a trifluoroborate salt, in a Suzuki coupling reaction, in the presence of a palladium catalyst, such as palladium acetate or tetrakis(triphenylphosphine) palladium, in a suitable solvent, such as 1,4-dioxane, toluene, acetonitrile or N, N-dimethylformamide. The reaction is carried out at a temperature of from −20° C. to 150° C., preferably from ambient temperature to 100° C.
7) Alternatively, compounds of formula IA (and compounds of formula IB) wherein Px is P as defined in the claims, a leaving group for example a halogen, such as bromo, a cyano or C(O)R wherein R is halogen, OH or $C_1$-$C_{15}$ alkoxy, can be prepared by reacting compounds of formula VIII (and respectively compounds of formula IX) wherein X is a leaving group, for example a halogen, such as bromo, or a triflate and wherein Px is P as defined in the claims, a leaving group for example a halogen, such as bromo, a cyano or C(O)R wherein R is halogen, OH or $C_1$-$C_{15}$alkoxy, with a compound of formula VII wherein $X^1$ is a trialkylstannane derivative, such as tributyltin, or respectively an organozinc derivative in a Stille or Negishi coupling reaction, in the presence of a palladium catalyst, such as palladium acetate or tetrakis(triphenylphosphine) palladium, in a suitable solvent, such as 1,4-dioxane, touene, acetonitrile or N, N-dimethylformamide.

8) Compounds of formula (VIII) (and compounds of formula (IX)) wherein X is a halogen, such as bromo, can be prepared by reacting compounds of formula (X) with a brominating agent, such as phosphoric tribromide, in a suitable solvent, such as tetrahydrofuran, chloroform or dichloromethane. The reaction is carried out at a temperature of from −40° C. to 100° C., preferably from −40° C. to ambient temperature.

9) Alternatively, compounds of formula (VIII) (and compounds of formula (IX)) wherein X is a triflate, can be prepared by reacting compounds of formula (X) with a triflating agent, such as triflic anhydride or N,N-bis(trifluoromethanesulfonyl)aniline, in the presence of a base, such as 4-picoline, sodium or potassium hexamethyldisilylamide, lithium diisopropylamide, triethylamine or 2,6-lutidine in a suitable solvent, such as tetrahydrofuran, chloroform or dichloromethane. The reaction is carried out at a temperature of from −100° C. to 150° C., preferably from −40° C. to 100° C.

10) Compounds of formula (X) can be prepared from compounds of formula (XI) by hydrolysis followed by decarboxylation using bases such as alkali-alkaline earth metals hydroxides at temperatures temperatures from 0° C. to 120° C. or by other general methods known in the art.

11) Compounds of formula XI can be prepared from chalcones of formula XII by reaction with alkylthioglycolates of formula A, wherein $R^{30}$ is $C_1$-$C_{15}$ alkyl, using methods similar to those described in *Bioorganic & Medicinal Chemistry*, 11(22), 4729-4742; 2003 or by other general methods known in the art.

12) Compounds of formula IA and IB wherein Px is P as defined in the claims, a leaving group for example a halogen, such as bromo, a cyano or C(O)R wherein R is halogen, OH or $C_1$-$C_{15}$alkoxy, can be prepared by reacting compounds of formula VII wherein $X^1$ is a leaving group, for example a halogen, such as iodo or bromo and wherein Px is P as defined in the claims, a leaving group for example a halogen, such as bromo, a cyano or C(O)R wherein R is halogen, OH or $C_1$-$C_{15}$ alkoxy, with a compound of formula X, in the presence of a metal, such as magnesium, lithium, indium, cerium or zinc, in a suitable solvent, such as tetrahydrofuran, diethyl ether or N, N-dimethylformamide. The reaction is carried out at a temperature of from −78° C. to 100° C., preferably from −78° C. to ambient temperature.

13) Alternatively, compounds of formula IA and IB wherein Px is P as defined in the claims, a leaving group for example a halogen, such as bromo, a cyano or C(O)R wherein R is halogen, OH or $C_1$-$C_{15}$ alkoxy, can be prepared by reacting a compound of formula XIII wherein Px is P as defined in the claims, a leaving group for example a halogen, such as bromo, a cyano or C(O)R wherein R is halogen, OH or $C_1$-$C_{15}$ alkoxy, in the presence of an acid, such as p-toluenesulfonic acid or sulphuric acid, or in the presence of a dehydrating agent, such as phosphorus trichloride in a suitable solvent, such as tetrahydrofuran, diethyl ether or dichloromethane. The reaction is carried out at a temperature of from −78° C. to 100° C., preferably from −40° C. to ambient temperature.

14) Alternatively, compounds of formula IA and IB wherein Px is P as defined in the claims, a leaving group for example a halogen, such as bromo, a cyano or C(O)R wherein R is halogen, OH or $C_1$-$C_{15}$ alkoxy, can be prepared by reacting a compound of formula XIII wherein Px is P as defined in the claims, a leaving group for example a halogen, such as bromo, a cyano or C(O)R wherein R is halogen, OH or $C_1$-$C_{15}$ alkoxy, in the presence of a chlorinating agent, such as thionyl chloride or oxalyl chloride, or an acetylating agent, such as acetic anhydride in the presence of a base, such as triethylamine, potassium carbonate or pyridine, in a suitable solvent, such as tetrahydrofuran, diethyl ether or dichloromethane. The reaction is carried out at a temperature of from −78° C. to 100° C., preferably from −40° C. to ambient temperature.

15) Compounds of formula XIII can be prepared by reacting compounds of formula VII wherein $X^1$ is a leaving group, Scheme 3

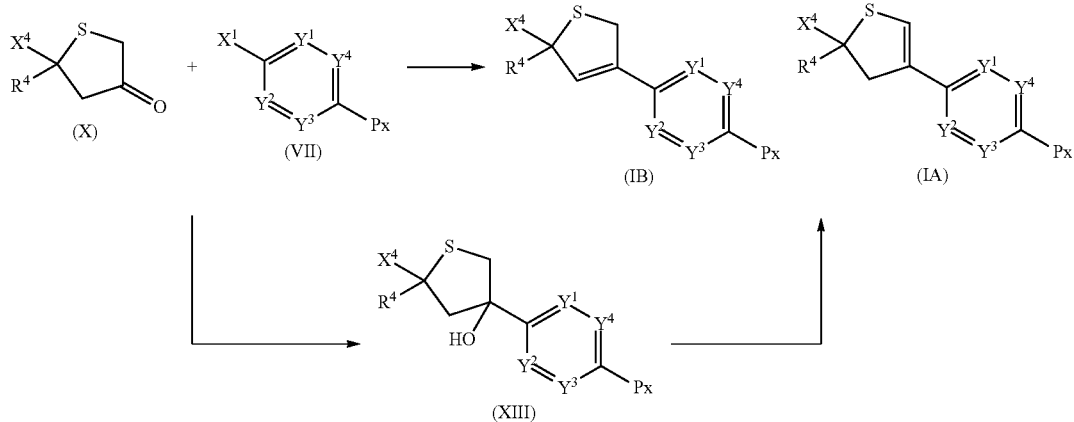

lithium, in a suitable solvent, such as tetrahydrofuran, diethyl ether or N, N-dimethylformamide. The reaction is carried out at a temperature of from −100° C. to 100° C., preferably from −100° C. to ambient temperature.

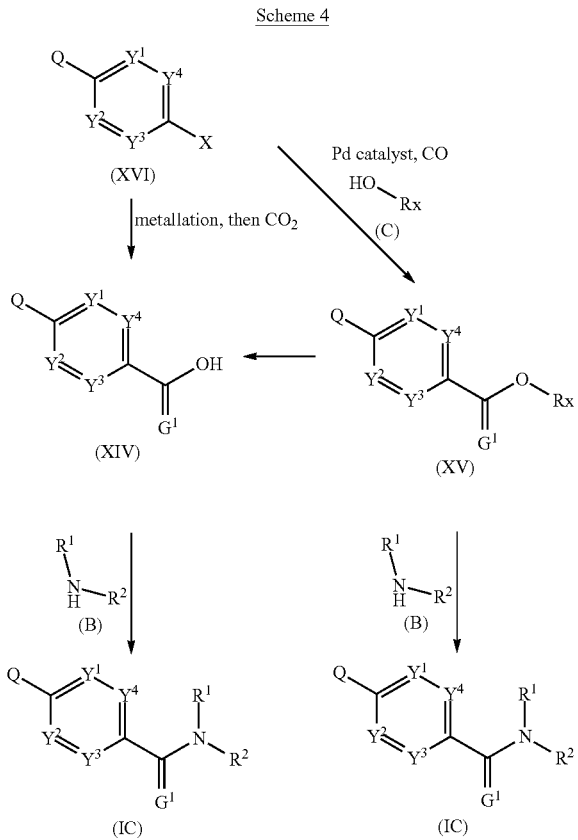

16) Compounds of formula IC can be prepared by treating compounds of formula XIV with compounds of formula B and a dehydrating reagent. Alternatively, compounds of formula XIV can be transformed to an activated derivative, such as an acid chloride, for example by treatment with thionyl chloride, or a mixed anhydride, for example by treatment with ethyl chloroformate, and reacting the activated derivative with a compound of formula B, optionally in the presence of a base, and in a suitable solvent, such as, for example, tetrahydrofuran. The reaction is carried out at a temperature of from −120° C. to +130° C., preferably from −100° C. to 100° C.

17) Alternatively, compounds of formula IC can be prepared from compounds of formula XV wherein Rx is $C_1$-$C_{15}$ alkoxy by heating the ester and an amine of formula B together in a thermal process. Amines of formula B are known and can be prepared using general methods known in the art.

18) Compounds of formula XIV can be prepared by treating a compound of formula XVI, wherein X is a halogen, for example bromine, with a metallating agent, such as a metal, for example magnesium, or an organometallic compound, for example butyllithium, followed by the treatment with carbon dioxide. The reaction is carried out at a temperature of from −120° C. to +130° C., preferably from −100° C. to 100° C.

19) Alternatively compounds of formula XIV can be prepared by hydrolysis of compounds of formula XV, wherein $R_x$ is $C_1$-$C_{15}$ alkyl, such as methyl or tert-butyl. For example, in the case where $R_x$ is methyl or ethyl, the hydrolysis can be done with water and a base, such as potassium hydroxide, in the absence or in the presence of a solvent, such as, for instance, tetrahydrofuran or methynol. In the case where $R_x$ is, for example, tert-butyl, the hydrolysis can be done in the presence of acid, such as trifluoroacetic acid or hydrochloric acid. The reaction is carried out at a temperature of from −120° C. to +130° C., preferably from −100° C. to 100° C.

20) Compounds of formula XV wherein Rx is $C_1$-$C_{15}$ alkoxy, can be prepared by reacting compounds of formula XVI wherein X is a leaving group, for example a halogen, such as bromo, with carbon monoxide and an alcohol of formula Rx-OH, such as ethanol, in the presence of a catalyst, such as bis-(triphenylphosphine)palladium(II) dichloride, and a base, such as pyridine, triethylamine, 4-(dimethylamino)-pyridine ("DMAP") or diisopropylethylamine (Hunig's base). The reaction is carried out at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar.

Scheme 5

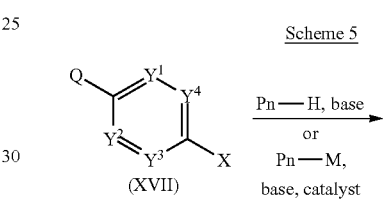

21) Compounds of formula ID, wherein Pn is an optionally substituted heterocycle, can be made, for example in the case where the heterocycle is attached via a nitrogen atom, by treatment of a compound XVII wherein X is a halogen, such as fluorine, with a heterocyclic compound Pn-H and a suitable base, such as potassium carbonate.

22) Alternatively, compounds of formula ID, wherein Pn is an optionally substituted heterocycle, can be made, for example in the case where the heterocycle is attached via a carbon atom, by treatment of a compound XVII wherein X is a halogen, such as bromine, with a heterocyclic compound Pn-M, wherein M is hydrogen or a metal, such as boron, magnesium or zinc, in which case M can be optionally substituted, with a base and a suitable catalyst, such as a palladium or a copper catalyst, in the presence of a suitable ligand for the catalyst, such as, for example, a diamine ligand, or a phosphine ligand. Such reactions are carried out at a temperature of from −120° C. to +130° C., preferably from −100° C. to 100° C.

23) In the above descriptions reference to leaving groups includes leaving groups such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. the leaving group may be selected from —$N_2^+Cl^-$, —$N_2^+$, $BF_4^+$, —$N_2^+Br$, —$N_2^+$, $PF_6^+$) and phosphonate esters (e.g. —OP(O)(OR)$_2$, wherein R is methyl or ethyl).

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars. "Control of infestations" of the pest can result in death (i.e. mortality or lethal control) of the pest, impact on the pest's growth cycle or a reduction in the damage the pest can cause (such as its feeding damage).

Furthermore, the compounds of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount appled, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by the compounds of formula (I) include: coleopterans, for example, *Callosobruchus chinensis, Sitophilus zeamais, Tribolium castaneum, Epilachna vigintioctomaculata, Agriotesfuscicollis, Anomala rufocuprea, Leptinotarsa decemlineata, Diabrotica* spp., *Monochamus alternatus, Lissorhoptrus oryzophilus, Lyctus bruneus, Aulacophora femoralis;* lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella;* hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental;* orthopterans, for example, *Blatella germanica, Periplaneta americana, Gryllotalpa Africana, Locusta migratoria migratoriodes;* isopterans, for example, *Reticulitermes speratus, Coptotermes formosanus;* dipterans, for example, *Musca domestica, Aedes aegypti, Hylemia platura, Culex pipiens, Anopheles sinensis, Culex tritaeniorhynchus, Liriomyza trifolii;* acari, for example, *Tetranychus cinnabarinus, Tetranychus urticae, Panonychus citri, Aculops pelekassi, Tarsonemus* spp.; nematodes, for example, *Meloidogyne incognita, Bursaphelenchus lignicolus Mamiya et Kiyohara, Aphelenchoides besseyi, Heterodera glycines, Pratylenchus* spp.

Examples of further pest species which may be controlled by the compounds of formula (I) include: from the order of the Anoplura (Phthiraptera), for example, *Damalinia* spp., *Haematopinus* spp., *Linognathus* spp., *Pediculus* spp., *Trichodectes* spp.; from the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* Spp., *Vasates lycopersici;* from the class of the Bivalva, for example, *Dreissena* spp.; from the order of the Chilopoda, for example, *Geophilus* spp., *Scutigera* spp.; from the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.; from the order of the Collembola, for example, *Onychiurus armatus;* from the order of the Dermaptera, for example, *Forficula auricularia;* from the order of the Diplopoda, for example, *Blaniulus guttulatus;* from the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis,* Faciola spp., *Haemonchus* spp., *Heterakis* spp., *Hymenolepis nana, Hyostrongulus* spp., *Loa Loa, Nematodirus* spp., *Oesoph-* agostomum spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Strongyloides* spp., *Taenia saginata*, *Taenia solium*, *Trichinella spiralis*, *Trichinella nativa*, *Trichinella britovi*, *Trichinella nelsoni*, *Trichinella pseudpsiralis*, *Trichostrongulus* spp., *Trichuris trichiura*, *Wuchereria bancrofti*; ft may be furthermore possible to control protozoa, such as *Eimeria*; from the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.; from the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*; from the order of the Hymenoptera, for example, *Diprion* spp., *Hoplocampa* spp., *Lasius* spp., *Mono-morium pharaonis*, *Vespa* spp.; from the order of the Isopoda, for example, *Armadillidium Vulgare*, *Oniscus Asellus*, *Porcellio scaber*; from the order of the Isoptera, for example, *Reticulitermes* spp., *Odontotermes* spp.; from the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.; from the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*; from the order of the Siphonaptera, for example, *Ceratophyllus* spp., *Xenopsylla cheopis*. From the order of the Symphyla, for example, *Scutigerella immaculata*; from the order of the Thysanoptera, for example, *Baliothrips biformis*, *Enneothripsflavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.; from the order of the Thysanura, for example, *Lepisma saccharina*. The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

In particular, the compounds of the invention may be used to control the following pest spcies:

*Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta_migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus*, *Reticulitermes flavipes*, *R. speratu*, *R. virginicus*, *R. hesperus*, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compound of formula I may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables, cucurbits and pulses (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The compounds of the invention may be used on soybean to control, for example, *Elasmopalpus lignosellus*, *Diloboderus abderus*, *Diabrotica speciosa*, *Trialeurodes* spp., *Bemisia* spp., aphids, *Sternechus subsignatus*, Formicidae, *Agrotis ipsilon*, *Julus* spp., *Murgantia* spp., *Halyomorpha* spp., *Thyanta* spp., *Megascelis* ssp., *Procornitermes* ssp., Gryllotalpidae, *Nezara viridula*, *Piezodorus* spp., *Acrosternum* spp., *Neomegalotomus* spp., *Cerotoma trifurcata*, *Popillia japonica*, *Edessa* spp., *Liogenys fuscus*, *Euschistus heros*, stalk borer, *Scaptocoris castanea*, *phyllophaga* spp., *Migdolus* spp., *Pseudoplusia includens*, *Anticarsia gemmatalis*, *Epinotia* spp., *Rachiplusia* spp., *Spodoptera* spp., *Bemisia tabaci*, *Tetranychus* spp., *Agriotes* spp., *Euschistus* spp. The compounds of the invention are preferably used on soybean to control *Diloboderus abderus*, *Diabrotica speciosa*, *Trialeurodes* spp., *Bemisia* spp., *Nezara viridula*, *Piezodorus* spp., *Acrosternum* spp., *Cerotoma trifurcata*, *Popillia japonica*, *Euschistus heros*, *Scaptocoris castanea*, *phyllophaga* spp., *Migdolus* spp., *Agriotes* spp., *Euschistus* spp.

The compounds of the invention may be used on corn to control, for example, *Euschistus heros*, *Euschistus* spp., *Dichelops furcatus*, *Diloboderus abderus*, *Thyanta* spp., *Elasmopalpus lignosellus*, *Halyomorpha* spp., *Spodoptera-frugiperda*, *Nezara viridula*, *Cerotoma trifurcata*, *Popillia japonica*, *Agrotis ipsilon*, *Diabrotica speciosa*, aphids, Heteroptera, *Procornitermes* spp., *Scaptocoris castanea*, Formicidae, *Julus* ssp., *Dalbulus maidis*, *Diabrotica virgifera*, *Diabrotica* spp., *Mocis latipes*, *Bemisia tabaci*, *heliothis* spp., *Tetranychus* spp., *thrips* spp., *phyllophaga* spp., *Migdolus* spp., *scaptocoris* spp., *Liogenysfuscus*, *Spodoptera* spp., *Ostrinia* spp., *Sesamia* spp., wireworms, *Agriotes* spp., *Halotydeus destructor*. The compounds of the invention are preferably used on corn to control *Euschistus heros*, *Euschistus* spp., *Dichelops furcatus*, *Diloboderus abderus*, *Nezara viridula*, *Cerotoma trifurcata*, *Popillia japonica*, *Diabrotica speciosa*, *Diabrotica virgifera*, *Diabrotica* spp., *Tetranychus* spp., *Thrips* spp., *Phyllophaga* spp., *Migdolus* spp., *Scaptocoris* spp., *Agriotes* spp.

The compounds of the invention may be used on sugar cane to control, for example, *Sphenophorus* spp., termites, *Migdolus* spp., *Diloboderus* spp., *Telchin licus*, *Diatrea saccharalis*, *Mahanarva* spp., Mealybugs.

The compounds of the invention may be used on alfalfa to control, for example, *Hypera brunneipennis*, *Hypera postica*, *Colias eurytheme*, *Collops* spp., *Empoasca solana*, *Epitrix* spp., *Geocoris* spp., *Lygus hesperus*, *Lygus lineolaris*, *Spissistilus* spp., *Spodoptera* spp., Aphids, *Trichoplusia ni*. The compounds of the invention are preferably used on alfalfa to control *Hypera brunneipennis*, *Hypera postica*, *Empoasca solana*, *Epitrix* spp., *Lygus hesperus*, *Lygus lineolaris*, *Trichoplusia ni*.

The compounds of the invention may be used on brassicas to control, for example, *Plutella xylostella*, *Pieris* spp., *Mamestra* spp., *Plusia* spp., *Trichoplusia ni*, *Phyllotreta* spp., *Spodoptera* spp., *Empoasca* spp., *thrips* spp., *Delia* spp., *Murgantia* spp., *Trialeurodes* spp., *Bemisia* spp., *Microtheca* spp., Aphids. The compounds of the invention are preferably used on brassicas to control *Plutella xylostella*, *Pieris* spp., *Plusia* spp., *Trichoplusia ni*, *Phyllotreta* spp., *Thrips* spp.

The compounds of the invention may be used on oil seed rape, e.g. canola, to control, for example, *Meligethes* spp., *Ceutorhynchus napi*, *Halotydeus destructor*, *Psylloides* spp.

The compounds of the invention may be used on potatoes, including sweet potatoes, to control, for example, *Empoasca* spp., *Leptinotarsa* spp., *Diabrotica speciosa*, *Phthorimaea* spp., *Paratrioza* spp., *Maladera matrida*, *Agriotes* spp., Aphids, wireworms. The compounds of the invention are preferably used on potatoes, including sweet potatoes, to control *Empoasca* spp., *Leptinotarsa* spp., *Diabrotica speciosa*, *Phthorimaea* spp., *Paratrioza* spp., *Agriotes* spp.

The compounds of the invention may be used on cotton to control, for example, *Anthonomus grandis*, *Pectinophora* spp., *heliothis* spp., *Spodoptera* spp., *Tetranychus* spp., *Empoasca* spp., *Thrips* spp., *Bemisia tabaci*, *Trialeurodes* spp., Aphids, *Lygus* spp., *phyllophaga* spp., *Scaptocoris* spp., *Austroasca viridigrisea*, *Creontiades* spp., *Nezara* spp., *Piezodorus* spp., *Halotydeus destructor*, *Oxycaraenus hyalinipennis*, *Dysdercus cingulatus*. The compounds of the invention are preferably used on cotton to control *Anthonomus grandis*, *Tetranychus* spp., *Empoasca* spp., *thrips* spp., *Lygus* spp., *phyllophaga* spp., *Scaptocoris* spp.

The compounds of the invention may be used on rice to control, for example, *Leptocorisa* spp., *Cnaphalocrosis* spp., *Chilo* spp., *Scirpophaga* spp., *Lissorhoptrus* spp., *Oebalus pugnax*, *Scotinophara* spp., *Nephotettix malayanus*, *Nephotettix nigropictus*, *Nephotettix parvus*, *Nephottetix virescens*, *Nephotettix* spp., Mealybugs, *Sogatella furcifera*, *Nilaparvata lugens*, *Orseolia* spp., *Cnaphalocrocis medinalis*, *Marasmia* spp., *Stenchaetothrips biformis*, *Thrips* spp., *Hydrellia philippina*, Grasshoppers, *Pomacea canaliculata*, *Scirpophaga innotata*, *Chilo suppressalis*, *Chilo auricilius*, *Chilo polychrysus*, *Sesamia inferens*, *Laodelphax striatellus*, *Nymphula depunctalis*, *Oulema oryzae*, Stinkbugs. The compounds of the invention are preferably used on rice to control *Leptocorisa* spp., *Lissorhoptrus* spp., *Oebalus pugnax, *Nephotettix malayanus, Nephotettix nigropictus, Nephotettix parvus, Nephottetix virescens, Nephotettix* spp., *Sogatella furcifera, Stenchaetothrips biformis, Thrips* spp., *Hydrellia philippina,* Grasshoppers, *Pomacea canaliculata, Scirpophaga innotata, Chilo suppressalis, Chilo polychrysus, Oulema oryzae.*

The compounds of the invention may be used on coffee to control, for example, *Hypothenemus Hampei, Perileucoptera Coffeella, Tetranychus* spp., *Brevipalpus* spp., Mealybugs. The compounds of the invention are preferably used on coffee to control *Hypothenemus Hampei, Perileucoptera Coffeella.*

The compounds of the invention may be used on citrus to control, for example, *Panonychus citri, Phyllocoptruta oleivora, Brevipalpus* spp., *Diaphorina citri, Scirtothrips* spp., *Thrips* spp., *Unaspis* spp., *Ceratitis capitata, Phyllocnistis* spp., Aphids, Hardscales, Softscales, Mealybugs. The compounds of the invention are preferably used on citrus to control *Panonychus citri, Phyllocoptruta oleivora, Brevipalpus* spp., *Diaphorina citri, Scirtothrips* spp., *thrips* spp., *Phyllocnistis* spp.

The compounds of the invention may be used on almonds to control, for example, *Amyelois transitella, Tetranychus* spp.

The compounds of the invention may be used on fruiting vegetables, cucurbits and pulses, including tomatoes, pepper, chili, eggplant, cucumber, squash etc., to control, for example, *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., Aphids, *Paratrioza* spp., *Frankliniella occidentalis, Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. *Maruca* spp., Fruit flies, Stinkbugs, Lepidopteras, Coleopteras. The compounds of the invention are preferably used on fruiting vegetables, cucurbits and pulses, including tomatoes, pepper, chili, eggplant, cucumber, squash etc., to control *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The compounds of the invention may be used on tea to control, for example, *Pseudaulacaspis* spp., *Empoasca* spp., *Scirtothrips* spp., *Caloptilia theivora, Tetranychus* spp. The compounds of the invention are preferably used on tea to control *Empoasca* spp., *Scirtothrips* spp.

The compounds of the invention may be used on bulb vegetables, including onion, leek etc. to control, for example, *Thrips* spp., *Spodoptera* spp., *heliothis* spp. The compounds of the invention are preferably used on bulb vegetables, including onion, leek etc. to control *Thrips* spp.

The compounds of the invention may be used on grapes to control, for example, *Empoasca* spp., *Lobesia* spp., *Eupoecilia ambiguella, Frankliniella* spp., *Thrips* spp., *Tetranychus* spp., *Rhipiphorothrips Cruentatus, Eotetranychus Willamettei, Erythroneura Elegantula, Scaphoides* spp., *Scelodonta strigicollis,* Mealybugs. The compounds of the invention are preferably used on grapes to control *Frankliniella* spp., *Thrips* spp., *Tetranychus* spp., *Rhipiphorothrips Cruentatus, Scaphoides* spp.

The compounds of the invention may be used on pome fruit, including apples, pears etc., to control, for example, *Cacopsylla* spp., *Psylla* spp., *Panonychus ulmi, Cydia pomonella,* Lepidopteras, Aphids, Hardscales, Softscales. The compounds of the invention are preferably used on pome fruit, including apples, pears etc., to control *Cacopsylla* spp., *Psylla* spp., *Panonychus ulmi.*

The compounds of the invention may be used on stone fruit to control, for example, *Grapholita molesta, Scirtothrips* spp., *Thrips* spp., *Frankliniella* spp., *Tetranychus* spp., Aphids, Hardscales, Softscales, Mealybugs. The compounds of the invention are preferably used on stone fruit to control *Scirtothrips* spp., *Thrips* spp., *Frankliniella* spp., *Tetranychus* spp.

The compounds of the invention may be used on cereals to control, for example, Aphids, Stinkbugs, earthmites, *Eurygaster integriceps, Zabrus tenebrioides, Anisoplia austriaca, Chaetocnema aridula, Phyllotreta* spp., *Oulema melanopus, Oscinella* spp., *Delia* spp., *Mayetiola* spp., *Contarinia* spp., *Cephus* spp., *Steneotarsonemus* spp., *Apamea* spp.

In another embodiment compounds of formula I and mixtures of the invention may be used on rice to control *Baliothrips biformis (Thrips), Chilo* spp. (e.g. *Chilo polychrysus* (Dark headed striped borer), *Chilo suppressalis* (Rice stemborer), *Chilo indicus* (Paddy stem borer), *Chilo polychrysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema oryzae* (Rice leafbeetle), *Leptocorsia acuta* (Rice bug), *Leptocorsia oratorius* (rice bug), *Lissorhoptrus oryzophilus* (rice water weevil), *Mythemina separata* (armyworm), *Nephottetix* spp. (Green leafhopper) (e.g. *Nephotettix cincticeps, Nephotettix malayanus, Nephotettix nigropictus, Nephotettix parvus, Nephottetix virescens*), *Nilaparvata lugens* (Brown Planthopper), *Nymphula depunctalis* (Rice caseworm), *Orseolia oryzae* (Rice Gall midge), *Oulema oryzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki.*

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, *Oleander* moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, *Thrips,* Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of formula (I) and mixture of the invention, in particular those in the tables above, may be used for soil applications, including as a seed application, to target at least the following: sucking pests such as aphids, *thrips*, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on lepidoptera, such as *spodoptera*, cutworms, *elasmoplpus, plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. oncorn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The compounds of formula (I) and mixture of the invention, in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenysfuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp *Hipnodes bicolor; Ctenicera destructor; Limonius canu; Limonius californicus*; rice water weevil: *Lissorhoptrus oryzophilus*; Red Legged earth mites: *Halotydeus destructor*.

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive ("synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A.105, Cry2Ab2, Cry1F, Cry34/35, Cry3Bb); Herculex®I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT® (cotton cultivars producing a Vip3Aa). Soybean Cyst Nematode resistance soybean (SCN®—Syngenta) and soybean with Aphid resistant trait (AMT®) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4 D (e.g. Enlist®) (e.g. WO 2011066384), glyphosate (e.g. Roundup Ready®, Roundup Ready 2 Yield®), sulfonylurea (e.g. STS®), glufosinate (e.g. Liberty Link®, Ignite®), Dicamba (Monsanto), HPPD tolerance (e.g. isoxaflutole herbicide) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®), dicamba and glyphosate tolerance (Monsanto). Of particular interest are soybean plants carrying trains conferring resistance to 2.4 D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®—Monsanto), MON1445 (Roundup ready Cotton®—Monsanto), MON531×MON1445 (Bollgard I+RR®—Monsanto), MON15985 (Genuity Bollgard II Cotton®—Monsanto), MON88913 (Genuity RR FLEX Cotton®—Monsanto), MON15985×MON1445 (Genuity Bollgard II+RR FELX Cotton®—Monsanto), MON15983× MON88913 (Genuity Bollgard II+RR FLEX Cotton®—Monsanto), MON15985 (FibreMax Bollgard II Cotton®—Monsanto), LL25 (FibreMax LL Cotton®—BCS Stoneville), GHB614 (FibreMax GlyTol Cotton®—BCS Stoneville), LL25×MON15985 (FibreMax LL Bollgard II Cotton®—BCS Stoneville/Monsanto), GHB614×LL25 (FibreMax LL GlyTol Cotton®—BCS Stoneville), GHB614× LL25×MON15985 (FibreMax RR GlyTol Bollgard II Cotton®—BCS Stoneville), MON88913×MON15985 (FibreMax LL GlyTol Bollgard II Cotton®—Monsanto), MON88913 (FibreMax RR Flex Cotton®—Monsanto), GHB119+T304-40 (Twinlink®—BCS Stoneville), GHB119+T304-40×LL25×GHB614 (Twinlink LL GT®—BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX—® Dow/Monsanto), 3006-210-23×281-24-236×MON1445 ((PhytoGen Widestrike Insect Protection+RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102×COT67B×MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701× MON89788 (Genuity Roundup ready 2 Yield Soybeans®—Monsanto), MON89788 (Roundup Ready2Yield®, $RR^2Y$®—Monsanto), MON87708 (Monsanto), 40-3-2 (Roundup Ready®, $RR^1$®—Monsanto), MON87701 (Monsanto), DAS-68416 (Enlist Weed Control System®—Dow), DP356043 (Optimum GAT®—Pioneer), A5547-127 (LibertyLink Soybean®—Bayercropscience), A2704-12 (Bayercropscience), GU262 (Bayercropscience), W62 W98 (Bayercropscience), CRV127 (Cultivance®—BASF/EMBRAPA) SYHTOH2 (WO2012/082548).

Examples of Maize transgenic events include T25 (LibertyLink@, LL®—Bayerscropscience), DHT-1 (Dow), TC1507 (Herculex I®—Dow), DAS59122-7 (Herculex RW®—Dow), TC1507+DAS59122-7—Herculex Xtra®—Dow), TC1507×DAS-59122-7×NK603 (Herculex Xtra+ RR®—Dow), TC1507×DAS-59122-×MON88017× MON89034 (Genuity Smartstax Corn®, Genuity Smartstax RIB Complete®—Monsanto/Dow), MON89034×NK603 (Genuity VT double PRO®—Monsanto), MON89034+ MON88017 (Genuity VT Triple PRO®—Monsanto), NK603 (Roundup Ready 2®, $RR^2$®—Monsanto), MON810 (YieldGard BT®, Yieldgard Cornborer®—Monsanto), MON810×NK603 (YieldGard cornborer RR Corn 2®—Monsanto), MON810×MON863 (YieldGard Plus®—Monsanto), MON863×MON810×NK603 (YieldGard Plus+ RR Corn2®/YieldGard RR Maize®—Monsanto), MON863×NK603 (YieldGard Rotworm+RR Corn 2®—Monsanto), MON863 (YieldBard RW®—Monsanto), MON89034 (YieldGard RW®—Monsanto), MON88017 (YieldGard VT RW®—Monsanto), MON810+MON88017 (YieldGard VT Triple®—Monsanto), MON88017+ MON89034 (YieldGard VT Triple Pro®—Monsanto), Bt11+MIR604+GA21 (Agrisure 3000®—Syngenta), Bt11+ TC1507+MIR604+5307+GA21 (Syngenta), Bt11+ TC1507+MIR604+DAS59122+GA21 (Agrisure 3122®—Syngenta), BT11 (Agrisure CB®—Syngenta), GA21—(Agrisure GT®—Syngenta), MIR604 (Agrisure RW®—Syngenta), Bt11+MIR162 (Agrisure TL VIP®—Syngenta), BT11+MIR162+GA21 (Agrisure Viptra 3110®—Syngenta), BT11+MIR162+MIR604 (Agrisure™ 3100®—Syngenta), Event3272+BT11+MIR604+GA21 (Syngenta), BT11+ MIR1692+MIR604+GA21 (Agrisure Viptera 3111®—Syngenta), BT11+MIR162+TC1507+GA21 (Agrisure Viptera 3220®—Syngenta), BT11+MIR162+TC1507+ MIR604+5307+GA21 (Agrisure Viptera 3222®—Syngenta), MIR162 (Syngenta), BT11+GA21+MIR162+ MIR604+5307 (Syngenta), 5307 (Syngenta).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following
a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin, acrinathirin, etofenprox or 5-benzyl-3-furylmethyl-(E)-(1R,3S)-2,2-dimethyl-3-(2-oxothiolan-3-ylidenemethyl)cyclopropane carboxylate;
b) Organophosphates, such as profenofos, sulprofos, acephate, methyl parathion, azinphos-methyl, demeton-s-methy 1, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron, diafenthiuron, lufeneron, novaluron, noviflumuron or chlorfluazuron;

e) Organic tin compounds, such as cyhexatin, fenbutatin oxide or azocyclotin;
f) Pyrazoles, such as tebufenpyrad, tolfenpyrad, ethiprole, pyriprole, fipronil, and fenpyroximate;
g) Macrolides, such as avermectins or milbemycins, for example abamectin, emamectin benzoate, ivermectin, milbemycin, spinosad, azadirachtin, milbemectin, lepimectin or spinetoram;
h) Hormones or pheromones;
i) Organochlorine compounds, such as endosulfan (in particular alpha-endosulfan), benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds, such as imidacloprid, thiacloprid, acetamiprid, nitenpyram, dinotefuran, thiamethoxam, clothianidin, or nithiazine;
m) Diacylhydrazines, such as tebufenozide, chromafenozide or methoxyfenozide;
n) Diphenyl ethers, such as diofenolan or pyriproxifen;
o) Ureas such as Indoxacarb or metaflumizone;
p) Ketoenols, such as Spirotetramat, spirodiclofen or spiromesifen;
q) Diamides, such as flubendiamide, chlorantraniliprole (Rynaxypyr®) or cyantraniliprole;
r) Essential oils such as Bugoil®—(PlantImpact); or
s) a compound selected from buprofezine, flonicamid, acequinocy 1, bifenazate, cyenopyrafen, cyflumetofen, etoxazole, flometoquin, fluacrypyrim, fluensulfone, flufenerim, flupyradifuone, harpin, iodomethane, dodecadienol, pyridaben, pyridalyl, pyrimidifen, flupyradifurone, 4-[(6-Chloropyridin-3-ylmethyl)-(2,2-difluoro-ethyl)-amino]-5H-furan-2-one (DE 102006015467), CAS: 915972-17-7 (WO 2006129714; WO2011/147953; WO2011/147952), CAS: 26914-55-8 (WO 2007020986), chlorfenapyr, pymetrozine, sulfoxaflor and pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap) or hopper specific insecticides (combinations such as buprofezin) for use in rice may be employed. Alternatively insecticides or acaricides specific for particular insect species/stages may also be included in the compositions (for example acaricidal ovo-larvicides, to give combinations such as clofentezine, flubenzimine, hexythiazox or tetradifon; acaricidal motilicides, to give combinations such as dicofol or propargite; acaricides, to give combinations such as bromopropylate or chlorobenzilate; or growth regulators, such as hydramethylnon cyromazine, methoprene, chlorfluazuron or diflubenzuron).

Examples of fungicidal compounds and combinations which may be included in the composition of the invention are (E)-N-methyl-2-[2-(2,5- dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim, chlorhydrate, carboxin, carpropamid, carvone, CGA41396, CGA41397, chinomethionate, chlorothalonil, chlorozolinate, clozylacon, copper containing compounds to give combinations such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimo 1, ethyl-(Z)-N- benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-A1, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]-amide.

The active ingredients combinations described above comprising a compound selected of the invention, in particularly from Tables 1P to 120P and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In addition, biological agents may be included in the composition of the invention e.g. *Bacillus* species such as *Bacillus firmus, Bacillus cereus, Bacillus subtilis*, and *Pasteuria* species such as *Pasteuria penetrans* and *Pasteuria nishizawae*. A suitable *Bacillus firmus* strain is strain CNCM I-1582 which is commercially available as BioNem™. A suitable *Bacillus cereus* strain is strain CNCM I-1562. Of both *Bacillus* strains more details can be found in U.S. Pat. No. 6,406,690. Other biological organisms that may be included in the compositions of the invention are bacteria such as *Streptomyces* spp. such as *S. avermitilis*, and fungi such as *Pochonia* spp. such as *P. chlamydosporia*. Also of interest are *Metarhizium* spp. such as *M. anisopliae; Pochonia* spp. such as *P. chlamydosporia*.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, Buprofezine pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means a compound of formula (I), and in particular a compound selected from Tables 1P to 90P and 1Q to 36Q, which may result in a synergistic combination with the given active ingredient): imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Examples of ratios of the compound of formula I to any mixing partner described herein include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool), cultured fish, honeybees. By combating parasites, fatalities and performance reduction (in terms of meat, milk, wool, skins, eggs, etc.) are reduced, so that applying the compounds of the invention allows more economic and simple husbandry of animals.

By controlling these pests it is intended to reduce deaths and improve performance (in the case of meat, milk, wool, hides, eggs, honey and the like) and health of the host animal. Also, controlling parasites may help to prevent the transmittance of infectious agents, the term "controlling" referring to the veterinary field, meaning that the active compounds are effective in reducing the incidence of the respective parasite in an animal infected with such parasites to innocuous levels, e.g. the active compound is effective in killing the respective parasite, inhibiting its growth, or inhibiting its proliferation.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc. and protozoae, such as coccidia).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia,* Nematodirus, *Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as Nematodirus, *Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma.*

Cestodes that are contemplated to be treated by the invention and by the inventive methods include, without limitation, the following genera: *Diphyllobothrium, Diplydium, Spirometra* and *Taenia.*

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella.*

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus*, *Dermacentor variabilis*, *Dermacentor andersoni*, *Amblyomma americanum*, *Ixodes scapularis* and other *Rhipicephalus* spp. (including the former *Boophilus genera*).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., Cimicidae or e.g., the common bed bug (*Cimex lectularius*); Triatominae spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites, e.g. insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like. These include e.g. flies such as *Haematobia* (*Lyperosia*) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis*, *Hypoderma lineatum*, *Lucilia sericata*, *Lucilia cuprina* (green blowfly), *Calliphora* spp. (blowfly), *Protophormia* spp., *Oestrus ovis* (nasal botfly), *Culicoides* spp. (midges), *Hippobosca equine*, *Gastrophilus intestinalis*, *Gastrophilus haemorrhoidalis* and *Gastrophilus nasalis*; lice such as *Bovicola* (*Damalinia*) *bovis*, *Bovicola equi*, *Haematopinus asini*, *Felicola subrostratus*, *Heterodoxus spiniger*, *Lignonathus setosus* and *Trichodectes canis*; keds such as *Melophagus ovinus*; and mites such as *Psoroptes* spp., *Sarcoptes scabei*, *Chorioptes bovis*, *Demodex equi*, *Cheyletiella* spp., *Notoedres cati*, *Trombicula* spp. and *Otodectes cyanotis* (ear mites).

Examples of species of animal health pesets include those from the order of the Anoplurida, for example *Haematopinus* spp., *Linognathus* spp., *Pediculus* spp., *Phtirus* spp., *Solenopotes* spp.; particular examples are: *Linognathus setosus*, *Linognathus vituli*, *Linognathus ovillus*, *Linognathus oviformis*, *Linognathus pedalis*, *Linognathus stenopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*, *Solenopotes capillatus*; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Fannia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*,

*Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis*; from the order of the Heteropterida, for example *Cimex* spp., *Triatoma* spp., *Rhodnius* spp., *Panstrongylus* spp; from the order of the Blattarida, for example *Blatta orientalis, Periplaneta americana, Blattela germanica, Supella* spp. (e.g. *Suppella longipalpa*); from the subclass of the Acari (*Acarina*) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*; from the order of the Actinedida (*Prostigmata*) and Acaridida (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi; Gasterophilus* spp., *Stomoxys* spp., *Trichodectes* spp., *Rhodnius* spp., *Ctenocephalides canis, Cimx lecturius, Ctenocephalides felis, Lucilia cuprina*; examples of acari include *Ornithodoros* spp., *Ixodes* spp., *Boophilus* spp.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration; or by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., *acacia*, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates.

Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

The following abbreviations were used in this section: DMF: dimethylformamide; THF: tetrahydrofuran; EtOAc: ethyl acetate; s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, [M+H]$^+$=molecular mass of the molecular cation, [M−H]$^-$=molecular mass of the molecular anion, TLC=thin Layer Chromatography.

The following abbreviations were used throughout this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; RT=retention time; MW=molecular cation.

The invention is now described by way of non-limiting Examples.

PREPARATION EXAMPLES

The following preparation examples describe the synthesis of compounds of formula I and intermediates thereof.

Example 1

Preparation of ethyl 3-(4-tert-butoxycarbonyl-3-methyl-phenyl)-5-(3,5-dichlorophenyl)-3-hydroxy-5-(trifluoromethyl)tetrahydrothiophene-2-carboxylate (IB1)

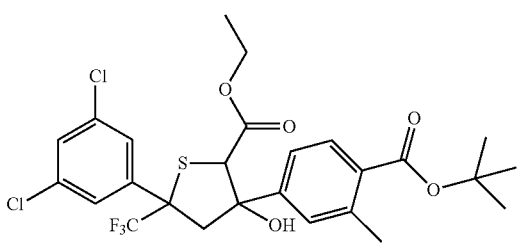 [SMILES: CCOC(=O)C1SC(c2cc(Cl)cc(Cl)c2)(C(F)(F)F)CC1(O)c1ccc(C(=O)OC(C)(C)C)c(C)c1]

To a solution of tert-butyl 5-[3-(3,5-dichlorophenyl)-4,4,4-trifluoro-but-2-enoyl]-2-methyl-benzoate (7 g) in tetrahydrofuran (40 mL), ethyl 2-sulfinylacetate (5.4 g,) was added followed by the addition of N,N,N-Triethylamine (1.05 mL). The stirring was continued overnight at room temperature. The completion of the reaction was monitored by Thin Layer Chromatography (TLC). After completion of the reaction, the reaction mixture was evaporated under reduced pressure, was diluted with ethyl acetate (50 ml), washed with water (25 ml×2) and dried over sodium sulphate. The combined organic phases were evaporated under reduced pressure and the crude residue was purified by column chromatography using 10% ethyl acetate and cyclohexane as an eluent.

Weight=6.5 g $^1$H-NMR (400 MHz, CDCl$_3$): 1.17 (d, 3H), 1.57 (s, 9H), 2.58 (s, 3H), 2.86 (d, 1H), 2.90 (d, 1H), 4.14-4.16 (m, 2H), 4.65 (d, 1H), 4.76 (s, 1H), 7.31-7.32 (m, 3H), 7.52-7.54 (m, 2H), 7.84 (d, 1H).

LC/MS (method B), RT 6.17, [M+H]$^+$ 569.88

Example 2

Preparation of 3-(4-tert-butoxycarbonyl-3-methyl-phenyl)-5-(3,5-dichlorophenyl)-3-hydroxy-5-(trifluoromethyl)tetrahydrothiophene-2-carboxylic acid (IB2)

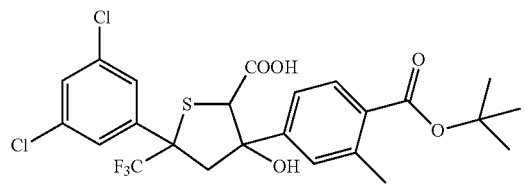 [SMILES: Cc1cc(C2(O)CC(c3cc(Cl)cc(Cl)c3)(C(F)(F)F)SC2C(=O)O)ccc1C(=O)OC(C)(C)C]

To a stirring solution of ethyl 3-(4-tert-butoxycarbonyl-3-methyl-phenyl)-5-(3,5-dichlorophenyl)-3-hydroxy-5-(trifluoromethyl)tetrahydrothiophene-2-carboxylate (15 g) in tetrahydrofuran (150 mL), alithium hydroxide solution (3.2 g, in 40 mL water) was added and the stirring was continued for two hours at room temperature. The completion of the reaction was monitored by TLC. After completion of the reaction, the reaction mixture was acidified with a solution of hydrochloric acid (2N), extracted with ethyl acetate (125 ml), washed with water (100 mL×2), dried over sodium sulphate and the solvent was evaporated under reduced pressure.

Weight=14.2 g $^1$H-NMR (400 MHz, CDCl$_3$): 1.55 (s, 9H), 2.44 (s, 3H), 2.79-2.87 (m, 3H), 4.09-4.14 (m, 2H), 7.22-7.47 (m, 6H).

Example 3

Preparation of tert-butyl 4-[2-(3,5-dichlorophenyl)-2-(trifluoromethyl)-3H-thiophen-4-yl]-2-methyl-benzoate (A55)

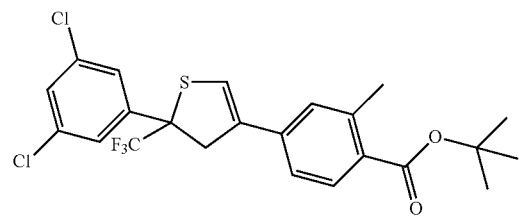 [SMILES: Cc1cc(C2=CSC(c3cc(Cl)cc(Cl)c3)(C(F)(F)F)C2)ccc1C(=O)OC(C)(C)C]

To a stirring solution of 3-(4-tert-butoxycarbonyl-3-methyl-phenyl)-5-(3,5-dichlorophenyl)-3-hydroxy-5-(trifluoromethyl)tetrahydrothiophene-2-carboxylic acid (15 g) in Dimethylformamide (50 mL), N,N-dimethylformamide dineopentylacetal (40 mL) was added and the reaction mixture was stirred under microwave irradiation at 160° C. for 50 min. The completion of the reaction was monitored by TLC. After completion of the reaction, the reaction mixture was diluted with ethyl acetate (50 ml), washed with water (25 ml, twice), dried over sodium sulphate, evaporated under reduced pressure and purified by column chromatography using 10% ethyl acetate and cyclohexane as an eluent.

Weight 5.5 g $^1$H-NMR (400 MHz, CDCl$_3$): 1.58 (s, 9H), 2.60 (s, 3H), 3.67 (d, 1H), 3.95 (d, 1H), 6.60 (d, 1H), 7.15-7.42 (m, 6H).

Example 4

Preparation of 4-[2-(3,5-dichlorophenyl)-2-(trifluoromethyl)-3H-thiophen-4-yl]-2-methyl-benzoic acid (A56)

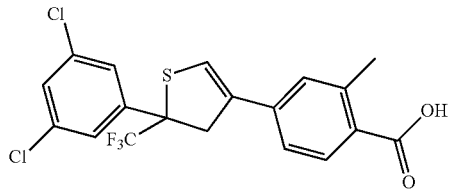 [SMILES: Cc1cc(C2=CSC(c3cc(Cl)cc(Cl)c3)(C(F)(F)F)C2)ccc1C(=O)O]

To a stirring solution of tert-butyl 4-[2-(3,5-dichlorophenyl)-2-(trifluoromethyl)-3H-thiophen-4-yl]-2-methyl-benzoate (1 g) in dichloromethane (20 mL) 2,2,2-trifluoroacetic acid (1.16 g) was added and stirring was continued overnight at room temperature. After completion of the reaction, monitored by TLC, the reaction mixture was quenched with water (30 ml), extracted with dichloromethane, dried with sodium sulphate and evaporated under reduced pressure. The residue was purified by column chromatography using 50% ethyl acetate and cyclohexane as an eluent Weight=0.5 g Melting point=197-199° C.

$^1$H-NMR (400 MHz, CDCl$_3$): 2.50 (s, 3H), 3.86 (d, 1H), 4.02 (d, 1H), 7.17-7.81 (m, 7H).

Example 5

Preparation of 4-[2-(3,5-dichlorophenyl)-2-(trifluoromethyl)-3H-thiophen-4-yl]-2-methyl-N-(2,2,2-trifluoroethyl)benzamide (A2)

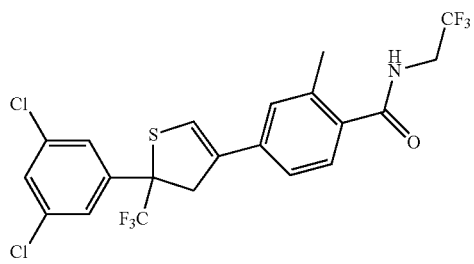 [SMILES: Cc1cc(C2=CSC(c3cc(Cl)cc(Cl)c3)(C(F)(F)F)C2)ccc1C(=O)NCC(F)(F)F]

To a stirring solution of 4-[2-(3,5-dichlorophenyl)-2-(trifluoromethyl)-3H-thiophen-4-yl]-2-methyl-benzoic acid (0.2 g) in dichloromethane (30 mL) 2 drops of N,N-dimethylformamide (DMF) and oxalyl dichloride (252 mg) was added and stirring continued for one hour at room temperature. The solvent was then evaporated under reduced pressure. The solid obtained was dissolved in dichloromethane (30 mL) and was added to a stirring solution of 2,2,2-trifluoroethanamine hydrochloride (68 mg) and triethylamine (0.27 mL) at 0° C. The reaction mixture was stirred overnight at room temperature. The reaction mixture was diluted with dichloromethane (30 mL) and washed with water (30 mL×2). The organic layer was dried with sodium sulphate and evaporated under reduced pressure. The compound was purified by column chromatography using 20% ethyl acetate and cyclohexane as an eluent Weight=0.1 g Melting point=78-80° C.

$^1$H-NMR (400 MHz, CDCl$_3$): 2.46 (s, 3H), 3.64 (d, 1H), 3.85 (d, 1H), 4.08-4.12 (m, 2H), 6.59 (s, 1H), 7.20-7.22 (m, 2H), 7.36-7.40 (m, 4H). LCMS=511.97 (−ESI, RT 5.75-5.92). LCMS (Method B) RT 5.83 min [M−H]$^+$ 511.97

Example 6

Preparation of 4-[2-(3,5-dichlorophenyl)-2-(trifluoromethyl)-3H-thiophen-4-yl]-2-methyl-N-[2-oxo-2-(2,2,2-trifluoroethylamino)ethyl]benzamide (A3)

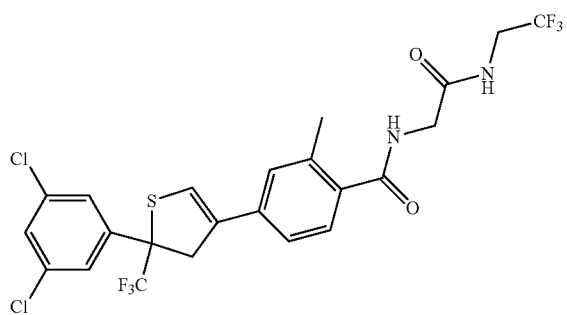 [SMILES: Cc1cc(C2=CSC(c3cc(Cl)cc(Cl)c3)(C(F)(F)F)C2)ccc1C(=O)NCC(=O)NCC(F)(F)F]

The compound (A3) was prepared using the same procedure as described for synthesis of (A2) using a different amine partner (glycine derived trifluoroethylamide).

$^1$H-NMR (400 MHz, CDCl$_3$): 2.47 (s, 3H), 3.66-3.67 (d, 1H), 3.83-3.87 (d, 1H), 3.95 (m, 2H), 4.17-4.18 (d, 2H), 6.59-6.61 (NH), 6.62-6.69 (s, 1H), 6.99 (s, 1H), 7.20 (m, 2H), 7.40 (m, 4H).

LC-MS Method B, RT=5.64 min, [M−H]$^+$ 568.96

Example 7

Preparation of 4-[2-(3,5-dichlorophenyl)-2-(trifluoromethyl)-3H-thiophen-4-yl]-N-(1,1-dioxothietan-3-yl)-2-methyl-benzamide (A4)

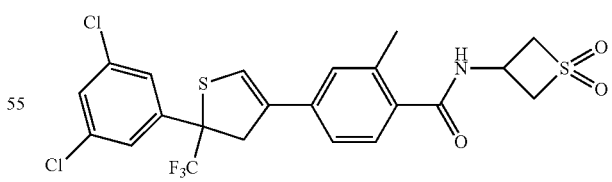

The compound was prepared using the same procedure as described for synthesis of (A1) using a different amine partner (4-amino thietanesulphone).

Melting point=88-90° C.

$^1$H-NMR (400 MHz, CDCl$_3$): 2.47 (s, 3H), 3.66 (d, 1H), 3.84 (d, 1H), 4.01-4.05 (m, 2H), 4.59-4.65 (m, 2H), 4.85-4.92 (m, 1H), 6.58-6.64 (m, 2H), 7.15-7.42 (m, 6H).

LC-MS (method B) RT 5.67 min, [M−H]$^+$ 533.88

Example 8

Preparation of (4-[2-(3,5-dichlorophenyl)-2-(trifluoromethyl)-3H-thiophen-4-yl]-2-methyl-N-(1-oxidothietan-1-ium-3-yl)benzamide (A7)

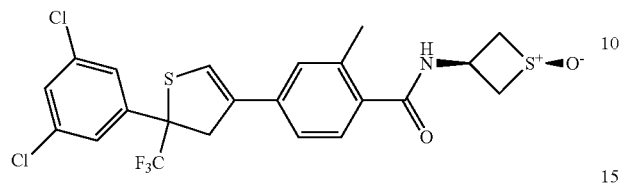

The compound was prepared using the same procedure as described for synthesis of (A1) using a different amine partner (cis-4-aminothietanesulphoxide).

Melting point=119-122° C.
$^1$H-NMR (400 MHz, CDCl$_3$): 2.46 (s, 3H), 3.22-3.28 (m, 2H), 3.66 (d, 1H), 3.84 (d, 1H), 4.17-4.22 (m, 2H), 4.67-4.69 (m, 1H), 6.66-6.48 (m, 1H), 6.59 (d, 1H), 7.18-7.48 (m, 6H).
LC-MS (method B) RT 5.70 min, [M+H]$^+$ 520.01

Example 9

Preparation of 4-[2-(3,5-dichlorophenyl)-2-(trifluoromethyl)-3H-thiophen-4-yl]-2-methyl-N-(thietan-3-yl)benzamide (A5)

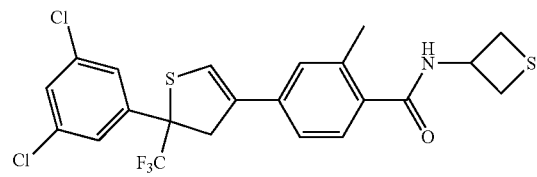 [SMILES: Cc1cc(C2=CSC(c3cc(Cl)cc(Cl)c3)(C(F)(F)F)C2)ccc1C(=O)NC1CSC1]

The compound was prepared using the same procedure as described for synthesis of (A1) using a different amine partner (thietanyl amine).

Melting point=68-70° C.
$^1$H-NMR (400 MHz, CDCl$_3$): 2.45 (s, 3H), 3.35-3.40 (m, 2H), 3.46-3.51 (m, 2H), 3.66 (d, 1H), 3.86 (d, 1H), 5.40-5.42 (m, 1H), 6.35 (d, NH), 6.59 (d, 1H), 7.18-7.42 (m, 6H).
LC-MS (method B), RT 5.90 min, [M+H]$^+$ 504.03

Example 10

Preparation of 4-[2-(3,5-dichlorophenyl)-2-(trifluoromethyl)-3H-thiophen-4-yl]-2-methyl-benzamide (A6)

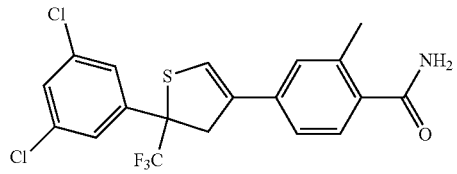 [SMILES: Cc1cc(C2=CSC(c3cc(Cl)cc(Cl)c3)(C(F)(F)F)C2)ccc1C(N)=O]

The compound was prepared using the same procedure as described for synthesis of (A1) using a different amine partner (ammonia).

Melting point=165-167° C.
$^1$H-NMR (400 MHz, CDCl$_3$): 2.52 (s, 3H), 3.66 (d, 1H), 3.85 (d, 1H), 5.71 (s, 2H), 6.59-6.62 (m, 1H), 7.19-7.46 (m, 5H), 8.08-8.11 (m, 1H).
LC-MS (method B), RT 5.70 min, [M−H]$^+$ 432.13

Example 11

Preparation of 4-[2-(3,5-dichlorophenyl)-2-(trifluoromethyl)-3H-thiophen-4-yl]-N-[(4R)-2-ethyl-3-oxo-isoxazolidin-4-yl]-2-methyl-benzamide (A9)

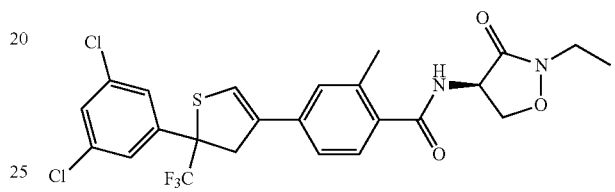

To a stirring solution of 4-[2-(3,5-dichlorophenyl)-2-(trifluoromethyl)-3H-thiophen-4-yl]-2-methyl-benzoic acid (0.15 g) in DMF (5 ml), N-[(Dimethylamino)-1H-1,2,3-triazolo-[4,5-b]pyridin-1-ylmethylene]-N-methylmethanaminium hexafluorophosphate N-oxide 190 mg), 1-oxothietan3-amine (109 mg) and triethylamine (0.27 mL) was added at 0° C. and stirring was continued overnight at room temperature. TLC showed the reaction was completed and the reaction mixture was diluted with ethyl acetate (30 ml) and washed with water (30 ml twice). The organic layer was dried with sodium sulphate and evaporated under reduced pressure. The compound was purified by column chromatography using 20% ethyl acetate and cyclohexane as an eluent Weight=0.12 g $^1$H-NMR (400 MHz, CDCl$_3$): 1.27 (m, 3H), 2.47 (s, 3H), 3.61-3.67 (m, 3H), 3.85 (d, 1H), 4.01-4.05 (m, 1H), 4.83-4.87 (m, 1H), 4.94-4.97 (m, 1H), 6.52 (d, 1H), 6.58 (d, 1H), 7.17-7.25 (m, 2H), 7.37-7.42 (m, 4H).
LC-MS (method), RT 5.78 min, [M+H]$^+$ 545.04.

Example 12

Preparation of 4-[2-(3,5-dichlorophenyl)-2-(trifluoromethyl)-3H-thiophen-4-yl]-2-methyl-N-(2-pyridylmethyl)benzamide (A8)

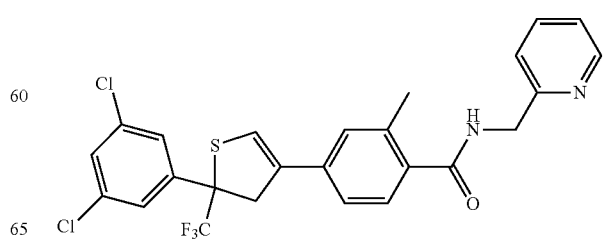

The compound was prepared using the same procedure as described for synthesis of (A1) using a different amine partner (2-aminomethylpyridine).

Melting point=161-163° C.

¹H-NMR (400 MHz, CDCl₃): 2.49 (s, 3H), 3.65 (d, 1H), 3.85 (d, 1H), 4.76 (d, 2H), 6.56 (d, 1H), 7.19-7.48 (m, 9H), 7.71-7.78 (t, 1H), 8.53 (d, 1H).

LC-MS (method B), RT 5.76 min, [M+H]⁺ 523.07

Example 13

Preparation of (NE)-4-[2-(3,5-dichlorophenyl)-2-(trifluoromethyl)-3H-thiophen-4-yl]-N-[(methoxyamino)methylene]-2-methyl-benzamide (A10)

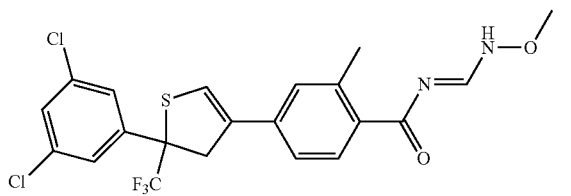 [SMILES: CON/C=N/C(=O)c1ccc(C2=CSC(c3cc(Cl)cc(Cl)c3)(C(F)(F)F)C2)cc1C]

A stirring solution of 4-[2-(3,5-dichlorophenyl)-2-(trifluoromethyl)-3H-thiophen-4-yl]-2-methyl-benzamide (99 mg) in dimethylformamide dimethyl acetal (2 ml) was heated at 120° C. for four hours. After completion of the reaction, the reaction mixture was concentrated under reduced pressure. The residue was dissolved in 1,4-Dioxane (10 ml) and treated with O-methylhydroxylamine hydrochloride (20 mg) and sodium hydroxide 10 mg). Then acetic acid (1.5 ml) was added and the reaction mixture was stirred overnight at room temperature. TLC showed the reaction was completed and the solution was evaporated under reduced pressure. The residue was diluted with ethyl acetate (30 ml) and washed with water (30 ml twice). The organic layer was dried with sodium sulphate and evaporated under reduced pressure.

Weight=0.06 g

¹H-NMR (400 MHz, CDCl₃): 2.52 (s, 3H), 3.65 (d, 1H), 3.82-3.89 (m, 4H), 6.64 (d, 1H), 7.23-7.46 (m, 6H), 8.50 (d, 1H).

LCMS (method B), RT 5.91 min, [M+H]⁺ 489.06

Example 14

Preparation of 4-[2-(3,5-dichlorophenyl)-1-oxido-2-(trifluoromethyl)-3H-thiophen-1-ium-4-yl]-2-methyl-N-(2,2,2-trifluoroethyl)benzamide (B1)

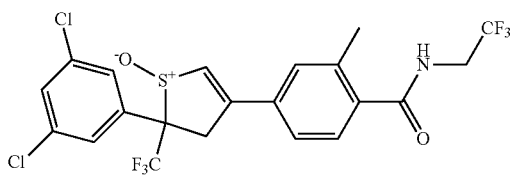

To a stirring solution of (1 4-[2-(3,5-dichlorophenyl)-2-(trifluoromethyl)-3H-thiophen-4-yl]-2-methyl-N-(2,2,2-trifluoroethyl)benzamide 150 mg) in dichloromethane (20 mL), m-chlor perbenzoic acid (100 mg) and potassium carbonate (80 mg) were added and stirring was continued overnight at room temperature. After completion of the reaction, as monitored by TLC, the reaction mixture was quenched with water (30 ml) and extracted with dichloromethane. The organic layer was dried with sodium sulphate and evaporated under reduced pressure. The compound was purified by column chromatography using 20% ethylacetate and cyclohexane as an eluent.

Weight=0.055 g

Melting point=114-116° C.

¹H-NMR (400 MHz, CDCl₃): 2.51 (s, 3H), 3.85 (d, 2H), 4.11-4.15 (m, 2H), 6.99 (d, 1H), 7.38-7.48 (m, 6H).

LC-MS (method B), RT 5.51 min, [M−H]⁺ 527.96

Example 15

Preparation of methyl 3-(4-tert-butoxycarbonyl-3-methyl-phenyl)-5-(3,5-dichlorophenyl)-3-hydroxy-5-(trifluoromethyl)tetrahydrothiophene-2-carboxylate

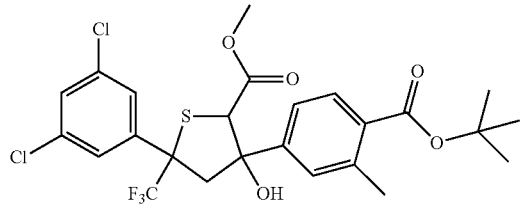 [SMILES: COC(=O)C1SC(c2cc(Cl)cc(Cl)c2)(C(F)(F)F)CC1(O)c1ccc(C(=O)OC(C)(C)C)c(C)c1]

A solution of tert-butyl 4-[(Z)-3-(3,5-dichlorophenyl)-4,4,4-trifluoro-but-2-enoyl]-2-methyl-benzoate (700 mg) in toluene (10 mL) was treated with methyl mercaptoacetate (194 mg) and piperidine (0.18 ml) and the mixture was stirred at 80° C. for four hours. Then, the reaction mixture was cooled to room temperature, diluted with ethyl acetate (20 ml) and washed with water (20 ml). The combined organic layers were dried over sodium sulfate, concentrated and purified by column chromatography (cyclohexane/ethyl acetate 1:9 as eluent) to give methyl 3-(4-tert-butoxycarbonyl-3-methyl-phenyl)-5-(3,5-dichlorophenyl)-3-hydroxy-5-(trifluoromethyl)tetrahydrothiophene-2-carboxylate (200 mg).

¹H-NMR (400 MHz, CDCl₃): 7.83 (1H, d), 7.52 (2H, s), 7.38 (1H, m), 7.33 (2H, m), 4.8 (1H, s), 4.6 (1H, brs), 3.65 (3H, s), 2.95 (1H, d), 2.86 (1H, d), 2.55 (3H, s), 1.60 (s, 9H)

Example 16

Preparation of methyl 4-(4-tert-butoxycarbonyl-3-methyl-phenyl)-2-(3,5-dichlorophenyl)-2-(trifluoromethyl)-3H-thiophene-5-carboxylate

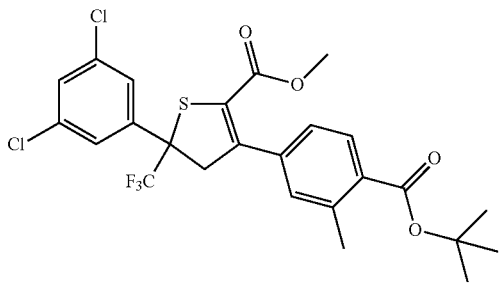 [SMILES: COC(=O)C1=C(c2ccc(C(=O)OC(C)(C)C)c(C)c2)CC(c2cc(Cl)cc(Cl)c2)(C(F)(F)F)S1]

A solution of methyl 3-(4-tert-butoxycarbonyl-3-methyl-phenyl)-5-(3,5-dichlorophenyl)-3-hydroxy-5-(trifluoromethyl)tetrahydrothiophene-2-carboxylate (1 g) in pyridine (5 mL) was cooled to 0° C., treated with thionyl chloride (0.39 ml) and stirred at 0° C. for four hours. The reaction was then slowly neutralized with a solution of hydrochloric acid (1N), diluted with water (20 ml) and extracted with ethyl acetate (25 ml×2). The combined organic layers were dried over sodium sulfate, concentrated and purified by column chromatography (cyclohexane/ethyl acetate 5:95 as eluent) to give a mixture of methyl 4-(4-tert-butoxycarbonyl-3-methyl-phenyl)-2-(3,5-dichlorophenyl)-2-(trifluoromethyl)-3H-thiophene-5-carboxylate and an uncharacterized component in 1:1 ratio. (700 mg).

$^1$H-NMR (400 MHz, CDCl$_3$): 7.83 (1H, dd), 7.50 (2H, s), 7.40 (1H, m), 7.35 (2H, m), 7.31 (1H, m), 7.29 (1H, m), 7.13 (2H, m), 6.5 (1H, s), 5.3 (1H, s), 3.9 (2H, dd), 3.7 (3H, s), 3.6 (3H, s), 2.60 (H, s), 2.55 (H, s), 1.6 (s, 18H).

Example 17

Preparation of ethyl 4-(4-tert-butoxycarbonyl-3-methyl-phenyl)-2-(3,5-dichlorophenyl)-2-(trifluoromethyl)-3H-thiophene-5-carboxylate

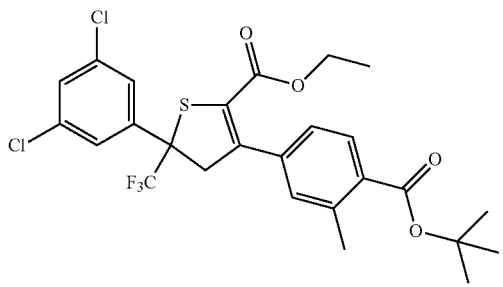 [SMILES: CCOC(=O)C1=C(c2ccc(C(=O)OC(C)(C)C)c(C)c2)CC(c2cc(Cl)cc(Cl)c2)(C(F)(F)F)S1]

A solution of ethyl 3-(4-tert-butoxycarbonyl-3-methyl-phenyl)-5-(3,5-dichlorophenyl)-3-hydroxy-5-(trifluoromethyl)tetrahydrothiophene-2-carboxylate (7 g) in pyridine (35 mL) was cooled to 0° C., treated with thionyl chloride (2.6 ml) and stirred at 0° C. for four hours. It was slowly neutralized with a solution of hydrochloric acid (1N), diluted water (20 ml) and extracted with ethyl acetate (25 ml×2). The combined organic layers were dried over sodium sulfate, concentrated and purified by column chromatography (cyclohexane/ethyl acetate 0.5:9.5 as eluent) to give a mixture of methyl 4-(4-tert-butoxycarbonyl-3-methyl-phenyl)-2-(3,5-dichlorophenyl)-2-(trifluoromethyl)-3H-thiophene-5-carboxylate and an uncharacterized component in 1:1 ratio (5.5 g).

Example 18

Preparation of ethyl 4-[4-(cyclobutylcarbamoyl)-3-methyl-phenyl]-2-(3,5-dichlorophenyl)-2-(trifluoromethyl)-3H-thiophene-5-carboxylate

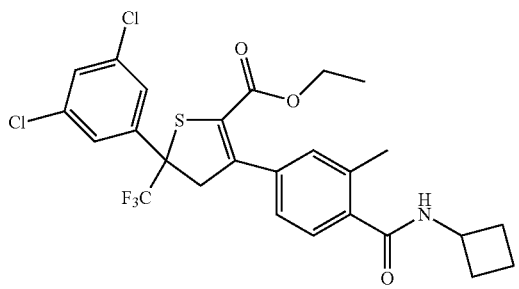 [SMILES: CCOC(=O)C1=C(c2ccc(C(=O)NC3CCC3)c(C)c2)CC(c2cc(Cl)cc(Cl)c2)(C(F)(F)F)S1]

A solution of ethyl 4-(3-tert-butoxycarbonyl-4-methyl-phenyl)-2-(3,5-dichlorophenyl)-2-(trifluoromethyl)-3H-thiophene-5-carboxylate (4.5 g) in dichloromethane (50 mL) was treated with trifluoroacetic acid (3 mL) and stirred for five hours at room temperature. The solvent was then removed in vacuo. The residue was diluted with dichloromethane (20 ml), treated with cyclobutylamine (1.1 g), N-ethyl-N-isopropyl-propan-2-amine (5.2 g), 1-hydroxybenzonitrile (1.1 g) and 1-Ethyl-3-(3-dimethylaminopropyl)carbodiimide hydrochloride (2.0 g). The suspension was stirred for 12 hours at room temperature. The reaction was diluted with dichloromethane (50 ml) and washed with water (25 ml). The organic phase was dried over sodium sulphate and purified by column chromatography (cyclohexane/ethyl acetate 4:6 as eluent) to give ethyl 4-[4-(cyclobutylcarbamoyl)-3-methyl-phenyl]-2-(3,5-dichlorophenyl)-2-(trifluoromethyl)-3H-thiophene-5-carboxylate along with an uncharacterized component in 1:1 ratio (2.5 g).

Example 19

Preparation of 4-[4-(cyclobutylcarbamoyl)-3-methyl-phenyl]-2-(3,5-dichlorophenyl)-2-(trifluoromethyl)-3H-thiophene-5-carboxylic acid

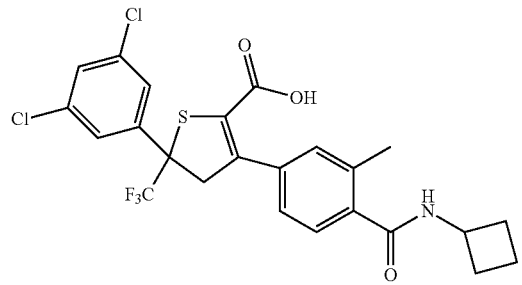 [SMILES: Cc1cc(C2=C(C(=O)O)SC(c3cc(Cl)cc(Cl)c3)(C(F)(F)F)C2)ccc1C(=O)NC1CCC1]

A solution of ethyl 4-[4-(cyclobutylcarbamoyl)-3-methyl-phenyl]-2-(3,5-dichlorophenyl)-2-(trifluoromethyl)-3H-thiophene-5-carboxylate (2.2 g) in tetrahydrofuran (25 mL) and water (5 mL) was heated at 80° C., treated with lithium hydroxide (332 mg) and stirred for two hours. The reaction mixture was cooled to room temperature, acidified with a solution of hydrochloric acid (2N), and the solvent was removed in vacuo. The reaction mixture was diluted with ethyl acetate (50 ml) and washed with water (20 ml). The organic layer was dried over sodium sulphate and concentrated in vacuo to give 4-[4-(cyclobutylcarbamoyl)-3-methyl-phenyl]-2-(3,5-dichlorophenyl)-2-(trifluoromethyl)-3H-thiophene-5-carboxylic acid along with an uncharacterized component in 1:1 ratio (2 g) LC-MS (method B), RT 2.25 min, [M+H]$^+$ 530.

Example 20

Preparation of N-cyclobutyl-4-[2-(3,5-dichlorophenyl)-2-(trifluoromethyl)-3H-thiophen-4-yl]-2-methyl-benzamide (A1)

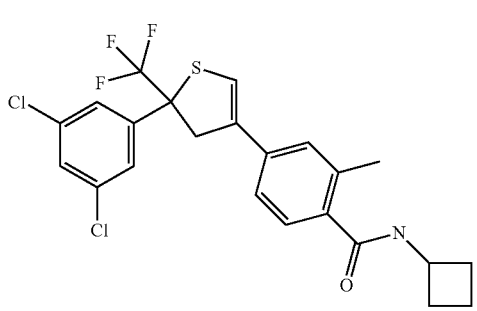

(A1)

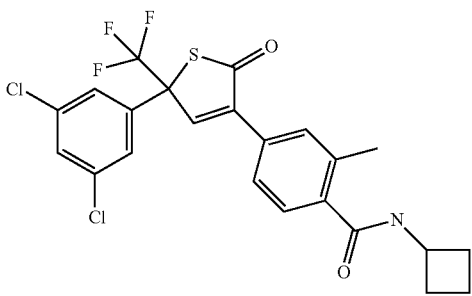

(A1')

A solution of 4-[4-(cyclobutylcarbamoyl)-3-methyl-phenyl]-2-(3,5-dichlorophenyl)-2-(trifluoromethyl)-3H-thiophene-5-carboxylic acid (194 mg) in dimethylsulfoxide (10 ml) was treated with silver carbonate (22 mg) and stirred overnight at 120° C. The reaction mixture was diluted with ethyl acetate (50 ml) and washed with sodium bicarbonate solution (20 ml) and water (20 ml). The organic layer was dried over sodium sulphate, purified by column chromatography (cyclohexane/ethyl acetate 1:9 as eluent) to give 400 mg of a crude mixture. This residue was further purified by preparative HPLC to give 60 mg of N-cyclobutyl-4-[2-(3,5-dichlorophenyl)-2-(trifluoromethyl)-3H-thiophen-4-yl]-2-methyl-benzamide (A1) and 50 mg of new product (A1') characterized as N-cyclobutyl-4-[5-(3,5-dichlorophenyl)-2-oxo-5-(trifluoromethyl)-3-thienyl]-2-methyl-benzamide.

N-cyclobutyl-4-[2-(3,5-dichlorophenyl)-2-(trifluoromethyl)-3H-thiophen-4-yl]-2-methyl-benzamide (A1): $^1$H-NMR (400 MHz, CDCl$_3$): 7.42 (2H, s), 7.40 (1H, s), 7.33 (1H, d), 7.15 (1H, d), 6.55 (1H, s), 5.85 (1H, m), 4.58 (1H, m), 3.6 (1H, d), 3.8 (1H, d), 2.5 (3H, s), 2.5 (2H, m), 1.9 (2H, m), 1.8 (2H, m).

LC-MS (method B), RT 2.51 min, [M+H]$^+$ 486.

N-cyclobutyl-4-[5-(3,5-dichlorophenyl)-2-oxo-5-(trifluoromethyl)-3-thienyl]-2-methyl-benzamide (A1'): $^1$H-NMR (400 MHz, CDCl$_3$): 7.70 (1H, s), 7.45 (5H, m), 5.1 (1H, m), 4.60 (1H, m), 2.48 (3H, s), 2.45 (2H, m), 1.9 (2H, m), 1.8 (2H, m). LC-MS (method B), RT 2.50, [M+H]$^+$ 500.

Example 21

Preparation of 4-[2-(3,5-dichlorophenyl)-1,1-dioxo-2-(trifluoromethyl)-3H-thiophen-4-yl]-2-methyl-N-(2,2,2-trifluoroethyl)benzamide (B2)

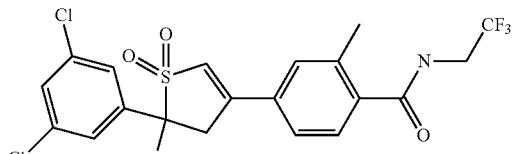

To a stirring solution of 4-[2-(3,5-dichlorophenyl)-2-(trifluoromethyl)-3H-thiophen-4-yl]-2-methyl-benzoic acid (70 mg) in acetic acid (2 mL), hydrogen peroxide (1.8 ml 10% solution) was added and stirring was continued at RT for 38 h. Reaction was diluted with ethyl acetate 30 ml and washed with 10% sodium carbonate solution followed by washing with water (30 ml). The combined organic layer was dried with sodium sulphate and evaporated under reduced pressure. Compound was purified by column chromatography using 20% ethylacetate and cyclohexane as an eluent to obtain titled compound.

Weight=0.018 g

1H NMR (DMSO, 400 MHz) δ: 9.07-9.08 (d, 1H), 8.10 (t, 1H), 7.92 (t, 1H), 7.79-7.84 (d, 1H), 7.72-7.73 (d, 1H), 7.46-7.48 (d, 2H), 4.14 (m, 2H), 3.30 (S, 3H), 2.50-2.51 (d, 1H), 2.40-2.44 (d, 1H). LC-MS (method B), RT 5.84 min, [M−H]$^+$ 544.06.

Example 22

Preparation of intermediate tert-butyl 2-bromo-4-[3-(3,5-dichlorophenyl)-4,4,4-trifluoro-but-2-enoyl]benzoate (IA1)

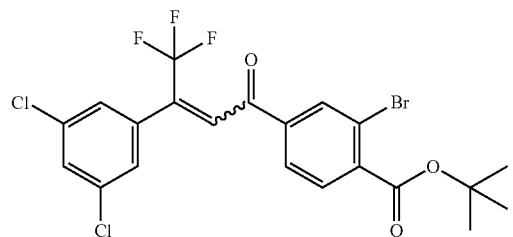 [SMILES: CC(C)(C)OC(=O)c1ccc(C(=O)C=C(c2cc(Cl)cc(Cl)c2)C(F)(F)F)cc1Br]

To a solution of tert-butyl 4-acetyl-2-bromo-benzoate (10 g) in acetonitrile (100 mL) was added 1-(3,5-dichlorophenyl)-2,2,2-trifluoro-ethanone (8.9 g) and potassium carbonate (465 mg). The r resulting mixture was heated at 120° C. under a nitrogen atmosphere for 16 hours. The reaction mixture was concentrated under reduced pressure to remove all volatiles, diluted with water (30 mL) and extracted with ethyl acetate (3×30 mL). The combined organic layers were dried over sodium sulphate, filtered and concentrated under reduced pressure. The crude product was purified by column chromatography eluted with cyclohexane/ethyl acetate (9:1) to obtain the titled compound as a solid (17 g). LC-MS (Method B) RT 5.90 min [M−H]$^+$ 521.68

Example 23

Preparation of intermediate ethyl 3-(3-bromo-4-tert-butoxycarbonyl-phenyl)-5-(3,5-dichlorophenyl)-3-hydroxy-5-(trifluoromethyl)tetrahydrothiophene-2-carboxylate (IB3)

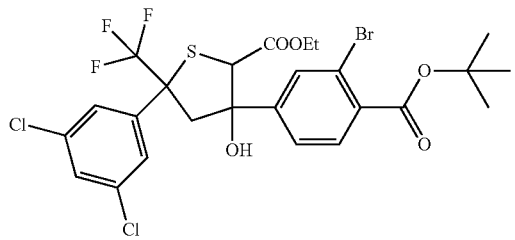 [SMILES: CC(C)(C)OC(=O)c1ccc(C2(O)CC(c3cc(Cl)cc(Cl)c3)(C(F)(F)F)SC2C(=O)O)cc1Br]

To a solution of tert-butyl 2-bromo-4-[(Z)-3-(3,5-dichlorophenyl)-4,4,4-trifluoro-but-2-enoyl]benzoate (5.6 g) in tetrahydrofuran (30 mL) was added ethyl 2-sulfanylacetate (3.5 mL) and triethylamine (0.74 mL). The resulting mixture was stirred at room temperature under a nitrogen atmosphere for 16 hours. The reaction mixture was concentrated under reduced pressure, diluted with water (30 mL) and extracted with ethyl acetate (3×30 mL). The combined organic layers were dried over sodium sulphate, filtered and concentrated under reduced pressure. The crude product was purified by silica gel column chromatography using cyclohexane/ethyl acetate (9:1) as eluent to obtain the titled compound as a solid (3.5 g). LC-MS (Method B) RT 6.33 min [M−H]+ 641.14. $^1$H NMR (CDCl$_3$, 400 MHz): 7.77 (d, 1H), 7.69-7.72 (m, 1H), 7.52 (d, 2H), 7.44 (dd, 1H), 7.37 (t, 1H), 4.72 (s, 1H), 4.69 (d, 1H), 4.05-4.20 (m, 2H), 2.93-3.00 (m, 1H), 2.80-2.86 (m, 1H), 1.59 (s, 9H), 1.20 (t, 3H)

Example 24

Preparation of intermediate 3-(3-bromo-4-tert-butoxycarbonyl-phenyl)-5-(3,5-dichlorophenyl)-3-hydroxy-5-(trifluoromethyl)tetrahydrothiophene-2-carboxylic acid (IB4)

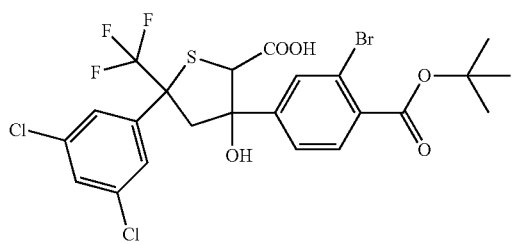

To a solution of ethyl 3-(3-bromo-4-tert-butoxycarbonyl-phenyl)-5-(3,5-dichlorophenyl)-3-hydroxy-5-(trifluoromethyl)tetrahydrothiophene-2-carboxylate (1.7 g) in tetrahydrofuran (10 mL) was added lithium hydroxide monohydrate (330 mg) in water (2 mL). The resulting mixture was stirred at room temperature for 16 hours. The reaction mixture was concentrated under reduced pressure, acidified with a 10% hydrochloric acid solution and extracted with ethyl acetate (3×30 mL). The combined organic layers were dried over sodium sulphate, filtered and concentrated under reduced pressure to obtain the titled compound as a solid (1.6 g).

Example 25

Preparation of tert-butyl 2-bromo-4-[2-(3,5-dichlorophenyl)-2-(trifluoromethyl)-3H-thiophen-4-yl]benzoate (A57)

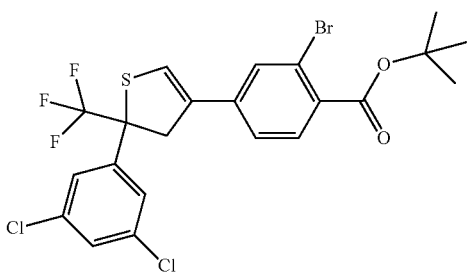 [SMILES: CC(C)(C)OC(=O)c1ccc(C2=CSC(c3cc(Cl)cc(Cl)c3)(C(F)(F)F)C2)cc1Br]

To a solution of 3-(3-bromo-4-tert-butoxycarbonyl-phenyl)-5-(3,5-dichlorophenyl)-3-hydroxy-5-(trifluoromethyl)tetrahydrothiophene-2-carboxylic acid (1.5 g) in pyridine (15 mL) was slowly added methanesulfonyl chloride (685 mg) at 0° C. The resulting mixture was stirred at room temperature under a nitrogen atmosphere for 12 hours. The reaction mixture was diluted with water (10 mL) and extracted with ethyl acetate (3×15 mL). The combined organic layers were dried over sodium sulphate, filtered and concentrated under reduced pressure to obtain a crude residue. This residue was diluted in DMF (5 mL) and the resulting mixture was heated at 120° C. for one hour. The reaction mixture was diluted with water (15 mL) and extracted with ethyl acetate (3×15 mL). The combined organic layers were dried over sodium sulphate, filtered and concentrated under reduced pressure. The crude product was purified by column chromatography using cyclohexane/ethyl acetate (9:1) as eluent to obtain the titled compound as a solid (950 mg). LC-MS (Method B) RT 6.66 min [M−H]+ 550.91. $^1$H NMR (CDCl$_3$, 400 MHz): 7.70 (d, 1H), 7.56 (d, 1H), 7.38-7.43 (m, 3H), 7.30 (dd, 1H), 6.67 (s, 1H), 3.83 (dd, 1H), 3.63 (dd, 1H), 1.60 (s, 9H)

Example 26

Preparation of 2-bromo-4-[2-(3,5-dichlorophenyl)-2-(trifluoromethyl)-3H-thiophen-4-yl]benzoic acid (A58)

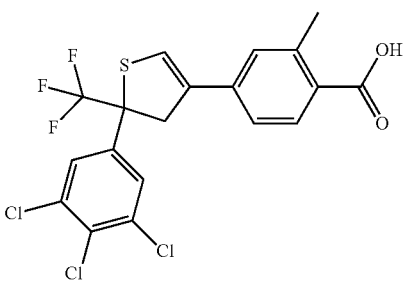 [SMILES: Cc1cc(C2=CSC(c3cc(Cl)c(Cl)c(Cl)c3)(C(F)(F)F)C2)ccc1C(=O)O]

To a solution of tert-butyl 2-bromo-4-[2-(3,5-dichlorophenyl)-2-(trifluoromethyl)-3H-thiophen-4-yl]benzoate (4 g) in dichloromethane (20 mL), was added 2,2,2-trifluoroacetic acid (5 mL). The resulting mixture was stirred at room temperature under a nitrogen atmosphere for 12 hours. The reaction mixture was diluted with water (20 mL), extracted with dichloromethane (3×30 mL). The combined organic layers were dried over sodium sulphate, filtered and concentrated under reduced pressure to obtain the titled compound (3 g). LCMS (Method B) RT 2.58 min [M−H]464.9. $^1$H NMR (CDCl$_3$, 400 MHz): 11.54 (br. s, 1H), 7.69-7.74 (m, 1H), 7.39 (s, 2H), 6.99-7.05 (m, 2H), 6.47 (s, 1H), 3.68 (dd, 1H), 3.47 (dd, 1H), 2.40 (s, 3H).

Example 27

Preparation of ethyl 3-[3-cyano-4-(1,2,4-triazol-1-yl)phenyl]-5-(3,5-dichlorophenyl)-3-hydroxy-5-(trifluoromethyl)tetrahydrothiophene-2-carboxylate (IB10

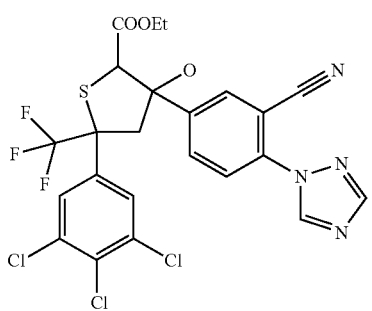 [SMILES: CCOC(=O)C1SC(c2cc(Cl)c(Cl)c(Cl)c2)(C(F)(F)F)CC1(O)c1ccc(-n2cncn2)c(C#N)c1]

The titled compound was prepared according to the steps described for the preparation of IB3.

$^1$H NMR (CDCl$_3$, 400 MHz): 8.80-8.83 (m, 1H), 8.19-8.21 (m, 1H), 8.01 (d, 1H), 7.87-7.91 (m, 1H), 7.83-7.87 (m, 1H), 7.64-7.68 (m, 2H), 4.84 (d, 1H), 4.76 (s, 1H), 4.76 (s, 1H), 4.08-4.18 (m, 2H), 2.97-3.04 (m, 1H), 2.86 (dd, 1H), 1.18-1.26 (m, 3H)

Example 28

Preparation of 2-(1,2,4-triazol-1-yl)-5-[2-(3,4,5-trichlorophenyl)-2-(trifluoromethyl)-3H-thiophen-4-yl]benzonitrile (C1)

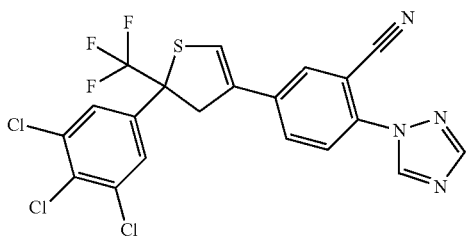 [SMILES: N#Cc1cc(C2=CSC(c3cc(Cl)c(Cl)c(Cl)c3)(C(F)(F)F)C2)ccc1-n1cncn1]

The titled compound was prepared from IB10 according to the steps described for the preparation of A57 from IB3?

LC-MS (Method B) RT 6.24 min [M+H]+ 501.22. $^1$H NMR (CDCl$_3$, 400 MHz): 8.79 (s, 1H), 8.19 (s, 1H), 7.68-7.79 (m, 3H), 7.57 (s, 2H), 6.77 (s, 1H), 3.89 (dd, 1H), 3.61-3.71 (m, 1H).

Example 29

General Procedure Used for the Preparation of Compound A20-A40

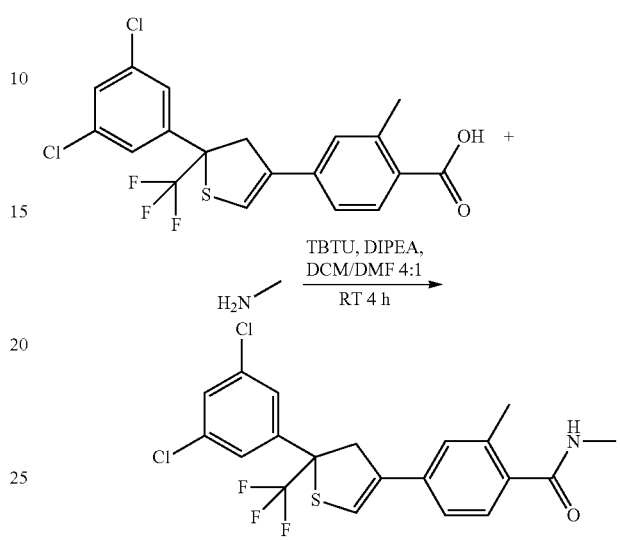

To a solution of 4-[2-(3,5-dichlorophenyl)-2-(trifluoromethyl)-3H-thiophen-4-yl]-2-methyl-benzoic acid (0.03 mmol) in a solvent mixture of DCM/DMF 4:1 (0.8 ml) was added N,N,N',N'-Tetramethyl-O-(benzotriazol-1-yl)uronium tetrafluoroborate (1.3 eq) and N,N-Diisopropylethylamine (5 eq). The mixture was stirred at room temperature for one hour after which the amine (2 eq) was added to the reaction mixture and stirring was continued for 4 hours at room temperature. After LC-MS analysis, dichloromethane was evaporated and the crude mass was dissolved in dimethylformamide to be purified by preparative HPLC-MS under acidic conditions.

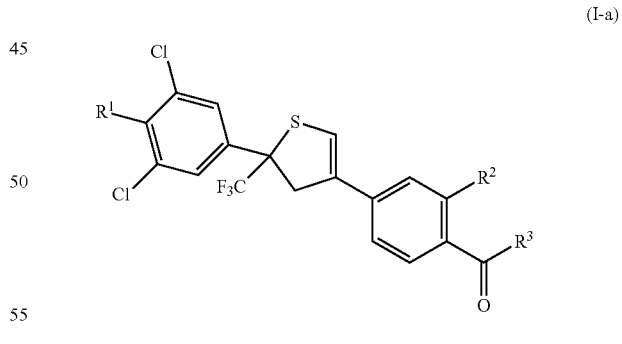

(I-a)

| Cmpd No. | R3 | R2 | R1 | RT (minute) | [M]+ (+ or − mode) | LC-MS method |
|---|---|---|---|---|---|---|
| A1 | cyclobutanamine; | Me | H | 2.51 (*) | 486.00 (+) | B |
| A2 | 2,2,2-trifluoroethanamine | Me | H | 5.83 (*) | 511.97 (−) | B |
| A3 | 2-amino-N-(2,2,2-trifluoroethyl)acetamide | Me | H | 5.70 (*) | 568.96 (−) | B |
| A4 | 1,1-dioxothietan-3-amine; | Me | H | 5.69 (*) | 533.88 (−) | B |

| Cmpd No. | R3 | R2 | R1 | RT (minute) | [M]+ (+ or – mode) | LC-MS method |
|---|---|---|---|---|---|---|
| A5 | thietan-3-amine | Me | H | 5.90 (*) | 504.03 (+) | B |
| A6 | ammonia | Me | H | 5.70 (*) | 432.13 (−) | B |
| A7 | 1-oxidothietan-1-ium-3-amine | Me | H | 5.71 (*) | 520.01 (−) | B |
| A8 | 2-pyridylmethanamine; | Me | H | 5.76 (*) | 523.07 (+) | B |
| A9 | (4R)-4-amino-2-ethyl-isoxazolidin-3-one | Me | H | 5.78 (*) | 545.04 (+) | B |
| A10 | N'-methoxyformamidine | Me | H | 5.92 (*) | 489.06 (+) | B |
| A11 | butan-1-amine | Br | H | 6.31 (*) | 552.16 (+) | B |
| A12 | 1-oxidothietan-1-ium-3-amine; | Br | H | 6.17 (*) | 581.99 (−) | B |
| A13 | butan-1-amine | Br | Cl | 2.65 (*) | 586.00 (+) | B |
| A14 | 2,2,2-trifluoroethanamine | Br | Cl | 2.23 (*) | 537.90 (+) | B |
| A15 | 1-oxidothietan-1-ium-3-amine; | Br | Cl | 6.16 (*) | 618.00 (+) | B |
| A16 | butan-1-amine | Me | F | 6.27 (*) | 506.27 (+) | B |
| A17 | 2,2,2-trifluoroethanamine | Me | F | 6.24 (*) | 530.13 (−) | B |
| A18 | 1-oxidothietan-1-ium-3-amine; | Me | F | 2.59 (*) | 611.80 (+) | B |
| A19 | ethanamine | Me | H | 2.41 (*) | 460.00 (+) | B |
| A20 | methanamine | Me | H | 1.98 | 446.25 (+) | A |
| A21 | 2-aminoacetonitrile | Me | H | 2.00 | 471.23 (+) | A |
| A22 | cyclopropyl-methanamine | Me | H | 2.16 | 486.27 (+) | A |
| A23 | 2-methyl-sulfanylethanamine | Me | H | 2.13 | 505.53 (+) | A |
| A24 | isoxazol-3-ylmethanamine | Me | H | 2.02 | 513.18 (+) | A |
| A25 | tetrahydrofuran-2-ylmethanamine | Me | H | 2.09 | 516.49 (+) | A |
| A26 | (3-methyloxetan-3-yl)methanamine | Me | H | 2.02 | 516.41 (+) | A |
| A27 | 4,5-dihydrothiazol-2-amine | Me | H | 1.96 | 517.17 (+) | A |
| A28 | 3-methylthietan-3-amine | Me | H | 2.23 | 518.26 (+) | A |
| A29 | phenylmethanamine | Me | H | 2.22 | 522.19 (+) | A |
| A30 | pyrimidin-2-ylmethanamine | Me | H | 1.98 | 524.19 (+) | A |
| A31 | oxetan-3-amine | Me | H | 1.95 | 488.18 (+) | A |
| A32 | 1-(ethoxymethyl)cyclopropanamine | Me | H | 2.16 | 530.28 (+) | A |
| A33 | 1-aminocyclopropane-carbonitrile | Me | H | 2.04 | 497.18 (+) | A |
| A34 | cyclopent-3-en-1-amine | Me | H | 2.19 | 498.02 (+) | A |
| A35 | (1S)-1-phenylethanamine | Me | H | 2.26 | 535.67 (+) | A |
| A36 | (2-fluorophenyl)methanamine | Me | H | 2.23 | 539.58 (+) | A |
| A37 | 1-(3-pyridyl)cyclopropanamine | Me | H | 1.73 | 549.24 (+) | A |
| A38 | oxazol-4-ylmethanamine | Me | H | 1.97 | 513.2 (+) | A |
| A39 | thiazol-2-ylmethanamine | Me | H | 2.04 | 529.2 (+) | A |
| A40 | 3,3-dichloroprop-2-en-1-amine | Me | H | 2.27 | 540.1 (+) | A |
| A41 | 2-amino-N-(2,2,2-trifluoroethyl)acetamide | CF3 | H | 6.08 (*) | 624.94 (−) | B |
| A42 | 2,2,2-trifluoroethanamine | CF3 | H | 6.13 (*) | 566.02 (−) | B |
| A43 | butan-1-amine; | CF3 | H | 6.22 | 542.09 (−) | B |
| A44 | 1-oxidothietan-1-ium-3-amine; | CF3 | H | 6.02 (*) | 574.17 (+) | B |
| A45 | (4R)-4-amino-2-ethyl-isoxazolidin-3-one; | CF3 | H | 6.14 (*) | 599.00 (+) | B |
| A46 | cyclopropanamine; | Me | H | 2.41 (*) | 471.90 (+) | B |
| A47 | (4R)-4-amino-2-ethyl-isoxazolidin-3-one; | Me | Cl | 2.45 (*) | 578.9 (+) | B |
| A48 | butan-1-amine; | Me | H | 2.55 (*) | 488.00 (+) | B |
| A49 | 1-oxidothietan-1-ium-3-amine; | Me | Cl | 2.33 | 552.00 (−) | B |
| A50 | butan-1-amine; | Cl | Cl | 5.46 (*) | 541.44 (−) | B |
| A51 | 2,2,2-trifluoroethanamine | Cl | Cl | 5.42 (*) | 565.69 (−) | B |
| A52 | 2-pyridylmethanamine; | Cl | Cl | 5.51 (*) | 578.82 (+) | B |
| A53 | 2-amino-N-(2,2,2-trifluoroethyl)acetamide | Cl | Cl | 5.48 (*) | 624.92 (+) | B |
| A54 | (4R)-4-amino-2-ethyl-isoxazolidin-3-one | Cl | Cl | 5.49 (*) | 601.85 (+) | B |
| A55 | tert-butoxy | Me | H | 6.17 (*) | 487.01 (−) | B |
| A56 | hydroxyl | Me | H | (*) | 431.01 (−) | B |
| A57 | tert-butoxy | Br | H | 6.66 (*) | 550.91 (−) | B |
| A58 | hydroxyl | Me | Cl | 2.58 (*) | 464.90 (−) | B |
| A59 | tert-butoxy | Br | Cl | (*) | | |
| A60 | tert-butoxy | Me | Cl | 2.95 (*) | 521.10 (−) | B |
| A61 | tert-butoxy | Cl | Cl | 5.85 (*) | 540.75 (−) | B |
| A62 | tert-butoxy | Me | F | 6.53 (*) | 505.08 (−) | B |
| A63 | hydroxyl | Cl | Cl | 4.28 | 484.71 (−) | B |

(*): NMR data as follows: $^1$H-NMR (400 MHz, CDCl$_3$, in ppm)

A1: 7.42 (2H, s), 7.40 (1H, s), 7.33 (1H, d), 7.15 (1H, d), 6.55 (1H, s), 5.85 (1H, m), 4.58 (1H, m), 3.6 (1H, d), 3.8 (1H, d), 2.5 (3H, s), 2.5 (2H, m), 1.9 (2H, m), 1.8 (2H, m)

A2: 2.46 (s, 3H), 3.64 (d, 1H), 3.85 (d, 1H), 4.08-4.12 (m, 2H), 6.59 (s, 1H), 7.20-7.22 (m, 2H), 7.36-7.40 (m, 4H).

A3: 2.47 (s, 3H), 3.66-3.67 (d, 1H), 3.83-3.87 (d, 1H), 3.95 (m, 2H), 4.17-4.18 (d, 2H), 6.59-6.61 (NH), 6.62-6.69 (s, 1H), 6.99 (s, 1H), 7.20 (m, 2H), 7.40 (m, 4H).

A4: 2.47 (s, 3H), 3.66 (d, 1H), 3.84 (d, 1H), 4.01-4.05 (m, 2H), 4.59-4.65 (m, 2H), 4.85-4.92 (m, 1H), 6.58-6.64 (m, 2H), 7.15-7.42 (m, 6H)

A5: 2.45 (s, 3H), 3.35-3.40 (m, 2H), 3.46-3.51 (m, 2H), 3.66 (d, 1H), 3.86 (d, 1H), 5.40-5.42 (m, 1H), 6.35 (d, NH), 6.59 (d, 1H), 7.18-7.42 (m, 6H).

A6: 2.52 (s, 3H), 3.66 (d, 1H), 3.85 (d, 1H), 5.71 (s, 2H), 6.59-6.62 (m, 1H), 7.19-7.46 (m, 5H), 8.08-8.11 (m, 1H).

A7: 2.46 (s, 3H), 3.22-3.28 (m, 2H), 3.66 (d, 1H), 3.84 (d, 1H), 4.17-4.22 (m, 2H), 4.67-4.69 (m, 1H), 6.66-6.48 (m, 1H), 6.59 (d, 1H), 7.18-7.48 (m, 6H).

A8: 2.49 (s, 3H), 3.65 (d, 1H), 3.85 (d, 1H), 4.76 (d, 2H), 6.56 (d, 1H), 7.19-7.48 (m, 9H), 7.71-7.78 (t, 1H), 8.53 (d, 1H)

A9: 1.27 (m, 3H), 2.47 (s, 3H), 3.61-3.67 (m, 3H), 3.85 (d, 1H), 4.01-4.05 (m, 1H), 4.83-4.87 (m, 1H), 4.94-4.97 (m, 1H), 6.52 (d, 1H), 6.58 (d, 1H), 7.17-7.25 (m, 2H), 7.37-7.42 (m, 4H).

A10: 2.52 (s, 3H), 3.65 (d, 1H), 3.82-3.89 (m, 4H), 6.64 (d, 1H), 7.23-7.46 (m, 6H), 8.50 (d, 1H).

A11: 7.50-7.56 (m, 2H), 7.36-7.41 (m, 3H), 7.31 (dd, 1H), 6.63 (s, 1H), 6.03 (br. s, 1H), 3.81 (dd, 1H), 3.62 (dd, 1H), 3.45 (td, 2H), 1.52-1.71 (m, 2H), 1.36-1.49 (m, 2H), 0.88-1.02 (m, 3H)

A12: 7.51-7.56 (m, 2H), 7.36-7.41 (m, 3H), 7.29-7.35 (m, 1H), 6.84 (d, 1H), 6.67 (s, 1H), 4.60-4.74 (m, 1H), 4.15-4.23 (m, 2H), 3.79-3.86 (m, 1H), 3.59-3.66 (m, 1H), 3.28-3.39 (m, 2H).

A13: 7.54 (t, 3H), 7.51 (d, 1H), 7.31 (dd, 1H), 6.62 (s, 1H), 6.01 (br. s, 1H), 3.82 (dd, 1H), 3.59 (dd, 1H), 3.42-3.49 (m, 2H), 1.55-1.66 (m, 2H), 1.37-1.48 (m, 2H), 0.91-0.99 (m, 3H)

A14: 7.51-7.60 (m, 4H), 7.33 (dd, 1H), 6.66 (s, 1H), 6.39-6.49 (m, 1H), 4.11 (qd, 2H), 3.82 (dd, 1H), 3.56-3.64 (m, 1H)

A15: 7.54 (s, 2H), 7.49 (d, 1H), 7.45 (d, 1H), 7.25-7.34 (m, 2H), 6.64 (s, 1H), 4.58-4.73 (m, 1H), 4.10-4.19 (m, 2H), 3.82 (dd, 1H), 3.60 (dd, 1H), 3.37 (td, 2H)

A16: 7.51 (d, 2H), 7.32 (d, 1H), 7.08-7.22 (m, 2H), 6.54 (s, 1H), 5.73 (t, 1H), 3.84 (dd, 1H), 3.61 (dd, 1H), 3.38-3.48 (m, 2H), 2.45 (s, 3H), 1.54-1.65 (m, 2H), 1.36-1.47 (m, 2H), 0.96 (t, 3H)

A17: 7.51 (d, 2H), 7.31-7.43 (m, 1H), 7.19-7.21 (m, 2H), 6.59 (s, 1H), 6.02 (br. s, 1H), 4.02-4.21 (m, 2H), 3.85 (d, 1H), 3.62 (d, 1H), 2.46 (s, 3H)

A18: 7.50 (d, 2H), 7.38 (d, 1H), 7.15-7.21 (m, 2H), 6.52-6.60 (m, 2H), 4.61-4.71 (m, 1H), 4.13-4.21 (m, 2H), 3.84 (dd, 1H), 3.61 (d, 1H), 3.29-3.39 (m, 2H), 2.45 (s, 3H)

A19: 7.42 (d, 2H), 7.36-7.39 (m, 1H), 7.30-7.34 (m, 1H), 7.12-7.21 (m, 2H), 6.55 (s, 1H), 5.69-5.87 (m, 1H), 3.84 (dd, 1H), 3.64 (dd, 1H), 3.46 (qd, 2H), 2.45 (s, 3H), 1.18 (t, 3H)

A41: 7.62-7.66 (m, 1H), 7.49-7.59 (m, 2H), 7.36-7.47 (m, 3H), 7.06 (br. s, 1H), 6.73-6.84 (m, 2H), 4.24 (d, 2H), 3.83-4.00 (m, 3H), 3.68 (dd, 1H)

A42: 7.64 (s, 1H), 7.50-7.60 (m, 2H), 7.40-7.43 (m, 3H), 6.75 (s, 1H), 6.05 (br. s, 1H), 4.11 (qd, 2H), 3.79-3.95 (m, 1H), 3.68 (d, 1H)

A44: 7.46-7.65 (m, 3H), 7.38-7.44 (m, 3H), 6.74 (s, 1H), 6.62 (m, 1H), 5.03-5.11 (m, 1H), 4.63-4.74 (m, 1H), 4.13-4.22 (m, 2H), 3.83-3.91 (m, 1H), 3.67 (dd, 1H), 3.23-3.33 (m, 2H)

A45: 7.63 (s, 1H), 7.51-7.60 (m, 2H), 7.37-7.44 (m, 3H), 6.74 (s, 1H), 6.43 (d, 1H), 4.99 (t, 1H), 4.79-4.88 (m, 1H), 4.05 (dd, 1H), 3.87 (d, 1H), 3.58-3.75 (m, 3H), 1.26 (t, 3H)

A46: 7.22 (s, 2H), 7.17-7.19 (m, 1H), 7.08-7.12 (m, 1H), 6.92-7.03 (m, 2H), 6.38 (s, 1H), 3.64 (dd, 1H), 3.45 (dd, 1H), 2.60-2.75 (m, 1H), 2.20-2.24 (s, 3H), 0.51-0.66 (m, 2H), 0.30-0.45 (m, 2H)

A47: 7.57 (s, 2H), 7.42-7.46 (m, 1H), 7.16-7.21 (m, 2H), 6.59 (s, 1H), 6.43 (d, 1H), 4.95-5.02 (m, 1H), 4.80-4.91 (m, 1H), 3.93-4.14 (m, 2H), 3.86 (dd, 1H), 3.58-3.75 (m, 2H), 2.48 (s, 3H), 1.22-1.28 (t, 3H)

A48: 7.43 (s, 2H), 7.37-7.39 (m, 1H), 7.30-7.34 (m, 1H), 7.13-7.21 (m, 2H), 6.55 (s, 1H), 5.84 (br. s, 1H), 3.85 (dd, 1H), 3.64 (dd, 1H), 3.37-3.49 (m, 2H), 2.45 (s, 3H), 1.54-1.64 (m, 2H), 1.37-1.47 (m, 3H), 0.96 (t, 3H)

A50: 8.41-8.44 (m, 1H), 7.69 (d, 1H), 7.55 (s, 2H), 7.32 (d, 1H), 7.28 (dd 1H), 6.64 (s, 1H), 6.25-6.33 (m, 1H), 3.83 (dd, 1H), 3.61 (dd, 1H), 3.42-3.48 (m, 2H), 1.57-1.65 (m, 2H), 1.37-1.48 (m, 2H), 0.96 (t, 3H)

A51: 7.74 (d, 1H), 7.55 (s, 2H), 7.36 (d, J=1.8 Hz, 1H), 7.29-7.34 (m, 1H), 6.66-6.72 (m, 2H), 4.14 (qd, 2H), 3.84 (dd, 1H), 3.62 (dd, 1H)

A52: 8.49 (d, 1H), 7.94 (s, 1H), 7.65-7.76 (m, 3H), 7.49 (s, 2H), 7.39 (d, 1H), 7.29 (d, 1H), 7.21-7.26 (m, 2H), 6.53-6.63 (m, 1H), 4.75 (d, 2H), 3.71-3.85 (m, 1H), 3.55 (dd, 1H)

A53: 7.63 (d, 1H), 7.49 (s, 2H), 7.30 (d, 1H), 7.24 (dd, 1H), 7.02 (br. s, 1H), 6.62 (s, 1H), 4.19 (d, 2H), 3.83-3.93 (m, 2H), 3.78 (dd, 1H), 3.51-3.59 (m, 1H)

A54: 7.62-7.67 (m, 1H), 7.49 (s, 2H), 7.28 (d, 1H), 7.23 (dd, 1H), 7.01-7.07 (m, 1H), 6.61 (s, 1H), 4.86-4.93 (m, 1H), 4.76-4.84 (m, 1H), 3.91-4.08 (m, 1H), 3.73-3.81 (m, 1H), 3.51-3.68 (m, 3H), 1.16-1.22 (m, 5H)

A55: 1.58 (s, 9H), 2.60 (s, 3H), 3.67 (d, 1H), 3.95 (d, 1H), 6.60 (d, 1H), 7.15-7.42 (m, 6H)

A56: 2.50 (s, 3H), 3.86 (d, 1H), 4.02 (d, 1H), 7.17-7.81 (m, 7H).

A57: 7.70 (d, 1H), 7.56 (d, 1H), 7.38-7.43 (m, 3H), 7.30 (dd, 1H), 6.67 (s, 1H), 3.83 (dd, 1H), 3.63 (dd, 1H), 1.60 (s, 9H)

A58: 11.54 (br. s, 1H), 7.69-7.74 (m, 1H), 7.39 (s, 2H), 6.99-7.05 (m, 2H), 6.47 (s, 1H), 3.68 (dd, 1H), 3.47 (dd, 1H), 2.40 (s, 3H)

A59: 7.82 (s, 2H), 7.76 (d, 1H), 7.68-7.70 (m, 1H), 7.41 (dd, 1H), 4.87 (s, 1H), 3.50 (d, 1H), 3.01 (d, 1H), 1.61 (s, 9H).

A60: 7.67-7.73 (m, 1H), 7.54-7.62 (m, 1H), 7.15-7.22 (m, 1H), 7.06-7.14 (m, 2H), 6.53 (s, 1H), 3.74-3.83 (m, 1H), 3.52-3.61 (m, 1H), 2.44-2.49 (m, 3H), 1.48 (s, 9H)

A61: 7.73 (d, 1H), 7.56 (s, 2H), 7.35 (d, 1H), 7.23-7.26 (m, 1H), 6.66 (s, 1H), 3.84 (dd, 1H), 3.61 (dd, 1H), 1.59 (s, 9H).

A62: 7.81 (d, 1H), 7.49-7.54 (m, 2H), 7.13-7.22 (m, 2H), 6.60 (s, 1H), 3.86 (dd, 1H), 3.58-3.67 (m, 1H), 2.58 (s, 3H), 1.59 (m, 9H).

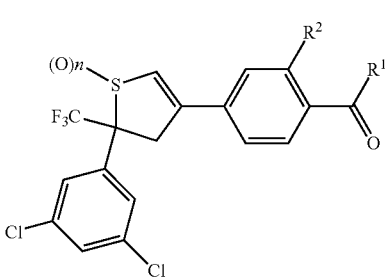

(I-b)

| Cmpd No. | R1 | R2 | n | RT (minute) | [M]+ (+ or −) mode) | LC-MS method |
|---|---|---|---|---|---|---|
| B1 | 2,2,2-trifluoroethanamine | Me | 1 | 5.50 (*) | 527.96 (−) | B |
| B2 | 2,2,2-trifluoroethanamine | Me | 2 | 5.84 (*) | 544.06 (−) | B |

(*): NMR data as follows: $^1$H-NMR (400 MHz, CDCl$_3$, in ppm)

B1: 2.51 (s, 3H), 3.85 (d, 2H), 4.11-4.15 (m, 2H), 6.99 (d, 1H), 7.38-7.48 (m, 6H)

B2: (NMR in DMSO d6): 9.07-9.08 (d, 1H), 8.10 (t, 1H), 7.92 (t, 1H), 7.79-7.84 (d, 1H), 7.72-7.73 (d, 1H), 7.46-7.48 (d, 2H), 4.14 (m, 2H), 3.30 (s, 3H), 2.50-2.51 (d, 1H), 2.40-2.44 (d, 1H).

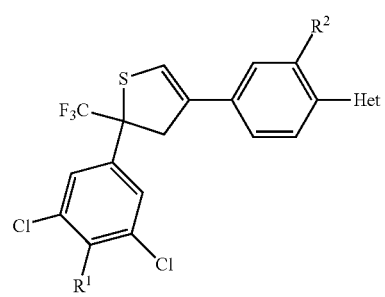

(I-c)

| Cmpd No. | Het | R1 | R2 | RT (minute) | [M]+ (+ or −) mode) | LC-MS method |
|---|---|---|---|---|---|---|
| C1 | 1,2,4-triazolyl | Cl | CN | 6.24 (*) | 501.22 (+) | B |

(*): NMR data as follows: $^1$H-NMR (400 MHz, CDCl$_3$, in ppm)

C1: 8.79 (s, 1H), 8.19 (s, 1H), 7.68-7.79 (m, 3H), 7.57 (s, 2H), 6.77 (s, 1H), 3.89 (dd, 1H), 3.61-3.71 (m, 1H)

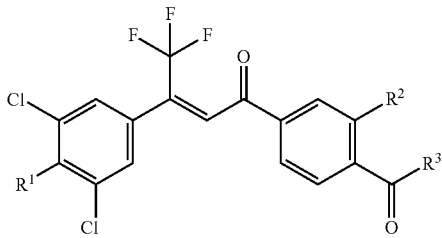

(IA-a)

| Cmpd No. | R1 | R2 | R3 | RT (minute) | [M]+ (+ or − mode) | LCMS method |
|---|---|---|---|---|---|---|
| IA1 | H | Br | OtBu | 5.90 | 521.68 (−) | B |
| IA2 | Cl | Br | OtBu | 5.90 | 556.91 (−) | B |

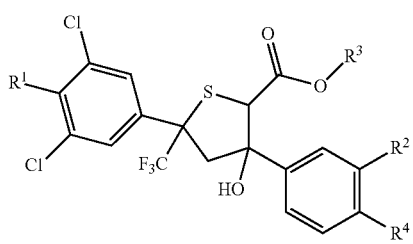

(IB-a)

| Cmpd No. | R1 | R2 | R3 | R4 | RT (minute) | [M]+ (+ or − mode) | LC-MS method |
|---|---|---|---|---|---|---|---|
| IB1 | H | Me | Et | COOtBu | 6.11 (*) | 577.11 (−) | B |
| IB2 | H | Me | H | COOtBu | (*) | | |
| IB3 | H | Br | Et | COOtBu | 6.33 (*) | 641.14 (−) | B |
| IB4 | H | Br | H | COOtBu | | | |
| IB5 | Cl | Br | Et | COOtBu | 6.42 (*) | 675.10 (−) | B |
| IB6 | Cl | Me | Et | COOtBu | 6.26 (*) | 610.97 (−) | B |
| IB7 | Cl | Cl | Et | COOtBu | (*) | | |
| IB8 | F | Me | Et | COOtBu | 6.34 (*) | 595.05 (−) | B |
| IB9 | H | CF3 | Et | COOtBu | (*) | | |
| IB10 | Cl | CN | Et | 1,2,4-triazolyl | 2.39 (*) | 591.00 (+) | B |

(*): NMR data as follows: $^1$H-NMR (400 MHz, CDCl$_3$, in ppm)

IB1: 1.17 (d, 3H), 1.57 (s, 9H), 2.58 (s, 3H), 2.86 (d, 1H), 2.90 (d, 1H), 4.14-4.16 (m, 2H), 4.65 (d, 1H), 4.76 (s, 1H), 7.31-7.32 (m, 3H), 7.52-7.54 (m, 2H), 7.84 (d, 1H).
IB2: 1.55 (s, 9H), 2.44 (s, 3H), 2.79-2.87 (m, 3H), 4.09-4.14 (m, 2H), 7.22-7.47 (m, 6H).
IB3: 7.77 (d, 1H), 7.69-7.72 (m, 1H), 7.52 (d, 2H), 7.44 (dd, 1H), 7.37 (t, 1H), 4.72 (s, 1H), 4.69 (d, 1H), 4.05-4.20 (m, 2H), 2.93-3.00 (m, 1H), 2.80-2.86 (m, 1H), 1.59 (s, 9H), 1.20 (t, 3H).
IB5: 7.76 (d, 1H), 7.70 (d, 1H), 7.66 (s, 2H), 7.44 (dd, 1H), 4.77 (dl H), 4.72 (s, 1H), 4.06-4.21 (m, 2H), 2.90-2.97 (m, 1H), 2.79-2.86 (m, 1H), 1.60 (s, 9H), 1.17-1.24 (m, 3H).
IB6: 7.83 (d, 1H), 7.68 (s, 2H), 7.29-7.35 (m, 2H), 4.77 (s, 1H), 4.72 (d, 1H), 4.10-4.20 (m, 2H), 2.90-2.95 (m, 1H), 2.83-2.89 (m, 1H), 2.59 (s, 3H), 1.59 (s, 9H), 1.19 (t, 3H).
IB7: 7.68 (d, 1H), 7.59 (s, 2H), 7.50 (d, 1H), 7.32 (dd, 1H), 4.69 (d, 1H), 4.65 (s, 1H), 4.00-4.12 (m, 2H), 2.83-2.90 (m, 1H), 2.72-2.80 (m, 1H), 1.36 (s, 9H), 1.10-1.17 (m, 3H).
IB8: 7.83 (d, 1H), 7.61 (d, 2H), 7.29-7.34 (m, 2H), 4.76 (s, 1H), 4.71 (d, 1H), 4.04-4.18 (m, 3H), 2.89-2.94 (m, 1H), 2.83-2.89 (m, 1H), 2.59 (s, 3H), 1.58-1.60 (m, 9H), 1.17-1.22 (m, 3H).
IB9: 7.86 (d, 1H), 7.74-7.79 (m, 1H), 7.67-7.73 (m, 1H), 7.50-7.55 (m, 2H), 7.38 (t, 1H), 4.76 (s, 1H), 4.70 (d, 1H), 4.04-4.18 (m, 2H), 2.96-3.03 (m, 1H), 2.86 (dd, 1H), 1.58 (s, 9H), 1.18 (t, 3H).
IB10: 8.80-8.83 (m, 1H), 8.19-8.21 (m, 1H), 8.01 (d, 1H), 7.87-7.91 (m, 1H), 7.83-7.87 (m, 1H), 7.64-7.68 (m, 2H), 4.84 (d, 1H), 4.76 (s, 1H), 4.08-4.18 (m, 2H), 2.97-3.04 (m, 1H), 2.86 (dd, 1H), 1.18-1.26 (m, 3H).

Example 30

Preparation of Chiral Dihydrothiophene Derivative

Step A: Synthesis of ethyl (5R)-3-(4-tert-butoxycarbonyl-3-methyl-phenyl)-5-(3,5-dichlorophenyl)-3-hydroxy-5-(trifluoromethyl)tetrahydrothiophene-2-carboxylate

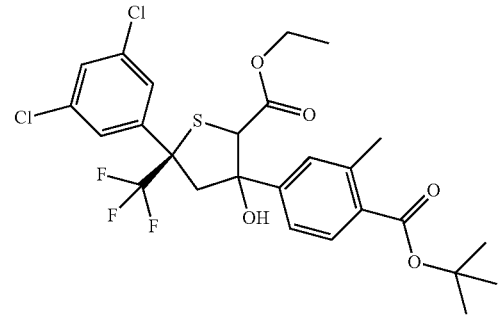 [SMILES: CCOC(=O)C1S[C@](c2cc(Cl)cc(Cl)c2)(C(F)(F)F)CC1(O)c1ccc(C(=O)OC(C)(C)C)c(C)c1]

In a 50 ml round bottom flask was dissolved tert-butyl 5-[(Z)-3-(3,5-dichlorophenyl)-4,4,4-trifluoro-but-2-enoyl]-2-methyl-benzoate (1.5 g) in toluene (10 mL). The reaction mixture was cooled at 0° C. and 1-[3,5-bis(trifluoromethyl) phenyl]-3-[(1S,2S)-2-(dimethylamino)cyclohexyl]thiourea (0.132 g) was added followed by the slow addition (3 h) of ethyl 2-sulfanylacetate (0.99 ml) at the same temperature. The reaction was stirred at room temperature overnight. Then, thin layer chromatogram showed 90% completion of the reaction. Water was added into the reaction mass and it was extracted using ethyl acetate. The combined organic layers were dried over sodium sulphate and concentrated under vacuo. Purification was done using silica gel chromatography using 5% ethyl acetate in cyclohexane as solvent, to obtain the titled compound (1.44 g)

The chiral purity of the isolated compound was assessed by Chiral HPLC and found to be 89:11.

Chiral HPLC Method:

Chiral column Chiralpak IE3 (250×4.6 mm)

Solvent Hexane (97%): isopropylalcohol (3%)

Flow 0.3 ml/min

Retention time (min) 17.4 and 18.3

Ratio of the peaks 89:11

Step B: Synthesis of 4-[(2R)-2-(3,5-dichlorophenyl)-2-(trifluoromethyl)-3H-thiophen-4-yl]-2-methyl-benzoate (D1)

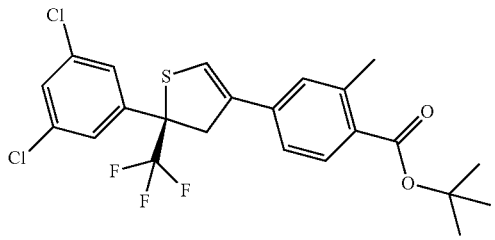 [SMILES: Cc1cc(C2=CS[C@](c3cc(Cl)cc(Cl)c3)(C(F)(F)F)C2)ccc1C(=O)OC(C)(C)C]

The titled compound was prepared according to the steps described for the preparation of compound A57 from intermediate IB3 via intermediate IB4.
Chiral HPLC Method:
Chiral column Chiral pakIB
Solvent Hexane (98%): isopropylalcohol (2%)
Flow 0.4 ml/min
Retention time (min) 10.07 and 10.59
Ratio of the peaks 90:10

Example 31

4-[(2R)-2-(3,5-dichlorophenyl)-2-(trifluoromethyl)-3H-thiophen-4-yl]-2-methyl-benzoic acid (D2)

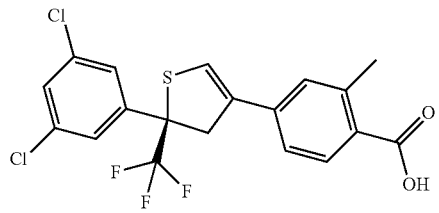 [SMILES: Cc1cc(C2=CS[C@](c3cc(Cl)cc(Cl)c3)(C(F)(F)F)C2)ccc1C(=O)O]

The titled compound was prepared according to the steps described for the preparation of compound A58.
Melting Point=197-199° C.

Example 32

4-[(2R)-2-(3,5-dichlorophenyl)-2-(trifluoromethyl)-3H-thiophen-4-yl]-N-[(4R)-2-ethyl-3-oxo-isoxazolidin-4-yl]-2-methyl-benzamide (D3)

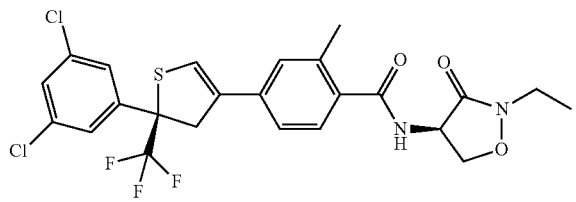 [SMILES: CCN1OC[C@@H](NC(=O)c2ccc(C3=CS[C@](c4cc(Cl)cc(Cl)c4)(C(F)(F)F)C3)cc2C)C1=O]

The titled compound was obtained similarly to the preparation of compound A9
Chiral HPLC Method
Chiral column Chiral pakIE 3 (250×4.6 mm)
Solvent Hexane (75%): isopropylalcohol (25%)
Flow 0.8 ml/min
Retention time (min) 31.31 and 38.91
Ratio of the peaks 89:10

Example 33

Preparation of 4-[(2R)-2-(3,5-dichlorophenyl)-2-(trifluoromethyl)-3H-thiophen-4-yl]-2-methyl-N-(1-oxothietan-3-yl)benzamide (D4)

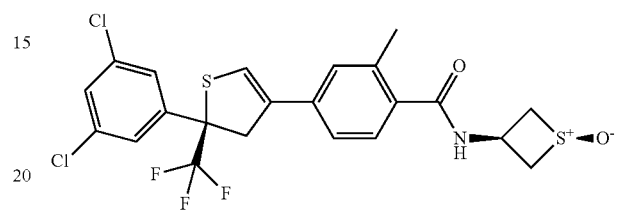

The titled compound was obtained similarly to the preparation of compound A7
Chiral HPLC Method
Chiral column Chiral pakIE 3 (250×4.6 mm)
Solvent Hexane (85%): isopropylalcohol (15%)
Flow 0.8 ml/min
Retention time (min) 28.26 and 30.74
Ratio of the peaks 92:7
Melting point 131-133° C.

Example 34

Preparation of Ethyl (5S)-3-(4-tert-butoxycarbonyl-3-methyl-phenyl)-5-(3,5-dichlorophenyl)-3-hydroxy-5-(trifluoromethyl)tetrahydrothiophene-2-carboxylate

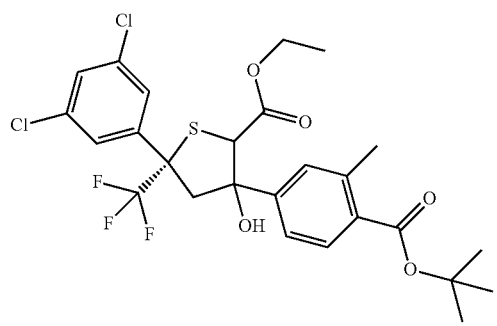 [SMILES: CCOC(=O)C1S[C@@](c2cc(Cl)cc(Cl)c2)(C(F)(F)F)CC1(O)c1ccc(C(=O)OC(C)(C)C)c(C)c1]

In a round bottom flask was dissolved tert-butyl 5-[(Z)-3-(3,5-dichlorophenyl)-4,4,4-trifluoro-but-2-enoyl]-2-methyl-benzoate (1 g) in toluene (100 mL). 1-[3,5-bis(trifluoromethyl)phenyl]-3-[(1R,2R)-2-(dimethylamino)cyclohexyl]thiourea (0.087 g) was added followed by slow addition (3 h) of ethyl 2-sulfanylacetate (0.66 ml) at the same temperature. The reaction was stirred at room temperature overnight. Then. thin layer chromatogram indicated 90% completion of the reaction. The reaction mixture was then diluted with water and extracted using ethyl acetate. The combined organic layers were dried over sodium sulphate and concentrated under reduced pressure. The purification was done using column chromatography using 5% ethyl acetate in cyclohexane as solvent to obtain 0.94 g of pure product.

Chiral HPLC Method
Chiral column Chiral pakIE3 (250×4.6 mm)
Solvent Hexane (97%): isopropylalcohol (3%)
Flow 0.3 ml/min
Retention time (min) 18.01 and 19.00
Ratio of the peaks 10:89

Example 35

Preparation of tert-butyl 4-[(2S)-2-(3,5-dichlorophenyl)-2-(trifluoromethyl)-3H-thiophen-4-yl]-2-methyl-benzoate (D5)

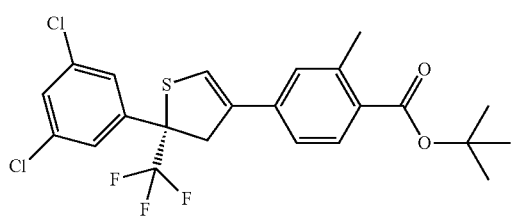 [SMILES: Cc1cc(C2=CS[C@@](c3cc(Cl)cc(Cl)c3)(C(F)(F)F)C2)ccc1C(=O)OC(C)(C)C]

The titled compound was prepared following the steps as described for the preparation of compound A57 from intermediate IB3 via intermediate IB4

Chiral HPLC Method
Chiral column Chiral pakIB
Solvent Hexane (98%): isopropylalcohol (2%)
Flow 0.4 ml/min
Retention time (min) 9.98 and 10.37
Ratio of the peaks 13:86

Example 36

Preparation of 4-[(2S)-2-(3,5-dichlorophenyl)-2-(trifluoromethyl)-3H-thiophen-4-yl]-2-methyl-benzoic acid (D6)

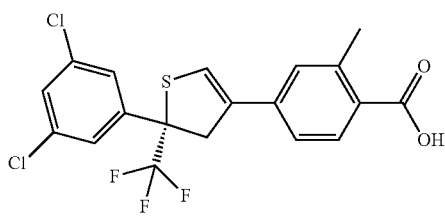 [SMILES: Cc1cc(C2=CS[C@@](c3cc(Cl)cc(Cl)c3)(C(F)(F)F)C2)ccc1C(=O)O]

The title compound was prepared following the steps as described for the preparation of compound A58

Melting Point 197-199° C.

Example 37

Synthesis of 4-[(2S)-2-(3,5-dichlorophenyl)-2-(trifluoromethyl)-3H-thiophen-4-yl]-N-(2-ethyl-3-oxo-isoxazolidin-4-yl)-2-methyl-benzamide (D7)

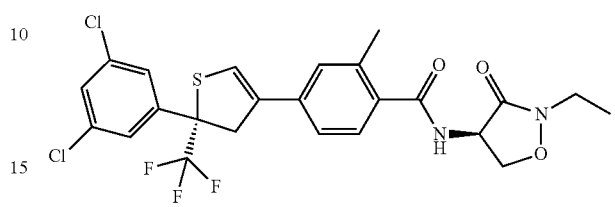

The title compound was obtained in a similar manner as for compound A9

Chiral HPLC Method
Chiral column Chiral pakIE 3 (250×4.6 mm)
Solvent Hexane (75%): isopropylalcohol (25%)
Flow 0.8 ml/min
Retention time (min) 29.61 and 36.63
Ratio of the peaks 15:85

Example 38

Preparation of 4-[(2S)-2-(3,5-dichlorophenyl)-2-(trifluoromethyl)-3H-thiophen-4-yl]-2-methyl-N-(1-oxothietan-3-yl)benzamide (D8)

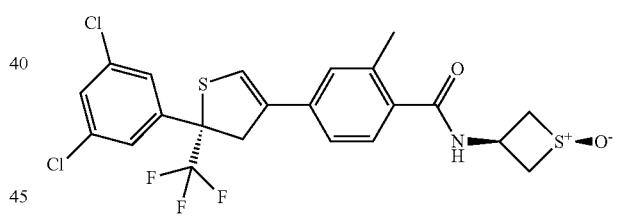

The title compound was obtained in a similar manner as for compound A7 Melting point 118-120° C.

Chiral HPLC Method
Chiral column Chiral pakIE 3 (250×4.6 mm)
Solvent Hexane (85%): isopropylalcohol (15%)
Flow 0.8 ml/min
Retention time (min) 26.81 and 28.55
Ratio of the peaks 13:87.

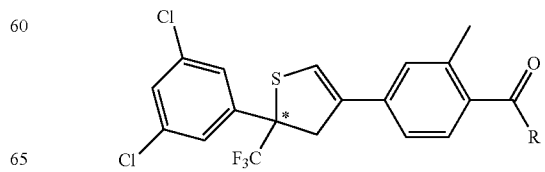

| Cmpd No. | Chiral centre | R1 | RT (minute) | [M]+ (+ or – mode) | LCMS method | RT (minute) in chiral HPLC | EE ratio |
|---|---|---|---|---|---|---|---|
| D1 | R | OtBu | 6.17 (*) | 487.01 (–) | B | 10.07 | 89:11 |
| D2 | R | OH | 2.49 (*) | 432.90 (+) | B | | |
| D3 | R | (4R)-4-amino-2-ethyl-isoxazolidin-3-one | 5.52 (*) | 544.84 (+) | B | 31.31 | 89:11 |
| D4 | R | 1-oxidothietan-1-ium-3-amine; | 2.23 (*) | 519.90 (+) | B | 28.26 | 92:8 |
| D5 | S | OtBu | 5.90 (*) | 486.99 (–) | B | 10.37 | 86:14 |
| D6 | S | OH | 2.47 (*) | 430.90 (–) | B | | |
| D7 | S | (4R)-4-amino-2-ethyl-isoxazolidin-3-one | 2.36 (*) | 544.80 (+) | B | 36.6 | 84:12 |
| D8 | S | 1-oxidothietan-1-ium-3-amine; | 2.22 (*) | 519.80 (+) | B | 28.55 | 37:13 |

(*): NMR data as follows: $^1$H-NMR (400 MHz, CDCl$_3$, in ppm)

D1: 7.81 (d, 1H), 7.43 (d, 2H), 7.37-7.39 (m, 1H), 7.12-7.17 (m, 2H), 6.61 (t, 1H), 3.81-3.99 (m, 1H), 3.48-3.71 (m, 1H), 2.58 (s, 3H), 1.59 (s, 9H)
D2: 7.93-8.13 (m, 1H), 7.34-7.50 (m, 3H), 7.12-7.25 (m, 2H), 6.69 (s, 1H), 3.89 (dd, 1H), 3.67 (dd, 1H), 2.67 (s, 3H)
D3: 7.31-7.52 (m, 4H), 7.15-7.23 (m, 2H), 6.60 (s, 1H), 6.41 (d, 1H), 4.93-5.05 (m, 1H), 4.80-4.88 (m, 1H), 4.12 (q, 1H), 4.04 (dd, 1H), 3.86 (dd, 1H), 3.60-3.76 (m, 3H), 2.49 (s, 2H), 1.24-1.29 (m, 3H)
D4: 7.30-7.54 (m, 4H), 7.15-7.23 (m, 2H), 6.60 (s, 1H), 6.48 (d, 1H), 4.60-4.75 (m, 1H), 4.14-4.27 (m, 2H), 3.86 (dd, 1H), 3.65 (dd, 1H), 3.17-3.35 (m, 2H), 2.46 (s, 3H)
D5: 7.74 (d, 1H), 7.24-7.40 (m, 3H), 7.02-7.16 (m, 2H), 6.47-6.66 (m, 1H), 3.80 (dd, 1H), 3.58 (dd, 1H), 2.51 (s, 3H), 1.36 (s, 9H)
D6: 7.97 (d, 1H), 7.28-7.48 (m, 3H), 6.98-7.22 (m, 2H), 6.62 (s, 1H), 3.71-4.02 (m, 1H), 3.52-3.66 (m, 1H), 2.60 (s, 3H)
D7: 7.33-7.50 (m, 4H), 7.14-7.22 (m, 2H), 6.60 (s, 1H), 6.41 (d, J=3.8 Hz, 1H), 4.94-5.05 (m, 1H), 4.73-4.90 (m, 1H), 4.12 (q, 1H), 4.04 (dd, 1H), 3.86 (dd, 1H), 3.50-3.74 (m, 3H), 2.48 (s, 2H), 1.26 (t, 3H)
D8: 7.30-7.48 (m, 4H), 7.07-7.21 (m, 1H), 6.60 (s, 1H), 6.46 (d, 1H), 4.58-4.79 (m, 1H), 4.20 (ddd, 2H), 3.85 (dd, 1H), 3.64 (d, 1H), 3.22-3.31 (m, 2H), 2.46 (s, 3H)

LC-MS (Liquid Chromatography-Mass Spectrometer) Acquisition
Method A: Details
ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400
Method Waters ACQUITY UPLC with the Following HPLC Gradient Conditions
(Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.
LC-MS (Liquid Chromatography-Mass Spectrometer) Acquisition
Method B: Details
Instrumentation: —
Mass Spectrometer: 6410 Triple Quadruple Mass Spectrometer from Agilent Technologies
HPLC: Agilent 1200 Series HPLC
Optimized Mass Parameter: —
Ionisation method: Electrospray (ESI)
Polarity: positive and Negative Polarity Switch
Scan Type: MS2 Scan
Capillary (kV): 4.00
Fragmentor (V): 100.00
Gas Temperature (° C.): 350
Gas Flow (L/min): 11
Nebulizer Gas (psi): 35
Mass range: 110 to 1000 Da
DAD Wavelength range (nm): 190 to 400
Optimized Chromatographic Parameter: —
Gradient Conditions
(Solvent A: Water, 0.1% formic acid and Solvent B: Acetonitrile, 0.1% formic acid)

| Time (minutes) | A (%) | B (%) | Flow rate (ml/min) |
|---|---|---|---|
| 0 | 90 | 10 | 1.8 |
| 2.0 | 0 | 100 | 1.8 |
| 3.0 | 0 | 100 | 1.8 |
| 3.2 | 90 | 10 | 1.8 |
| 4.0 | 90 | 10 | 1.8 |

Column: Waters Xterra MS C18
Column length: 30 mm
Internal diameter of column: 4.6 mm
Particle Size: 3.5 g
Temperature: Room Temperature

BIOLOGICAL EXAMPLES

The examples illustrate the pest control properties of the compounds of the invention. The tests were performed as follows:"

*Spodoptera littoralis* (Egyptian Cotton Leaf Worm)

Cotton leaf discs were placed on agar in 24-well microtiter plates and sprayed with aqueous test solutions prepared from 10'000 ppm DMSO stock solutions. After drying the leaf discs were infested with five L1 larvae. The samples were assessed for mortality, anti-feedant effect, and growth inhibition 3 days after infestation. Control of *Spodoptera littoralis* by a test sample is noted when at least one of mortality, anti-feedant effect, and growth inhibition is better than the untreated sample.

The following compounds resulted in at least 80% control at an application rate of 200 ppm:

A1, A2, A3, A4, A5, A6, A7, A8, A9, A10, A11, A12, A13, A14, A15, A16, A17, A18, A19, A20, A21, A22, A23, A24, A25, A26, A28, A29, A30, A31, A32, A33, A34, A35, A36, A37, A38, A39, A40, A41, A42, A43, A44, A45, A46, A47, A48, A50, A51, A52, A53, A54, B1, B2, C1, D3, D4, D7, D8

*Heliothis virescens* (Tobacco Budworm):

Eggs (0-24 h old) were placed in 24-well microtiter plates on artificial diet and treated with aqueous test solutions prepared from 10'000 ppm DMSO stock solutions by pipetting. The samples were assessed for egg mortality, larval mortality and growth inhibition 5 days after infestation. Control of *Heliothis virescens* by a test sample is noted when at least one of egg mortality, larval mortality and growth inhibition is better than the untreated sample.

The following compounds resulted in at least 80% control at an application rate of 200 ppm:

A1, A2, A3, A4, A5, A6, A7, A8, A9, A10, A11, A12, A13, A14, A15, A16, A17, A18, A19, A20, A21, A22, A23, A24, A25, A26, A28, A29, A30, A31, A32, A33, A34, A35, A36, A38, A39, A40, A41, A42, A43, A44, A45, A46, A47, A48, B1, B2, C1, D3, D4,

*Plutella xylostella* (Diamond Back Moth):

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition 5 days after infestation. Control of *Plutella xyllostella* by a test sample is noted when at least one of mortality and growth inhibition is better than the untreated sample.

The following compounds resulted in at least 80% control at an application rate of 200 ppm:

A1, A2, A3, A4, A5, A6, A7, A8, A9, A10, A11, A12, A13, A14, A15, A16, A17, A18, A19, A20, A21, A22, A23, A24, A25, A26, A28, A29, A30, A31, A32, A33, A34, A35, A36, A37, A38, A39, A40, A41, A42, A43, A44, A45, A46, A47, A48, A50, A51, A52, A53, A54, B1, B2, C1, D3, D4, D7, D8

*Diabrotica balteata* (Corn Root Worm):

24-well microtiter plates with artificial diet were treated with aqueous test solutions prepared from 10'000 ppm DMSO stock solutions by pipetting. After drying, the plates were infested with L2 larvae (6 to 10 per well). The samples were assessed for mortality and growth inhibition 5 days after infestation. Control of *Diabrotica balteata* by a test sample is noted when at least one of mortality and growth inhibition is better than the untreated sample.

The following compounds resulted in at least 80% control at an application rate of 200 ppm:

A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A36, A38, A39, A40, A41, A42, A43, A44, A45, A46, A47, A48, B2, C1

*Diabrotica balteata*, (Corn Root Worm)

Maize sprouts, placed on an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition 4 days after infestation. Control of *Diabrotica balteata* by a test sample is noted when at least one of mortality and growth inhibition is better than the untreated sample.

The following compounds resulted in at least 80% control at an application rate of 200 ppm:

A50, A51, A52, A53, A54, D3, D4, D7, D8

*Thrips tabaci* (Onion *Thrips*):

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation.

The following compounds resulted in at least 80% control at an application rate of 200 ppm:

A1, A2, A3, A4, A5, A7, A8, A9, A11, A12, A13, A14, A15, A16, A17, A18, A24, A33, AA38, A41, A42, A43, A44, A45, A47, A48, A50, A51, A52, A53, A54, D3, D4, D7, D8

*Tetranychus urticae* (Two-Spotted Spider Mite):

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality (mobile stages) 8 days after infestation.

The following compounds resulted in at least 80% control at an application rate of 200 ppm:

A1, A2, A3, A4, A5, A7, A8, A9, A10, A11, A12, A13, A14, A15, A16, A17, A18, A19, A20, A21, A22, A23, A24, A25, A26, A28, A30, A31, A32, A33, A34, A36, A37, A38, A39, A40, A41, A42, A43, A44, A45, A46, A47, A48, A50, A51, A52, A53, A54, D3, D4, D7, D8

*Euschistus heros* (Neotropical Brown Stink Bug)

Two weeks old soybean plants were sprayed in a turn table spray chamber with the diluted spray solutions. After drying 2 soybean seeds were added and plants were infested with 10 N2 nymphs of the neotropical brown stink bug *Euschistus heros* in plastic test boxes. The samples were assessed for mortality and growth inhibition 5 days after infestation. Control of *Euschistus heros* by a test sample is noted when at least one of mortality and growth inhibition is better than the untreated sample.

The following compounds resulted in at least 80% control at an application rate of 50 ppm:

A1, A2, A3, A4, A5, A7, A9, A12, A13, A15, A17, A18, A42, A43, A44, A45, A47

Test to Determine Biological Safety Profile

*Spodoptera littoralis* (Egyptian Cotton Leafworm)

Cotton plants in the 5 leaf stage (around 5 weeks old) are treated in an automated turn table spray chamber. Plants were stored in the greenhouse at 26° C. and 14 h day length during the whole test period. 2, 10 and 16 days after treatment, 4 leaves from each sample were excised, placed into 14 cm plastic petri dishes on wet filter paper. The infestation of 10 L-3 *Spodoptera littoralis* is made immediately afterwards. The samples were assessed for mortality, growth inhibition and anti-feedant effect after an incubation period of 6 days at 27° C. (without light). Control of *Spodoptera littoralis* by a test sample is noted when at least one of mortality, growth inhibition and anti-feedant effect is better than the untreated sample.

The invention claimed is:
1. A compound of formula (I)

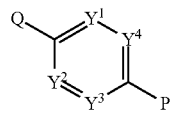
(I)

wherein Q is Q1 or Q2

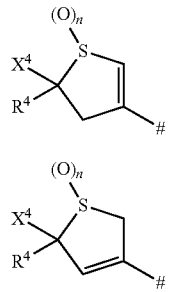

wherein
P is P0, heterocyclyl or heterocyclyl substituted by one to five Z;

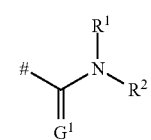
(P0)

$Y^2$, $Y^3$ and Y are independently of each other C—H, C—$R^5$, or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, $C_3$-$C_{10}$cycloalkyl-$C_1$-$C_4$alkanediyl or $C_3$-$C_{10}$cycloalkyl-$C_1$-$C_4$alkanediyl substituted by one to five $R^7$, $C_3$-$C_{10}$cycloalkenyl or $C_3$-$C_{10}$cycloalkenyl substituted by one to five $R^7$, $C_3$-$C_{10}$cycloalkenyl-$C_1$-$C_4$alkanediyl or $C_3$-$C_{10}$cycloalkenyl-$C_1$-$C_4$alkanediyl substituted by one to five $R^7$, aryl-$C_1$-$C_4$alkanediyl or aryl-$C_1$-$C_4$alkanediyl in which the aryl moiety is substituted by one to five $R^8$, heterocyclyl-$C_1$-$C_4$alkanediyl or heterocyclyl-$C_1$-$C_4$alkanediyl in which the heterocyclyl moiety is substituted by one to five $R^8$, aryl-N($R^{20}$)— or aryl-N($R^{20}$)— in which the aryl moiety is substituted by one to five $R^8$, heterocyclyl-N($R^{20}$)— or heterocyclyl-N($R^{20}$)— in which the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$alkanediyl, $C_1$-$C_8$haloalkylaminocarbonyl-$C_1$-$C_4$alkanediyl, $C_3$-$C_8$cycloalkyl-aminocarbonyl-$C_1$-$C_4$alkanediyl, $C_1$-$C_8$alkylaminocarbonyl-, $C_1$-$C_8$haloalkylaminocarbonyl, $C_3$-$C_8$cycloalkyl-aminocarbonyl, $C_1$-$C_8$alkyl-O—N=CH—, or $C_1$-$C_6$haloalkyl-O—N=CH—, and in which a bridging alkanediyl moiety optionally includes a —C($R^{21}$)($R^{22}$)— unit as bridge member;
or $R^1$ and $R^2$ together represent group A

(A)

$G^2$ is O($R^{13}$), N($R^{14}$)($R^{15}$) or S($R^{16}$);
$G^3$ is N($R^{17}$)($R^{18}$) or S($R^{19}$));
$X^4$ is $C_1$-$C_8$haloalkyl;
$R^4$ is aryl or aryl substituted by one to five $R^9$, or heteroaryl or heteroaryl substituted by one to five $R^9$;
each $R^5$ is independently hydrogen, halogen, cyano, nitro, $NH_2$, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-; or two $R^5$ on adjacent carbon atoms together form a —CH=CH—CH=CH— bridge;
each $R^6$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, $C_1$-$C_8$alkoxy-, $C_1$-$C_8$haloalkoxy-, aryloxy or aryloxy substituted by one to five $R^{10}$, aryloxy-$C_1$-$C_4$alkanediyl or aryloxy-$C_1$-$C_4$alkanediyl in which the aryl moiety is substituted by one to five $R^{10}$, $C_1$-$C_8$alkylcarbonyl-, $C_1$-$C_8$alkoxycarbonyl-, mercapto, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, aryl-$C_1$-$C_4$alkanediylthio or aryl-$C_1$-$C_4$alkanediylthio in which the aryl moiety is substituted by one to five $R^{10}$;
each $R^7$ is independently halogen, cyano, $C_1$-$C_8$alkyl, $C_2$-$C_8$alkenyl, $C_2$-$C_8$alkynyl, $C_1$-$C_8$alkyl-O—N=, $C_1$-$C_8$haloalkyl-O—N=, $C_1$-$C_8$alkoxy, $C_1$-$C_4$alkoxy-$C_1$-$C_4$alkyl, or $C_1$-$C_8$alkoxycarbonyl;
each $R^8$ is independently halogen, cyano, nitro, oxo, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkanediyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$haloalkylsulfinyl-, $C_1$-$C_8$alkylsulfonyl-, $C_1$-$C_8$haloalkylsulfonyl-, $C_1$-$C_8$alkylaminosulfonyl, ($C_1$-$C_8$alkyl)$_2$aminosulfonyl-, $C_1$-$C_8$alkylcarbonyl-, $C_1$-$C_8$alkoxycarbonyl-, aryl or aryl substituted by one to five $R^{10}$, heterocyclyl or heterocyclyl substituted by one to five $R^{10}$, aryl-$C_1$-$C_4$alkanediyl- or aryl-$C_1$-$C_4$alkanediyl- in which the aryl moiety is substituted by one to five $R^{10}$, heterocyclyl-$C_1$-$C_4$alkanediyl or heterocyclyl-$C_1$-$C_4$alkanediyl in which the heterocyclyl moiety is substituted by one to five $R^{10}$, aryloxy or aryloxy substituted by one to five $R^{10}$, aryloxy-$C_1$-$C_4$alkanediyl or aryloxy-$C_1$-$C_4$alkanediyl in which the aryl moiety is substituted by one to five $R^{10}$;

each $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$haloalkylthio-, $C_1$-$C_8$alkylsulfinyl-, $C_1$-$C_8$haloalkylsulfinyl-, $C_1$-$C_8$alkylsufonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{10}$, or heterocyclyl or heterocyclyl substituted by one to five $R^{10}$;

each $R^{10}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;

each Z is independently halogen, $C_1$-$C_{12}$alkyl or $C_1$-$C_{12}$alkyl substituted by one to five $R^6$, nitro, $C_1$-$C_{12}$alkoxy or $C_1$-$C_{12}$alkoxy substituted by one to five $R^6$, cyano, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, hydroxyl or thiol;

$R^{13}$, $R^{16}$ and $R^{19}$ are independently $C_1$-$C_4$alkyl;

$R^{14}$, $R^{15}$, $R^{17}$, and $R^{18}$ are independently hydrogen or $C_1$-$C_4$alkyl;

$R^{20}$ is hydrogen or $C_1$-$C_4$alkyl;

each $R^{21}$ and $R^{22}$ is independently halogen or $C_1$-$C_4$alkyl, or optionally together form a $C_3$-$C_4$alkanediyl bridge;

n is 0, 1 or 2;

or a salt or N-oxide thereof.

2. The compound according to claim 1, wherein Q is Q1.

3. The compound according to claim 1, wherein $Y^1$ is C—$R^5$, C—H or nitrogen, $Y^2$ and $Y^3$ are independently C—H or nitrogen and $Y^4$ is C—$R^5$; in which no more than two of $Y^1$, $Y^2$ and $Y^3$ are nitrogen and in which $Y^2$ and $Y^3$ are not both nitrogen, and wherein two $R^5$ when present on adjacent carbon atoms together form a —CH=CH—CH=CH— bridge.

4. The compound according to claim 1, wherein $G^1$ is oxygen.

5. The compound according to claim 1, wherein P is P0 or a heterocycle selected from H1 to H9

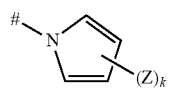

H1

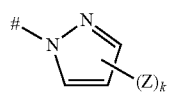

H2

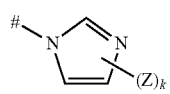

H3

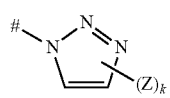

H4

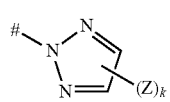

H5

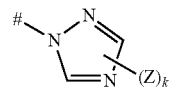

H6

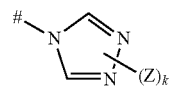

H7

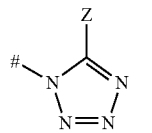

H8

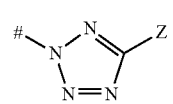

H9 k is 0, 1 or 2.

6. The compound according to claim 1, wherein $R^1$ is hydrogen, methyl, ethyl, methylcarbonyl-, or methoxycarbonyl-.

7. The compound according to claim 1, wherein $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, aryl-$C_1$-$C_4$alkanediyl or aryl-$C_1$-$C_4$alkanediyl in which the aryl moiety is substituted by one to five $R^8$, heterocyclyl-$C_1$-$C_4$alkanediyl or heterocyclyl-$C_1$-$C_4$alkanediyl in which the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$alkanediyl, $C_1$-$C_8$haloalkylaminocarbonyl-$C_1$-$C_4$ alkylene $C_1$-$C_8$haloalkylaminocarbonyl-$C_1$-$C_4$alkanediyl, $C_3$-$C_8$cycloalkyl-aminocarbonyl-$C_1$-$C_4$alkandiyl, or group C1

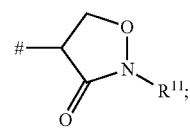

(C1)

$R^{11}$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^{12}$, or $R^{11}$ is pyridyl-methyl- or pyridyl-methyl-substituted by one to three $R^{12}$;

each $R^{12}$ is independently fluoro, chloro, bromo, trifluoromethyl, trifluoromethoxy, cyano or methoxy;

in which each aryl group is a phenyl group and each heterocyclyl group is independently selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, dihydrothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, morpholinyl, 2,3-dihydro-benzofuranyl, benzo[1,3]dioxolanyl, or 2,3-dihydro-benzo[1,4]dioxinyl.

8. The compound according to claim 7, wherein $R^2$ is $C_1$-$C_8$alkyl or $C_1$-$C_8$alkyl substituted by one to five $R^6$, $C_3$-$C_{10}$cycloalkyl or $C_3$-$C_{10}$cycloalkyl substituted by one to five $R^7$, phenyl-$C_1$-$C_4$alkanediyl or phenyl-$C_1$-$C_4$alkanediyl in which the phenyl moiety is substituted by one to five $R^8$, pyridyl-$C_1$-$C_4$alkandiyl or pyridyl-$C_1$-$C_4$alkandiyl in which the pyridyl moiety is substituted by one to four $R^8$, oxetanyl or oxetanyl substituted by one to five $R^8$, thietanyl-$C_1$-$C_4$alkanediyl or thietanyl-$C_1$-$C_4$alkanediyl in which the thietanyl moiety is substituted by one to five $R^8$, oxo-thietanyl-$C_1$-$C_4$alkanediyl or oxo-thietanyl-$C_1$-$C_4$alkanediyl in which the oxo-thietanyl moiety is substituted by one to five $R^8$, dioxo-thietanyl-$C_1$-$C_4$alkanediyl or dioxo-thietanyl-$C_1$-$C_4$alkanediyl in which the dioxo-thietanyl moiety is substituted by one to five $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$, $C_1$-$C_8$alkylaminocarbonyl-$C_1$-$C_4$alkanediyl, $C_1$-$C_8$haloalkylaminocarbonyl-$C_1$-$C_4$alkanediyl, or $C_3$-$C_8$cycloalkyl-aminocarbonyl-$C_1$-$C_4$alkanediyl or group C1

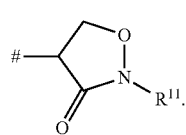

(C1)

9. The compound according to claim 1 wherein $X^4$ is chlorodifluoromethyl or trifluoromethyl.

10. The compound according to claim 1, wherein $R^4$ is aryl or aryl substituted by one to five $R^9$.

11. The compound according to claim 1, wherein the compound of formula I is a compound of formula Ik-1

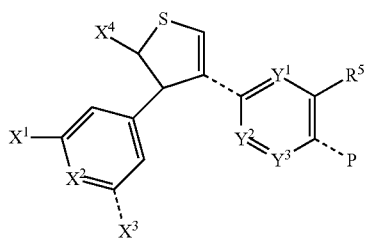

(Ik-1)

wherein
$Y^1$ is C—$R^5$, CH or nitrogen;
$Y^2$ and $Y^3$ are independently CH or nitrogen;
wherein no more than two of $Y^1$, $Y^2$ and $Y^3$ are nitrogen and in which $Y^2$ and $Y^3$ are not both nitrogen;
$R^5$ is hydrogen, halogen, cyano, nitro, $NH_2$, $C_1$-$C_2$haloalkyl, $C_3$-$C_5$cycloalkyl, $C_3$-$C_5$halocycloalkyl, $C_1$-$C_2$alkoxy, or $C_1$-$C_2$haloalkoxy;
two $R^5$ when present on adjacent carbon atoms together form a —CH=CH—CH=CH— bridge;
$X^2$ is C—$X^6$ or nitrogen;
$X^1$, $X^3$ and $X^6$ are independently hydrogen, halogen or trihalomethyl, in which at least two of $X^1$, $X^3$ and $X^6$ are not hydrogen;

$X^4$ is trifluoromethyl, difluoromethyl or chlorodifluoromethyl.

12. A compound of formula (Int-I)

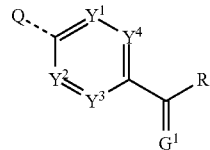

wherein Q, $G^1$, $Y^1$, $Y^2$, $Y^3$ and $Y^4$ are as defined for a compound of formula (I) in claim 1, and R is hydroxy, $C_1$-$C_{15}$alkoxy or halogen, or a salt or N-oxide thereof; or a compound of formula (Int-II)

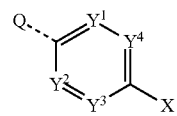

wherein Q, $Y^1$, $Y^2$, $Y^3$ and $Y^4$ are as defined for a compound of formula (I) in claim 1, and X is a leaving group chosen from halogen, $C_1$-$C_8$alkoxy, cyano, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy, diazonium salts, phosphonate esters; or a salt or N-oxide thereof; or a compound of formula (Int-III)

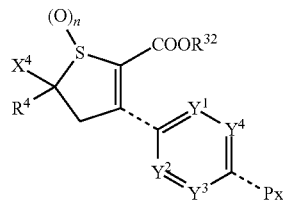

(Int-III)

wherein n, $X^4$, $Y^1$, $Y^2$, $Y^3$, $Y^4$ and $R^4$ are as defined for the compound of formula (I) in claim 1, Px is P as defined for the compound of formula I claim 1, a leaving group as defined for X in compounds of formula Int-II, or C(O)R in which R is halogen, OH or $C_1$-$C_{15}$alkoxy, and $R^{32}$ is hydrogen or $C_1$-$C_{15}$alkyl, or a salt or N-oxide thereof; or a compound of formula (Int-IV)

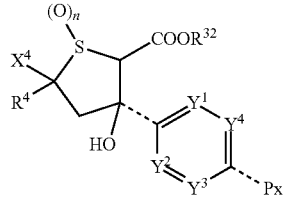

(Int-IV)

wherein n, $X^4$, $Y^1$, $Y^2$, $Y^3$, $Y^4$ and $R^4$ are as defined for compounds of formula (I) in claim 1, Px is P as defined for the compound of formula I in claim 1, a leaving group as defined for X in compounds of formula Int-II, or C(O)R wherein R is halogen, OH or $C_1$-$C_{15}$alkoxy, and $R^{32}$ is hydrogen or $C_1$-$C_{15}$alkyl, or a salt or N-oxide thereof;

a compound of formula (Int-V)

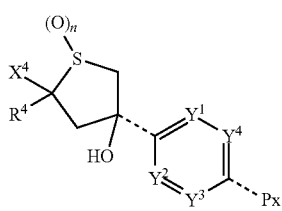

wherein n, $X^4$, $Y^1$, $Y^2$, $Y^3$, $Y^4$ and $R^4$ are as defined for compounds of formula (I), in claim 1, Px is P as defined for the compound of formula I in claim 1, a leaving group as defined for X in compounds of formula Int-II, or C(O)R in which R is halogen, OH or $C_1$-$C_{15}$alkoxy, or a salt or N-oxide thereof.

13. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

14. An insecticidal, acaricidal, nematicidal or molluscicidal composition comprising an insecticidally, acaricidally, nematicidally or molluscicidally effective amount of a compound of formula (I) as defined in claim 1.

15. The insecticidal, acaricidal, nematicidal or molluscicidal composition according to claim 14, wherein the composition comprises at least one additional compound having biological activity.

16. A combination product comprising a pesticidally effective amount of a component A and a pesticidally effective amount of component B, wherein component A is a compound of formula (I) as defined in claim 1, and compound B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene, S-methoprene, clorsulon, pyrantel, amitraz, triclabendazole, ivermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

17. The compound of claim 12, wherein the compound is the compound of formula (Int-I).

18. The compound of claim 12, wherein the compound is the compound of formula (Int-II).

19. The compound of claim 12, wherein the compound is the compound of formula (Int-III).

20. The compound of claim 12, wherein the compound is the compound of formula (Int-IV).

21. The compound of claim 12, wherein the compound is the compound of formula (Int-V).

22. The compound of claim 1, wherein
Q is Q1;
P is P0;
$Y^1$, $Y^2$, $Y^3$ and $Y^4$ are independently of each other C—H or C—$R^5$, provided at least three of $Y^1$, $Y^2$, $Y^3$ and $Y^4$ are C—H;
$G^1$ is O;
$R^1$ is hydrogen; and
$X^4$ is trifluoromethyl.

23. The compound of claim 22, wherein the compound of formula (I) is

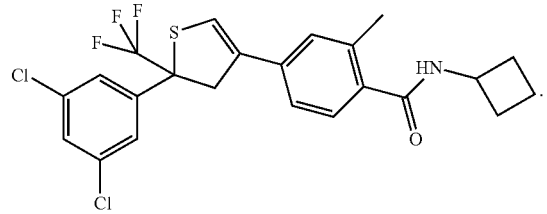 [SMILES: Cc1cc(C2=CSC(c3cc(Cl)cc(Cl)c3)(C(F)(F)F)C2)ccc1C(=O)NC1CCC1]

24. The method of claim 13, wherein the pest is *Myzus persicae*.

* * * * *